(12) United States Patent
Cooper et al.

(10) Patent No.: US 8,716,483 B2
(45) Date of Patent: May 6, 2014

(54) COMPOUNDS THAT ARE ERK INHIBITORS

(75) Inventors: Alan B. Cooper, Kenilworth, NJ (US); Yang Nan, Cambridge, MA (US); Yongqi Deng, Cambridge, MA (US); Gerald W. Shipps, Jr., Cambridge, MA (US); Neng-Yang Shih, Cambridge, MA (US); Hugh Y. Zhu, Kenilworth, NJ (US); Jagdish A. Desai, Kenilworth, NJ (US); James J-S Wang, Kenilworth, NJ (US); Sunil Paliwal, Kenilworth, NJ (US); Hon-Chung Tsui, Kenilworth, NJ (US); Sobhana Babu Boga, Kenilworth, NJ (US); Abdul-Basit Alhassan, Kenilworth, NJ (US); Xiaolei Gao, Kenilworth, NJ (US); Liang Zhu, Cambridge, MA (US); Ahmed Samatar, West Windsor, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 431 days.

(21) Appl. No.: 12/918,099

(22) PCT Filed: Feb. 19, 2009

(86) PCT No.: PCT/US2009/034447
§ 371 (c)(1),
(2), (4) Date: Mar. 23, 2011

(87) PCT Pub. No.: WO2009/105500
PCT Pub. Date: Aug. 27, 2009

(65) Prior Publication Data
US 2011/0189192 A1 Aug. 4, 2011

Related U.S. Application Data

(60) Provisional application No. 61/030,407, filed on Feb. 21, 2008.

(51) Int. Cl.
*C07D 401/04* (2006.01)
*A61K 31/444* (2006.01)

(52) U.S. Cl.
USPC .......................... 546/256; 514/333

(58) Field of Classification Search
USPC .......................... 546/256; 514/333
See application file for complete search history.

(56) References Cited

U.S. PATENT DOCUMENTS

| | | | |
|---|---|---|---|
| 6,696,443 B2 | 2/2004 | Mavunkel et al. | |
| 6,831,175 B2 | 12/2004 | Li et al. | |
| 6,897,231 B2 | 5/2005 | Bhagwat et al. | |
| 7,208,513 B2 | 4/2007 | Bhagwat et al. | |
| 7,211,594 B2 | 5/2007 | Bhagwat et al. | |
| 7,214,679 B2 | 5/2007 | Mavunkel et al. | |
| 7,220,771 B2 | 5/2007 | Bhagwat et al. | |
| 7,429,609 B2 | 9/2008 | Ohi et al. | |
| 2002/0103229 A1 | 8/2002 | Bhagwat et al. | |
| 2002/0198214 A1 | 12/2002 | Mavunkel et al. | |
| 2003/0055068 A1 | 3/2003 | Bebbington et al. | |
| 2003/0187026 A1 | 10/2003 | Li et al. | |
| 2004/0077877 A1 | 4/2004 | Bhagwat et al. | |
| 2004/0127536 A1 | 7/2004 | Bhagwat et al. | |
| 2004/0127538 A1 | 7/2004 | Oinuma et al. | |
| 2005/0009876 A1 | 1/2005 | Bhagwat et al. | |
| 2005/0107386 A1 | 5/2005 | Naria et al. | |
| 2005/0107457 A1 | 5/2005 | Bhagwat et al. | |
| 2007/0060616 A1 | 3/2007 | Bennett et al. | |
| 2007/0149484 A1 | 6/2007 | Claus et al. | |
| 2007/0185112 A1 | 8/2007 | Mavunkel et al. | |
| 2007/0191604 A1 | 8/2007 | Cooper et al. | |
| 2007/0232610 A1 | 10/2007 | Deng et al. | |
| 2007/0265333 A1 | 11/2007 | Fu et al. | |
| 2008/0004287 A1 | 1/2008 | Ma et al. | |
| 2008/0007509 A1 | 1/2008 | Lankhorst et al. | |
| 2009/0011284 A1 | 1/2009 | Wang et al. | |
| 2009/0062355 A1 | 3/2009 | Iizawa et al. | |
| 2009/0118284 A1 | 5/2009 | Cooper et al. | |

FOREIGN PATENT DOCUMENTS

| | | | |
|---|---|---|---|
| GB | 2306108 A | 4/1987 | |
| GB | 2323845 A | 7/1998 | |
| GB | 2400101 A | 10/2004 | |
| WO | 9745412 A1 | 12/1997 | |

(Continued)

OTHER PUBLICATIONS

Lima et. al. "Bioisosterism: A Useful Strategy for Molecular Modification and Drug Design" Current Medicinal Chemistry, Jan. 2005, 12, 23-49.*
Wolff, ME, Burger's Medicinal Chemistry, 5th Ed. Part 1, pp. 975-977 (1995).
Banker et al., Modern Pharmaceuticals, 3rd Ed., p. 596 (1996).
Pinedo et al., Translational Research: The Role of VEGF in Tumor Angiogenesis, The Oncologist 2000; 5 (suppl1); 102. (www.TheOncologist.com).
McMahon, G. VEGF Receptor Signaling in Tumor Anglogenisis. The Oncologist 2000; 5(suppl1):3-10 (www.TheOncologist.com).
(PCT/US2006/046959) International Preliminary Report on Patentability—6 pages (Jun. 18, 2008).

(Continued)

*Primary Examiner* — David K O Dell
(74) *Attorney, Agent, or Firm* — Richard S. Parr; Laura M. Ginkel

(57) ABSTRACT

Disclosed are the ERK inhibitors of formula 1.0: and the pharmaceutically acceptable salts, and solvates thereof. Q is a tetrahydropyridinyl ring. All other substitutents are as defined herein. Also disclosed are methods of treating cancer using the compounds of formula 1.0.

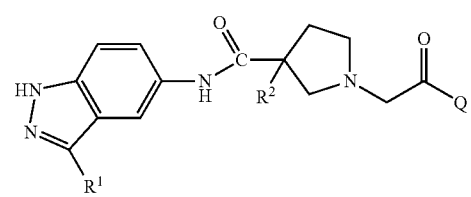

(1.0)

12 Claims, No Drawings

(56) References Cited

FOREIGN PATENT DOCUMENTS

| | | |
|---|---|---|
| WO | 9903498 A1 | 1/1999 |
| WO | 9910325 A1 | 3/1999 |
| WO | 0156557 A2 | 8/2001 |
| WO | 0157022 A2 | 8/2001 |
| WO | 0168619 A1 | 9/2001 |
| WO | 0172721 A2 | 10/2001 |
| WO | 0210137 A2 | 2/2002 |
| WO | 0222604 A1 | 3/2002 |
| WO | 0222610 A1 | 3/2002 |
| WO | 0246158 A2 | 6/2002 |
| WO | 0250065 A2 | 6/2002 |
| WO | 02064586 A2 | 8/2002 |
| WO | 02088090 A2 | 11/2002 |
| WO | 02088097 A1 | 11/2002 |
| WO | 03011854 A1 | 2/2003 |
| WO | 03011855 A2 | 2/2003 |
| WO | 03035626 A2 | 5/2003 |
| WO | 03091246 A1 | 11/2003 |
| WO | 03099212 A2 | 12/2003 |
| WO | 2004026867 A2 | 4/2004 |
| WO | 2004083203 A1 | 9/2004 |
| WO | 2005002673 A1 | 1/2005 |
| WO | 2005063258 A1 | 7/2005 |
| WO | 2005100338 A1 | 10/2005 |
| WO | 2005100342 A1 | 10/2005 |
| WO | 2005113541 A1 | 12/2005 |
| WO | 2005113546 A1 | 12/2005 |
| WO | 2006040569 A1 | 4/2006 |
| WO | 2006071644 A1 | 7/2006 |
| WO | 2006136008 A1 | 12/2006 |
| WO | 2007044401 A2 | 4/2007 |
| WO | 2007044420 A1 | 4/2007 |
| WO | 2007070398 A1 | 6/2007 |
| WO | 2007097937 A1 | 8/2007 |
| WO | 2008121742 A2 | 10/2008 |
| WO | 2008153858 A1 | 12/2008 |
| WO | 2008154241 A1 | 12/2008 |
| WO | 2008156739 A1 | 12/2008 |
| WO | 2011041152 A1 | 4/2011 |

OTHER PUBLICATIONS (PCT/US2006/046959) International Search Report—1 page, (May 18, 2007).

(PCT/US2008/006979)—International Preliminary Report on Patentability—8 pages (Jul. 12, 2009).

(PCT/US2009/034447)—International Search Report—3 pages (Oct. 6, 2009).

(PCT/US2009/034447)—International Preliminary Report on Patentability—5 pages (Aug. 24, 2010).

Translation of Chinese Office Action for CN200980113870.7 received from agent—11 pages (Sep. 25, 2012).

European Office Action for 09 712 601.5-2117—8 pages (Apr. 1, 2012).

(PCT/US2008/006979)—International Search Report—1 page (Oct. 8, 2010).

PCT International Search Report for PCT Application No. (PCT/US2008/007509)—Mailed date: Sep. 30, 2008—2 pages.

PCT International Search Report for PCT Application No. (PCT/US2007/003665)—Mailed date: Jul. 9, 2007—3 pages.

(PCT/US2006/046959) Written Opinion—5 pages (Jun. 13, 2008).

(PCT/US2009/034447)—Written Opinion—4 pages (Aug. 21, 2010).

(PCT/US2008/006979)—Written Opinion—7 pages (May 12, 2009).

* cited by examiner

COMPOUNDS THAT ARE ERK INHIBITORS

REFERENCE TO RELATED APPLICATIONS

This application is a 371 of PCT/US2009/034447 filed Feb. 19, 2009, which in turn claims the benefit of U.S. Provisional Application Ser. No. 61/030,407 filed Feb. 21, 2008.

BACKGROUND

The processes involved in tumor growth, progression, and metastasis are mediated by signaling pathways that are activated in cancer cells. The ERK pathway plays a central role in regulating mammalian cell growth by relaying extracellular signals from ligand-bound cell surface tyrosine kinase receptors such as erbB family, PDGF, FGF, and VEGF receptor tyrosine kinase. Activation of the ERK pathway is via a cascade of phosphorylation events that begins with activation of Ras. Activation of Ras leads to the recruitment and activation of Raf, a serine-threonine kinase. Activated Raf then phosphorylates and activates MEK1/2, which then phosphorylates and activates ERK1/2. When activated, ERK1/2 phosphorylates several downstream targets involved in a multitude of cellular events including cytoskeletal changes and transcriptional activation. The ERK/MAPK pathway is one of the most important for cell proliferation, and it is believed that the ERK/MAPK pathway is frequently activated in many tumors. Ras genes, which are upstream of ERK1/2, are mutated in several cancers including colorectal, melanoma, breast and pancreatic tumors. The high Ras activity is accompanied by elevated ERK activity in many human tumors. In addition, mutations of BRAF, a serine-threonine kinase of the Raf family, are associated with increased kinase activity. Mutations in BRAF have been identified in melanomas (60%), thyroid cancers (greater than 40%) and colorectal cancers. These observations indicate that the ERK1/2 signalling pathway is an attractive pathway for anticancer therapies in a broad spectrum of human tumours.

Therefore, a welcome contribution to the art would be small-molecules (i.e., compounds) that inhibit ERK activity (i.e., ERK1 and ERK2 activity), which small-molecules would be useful for treating a broad spectrum of cancers, such as, for example, melanoma, pancreatic cancer, thyroid cancer, colorectal cancer, lung cancer, breast cancer, and ovarian cancer. Such a contribution is provided by this invention.

SUMMARY OF THE INVENTION

This invention provides compounds that inhibit the activity of ERK1 and/or the activity of ERK2.

The compounds of this invention also inhibit the phosphorylation of ERK1 and ERK2.

Thus, this invention provides compounds that are ERK inhibitors (i.e., ERK1 inhibitors and/or ERK2 inhibitors), said compounds being of the formula 1.0:

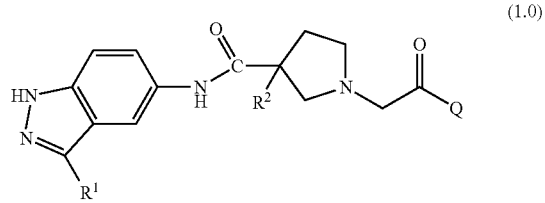

(1.0)

or the pharmaceutically acceptable salts, and solvates thereof, wherein: Q is a tetrahydropyridinyl (e.g., 1,2,3,6-tetrahydropyridinyl), or a substituted tetrahydropyridinyl (e.g., a substituted 1,2,3,6-tetrahydro-pyridinyl); and $R^1$ and $R^2$ are as defined below.

This invention provides compounds of formula 1.0.

This invention provides compounds of formula 1.0 in pure or isolated form.

This invention provides pharmaceutically acceptable salts of the compounds of formula 1.0.

This invention provides solvates of the compounds of formula 1.0.

This invention provides compounds of formula 1.0 wherein from one up to the total number of hydrogens are deuterium.

This invention provides compounds of formula 1.0 wherein at least one H is deuterium.

This invention provides compounds of formula 1.0 wherein 1 to 5H are deuterium.

This invention provides compounds of formula 1.0 wherein one H is deuterium.

This invention provides compounds A1 to A16 and A18 to A48.

This invention provides compounds A1 to A16 and A18 to A30.

This invention provides compounds A1 to A16 and A18 to A26.

This invention provides compounds A31 to A48.

This invention also provides a pharmaceutical composition comprising an effective amount of at least one compound of formula 1.0 and a pharmaceutically acceptable carrier.

This invention also provides a pharmaceutical composition comprising an effective amount of at least one compound of formula 1.0 and an effective amount of at least one other pharmaceutically active ingredient (such as, for example, a chemotherapeutic agent), and a pharmaceutically acceptable carrier.

This invention also provides a method of inhibiting ERK (i.e., inhibiting the activity of ERK) in a patient in need of such treatment comprising administering to said patient an effective amount of at least one compound of formula 1.0.

This invention also provides a method of inhibiting ERK1 (i.e., inhibiting the activity of ERK1) in a patient in need of such treatment comprising administering to said patient an effective amount of at least one compound of formula 1.0.

This invention also provides a method of inhibiting ERK2 (i.e., inhibiting the activity of ERK2) in a patient in need of such treatment comprising administering to said patient an effective amount of at least one compound of formula 1.0.

This invention also provides a method of inhibiting ERK1 and ERK2 (i.e., inhibiting the activity of ERK1 and ERK2) in a patient in need of such treatment comprising administering to said patient an effective amount of at least one compound of formula 1.0.

This invention also provides a method for treating cancer in a patient in need of such treatment, said method comprising administering to said patient an effective amount of at least one compound of formula 1.0.

This invention also provides a method for treating cancer in a patient in need of such treatment, said method comprising administering to said patient an effective amount of a pharmaceutical composition comprising an effective amount of at least one compound of formula 1.0.

This invention also provides a method for treating cancer in a patient in need of such treatment, said method comprising administering to said patient an effective amount of at least one compound of formula 1.0, in combination with an effective amount of at least one chemotherapeutic agent.

This invention also provides a method for treating cancer in a patient in need of such treatment, said method comprising administering to said patient an effective amount of a pharmaceutical composition comprising an effective amount of at least one compound of formula 1.0, in combination with an effective amount of at least one chemotherapeutic agent.

This invention also provides a method of treating cancer in a patient in need of such treatment, said method comprising administering to said patient an effective amount of at least one compound of formula 1.0 in combination with at least one signal transduction inhibitor.

This invention also provides a method of treating cancer in a patient in need of such treatment, said method comprising administering to said patient an effective amount of a pharmaceutical composition comprising an effective amount of at least compound of formula 1.0 in combination with at least one signal transduction inhibitor.

In the methods of this invention the compounds of this invention can be administered concurrently or sequentially (i.e., consecutively) with the chemotherapeutic agents or the signal transduction inhibitor.

The methods of treating cancers described herein can optionally include the administration of an effective amount of radiation (i.e., the methods of treating a cancers described herein optionally include the administration of radiation therapy).

DETAILED DESCRIPTION OF THE INVENTION

As described herein, unless otherwise indicated, the use of a drug or compound in a specified period is per treatment cycle. For example, once a day means once per day of each day of the treatment cycle. Twice a day means twice per day each day of the treatment cycle. Once a week means one time per week during the treatment cycle. Once every three weeks means once per three weeks during the treatment cycle.

The following abbreviations have the following meanings unless defined otherwise:

| | |
|---|---|
| ACN | Acetonitrile |
| AcOH | Acetic acid |
| Anhy | Anhydrous |
| DAST | (diethylamino)sulfur trifluoride |
| DCC | Dicyclohexylcarbodiimide |
| DCU | Dicyclohexylurea |
| DCM | Dichloromethane |
| DI | Deionized water |
| DIAD | Diisopropylazodicarboxylate |
| DIEA | Diisopropylethylamine |
| DMAP | 4-Dimethylaminopyridine |
| DME | Dimethoxyethane |
| DMF | Dimethylformamide |
| DMFDMA | N,N-Dimethylformamide dimethylacetal |
| DMSO | Dimethyl sulfoxide |
| DTT | Dithiothreitol |
| EDCl | 1-(3-dimethylamino-propyl)-3-ethylcarbodiimide hydrochloride |
| Et | Ethyl |
| EtOAc | Ethyl acetate |
| EtOH | Ethanol |
| HATU | N,N,N',N'-Tetramethyl-O-(7-Azabenzotriazol-1-yl) Uronium hexafluorophosphate |
| Hex | hexanes |
| HOBt | 1-Hydroxylbenzotriazole |
| HPLC | High pressure liquid chromatography |
| LCMS | Liquid chromatography mass spectrometry |
| LDA | Lithium diisopropylamide |
| mCPBA | meta-Chloroperoxybenzoic acid |
| MeOH | Methanol |
| MTT | (3-[4,5-dimethyl-thiazol-2-yl]-2,5-diphenyltetrazolium bromide, Thiazolyl blue) |
| NMR | Nuclear magnetic resonance |
| PFP | Pentafluorophenol |
| PMB | p-methoxybenzyl |
| Py | Pyridine |
| Pyr | Pyridine |
| Rb | Round bottom flask |
| Rbt | Round bottom flask |
| RT (r.t.) | Room temperature |
| SEMCl | 2-(Trimethylsily)ethoxy methyl chloride |
| TEA | Triethylamine |
| Tr | Triphenyl methane |
| Trt | Triphenyl methane |
| TrCl | Triphenyl methane chloride |
| TFA | Trifluoroacetic acid |
| THF | Tetrahydrofuran |
| TLC | Thin layer chromatography |
| TMS | Trimethylsilyl |

As used herein, unless otherwise specified, the following terms have the following meanings:

"anti-cancer agent" means a drug (medicament or pharmaceutically active ingredient) for treating cancer;

"antineoplastic agent" means a drug (medicament or pharmaceutically active ingredient) for treating cancer (i.e., a chemotherapeutic agent);

"at least one", as used in reference to the number of compounds of this invention means for example 1-6, generally 1-4, more generally 1, 2 or 3, and usually one or two, and more usually one; thus, in one example "at least one" means one, in another example "at least one" means two, and in another example "at least one" means three;

"at least one", as used in reference to the number of chemotherapeutic agents used, means for example 1-6, generally 1-4, more generally 1, 2 or 3, and usually one or two, or one; thus, in one example "at least one" means one, in another example "at least one" means two, and in another example "at least one" means three;

"chemotherapeutic agent" means a drug (medicament or pharmaceutically active ingredient) for treating cancer (i.e., and antineoplastic agent);

"compound" with reference to the antineoplastic agents, includes the agents that are antibodies;

"concurrently" means (1) simultaneously in time (e.g., at the same time); or (2) at different times during the course of a common treatment schedule;

"consecutively" means one following the other;

"different" as used in the phrase "different antineoplastic agents" means that the agents are not the same compound or structure; preferably, "different" as used in the phrase "different antineoplastic agents" means not from the same class of antineoplastic agents; for example, one antineoplastic agent is a taxane, and another antineoplastic agent is a platinum coordinator compound;

"effective amount" or "therapeutically effective amount" is meant to describe an amount of compound or a composition of the present invention, or an amount of radiation, effective in treating or inhibiting the diseases or conditions described herein, and thus producing the desired therapeutic, ameliorative, inhibitory or preventative effect; thus, for example, in the methods of treating cancer described herein "effective amount" (or "therapeutically effective amount") means, for example, the amount of the compound (or drug), or radiation, that results in: (a) the reduction, alleviation or disappearance of one or more symptoms caused by the cancer, (b) the reduction of tumor size, (c) the elimination of the tumor, and/or (d) long-term disease stabilization (growth arrest) of the tumor; for example, in the treatment of lung cancer (e.g., non small cell lung cancer) a therapeutically effective amount is that amount that alleviates or eliminates cough, shortness of breath and/or pain; also, for example, an effective amount, or a therapeutically effective amount of the ERK inhibitor (i.e., a compound of this invention) is that amount which results in the reduction in ERK (ERK1 and/or ERK2) activity and phosphorylation; the reduction in ERK activity may be determined by the analysis of pharmacodynamic markers such as phosphorylated RSK1,2 and phosphorylated ERK1,2, using techniques well known in the art;

"Ex" in the tables represents "Example";

"one or more" has the same meaning as "at least one";

"patient" means an animal, such as a mammal (e.g., a human being, and preferably a human being);

"prodrug" means compounds that are rapidly transformed, for example, by hydrolysis in blood, in vivo to the parent compound, i.e., to the compounds of formula 1.0 or to a salt and/or to a solvate thereof; a thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference; the scope of this invention includes Prodrugs of the novel compounds of this invention;

sequentially-represents (1) administration of one component of the method ((a) compound of the invention, or (b) chemotherapeutic agent, signal transduction inhibitor and/or radiation therapy) followed by administration of the other component or components; after administration of one component, the next component can be administered substantially immediately after the first component, or the next component can be administered after an effective time period after the first component; the effective time period is the amount of time given for realization of maximum benefit from the administration of the first component; and "solvate" means a physical association of a compound of this invention with one or more solvent molecules; this physical association involves varying degrees of ionic and covalent bonding, including hydrogen bonding; in certain instances the solvate will be capable of isolation, for example when one or more solvent molecules are incorporated in the crystal lattice of the crystalline solid; "solvate" encompasses both solution-phase and isolatable solvates; non-limiting examples of suitable solvates include ethanolates, methanolates, and the like; "hydrate" is a solvate wherein the solvent molecule is $H_2O$.

As used herein, unless otherwise specified, the following terms have the following meanings, and unless otherwise specified, the definitions of each term (i.e., moiety or substituent) apply when that term is used individually or as a component of another term (e.g., the definition of aryl is the same for aryl and for the aryl portion of arylalkyl, alkylaryl, arylalkynyl, and the like):

"acyl" means an H—C(O)—, alkyl-C(O)—, alkenyl-C(O)—, Alkynyl-C(O)—, cycloalkyl-C(O)—, cycloalkenyl-C(O)—, or cycloalkynyl-C(O)— group in which the various groups are as defined below (and as defined below, the alkyl, alkenyl, alkynyl, cycloalkyl, cycloalkenyl and cycloalkynyl moieties can be substituted); the bond to the parent moiety is through the carbonyl; preferred acyls contain a lower alkyl; Non-limiting examples of suitable acyl groups include formyl, acetyl, propanoyl, 2-methylpropanoyl, butanoyl and cyclohexanoyl;

"alkenyl" means an aliphatic hydrocarbon group (chain) comprising at least one carbon to carbon double bond, wherein the chain can be straight or branched, and wherein said group comprises about 2 to about 15 carbon atoms; Preferred alkenyl groups comprise about 2 to about 12 carbon atoms in the chain; and more preferably about 2 to about 6 carbon atoms in the chain; branched means that one or more lower alkyl groups, such as methyl, ethyl or propyl, or alkenyl groups are attached to a linear alkenyl chain; "lower alkenyl" means an alkenyl group comprising about 2 to about 6 carbon atoms in the chain, and the chain can be straight or branched; the term "substituted alkenyl" means that the alkenyl group is substituted by one or more independently selected substituents, and each substituent is independently selected from the group consisting of: halo, alkyl, aryl, cycloalkyl, cyano, alkoxy and —S(alkyl); non-limiting examples of suitable alkenyl groups include ethenyl, propenyl, n-butenyl, 3-methylbut-2-enyl, n-pentenyl, octenyl and decenyl;

"alkoxy" means an alkyl-O— group (i.e., the bond to the parent moiety is through the ether oxygen) in which the alkyl group is unsubstituted or substituted as described below; non-limiting examples of suitable alkoxy groups include methoxy, ethoxy, n-propoxy, isopropoxy, n-butoxy and heptoxy;

"alkoxycarbonyl" means an alkyl-O—CO— group (i.e., the bond to the parent moiety is through the carbonyl) wherein the alkyl group is unsubstituted or substituted as previously defined; non-limiting examples of suitable alkoxycarbonyl groups include methoxycarbonyl and ethoxycarbonyl;

"alkyl" (including the alkyl portions of other moieties, such as trifluoroalkyl and alkyloxy) means an aliphatic hydrocarbon group (chain) that can be straight or branched wherein said group comprises about 1 to about 20 carbon atoms in the chain; preferred alkyl groups comprise about 1 to about 12 carbon atoms in the chain; more preferred alkyl groups comprise about 1 to about 6 carbon atoms in the chain; branched means that one or more lower alkyl groups, such as methyl, ethyl or propyl, are attached to a linear alkyl chain; "lower alkyl" means a group comprising about 1 to about 6 carbon atoms in the chain, and said chain can be straight or branched; the term "substituted alkyl" means that the alkyl group is substituted by one or more independently selected substituents, and wherein each substituent is independently selected from the group consisting of: halo, aryl, cycloalkyl, cyano, hydroxy, alkoxy, alkylthio, amino, —NH(alkyl), —NH(cycloalkyl), —N(alkyl)$_2$, carboxy, —C(O)O-alkyl and —S(alkyl); non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl;

"alkylaryl" (or alkaryl) means an alkyl-aryl- group (i.e., the bond to the parent moiety is through the aryl group) wherein the alkyl group is unsubstituted or substituted as defined above, and the aryl group is unsubstituted or substituted as defined below; preferred alkylaryls comprise a lower alkyl group; non-limiting examples of suitable alkylaryl groups include o-tolyl, p-tolyl and xylyl;

"alkylheteroaryl" means an alkyl-heteroaryl- group (i.e., the bond to the parent moiety is through the heteroaryl group) wherein the alkyl is unsubstituted or substituted as defined above and the heteroaryl group is unsubstituted or substituted as defined below;

"alkylsulfinyl" means an alkyl-S(O)— group (i.e., the bond to the parent moiety is through the sulfinyl) wherein the alkyl group is unsubstituted or substituted as previously defined; preferred groups are those in which the alkyl group is lower alkyl;

"alkylsulfonyl" means an alkyl-S($O_2$)— group (i.e., the bond to the parent moiety is through the sulfonyl) wherein the alkyl group is unsubstituted or substituted as previously defined; preferred groups are those in which the alkyl group is lower alkyl;

"alkylthio" means an alkyl-S— group (i.e., the bond to the parent moiety is through the sulfur) wherein the alkyl group is unsubstituted or substituted as previously described; non-limiting examples of suitable alkylthio groups include methylthio, ethylthio, i-propylthio and heptylthio;

"alkynyl" means an aliphatic hydrocarbon group (chain) comprising at least one carbon to carbon triple bond, wherein the chain can be straight or branched, and wherein the group comprises about 2 to about 15 carbon atoms in the; preferred alkynyl groups comprise about 2 to about 12 carbon atoms in the chain; and more preferably about 2 to about 4 carbon atoms in the chain; Branched means that one or more lower alkyl groups, such as methyl, ethyl or propyl, are attached to a linear alkynyl chain; "lower alkynyl" means an alkynyl group comprising about 2 to about 6 carbon atoms in the chain, and the chain can be straight or branched; non-limiting examples of suitable alkynyl groups include ethynyl, propynyl, 2-butynyl, 3-methylbutynyl, n-pentynyl, and decynyl; the term "substituted alkynyl" means that the alkynyl group is substituted by one or more independently selected, and each substituent is independently selected from the group consisting of alkyl; aryl and cycloalkyl;

"amino means a —$NH_2$ group;

"aralkenyl" (or arylalkenyl) means an aryl-alkenyl- group (i.e., the bond to the parent moiety is through the alkenyl group) wherein the aryl group is unsubstituted or substituted as defined below, and the alkenyl group is unsubstituted or substituted as defined above; preferred aralkenyls contain a lower alkenyl group; non-limiting examples of suitable aralkenyl groups include 2-phenethenyl and 2-naphthylethenyl;

"aralkyl" (or arylalkyl) means an aryl-alkyl- group (i.e., the bond to the parent moiety is through the alkyl group) wherein the aryl is unsubstituted or substituted as defined below and the alkyl is unsubstituted or substituted as defined above; preferred aralkyls comprise a lower alkyl group; non-limiting examples of suitable aralkyl groups include benzyl, 2-phenethyl and naphthalenylmethyl;

"aralkyloxy" (or arylalkyloxy) means an aralkyl-O— group (i.e., the bond to the parent moiety is through the ether oxygen) wherein the aralkyl group is unsubstituted or substituted as previously described; non-limiting examples of suitable aralkyloxy groups include benzyloxy and 1- or 2-naphthalenemethoxy;

"aralkoxycarbonyl" means an aralkyl-O—C(O)— group (i.e., the bond to the parent moiety is through the carbonyl) wherein the aralkyl group is unsubstituted or substituted as previously defined; a non-limiting example of a suitable aralkoxycarbonyl group is benzyloxycarbonyl;

"aralkylthio" means an aralkyl-S— group (i.e., the bond to the parent moiety is through the sulfur) wherein the aralkyl group is unsubstituted or substituted as previously described; a non-limiting example of a suitable aralkylthio group is benzylthio;

"aroyl" means an aryl-C(O)— group (i.e., the bond to the parent moiety is through the carbonyl) wherein the aryl group is unsubstituted or substituted as defined below; non-limiting examples of suitable groups include benzoyl and 1- and 2-naphthoyl;

"aryl" (sometimes abbreviated "ar") means an aromatic monocyclic or multicyclic ring system comprising about 6 to about 14 carbon atoms, preferably about 6 to about 10 carbon atoms; the aryl group can be optionally substituted with one or more independently selected "ring system substituents" (defined below). Non-limiting examples of suitable aryl groups include phenyl and naphthyl;

"arylalkynyl" means an aryl-alkynyl- group (i.e., the bond to the parent moiety is through the alkynyl group) wherein the aryl group is unsubstituted or substituted as defined above, and the alkynyl group is unsubstituted or substituted as defined above;

"arylaminoheteroaryl" means an aryl-amino-heteroaryl group (i.e., the bond to the parent moiety is through the heteroaryl group) wherein the aryl group is unsubstituted or substituted as defined above, the amino group is as defined above (i.e., a —NH— here), and the heteroaryl group is unsubstituted or substituted as defined below;

"arylheteroaryl" means an aryl-heteroaryl group—(i.e., the bond to the parent moiety is through the heteroaryl group) wherein the aryl group is unsubstituted or substituted as defined above, and the heteroaryl group is unsubstituted or substituted as defined below;

"aryloxy" means an aryl-O— group (i.e., the bond to the parent moiety is through the ether oxygen) wherein the aryl group is unsubstituted or substituted as defined above; non-limiting examples of suitable aryloxy groups include phenoxy and naphthoxy;

"aryloxycarbonyl" means an aryl-O—C(O)— group (i.e., the bond to the parent moiety is through the carbonyl) wherein the aryl group is unsubstituted or substituted as previously defined; non-limiting examples of suitable aryloxycarbonyl groups include phenoxycarbonyl and naphthoxycarbonyl;

"arylsulfinyl" means an aryl-S(O)— group (i.e., the bond to the parent moiety is through the sulfinyl) wherein aryl is unsubstituted or substituted as previously defined;

"arylsulfonyl" means an aryl-S($O_2$)— group (i.e., the bond to the parent moiety is through the sulfonyl) wherein aryl is unsubstituted or substituted as previously defined;

"arylthio" means an aryl-S— group (i.e., the bond to the parent moiety is through the sulfur) wherein the aryl group is unsubstituted or substituted as previously described; non-limiting examples of suitable arylthio groups include phenylthio and naphthylthio;

"cycloalkenyl" means a non-aromatic mono or multicyclic ring system comprising about 3 to about 10 carbon atoms, preferably about 5 to about 10 carbon atoms that contains at least one carbon-carbon double bond; preferred cycloalkenyl rings contain about 5 to about 7 ring atoms; the cycloalkenyl can be optionally substituted with one or more independently selected "ring system substituents" (defined below); Non-limiting examples of suitable monocyclic cycloalkenyls include cyclopentenyl, cyclohexenyl, cycloheptenyl, and the like; a non-limiting example of a suitable multicyclic cycloalkenyl is norbornylenyl;

"cycloalkyl" means a non-aromatic mono- or multicyclic ring system comprising about 3 to about 7 carbon atoms, preferably about 3 to about 6 carbon atoms; the cycloalkyl can be optionally substituted with one or more independently selected "ring system substituents" (defined below); non-limiting examples of suitable monocyclic cycloalkyls include cyclopropyl, cyclopentyl, cyclohexyl, cycloheptyl and the like; non-limiting examples of suitable multicyclic cycloalkyls include 1-decalin, norbornyl, adamantyl and the like;

"cycloalkylalkyl" means a cycloalkyl-alkyl-group (i.e., the bond to the parent moiety is through the alkyl group) wherein the cycloalkyl moiety is unsubstituted or substituted as defined above, and the alkyl moiety is unsubstituted or substituted as defined above;

"halo" means fluoro, chloro, bromo, or iodo groups; preferred halos are fluoro, chloro or bromo, and more preferred are fluoro and chloro;

"halogen" means fluorine, chlorine, bromine, or iodine; preferred halogens are fluorine, chlorine and bromine;

"haloalkyl" means an alkyl, as defined above, wherein one or more hydrogen atoms on the alkyl is replaced by a halo group, as defined above;

"heteroaralkenyl" means a heteroaryl-alkenyl- group (i.e., the bond to the parent moiety is through the alkenyl group) wherein the heteroaryl group is unsubstituted or substituted as defined below, and the alkenyl group is unsubstituted or substituted as defined above;

"heteroaralkyl" (or heteroarylalkyl) means a heteroaryl-alkyl- group (i.e., the bond to the parent moiety is through the alkyl group) in which the heteroaryl is unsubstituted or substituted as defined below, and the alkyl group is unsubstituted or substituted as defined above; preferred heteroaralkyls comprise an alkyl group that is a lower alkyl group; non-limiting examples of suitable aralkyl groups include pyridylmethyl, 2-(furan-3-yl)ethyl and quinolin-3-ylmethyl;

"heteroaralkylthio" means a heteroaralkyl-S— group wherein the heteroaralkyl group is unsubstituted or substituted as defined above;

"heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination; preferred heteroaryls comprise about 5 to about 6 ring atoms; the "heteroaryl" can be optionally substituted by one or more independently selected "ring system substituents" (defined below); the prefix aza, oxa or thia before the heteroaryl root name means that at least a nitrogen, oxygen or sulfur atom, respectively, is present as a ring atom; a nitrogen atom of a heteroaryl can be optionally oxidized to the corresponding N-oxide; non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl, furopyridine

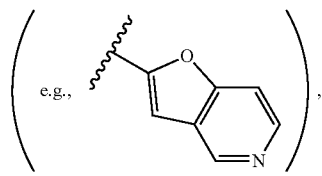

and the like;

"heteroarylalkynyl" (or heteroaralkynyl) means a heteroaryl-alkynyl- group (i.e., the bond to the parent moiety is through the alkynyl group) wherein the heteroaryl group is unsubstituted or substituted as defined above, and the alkynyl group is unsubstituted or substituted as defined above;

"heteroarylaryl" (or heteroararyl) means a heteroaryl-aryl-group (i.e., the bond to the parent moiety is through the aryl group) wherein the heteroaryl group is unsubstituted or substituted as defined above, and the aryl group is unsubstituted or substituted as defined above;

"heteroarylheteroarylaryl" means a heteroaryl-heteroaryl-group (i.e., the bond to the parent moiety is through the last heteroaryl group) wherein each heteroaryl group is independently unsubstituted or substituted as defined above;

"heteroarylsulfinyl" means a heteroaryl-SO— group wherein the heteroaryl group is unsubstituted or substituted as defined above;

"heteroarylsulfonyl" means a heteroaryl-$SO_2$— group wherein the heteroaryl group is unsubstituted or substituted as defined above;

"heteroarylthio" means a heteroaryl-S— group wherein the heteroaryl group is unsubstituted or substituted as defined above;

"heterocyclenyl" (or heterocycloalkenyl) means a non-aromatic monocyclic or multicyclic ring system comprising about 3 to about 10 ring atoms, preferably about 5 to about 10 ring atoms, in which one or more of the atoms in the ring system is an element other than carbon (for example one or more heteroatoms independently selected from the group consisting of nitrogen, oxygen and sulfur atom), and which contains at least one carbon-carbon double bond or carbon-nitrogen double bond; there are no adjacent oxygen and/or sulfur atoms present in the ring system; Preferred heterocyclenyl rings contain about 5 to about 6 ring atoms; the prefix aza, oxa or thia before the heterocyclenyl root name means that at least a nitrogen, oxygen or sulfur atom, respectively, is present as a ring atom; the heterocyclenyl can be optionally substituted by one or more independently selected "Ring system substituents" (defined below); the nitrogen or sulfur atom of the heterocyclenyl can be optionally oxidized to the corresponding N-oxide, S-oxide or S,S-dioxide; non-limiting examples of suitable monocyclic azaheterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like; Non-limiting examples of suitable oxaheterocyclenyl groups include 3,4-dihydro-2H-pyran, dihydrofuranyl, fluorodihydrofuranyl, and the like; A non-limiting example of a suitable multicyclic oxaheterocyclenyl group is 7-oxabicyclo[2.2.1]heptenyl; non-limiting examples of suitable monocyclic thiaheterocyclenyl rings include dihydrothiophenyl, dihydrothiopyranyl, and the like;

"heterocycloalkylalkyl" (or heterocyclylalkyl) means a heterocycloalkylalkyl- group (i.e., the bond to the parent moiety is through the alkyl group) wherein the heterocycloalkyl group (i.e., the heterocyclyl group) is unsubstituted or substituted as defined below, and the alkyl group is unsubstituted or substituted as defined above;

"heterocyclyl" (or heterocycloalkyl) means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination; there are no adjacent oxygen and/or sulfur atoms present in the ring system; preferred heterocyclyls contain about 5 to about 6 ring atoms; the prefix aza, oxa or thia before the heterocyclyl root name means that at least a nitrogen, oxygen or sulfur atom respectively is present as a ring atom; the heterocyclyl can be optionally substituted by one or more independently selected "ring system substituents" (defined below); the nitrogen or sulfur atom of the heterocyclyl can be optionally oxidized to the corresponding N-oxide, S-oxide or S,S-dioxide; non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like;

"hydroxyalkyl" means a HO-alkyl- group wherein the alkyl group is substituted or unsubstituted as defined above; preferred hydroxyalkyls comprise a lower alkyl; Non-limiting examples of suitable hydroxyalkyl groups include hydroxymethyl and 2-hydroxyethyl; and "ring system substituent" means a substituent attached to an aromatic or non-aromatic ring system that, for example, replaces an available hydrogen on the ring system; ring system substituents are each independently selected from the group consisting of: alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $R^{60}R^{65}N-$, $R^{60}R^{65}N$-alkyl-, $R^{60}R^{65}NC(O)-$ and $R^{60}R^{65}NSO_2-$, wherein $R^{60}$ and $R^{65}$ are each independently selected from the group consisting of: hydrogen, alkyl, aryl, and aralkyl; "Ring system substituent" also means a cyclic ring of 3 to 7 ring atoms, wherein 1-2 ring atoms can be heteroatoms, attached to an aryl, heteroaryl, heterocyclyl or heterocyclenyl ring by simultaneously substituting two ring hydrogen atoms on said aryl, heteroaryl, heterocyclyl or heterocyclenyl ring; Non-limiting examples include:

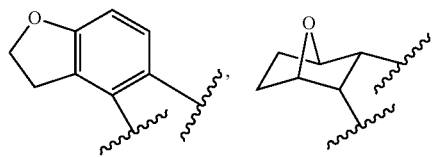

and the like

Lines drawn into a ring mean that the indicated bond may be attached to any of the substitutable ring carbon atoms.

Any carbon or heteroatom with unsatisfied valences in the text, schemes, examples, structural formulae, and any Tables herein is assumed to have the hydrogen atom or atoms to satisfy the valences. And any one or more of these hydrogen atoms can be deuterium.

One or more compounds of the invention may also exist as, or optionally converted to, a solvate. Preparation of solvates is generally known. Thus, for example, M. Caira et al, J. Pharmaceutical Sci., 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, AAPS Pharm Sci Tech., 5(1), article 12 (2004); and A. L. Bingham et al, Chem. Commun., 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I.R. spectroscopy, show the presence of the solvent (or water) in the crystals as a solvate (or hydrate).

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, capsules, pills and the like. Similarly, the herein-described methods of treating a patient by administering a pharmaceutical composition of the present invention is also intended to encompass the administration of the afore-said bulk composition and individual dosage units.

Prodrugs of the compounds of the invention are also contemplated herein. The term "prodrug", as employed herein, denotes a compound that is a drug precursor which, upon administration to a subject, undergoes chemical conversion by metabolic or chemical processes to yield a compound of formula 1.0 or a salt and/or solvate thereof. A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press, both of which are incorporated herein by reference thereto.

For example, if a compound of formula 1.0, or a pharmaceutically acceptable salt, hydrate or solvate of the compound, contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as (3-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$ alkyl, and the like.

Similarly, if a compound of formula 1.0 contains an alcohol functional group, a prodrug can be formed by the replacement of the hydrogen atom of the alcohol group with a group such as, for example, $(C_1-C_6)$alkanoyloxymethyl, 1-($(C_1-C_6)$alkanoyloxy)ethyl, 1-methyl-1-($(C_1-C_6)$alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino $(C_1-C_4)$alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)alkyl)_2$ or glycosyl (the radical resulting from the removal of a hydroxyl group of the hemiacetal form of a carbohydrate), and the like.

If a compound of formula 1.0 incorporates an amine functional group, a prodrug can be formed by the replacement of a hydrogen atom in the amine group with a group such as, for example, $R^{70}$-carbonyl, $R^{70}$O-carbonyl, $NR^{70}R^{75}$-carbonyl where $R^{70}$ and $R^{75}$ are each independently $(C_1-C_{10})$alkyl, $(C_3-C_7)$ cycloalkyl, benzyl, or $R^{70}$-carbonyl is a natural α-aminoacyl or natural α-aminoacyl, —$C(OH)C(O)OY^{80}$ wherein $Y^{80}$ is H, $(C_1-C_6)$alkyl or benzyl, —$C(OY^{82})Y^{84}$ wherein $Y^{82}$ is $(C_1-C_4)$ alkyl and $Y^{84}$ is $(C_1-C_6)$alkyl, carboxy $(C_1-C_6)$alkyl, amino$(C_1-C_4)$alkyl or mono-N- or di-N,N—$(C_1-C_6)$alkylaminoalkyl, —$C(Y^{86})Y^{88}$ wherein $Y^{86}$ is H or methyl and $Y^{88}$ is mono-N- or di-N,N—$(C_1-C_6)$alkylamino morpholino, piperidin-1-yl or pyrrolidin-1-yl, and the like.

This invention also includes the compounds of this invention in isolated and purified form.

Polymorphic forms of the compounds of formula 1.0, and of the salts, solvates and prodrugs of the compounds of formula 1.0, are intended to be included in the present invention.

Certain compounds of the invention may exist in different isomeric (e.g., enantiomers, diastereoisomers, atropisomers) forms. The invention contemplates all such isomers both in pure form and in admixture, including racemic mixtures. Enol forms are also included.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

Diasteromeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

The compounds of formula 1.0 form salts that are also within the scope of this invention. Reference to a compound of formula 1.0 herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula 1.0 contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable salts) are preferred. Salts of the compounds of the formula 1.0 may be formed, for example, by reacting a compound of formula 1.0 with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in *The Orange Book* (Food & Drug Administration, Washington, D.C. on their website); and P. Heinrich Stahl, Camille G. Wermuth (Eds.), *Handbook of Pharmaceutical Salts: Properties, Selection, and Use*, (2002) Intl. Union of Pure and Applied Chemistry, pp. 330-331. These disclosures are incorporated herein by reference thereto.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis(dehydroabietyl)ethylenediamine), N-methyl-D-glucamines, N-methyl-D-glucamides, t-butyl amines, piperazine, phenylcyclohexylamine, choline, tromethamine, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid and base salts are intended to be pharmaceutically acceptable salts within the scope of the invention and all acid and base salts are considered equivalent to the free forms of the corresponding compounds for purposes of the invention.

Compounds of formula 1.0, and salts, solvates and prodrugs thereof, may exist in their tautomeric form (for example, as an amide or imino ether). All such tautomeric forms are contemplated herein as part of the present invention.

In hetero-atom containing ring systems of this invention, there are no hydroxyl groups on carbon atoms adjacent to a N, O or S, and there are no N or S groups on carbon adjacent to another heteroatom. Thus, for example, in the ring:

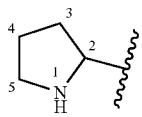

there is no —OH attached directly to carbons marked 2 and 5.

The compounds of formula 1.0 may exist in different tautomeric forms, and all such forms are embraced within the scope of the invention. Also, for example, all keto-enol and imine-enamine forms of the compounds are included in the invention.

Tautomeric forms such as, for example, the moieties:

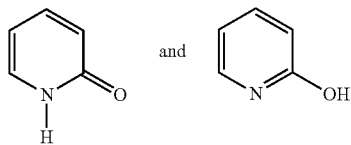 [SMILES: O=c1cccc[nH]1 ; Oc1ccccn1]

are considered equivalent in certain embodiments of this invention.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, in sufficient purity to be characterizable by standard analytical techniques described herein or well known to the skilled artisan.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^3$, etc.) occurs more than one time in any moiety or in any compound of formula 1.0, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine, chlorine, and iodine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{123}I$, respectively.

Certain isotopically-labelled compounds of formula 1.0 (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Certain isotopically-labelled compounds of Formula (I) can be useful for medical imaging purposes. E.g., those labeled with positron-emitting isotopes like $^{11}C$ or $^{18}F$ can be useful for application in Positron Emission Tomography (PET) and those labeled with gamma ray emitting isotopes like $^{123}I$ can be useful for application in Single photon emission computed tomography (SPECT). Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of Formula (I), in particular those containing isotopes with longer half lives (T1/2>1 day), can generally be prepared by following procedures analogous to those disclosed in the Schemes and/or in the Examples herein below, by substituting an appropriate isotopically labeled reagent for a non-isotopically labeled reagent.

This invention provides compounds of formula 1.0:

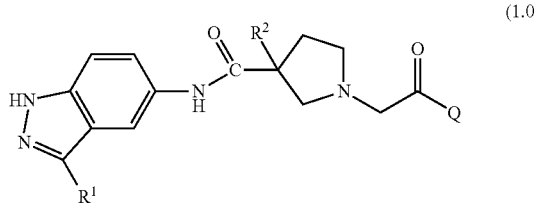

(1.0)

or the pharmaceutically acceptable salts, or solvates thereof, wherein $R^1$, $R^2$ and Q are independently selected, and wherein:

Q is:

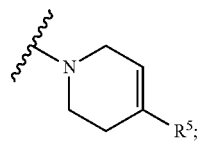

$R^1$ is selected from the group consisting of: heteroaryl and substituted heteroaryl, wherein said substituted heteroaryl is substituted with 1 to 3 (preferably 1) substituents independently selected from the group consisting of: —OH, alkoxy, and —O-alkylene-O-alkyl;

$R^2$ is selected from the group consisting of: —O-alkyl and —S-alkyl; and $R^5$ is selected from the group consisting of:
(a) triazolyl-phenyl-,
(b) triazolyl-phenyl- wherein said phenyl is optionally substituted with 1 to 3 substituents independently selected from the group consisting of: halo (e.g., Br, Cl, F, and in one example F) and alkoxy (e.g., $C_1$-$C_6$alkoxy, and in one example, $C_1$-$C_2$alkoxy, and in another example —$OCH_3$),
(c) substituted triazolyl-phenyl- wherein said phenyl is optionally substituted with 1 to 3 substituents independently selected from the group consisting of: halo (e.g., Br, Cl, F, and in one example F) and alkoxy (e.g., $C_1$-$C_6$alkoxy, and in one example, $C_1$-$C_2$alkoxy, and in another example —$OCH_3$), and said triazolyl group is substituted with one or two substitutents independently selected from the group consisting of: alkyl, hydroxy substituted alkyl, -alkylene-O-alkyl, and amino (i.e., —$NH_2$),
(d) triazolyl-thienyl-,
(e) triazolyl-thienyl- wherein said thienyl is optionally substituted with 1 to 2 substituents independently selected from the group consisting of: halo (e.g., Br, Cl, F, and in one example F) and alkoxy (e.g., $C_1$-$C_6$alkoxy, and in one example, $C_1$-$C_2$alkoxy, and in another example —$OCH_3$),
(f) substituted triazolyl-thienyl- wherein said thienyl is optionally substituted with 1 to 2 substituents independently selected from the group consisting of: halo (e.g., Br, Cl, F, and in one example F) and alkoxy (e.g., $C_1$-$C_6$alkoxy, and in one example, $C_1$-$C_2$alkoxy, and in another example —$OCH_3$), and said triazolyl group is substituted with one or two substitutents independently selected from the group consisting of: alkyl, hydroxy substituted alkyl, -alkylene-O-alkyl, and amino (i.e., —$NH_2$),
(g) triazolyl-pyridyl-,
(h) triazolyl-pyridyl- wherein said pyridyl is optionally substituted with 1 to 3 substituents independently selected from the group consisting of: halo (e.g., Br, Cl, F, and in one example F), alkyl, and alkoxy (e.g., $C_1$-$C_6$alkoxy, and in one example, $C_1$-$C_2$alkoxy, and in another example —$OCH_3$), provided that the carbon atoms adjacent to the nitrogen atom in said pyridyl are not substituted with halo, and
(i) substituted triazolyl-pyridyl- wherein: (1) said pyridyl is optionally substituted with 1 to 3 substituents independently selected from the group consisting of: halo (e.g., Br, Cl, F, and in one example F), alkyl, and alkoxy (e.g., $C_1$-$C_6$alkoxy, and in one example, $C_1$-$C_2$alkoxy, and in another example —$OCH_3$), provided that the carbon atoms adjacent to the nitrogen atom in said pyridyl are not substituted with halo, and (2) said triazolyl group is substituted with one or two substitutents independently selected from the group consisting of: alkyl, hydroxy substituted alkyl, -alkylene-O-alkyl, and amino (i.e., —$NH_2$),
(j) triazolyl-thiazolyl-,
(k) triazolyl-thiazolyl- wherein said thiazolyl is optionally substituted with 1 substituent independently selected from the group consisting of: halo (e.g., Br, Cl, F, and in one example F), alkyl, and alkoxy (e.g., $C_1$-$C_6$alkoxy, and in one example, $C_1$-$C_2$alkoxy, and in another example —$OCH_3$), amino (i.e., $NH_2$), alkylamino, and dialkylamino wherein each alkyl is independently selected, and
(l) substituted triazolyl-thiazolyl- wherein (1) said thiazolyl is optionally substituted with 1 substituent independently selected from the group consisting of: halo (e.g., Br, Cl, F, and in one example F), alkyl, and alkoxy (e.g., $C_1$-$C_6$alkoxy, and in one example, $C_1$-$C_2$alkoxy, and in another example —$OCH_3$), amino (i.e., $NH_2$), alkylamino, and dialkylamino wherein each alkyl is independently selected, and (2) said triazolyl group is substituted with one or two substitutents independently selected from the group consisting of: alkyl, hydroxy substituted alkyl, -alkylene-O-alkyl, and amino (i.e., —$NH_2$),
(m) pyridazinyl-thienyl-,
(n) pyridazinyl-thienyl- wherein said thienyl is optionally substituted with 1 to 2 substituents independently selected from the group consisting of: halo (e.g., Br, Cl, F, and in one example F) and alkoxy (e.g., $C_1$-$C_6$alkoxy, and in one example, $C_1$-$C_2$alkoxy, and in another example —$OCH_3$), and
(o) substituted pyridazinyl-thienyl- wherein (1) said thienyl is optionally substituted with 1 to 2 substituents independently selected from the group consisting of: halo (e.g., Br, Cl, F, and in one example F) and alkoxy (e.g., $C_1$-$C_6$alkoxy, and in one example, $C_1$-$C_2$alkoxy, and in another example —$OCH_3$), and (2) said pyridazinyl group is substituted with 1 to 3 substitutents independently selected from the group consisting of: =O, alkyl, amino (i.e., —$NH_2$), alkylamino, dialkylamino wherein each alkyl is independently selected, and halo (e.g., Br, Cl, F, and in one example F), provided that the carbon atoms adjacent to the nitrogen atoms in said pyridazinyl are not substituted with halo, and provided that when said -alkylene-O-alkyl group is bound to the nitrogen of said triazolyl in (c), (f), (i) and (l) of $R^5$ the alkylene moiety of said -alkylene-O-alkyl group is not —$CH_2$— (i.e., the alkylene moiety is 2 or more carbons in length).

This invention provides compounds of formula 1.0:

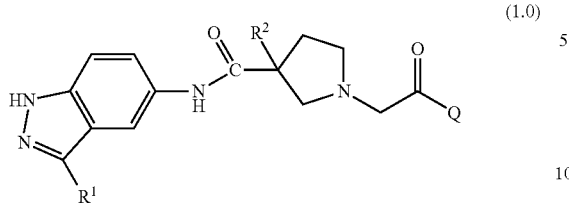

(1.0)

or the pharmaceutically acceptable salts, or solvates thereof, wherein:

Q is:

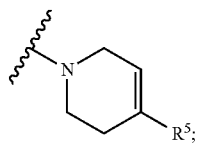

$R^1$ is selected from the group consisting of: heteroaryl and substituted heteroaryl, wherein said substituted heteroaryl is substituted with 1 to 3 (preferably 1) substituents independently selected from the group consisting of: —OH, alkoxy, and —O-alkylene-O-alkyl;

$R^2$ is selected from the group consisting of: —O-alkyl and —S-alkyl; and $R^5$ is selected from the group consisting of:
(a) triazolyl-phenyl-,
(b) triazolyl-phenyl- wherein said phenyl is optionally substituted with 1 to 3 substituents independently selected from the group consisting of: halo (e.g., Br, Cl, F, and in one example F) and alkoxy (e.g., $C_1$-$C_6$alkoxy, and in one example, $C_1$-$C_2$alkoxy, and in another example —$OCH_3$),
(c) substituted triazolyl-phenyl- wherein said phenyl is optionally substituted with 1 to 3 substituents independently selected from the group consisting of: halo (e.g., Br, Cl, F, and in one example F) and alkoxy (e.g., $C_1$-$C_6$alkoxy, and in one example, $C_1$-$C_2$alkoxy, and in another example —$OCH_3$), and said triazolyl group is substituted with one or two substitutents independently selected from the group consisting of: alkyl, hydroxy substituted alkyl, -alkylene-O-alkyl, and amino (i.e., —$NH_2$);
(d) triazolyl-thienyl-,
(e) triazolyl-thienyl- wherein said thienyl is optionally substituted with 1 to 2 substituents independently selected from the group consisting of: halo (e.g., Br, Cl, F, and in one example F) and alkoxy (e.g., $C_1$-$C_6$alkoxy, and in one example, $C_1$-$C_2$alkoxy, and in another example —$OCH_3$), and
(f) substituted triazolyl-thienyl- wherein said thienyl is optionally substituted with 1 to 2 substituents independently selected from the group consisting of: halo (e.g., Br, Cl, F, and in one example F) and alkoxy (e.g., $C_1$-$C_6$alkoxy, and in one example, $C_1$-$C_2$alkoxy, and in another example —$OCH_3$), and said triazolyl group is substituted with one or two substitutents independently selected from the group consisting of: alkyl, hydroxy substituted alkyl, -alkylene-O-alkyl, and amino (i.e., —$NH_2$), and provided that when said -alkylene-O-alkyl group is bound to the nitrogen of said triazolyl in (c) and (f) of $R^5$ the alkylene moiety of said -alkylene-O-alkyl group is not —$CH_2$— (i.e., the alkylene moiety is 2 or more carbons in length).

Those skilled in the art will appreciate that the term "alkylene", as used in the substituents —O-alkylene-O-alkyl and -alkylene-O-alkyl, means a divalent saturated hydrocarbon group. Thus, an example of an alkylene moiety is —$CH_2$—$CH_2$—, and an example of an —O-alkylene-O-alkyl moiety is —O—$(CH_2)_2$—O—$CH_3$, and an example of an -alkylene-O-alkyl moiety is —$(CH_2)_2$—O—$CH_3$.

Those skilled in the art will also appreciate that the term alkylene also includes the moiety —$CH_2$—.

Examples of the $R^1$ heteroaryl group include, but are not limited to, pyridyl, pyrrolyl, pyrazolyl, imidazolyl, furanyl, thienyl, thiazolyl, pyridyl N-0, and pyrimidinyl.

Examples of the $R^1$ substituted heteroaryl group include, but are not limited to, substituted pyridyl, substituted pyrrolyl, substituted pyrazolyl, substituted imidazolyl, substituted furanyl, substituted thienyl, substituted thiazolyl, substituted pyridyl N—O, and substituted pyrimidinyl.

In one embodiment of this invention $R^1$ is pyridyl.

In another embodiment of this invention $R^1$ is substituted pyridyl.

In another embodiment of this invention $R^1$ is pyridyl substituted with one substitutent.

The substitutents on the substituted $R^1$ groups (e.g., the substituted pyridyl) are independently selected from the group consisting of: —OH, alkoxy, and —O-alkylene-O-alkyl. Examples of the alkoxy group include, for example, $C_1$ to $C_6$alkoxy (such as, for example, —O—$CH_3$, —O—$C_2H_5$, and —O—$CH(CH_3)_2$). Examples of the —O-alkylene-O-alkyl group include, for example, —O—$(C_1$-$C_4)$alkylene-O—$(C_1$-$C_6)$alkyl, —O—$(C_1$-$C_2)$alkylene-O—$(C_1$-$C_3$alkyl), and —O—$(CH_2)_2$—O—$CH_3$).

Examples of $R^1$ include, for example,

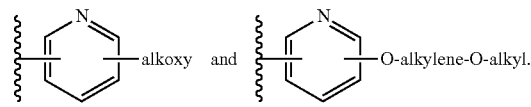

In one embodiment of this invention $R^1$ is pyridyl substituted with alkoxy.

In another embodiment of this invention $R^1$ is substituted with —$OCH(CH_3)_2$.

In another embodiment of this invention $R^1$ is substituted with —$OC_2H_6$.

In another embodiment of this invention $R^1$ is:

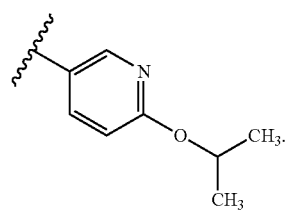 [SMILES: *c1ccc(OC(C)C)nc1]

In another embodiment of this invention R¹ is:

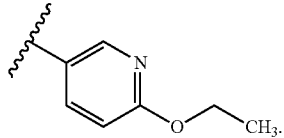 [SMILES: *c1ccc(OCC)nc1]

In another embodiment of this invention R¹ is substituted with —O-alkylene-O-alkyl.

In another embodiment of this invention R¹ is substituted with —OCH₂CH₂OCH₃.

In another embodiment of this invention R¹ is:

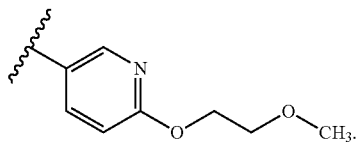 [SMILES: *c1ccc(OCCOC)nc1]

Examples of the R²—O-alkyl group include, for example, —O—(C₁-C₆)alkyl, —O—(C₁-C₂)alkyl, and —OCH₃.

Examples of the R²—S-alkyl group include, for example, —S—(C₁-C₆)alkyl, —S—(C₁-C₂)alkyl, and —SCH₃.

In one embodiment of this invention R² is a —O—(C₁-C₂)alkyl group.

In another embodiment of this invention R² is —OCH₃.

In another embodiment of this invention R² is a —S—(C₁-C₂)alkyl group.

In another embodiment of this invention R² is —SCH₃.

In one embodiment of this invention R⁵ is a triazolyl-phenyl moiety wherein the triazolyl moiety is bonded to the phenyl moiety by a ring carbon of the triazolyl moiety In one embodiment of this invention R⁵ is a triazolyl-phenyl- moiety, such as, for example,

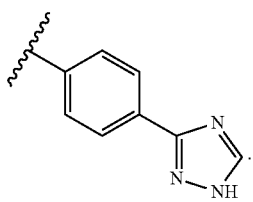 [SMILES: *c1ccc(-c2nc[nH]n2)cc1]

In another embodiment of this invention R⁵ is a triazolyl-thienyl- moiety, such as, for example,

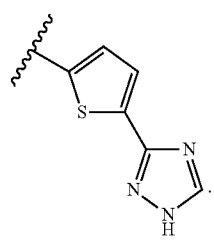 [SMILES: *c1ccc(-c2nc[nH]n2)s1]

In another embodiment of this invention R⁵ is a triazolyl-thienyl- moiety, such as, for example,

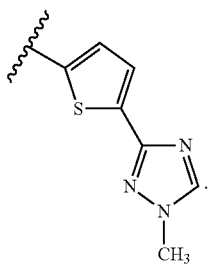 [SMILES: *c1ccc(-c2ncn(C)n2)s1]

In another embodiment of this invention the substituted triazolyl moiety of said R⁵ group is substituted on the ring nitrogen.

When the triazolyl moiety of R⁵ is substituted with alkyl, examples of the alkyl groups include, for example, —C₁-C₆alkyl, —C₁-C₄alkyl, —C₁-C₂alkyl, and —CH₃. And in one embodiment, there is alkyl substitution on the triazolyl moiety of R⁵ and said alkyl is —CH₃.

When the triazolyl moiety of R⁵ is substituted with -alkylene-O-alkyl groups, examples of the -alkylene-O-alkyl groups include, for example, —C₁-C₄alkylene-O—C₁-C₆alkyl, —C₁-C₂alkylene-O—C₁-C₂alkyl, —C₁-C₄alkylene-O—CH₃, and —CH₂CH₂OCH₃. And in one embodiment, there is -alkylene-O-alkyl substitution on the triazolyl moiety of R⁵ and said -alkylene-O-alkyl is —CH₂CH₂OCH₃. When the nitrogen of the triazolyl moiety of R⁵ is substituted with -alkylene-O-alkyl group, examples of the -alkylene-β-alkyl group includes, for example, —C₂-C₄alkylene-O—C₁-C₆alkyl, —C₂alkylene-O—C₁-C₂alkyl, —C₂-C₄alkylene-O—CH₃, and —CH₂CH₂OCH₃. And in one embodiment, there is -alkylene-O-alkyl substitution on the nitrogen of the triazolyl moiety of R⁵ and said -alkylene-O-alkyl is —CH₂CH₂OCH₃.

When the triazolyl moiety of R⁵ is substituted with hydroxy substituted alkyl groups, examples of the hydroxy substituted alkyl groups include, for example, hydroxy substituted —C₁-C₄alkyl, hydroxy substituted —C₁-C₂alkyl, and hydroxy substituted —CH₃. Examples also include, for example, —CH₂COH(CH₃)₂, and —CH₂CH₂OH.

When the phenyl moiety of R⁵ is substituted with halo atoms, examples of the halo atoms include, for example, Cl, F and Br. In one embodiment of this invention the halo on the phenyl is F. In another embodiment of this invention the phenyl is substituted with one F.

In one embodiment of this invention R⁵ is a substituted triazolyl-phenyl- wherein said triazolyl is substituted and said phenyl is unsubstituted.

In another embodiment of this invention R⁵ is a substituted triazolyl-phenyl- wherein said triazolyl is substituted on the nitrogen and said phenyl is unsubstituted.

In another embodiment of this invention R⁵ is a substituted triazolyl-phenyl- wherein said triazolyl is substituted on the carbon and said phenyl is unsubstituted.

In another embodiment of this invention R⁵ is a substituted triazolyl-phenyl- wherein said triazolyl is substituted on the nitrogen and on the carbon, and said phenyl is unsubstituted.

In another embodiment of this invention R⁵ is a substituted triazolyl-phenyl- wherein said triazolyl is substituted and said phenyl is substituted.

In another embodiment of this invention R⁵ is a substituted triazolyl-phenyl- wherein said triazolyl is substituted on the nitrogen and said phenyl is substituted.

In another embodiment of this invention $R^5$ is a substituted triazolyl-phenyl- wherein said triazolyl is substituted on the carbon and said phenyl is substituted.

In another embodiment of this invention $R^5$ is a substituted triazolyl-phenyl- wherein said triazolyl is substituted on the nitrogen and on the carbon, and said phenyl is substituted.

In another embodiment of this invention $R^5$ is a substituted triazolyl-phenyl- wherein said triazolyl is unsubstituted and said phenyl is substituted.

In another embodiment of this invention $R^5$ is all unsubstituted triazolyl-phenyl-.

In another embodiment of this invention $R^5$ is a substituted triazolyl-phenyl- wherein the triazolyl is substituted on the nitrogen with $-CH_2COH(CH_3)_2$.

In another embodiment of this invention $R^5$ is a substituted triazolyl-phenyl- wherein the triazolyl is substituted on the nitrogen with $-CH_2CH_2OH$.

In another embodiment of this invention $R^5$ is a substituted triazolyl-phenyl- wherein the triazolyl is substituted on the nitrogen with an alkyl group.

In another embodiment of this invention $R^5$ is a substituted triazolyl-phenyl- wherein the triazolyl is substituted on the nitrogen with an alkyl group and substituted on the carbon with an alkyl group, wherein each alkyl group is independently selected.

In another embodiment of this invention $R^5$ is a substituted triazolyl-phenyl- wherein the triazolyl is substituted on the nitrogen with a $-CH_3$ group.

In another embodiment of this invention $R^5$ is a substituted triazolyl-phenyl- wherein the triazolyl is substituted on the nitrogen with a $-CH_3$ group and on the carbon with a $-CH_3$ group.

In another embodiment of this invention $R^5$ moiety is a substituted triazolyl-phenyl- wherein the triazolyl is substituted on the carbon with a $-NH_2$ group.

In another embodiment of this invention $R^5$ is a substituted triazolyl-phenyl- wherein the triazolyl is substituted on the nitrogen with an -alkylene-O-alkyl group.

In another embodiment of this invention $R^5$ is a substituted triazolyl-phenyl- wherein the triazolyl is substituted on the nitrogen with a $-CH_2CH_2OCH_3$ group.

In another embodiment of this invention $R^5$ moiety is a substituted triazolyl-phenyl- wherein said phenyl moiety is substituted with halo, and said triazolyl moiety is substituted as described in any of the above embodiments.

In another embodiment of this invention $R^5$ is a substituted triazolyl-phenyl- wherein said phenyl moiety is substituted with one halo, and said triazolyl moiety is substituted as described in any one of the above embodiments.

In another embodiment of this invention $R^5$ is a substituted triazolyl-phenyl- wherein said phenyl moiety is substituted with F, and said triazolyl moiety is substituted as described in any one of the above embodiments.

In another embodiment of this invention $R^5$ is a substituted triazolyl-phenyl- wherein said phenyl moiety is substituted with one F, and said triazolyl moiety is substituted as described in any one of the above embodiments.

In another embodiment of this invention $R^5$ is a substituted triazolyl-phenyl- group wherein said phenyl moiety is substituted with one F, and said triazolyl moiety is substituted on the nitrogen with a hydroxyl substituted alkyl group.

In another embodiment of this invention $R^5$ is a substituted triazolyl-phenyl- wherein said phenyl moiety is substituted with one F, and said triazolyl moiety is substituted on the nitrogen with a $-CH_2CH_2OH$ group.

In another embodiment of this invention $R^5$ is a substituted triazolyl-phenyl- wherein said phenyl moiety is substituted with one F, and said triazolyl moiety is substituted on the nitrogen with α-alkylene-O-alkyl group.

In another embodiment of this invention $R^5$ is a substituted triazolyl-phenyl- wherein said phenyl moiety is substituted with one F, and said triazolyl moiety is substituted on the nitrogen with $-CH_2CH_2OCH_3$ group.

In another embodiment of this invention $R^5$ is a substituted triazolyl-phenyl- wherein said phenyl moiety is substituted with halo, and said triazolyl moiety is unsubstituted.

In another embodiment of this invention $R^5$ is a substituted triazolyl-phenyl- wherein said phenyl moiety is substituted with one halo, and said triazolyl moiety is unsubstituted.

In another embodiment of this invention $R^5$ is a substituted triazolyl-phenyl- wherein said phenyl moiety is substituted with F, and said triazolyl moiety is unsubstituted.

In another embodiment of this invention $R^5$ is a substituted triazolyl-phenyl- wherein said phenyl moiety is substituted with one F, and said triazolyl moiety is unsubstituted.

In another embodiment of this invention $R^5$ moiety is a substituted triazolyl-phenyl- wherein said phenyl moiety is substituted with alkoxy, and said triazolyl moiety is substituted as described in any of the above embodiments.

In another embodiment of this invention $R^5$ is a substituted triazolyl-phenyl- wherein said phenyl moiety is substituted with one alkoxy, and said triazolyl moiety is substituted as described in any one of the above embodiments.

In another embodiment of this invention $R^5$ is a substituted triazolyl-phenyl- wherein said phenyl moiety is substituted with $-OCH_3$, and said triazolyl moiety is substituted as described in any one of the above embodiments.

In another embodiment of this invention $R^5$ is a substituted triazolyl-phenyl- wherein said phenyl moiety is substituted with one $-OCH_3$, and said triazolyl moiety is substituted as described in any one of the above embodiments.

In another embodiment of this invention $R^5$ is a substituted triazolyl-phenyl- group wherein said phenyl moiety is substituted with one $-OCH_3$, and said triazolyl moiety is substituted on the nitrogen with a hydroxyl substituted alkyl group.

In another embodiment of this invention $R^5$ is a substituted triazolyl-phenyl- wherein said phenyl moiety is substituted with one $-OCH_3$, and said triazolyl moiety is substituted on the nitrogen with a $-CH_2CH_2OH$ group.

In another embodiment of this invention $R^5$ is a substituted triazolyl-phenyl- wherein said phenyl moiety is substituted with one $-OCH_3$, and said triazolyl moiety is substituted on the nitrogen with α-alkylene-O-alkyl group.

In another embodiment of this invention $R^5$ is a substituted triazolyl-phenyl- wherein said phenyl moiety is substituted with one $-OCH_3$, and said triazolyl moiety is substituted on the nitrogen with a $-CH_2CH_2OCH_3$ group.

In another embodiment of this invention $R^5$ is a substituted triazolyl-phenyl- wherein said phenyl moiety is substituted with alkoxy, and said triazolyl moiety is unsubstituted.

In another embodiment of this invention $R^5$ is a substituted triazolyl-phenyl- wherein said phenyl moiety is substituted with one alkoxy, and said triazolyl moiety is unsubstituted.

In another embodiment of this invention $R^5$ is a substituted triazolyl-phenyl- wherein said phenyl moiety is substituted with $-OCH_3$, and said triazolyl moiety is unsubstituted.

In another embodiment of this invention $R^5$ is a substituted triazolyl-phenyl- wherein said phenyl moiety is substituted with one $-OCH_3$, and said triazolyl moiety is unsubstituted.

In another embodiment of this invention R⁵ is:

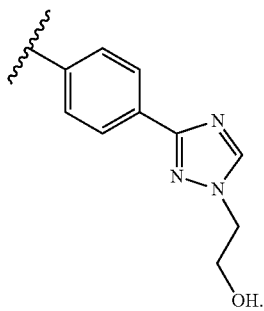 [SMILES: *c1ccc(-c2ncn(CCO)n2)cc1]

In another embodiment of this invention R⁵ is:

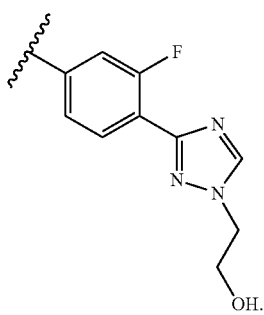 [SMILES: *c1ccc(-c2ncn(CCO)n2)c(F)c1]

In another embodiment of this invention R⁵ is:

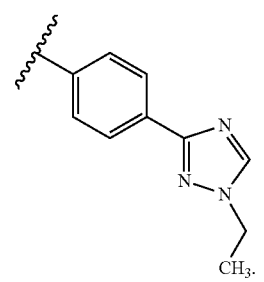 [SMILES: *c1ccc(-c2ncn(CC)n2)cc1]

In another embodiment of this invention R⁵ is:

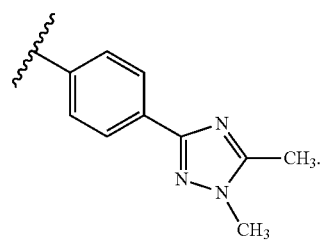 [SMILES: *c1ccc(-c2nc(C)n(C)n2)cc1]

In another embodiment of this invention R⁵ is:

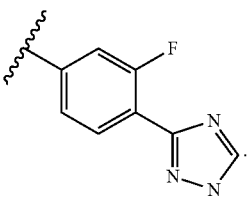 [SMILES: *c1ccc(-c2nc[nH]n2)c(F)c1]

In another embodiment of this invention R⁵ is:

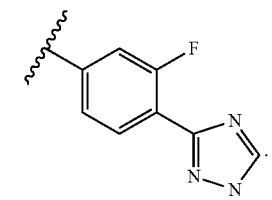

In another embodiment of this invention R⁵ is:

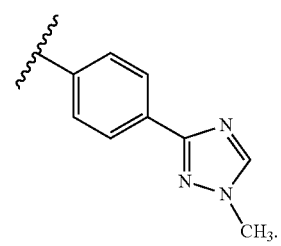 [SMILES: *c1ccc(-c2ncn(C)n2)cc1]

In another embodiment of this invention R⁵ is:

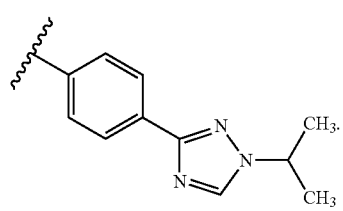 [SMILES: *c1ccc(-c2ncn(C(C)C)n2)cc1]

In another embodiment of this invention R⁵ is:

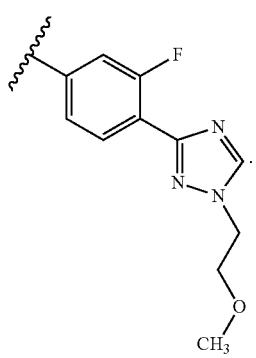 [SMILES: *c1ccc(-c2ncn(CCOC)n2)c(F)c1]

In another embodiment of this invention R⁵ is:

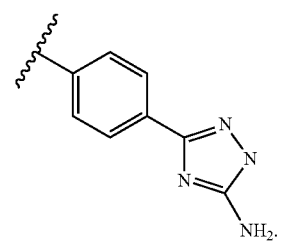 [SMILES: *c1ccc(-c2n[nH]c(N)n2)cc1]

In another embodiment of this invention R⁵ is:

[Structure: phenyl substituted with triazolyl-CH₂-C(CH₃)₂-OH]

In another embodiment of this invention R⁵ is:

[Structure: 2-fluorophenyl substituted with triazolyl-CH₂CH₂-OH]

In another embodiment of this invention R⁵ is a substituted triazolyl-thienyl- wherein said triazolyl is substituted and said thienyl is unsubstituted.

In another embodiment of this invention R⁵ is a substituted triazolyl-thienyl- wherein said triazolyl is substituted on the nitrogen and said thienyl is unsubstituted.

In another embodiment of this invention R⁵ is a substituted triazolyl-thienyl- wherein said triazolyl is substituted on the carbon and said thienyl is unsubstituted.

In another embodiment of this invention R⁵ is a substituted triazolyl-thienyl- wherein said triazolyl is substituted on the nitrogen and on the carbon, and said thienyl is unsubstituted.

In another embodiment of this invention R⁵ is a substituted triazolyl-thienyl- wherein said triazolyl is substituted and said thienyl is substituted.

In another embodiment of this invention R⁵ is a substituted triazolyl-thienyl- wherein said triazolyl is substituted on the nitrogen and said thienyl is substituted.

In another embodiment of this invention R⁵ is a substituted triazolyl-thienyl- wherein said triazolyl is substituted on the carbon and said thienyl is substituted.

In another embodiment of this invention R⁵ is a substituted triazolyl-thienyl- wherein said triazolyl is substituted on the nitrogen and on the carbon, and said thienyl is substituted.

In another embodiment of this invention R⁵ is a substituted triazolyl-thienyl- wherein said triazolyl is unsubstituted and said thienyl is substituted.

In another embodiment of this invention R⁵ is an unsubstituted triazolyl-thienyl-.

In another embodiment of this invention R⁵ is a substituted triazolyl-thienyl- wherein the triazolyl is substituted on the nitrogen with —CH₂COH(CH₃)₂.

In another embodiment of this invention R⁵ is a substituted triazolyl-thienyl- wherein the triazolyl is substituted on the nitrogen with —CH₂CH₂OH.

In another embodiment of this invention R⁵ is a substituted triazolyl-thienyl- wherein the triazolyl is substituted on the nitrogen with an alkyl group.

In another embodiment of this invention R⁵ is a substituted triazolyl-thienyl- wherein the triazolyl is substituted on the nitrogen with an alkyl group and substituted on the carbon with an alkyl group, wherein each alkyl group is independently selected.

In another embodiment of this invention R⁵ is a substituted triazolyl-thienyl- wherein the triazolyl is substituted on the nitrogen with a —CH₃ group.

In another embodiment of this invention R⁵ is a substituted triazolyl-thienyl- wherein the triazolyl is substituted on the nitrogen with a —CH₃ group and on the carbon with a —CH₃ group.

In another embodiment of this invention R⁵ moiety is a substituted triazolyl-thienyl- wherein the triazolyl is substituted on the carbon with a —NH₂ group.

In another embodiment of this invention R⁵ is a substituted triazolyl-thienyl- wherein the triazolyl is substituted on the nitrogen with an -alkylene-O-alkyl group.

In another embodiment of this invention R⁵ is a substituted triazolyl-thienyl- wherein the triazolyl is substituted on the nitrogen with a —CH₂CH₂OCH₃ group.

In another embodiment of this invention R⁵ moiety is a substituted triazolyl-thienyl- wherein said thienyl moiety is substituted with halo, and said triazolyl moiety is substituted as described in any of the above embodiments.

In another embodiment of this invention R⁵ is a substituted triazolyl-thienyl- wherein said thienyl moiety is substituted with one halo, and said triazolyl moiety is substituted as described in any one of the above embodiments.

In another embodiment of this invention R⁵ is a substituted triazolyl-thienyl- wherein said thienyl moiety is substituted with F, and said triazolyl moiety is substituted as described in any one of the above embodiments.

In another embodiment of this invention R⁵ is a substituted triazolyl-thienyl- wherein said thienyl moiety is substituted with one F, and said triazolyl moiety is substituted as described in any one of the above embodiments.

In another embodiment of this invention R⁵ is a substituted triazolyl-thienyl- group wherein said thienyl moiety is substituted with one F, and said triazolyl moiety is substituted on the nitrogen with a hydroxyl substituted alkyl group.

In another embodiment of this invention R⁵ is a substituted triazolyl-thienyl- wherein said thienyl moiety is substituted with one F, and said triazolyl moiety is substituted on the nitrogen with a —CH₂CH₂OH group.

In another embodiment of this invention R⁵ is a substituted triazolyl-thienyl- wherein said thienyl moiety is substituted with one F, and said triazolyl moiety is substituted on the nitrogen with α-alkylene-O-alkyl group.

In another embodiment of this invention R⁵ is a substituted triazolyl-thienyl- wherein said thienyl moiety is substituted with one F, and said triazolyl moiety is substituted on the nitrogen with a —CH₂CH₂OCH₃ group.

In another embodiment of this invention R⁵ is a substituted triazolyl-thienyl- wherein said thienyl moiety is substituted with halo, and said triazolyl moiety is unsubstituted.

In another embodiment of this invention R⁵ is a substituted triazolyl-thienyl- wherein said thienyl moiety is substituted with one halo, and said triazolyl moiety is unsubstituted.

In another embodiment of this invention R⁵ is a substituted triazolyl-thienyl- wherein said thienyl moiety is substituted with F, and said triazolyl moiety is unsubstituted.

In another embodiment of this invention $R^5$ is a substituted triazolyl-thienyl- wherein said thienyl moiety is substituted with one F, and said triazolyl moiety is unsubstituted.

In another embodiment of this invention $R^5$ moiety is a substituted triazolyl-thienyl- wherein said thienyl moiety is substituted with alkoxy, and said triazolyl moiety is substituted as described in any of the above embodiments.

In another embodiment of this invention $R^5$ is a substituted triazolyl-thienyl- wherein said thienyl moiety is substituted with one alkoxy, and said triazolyl moiety is substituted as described in any one of the above embodiments.

In another embodiment of this invention $R^5$ is a substituted triazolyl-thienyl- wherein said thienyl moiety is substituted with —$OCH_3$, and said triazolyl moiety is substituted as described in any one of the above embodiments.

In another embodiment of this invention $R^5$ is a substituted triazolyl-thienyl- wherein said thienyl moiety is substituted with one —$OCH_3$, and said triazolyl moiety is substituted as described in any one of the above embodiments.

In another embodiment of this invention $R^5$ is a substituted triazolyl-thienyl- group wherein said thienyl moiety is substituted with one —$OCH_3$, and said triazolyl moiety is substituted on the nitrogen with a hydroxyl substituted alkyl group.

In another embodiment of this invention $R^5$ is a substituted triazolyl-thienyl- wherein said thienyl moiety is substituted with one —$OCH_3$, and said triazolyl moiety is substituted on the nitrogen with a —$CH_2CH_2OH$ group.

In another embodiment of this invention $R^5$ is a substituted triazolyl-thienyl- wherein said thienyl moiety is substituted with one —$OCH_3$, and said triazolyl moiety is substituted on the nitrogen with α-alkylene-O-alkyl group.

In another embodiment of this invention $R^5$ is a substituted triazolyl-thienyl- wherein said thienyl moiety is substituted with one —$OCH_3$, and said triazolyl moiety is substituted on the nitrogen with a —$CH_2CH_2OCH_3$ group.

In another embodiment of this invention $R^5$ is a substituted triazolyl-thienyl- wherein said thienyl moiety is substituted with alkoxy, and said triazolyl moiety is unsubstituted.

In another embodiment of this invention $R^5$ is a substituted triazolyl-thienyl- wherein said thienyl moiety is substituted with one alkoxy, and said triazolyl moiety is unsubstituted.

In another embodiment of this invention $R^5$ is a substituted triazolyl-thienyl- wherein said thienyl moiety is substituted with —$OCH_3$, and said triazolyl moiety is unsubstituted.

In another embodiment of this invention $R^5$ is a substituted triazolyl-thienyl- wherein said thienyl moiety is substituted with one —$OCH_3$, and said triazolyl moiety is unsubstituted.

In another embodiment of this invention $R^5$ is triazolyl-pyridyl-.

In another embodiment of this invention $R^5$ is

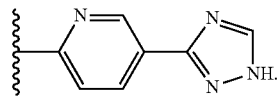

In another embodiment of this invention $R^5$ is a substituted triazolyl-pyridyl- wherein said triazolyl is substituted and said pyridyl is unsubstituted.

In another embodiment of this invention $R^5$ is a substituted triazolyl-pyridyl- wherein said triazolyl is substituted on the nitrogen and said pyridyl is unsubstituted.

In another embodiment of this invention $R^5$ is a substituted triazolyl-pyridyl- wherein said triazolyl is substituted on the carbon and said pyridyl is unsubstituted.

In another embodiment of this invention $R^5$ is a substituted triazolyl-pyridyl- wherein said triazolyl is substituted on the nitrogen and on the carbon, and said pyridyl is unsubstituted.

In another embodiment of this invention $R^5$ is a substituted triazolyl-pyridyl- wherein said triazolyl is substituted and said pyridyl is substituted.

In another embodiment of this invention $R^5$ is a substituted triazolyl-pyridyl- wherein said triazolyl is substituted on the nitrogen and said pyridyl is substituted.

In another embodiment of this invention $R^5$ is a substituted triazolyl-pyridyl- wherein said triazolyl is substituted on the carbon and said pyridyl is substituted.

In another embodiment of this invention $R^5$ is a substituted triazolyl-pyridyl- wherein said triazolyl is substituted on the nitrogen and on the carbon, and said pyridyl is substituted.

In another embodiment of this invention $R^5$ is a substituted triazolyl-pyridyl- wherein said triazolyl is unsubstituted and said pyridyl is substituted.

In another embodiment of this invention $R^5$ is a substituted triazolyl-pyridyl- wherein the triazolyl is substituted on the nitrogen with alkyl.

When the pyridyl moiety of $R^5$ is substituted with alkyl, examples of the alkyl groups include, for example, —$C_1$-$C_6$alkyl, —$C_1$-$C_4$alkyl, —$C_1$-$C_2$alkyl, and —$CH_3$.

When the pyridyl moiety of $R^5$ is substituted with halo atoms, examples of the halo atoms include, for example, Cl, F and Br, provided that the carbon atoms adjacent to the nitrogen atom in said pyridyl are not substituted with halo. In one embodiment of this invention the halo on the pyridyl is F. In another embodiment of this invention the pyridyl is substituted with one F.

In another embodiment of this invention $R^5$ is a substituted triazolyl-pyridyl- wherein the triazolyl is substituted on the nitrogen with —$CH_2COH(CH_3)_2$, and the pyridyl is unsubstituted.

In another embodiment of this invention $R^5$ is a substituted triazolyl-pyridyl- wherein the triazolyl is substituted on the nitrogen with —$CH_2CH_2OH$, and the pyridyl is unsubstituted.

In another embodiment of this invention $R^5$ is a substituted triazolyl-pyridyl- wherein the triazolyl is substituted on the nitrogen with an alkyl group, and the pyridyl is unsubstituted.

In another embodiment of this invention $R^5$ is a substituted triazolyl-pyridyl- wherein the triazolyl is substituted on the nitrogen with an alkyl group and substituted on the carbon with an alkyl group, wherein each alkyl group is independently selected, and the pyridyl is unsubstituted.

In another embodiment of this invention $R^5$ is a substituted triazolyl-pyridyl- wherein the triazolyl is substituted on the nitrogen with a —$CH_3$ group, and the pyridyl is unsubstituted.

In another embodiment of this invention $R^5$ is a substituted triazolyl-pyridyl- wherein the triazolyl is substituted on the nitrogen with a —$CH_3$ group and on the carbon with a —$CH_3$ group, and the pyridyl is unsubstituted.

In another embodiment of this invention $R^5$ moiety is a substituted triazolyl-pyridyl- wherein the triazolyl is substituted on the carbon with a —$NH_2$ group, and the pyridyl is unsubstituted.

In another embodiment of this invention $R^5$ is a substituted triazolyl-pyridyl- wherein the triazolyl is substituted on the nitrogen with an -alkylene-O-alkyl group, and the pyridyl is unsubstituted, and provided that the alkylene moiety of said -alkylene-O-alkyl group is not —$CH_2$— (i.e., the alkylene moiety is 2 or more carbons in length).

In another embodiment of this invention $R^5$ is a substituted triazolyl-pyridyl- wherein the triazolyl is substituted on the nitrogen with a —$CH_2CH_2OCH_3$ group, and the pyridyl is unsubstituted.

In another embodiment of this invention $R^5$ moiety is a substituted triazolyl-pyridyl- wherein said pyridyl moiety is substituted with halo, provided that the carbon atoms adjacent to the nitrogen atom in said pyridyl are not substituted with halo, and said triazolyl moiety is substituted as described in any of the above embodiments describing substituted triazolyl groups.

In another embodiment of this invention $R^5$ is a substituted triazolyl-pyridyl- wherein said pyridyl moiety is substituted with one halo, provided that a carbon atom adjacent to the nitrogen atom in said pyridyl is not substituted with said halo, and said triazolyl moiety is substituted as described in any one of the above embodiments, describing triazolyl groups.

In another embodiment of this invention $R^5$ is a substituted triazolyl-pyridyl- wherein said pyridyl moiety is substituted with F, provided that a carbon atom adjacent to the nitrogen atom in said pyridyl is not substituted with said F, and said triazolyl moiety is substituted as described in any one of the above embodiments, describing triazolyl groups.

In another embodiment of this invention $R^5$ is a substituted triazolyl-pyridyl- wherein said pyridyl moiety is substituted with one F, provided that a carbon atom adjacent to the nitrogen atom in said pyridyl is not substituted with said F, and said triazolyl moiety is substituted as described in any one of the above embodiments describing triazolyl groups.

In another embodiment of this invention $R^5$ is a substituted triazolyl-pyridyl- group wherein said pyridyl moiety is substituted with one F, provided that a carbon atom adjacent to the nitrogen atom in said pyridyl is not substituted with said F, and said triazolyl moiety is substituted on the nitrogen with a hydroxyl substituted alkyl group.

In another embodiment of this invention $R^5$ is a substituted triazolyl-pyridyl- wherein said pyridyl moiety is substituted with one F, provided that a carbon atom adjacent to the nitrogen atom in said pyridyl is not substituted with said F, and said triazolyl moiety is substituted on the nitrogen with a —$CH_2CH_2OH$ group.

In another embodiment of this invention $R^5$ is a substituted triazolyl-pyridyl- wherein said pyridyl moiety is substituted with one F, provided that a carbon atom adjacent to the nitrogen atom in said pyridyl is not substituted with said F, and said triazolyl moiety is substituted on the nitrogen with an -alkylene-O-alkyl group, and the alkylene moiety of said -alkylene-O-alkyl group is not —$CH_2$— (i.e., the alkylene moiety is 2 or more carbons in length).

In another embodiment of this invention $R^5$ is a substituted triazolyl-pyridyl- wherein said pyridyl moiety is substituted with one F, provided that a carbon atom adjacent to the nitrogen atom in said pyridyl is not substituted with said F, and said triazolyl moiety is substituted on the nitrogen with a —$CH_2CH_2OCH_3$ group.

In another embodiment of this invention $R^5$ is a substituted triazolyl-pyridyl- wherein said pyridyl moiety is substituted with halo, provided that the carbon atoms adjacent to the nitrogen atom in said pyridyl are not substituted with halo, and said triazolyl moiety is unsubstituted.

In another embodiment of this invention $R^5$ is a substituted triazolyl-pyridyl- wherein said pyridyl moiety is substituted with one halo, provided that a carbon atom adjacent to the nitrogen atom in said pyridyl is not substituted with said halo, and said triazolyl moiety is unsubstituted.

In another embodiment of this invention $R^5$ is a substituted triazolyl-pyridyl- wherein said pyridyl moiety is substituted with F, provided that a carbon atom adjacent to the nitrogen atom in said pyridyl is not substituted with said F, and said triazolyl moiety is unsubstituted.

In another embodiment of this invention $R^5$ is a substituted triazolyl-pyridyl- wherein said pyridyl moiety is substituted with one F, provided that a carbon atom adjacent to the nitrogen atom in said pyridyl is not substituted with said F, and said triazolyl moiety is unsubstituted.

In another embodiment of this invention $R^5$ moiety is a substituted triazolyl-pyridyl- wherein said pyridyl moiety is substituted with alkoxy, and said triazolyl moiety is substituted as described in any of the above embodiments describing substituted triazolyl groups.

In another embodiment of this invention $R^5$ is a substituted triazolyl-pyridyl- wherein said pyridyl moiety is substituted with one alkoxy, and said triazolyl moiety is substituted as described in any one of the above embodiments describing substituted triazolyl groups.

In another embodiment of this invention $R^5$ is a substituted triazolyl-pyridyl- wherein said pyridyl moiety is substituted with —$OCH_3$, and said triazolyl moiety is substituted as described in any one of the above embodiments describing substituted triazolyl groups.

In another embodiment of this invention $R^5$ is a substituted triazolyl-pyridyl- wherein said pyridyl moiety is substituted with one —$OCH_3$, and said triazolyl moiety is substituted as described in any one of the above embodiments describing substituted triazolyl groups.

In another embodiment of this invention $R^5$ is a substituted triazolyl-pyridyl- group wherein said pyridyl moiety is substituted with one —$OCH_3$, and said triazolyl moiety is substituted on the nitrogen with a hydroxyl substituted alkyl group.

In another embodiment of this invention $R^5$ is a substituted triazolyl-pyridyl- wherein said pyridyl moiety is substituted with one —$OCH_3$, and said triazolyl moiety is substituted on the nitrogen with a —$CH_2CH_2OH$ group.

In another embodiment of this invention $R^5$ is a substituted triazolyl-pyridyl- wherein said pyridyl moiety is substituted with one —$OCH_3$, and said triazolyl moiety is substituted on the nitrogen with α-alkylene-O-alkyl group, and the alkylene moiety of said -alkylene-O-alkyl group is not —$CH_2$— (i.e., the alkylene moiety is 2 or more carbons in length).

In another embodiment of this invention $R^5$ is a substituted triazolyl-pyridyl- wherein said pyridyl moiety is substituted with one —$OCH_3$, and said triazolyl moiety is substituted on the nitrogen with a —$CH_2CH_2OCH_3$ group.

In another embodiment of this invention $R^5$ is a substituted triazolyl-pyridyl- wherein said pyridyl moiety is substituted with alkoxy, and said triazolyl moiety is unsubstituted.

In another embodiment of this invention $R^5$ is a substituted triazolyl-pyridyl- wherein said pyridyl moiety is substituted with one alkoxy, and said triazolyl moiety is unsubstituted.

In another embodiment of this invention $R^5$ is a substituted triazolyl-pyridyl- wherein said pyridyl moiety is substituted with —$OCH_3$, and said triazolyl moiety is unsubstituted.

In another embodiment of this invention $R^5$ is a substituted triazolyl-pyridyl- wherein said pyridyl moiety is substituted with one —$OCH_3$, and said triazolyl moiety is unsubstituted.

In another embodiment of this invention $R^5$ is a substituted triazolyl-pyridyl- wherein said triazolyl is substituted with 1 or 2 groups independently selected from the group consisting of: (a) hydroxyl substituted alkyl group (e.g., —$CH_2COH(CH_3)_2$, and —$CH_2CH_2OH$), (b) alkyl (e.g., —$C_1$-$C_6$alkyl, —$C_1$-$C_4$alkyl, —$C_1$-$C_2$alkyl, and —$CH_3$), (c) —$NH_2$, and (d)-alkylene-O-alkyl (e.g., —$CH_2CH_2OCH_3$), provided that the alkylene moiety of said -alkylene-O-alkyl group is not —CH$_2$— (i.e., the alkylene moiety is 2 or more carbons in length) when said -alkylene-O-alkyl group is bound to the nitrogen of said triazolyl; and said pyridyl is substituted with 1 to 3 groups independently selected from the group consisting of: (a) alkyl (e.g., —C$_1$-C$_6$alkyl, —C$_1$-C$_4$alkyl, —C$_1$-C$_2$alkyl, and —CH$_3$), (b) halo (e.g., Cl, F and Br) and provided that carbon atoms adjacent to the nitrogen atom in said pyridyl are not substituted with halo, and (c) alkoxy (e.g., —OCH$_3$).

In another embodiment of this invention R$^5$ is

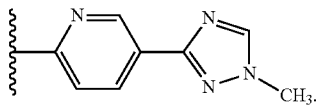

In another embodiment of this invention R$^5$ is triazolyl-thiazolyl-.

In another embodiment of this invention R$^5$ is

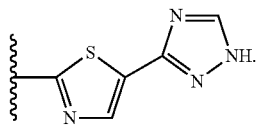 [SMILES: *c1ncc(-c2nc[nH]n2)s1]

In another embodiment of this invention R$^5$ is a substituted triazolyl-thiazolyl- wherein said triazolyl is substituted and said thiazolyl is unsubstituted.

In another embodiment of this invention R$^5$ is a substituted triazolyl-thiazolyl- wherein said triazolyl is substituted on the nitrogen and said thiazolyl is unsubstituted.

In another embodiment of this invention R$^5$ is a substituted triazolyl-thiazolyl- wherein said triazolyl is substituted on the carbon and said thiazolyl is unsubstituted.

In another embodiment of this invention R$^5$ is a substituted triazolyl-thiazolyl- wherein said triazolyl is substituted on the nitrogen and on the carbon, and said thiazolyl is unsubstituted.

When the thiazolyl moiety of R$^5$ is substituted with alkyl, examples of the alkyl groups include, for example, —C$_1$-C$_6$alkyl, —C$_1$-C$_4$alkyl, —C$_1$-C$_2$alkyl, and —CH$_3$.

When the thiazolyl moiety of R$^5$ is substituted with halo atoms, examples of the halo atoms include, for example, Cl, F and Br. In one embodiment of this invention the halo on the thiazolyl is F. In another embodiment of this invention the thiazolyl is substituted with one F.

When the thiazolyl moiety of R$^5$ is substituted with an alkylamino group, examples of the alkylamino group include, for example, C$_1$-C$_6$alkyl-NH—, C$_1$-C$_2$alkyl-NH—, CH$_3$—NH—, and CH$_3$CH$_2$—NH—.

When the thiazolyl moiety of R$^5$ is substituted with a dialkylamino group, examples of the dialkylamino group include, for example, (C$_1$-C$_6$alkyl)$_2$-N— wherein each alkyl is independently selected, (C$_1$-C$_2$alkyl)$_2$-N— wherein each alkyl is independently selected, (CH$_3$)$_2$N—, (CH$_3$CH$_2$)$_2$—N—, and (CH$_3$)(CH$_3$CH$_2$)N—.

In another embodiment of this invention R$^5$ is a substituted triazolyl-thiazolyl- wherein said triazolyl is substituted and said thiazolyl is substituted.

In another embodiment of this invention R$^5$ is a substituted triazolyl-thiazolyl- wherein said triazolyl is substituted on the nitrogen and said thiazolyl is substituted.

In another embodiment of this invention R$^5$ is a substituted triazolyl-thiazolyl- wherein said triazolyl is substituted on the carbon and said thiazolyl is substituted.

In another embodiment of this invention R$^5$ is a substituted triazolyl-thiazolyl- wherein said triazolyl is substituted on the nitrogen and on the carbon, and said thiazolyl is substituted.

In another embodiment of this invention R$^5$ is a substituted triazolyl-thiazolyl- wherein said triazolyl is unsubstituted and said thiazolyl is substituted.

In another embodiment of this invention R$^5$ is a substituted triazolyl-thiazolyl- wherein the triazolyl is substituted on the nitrogen with alkyl, and said thiazolyl is unsubstituted.

In another embodiment of this invention R$^5$ is a substituted triazolyl-thiazolyl- wherein the triazolyl is substituted on the nitrogen with —CH$_2$COH(CH$_3$)$_2$, and said thiazolyl is unsubstituted.

In another embodiment of this invention R$^5$ is a substituted triazolyl-thiazolyl- wherein the triazolyl is substituted on the nitrogen with —CH$_2$CH$_2$OH, and said thiazolyl is unsubstituted.

In another embodiment of this invention R$^5$ is a substituted triazolyl-thiazolyl- wherein the triazolyl is substituted on the nitrogen with an alkyl group and substituted on the carbon with an alkyl group, wherein each alkyl group is independently selected, and said thiazolyl is unsubstituted.

In another embodiment of this invention R$^5$ is a substituted triazolyl-thiazolyl- wherein the triazolyl is substituted on the nitrogen with a —CH$_3$ group, and said thiazolyl is unsubstituted.

In another embodiment of this invention R$^5$ is a substituted triazolyl-thiazolyl- wherein the triazolyl is substituted on the nitrogen with a —CH$_3$ group and on the carbon with a —CH$_3$ group, and said thiazolyl is unsubstituted.

In another embodiment of this invention R$^5$ moiety is a substituted triazolyl-thiazolyl- wherein the triazolyl is substituted on the carbon with a —NH$_2$ group, and said thiazolyl is unsubstituted.

In another embodiment of this invention R$^5$ is a substituted triazolyl-thiazolyl- wherein the triazolyl is substituted on the nitrogen with an -alkylene-O-alkyl group, provided that the alkylene moiety of said -alkylene-O-alkyl group is not —CH$_2$— (i.e., the alkylene moiety is 2 or more carbons in length), and said thiazolyl is unsubstituted.

In another embodiment of this invention R$^5$ is a substituted triazolyl-thiazolyl- wherein the triazolyl is substituted on the nitrogen with a —CH$_2$CH$_2$OCH$_3$ group, and said thiazolyl is unsubstituted.

In another embodiment of this invention R$^5$ moiety is a substituted triazolyl-thiazolyl- wherein said thiazolyl moiety is substituted with halo, and said triazolyl moiety is substituted as described in any of the above embodiments describing substituted triazolyl groups.

In another embodiment of this invention R$^5$ is a substituted triazolyl-thiazolyl- wherein said thiazolyl moiety is substituted with F, and said triazolyl moiety is substituted as described in any one of the above embodiments describing substituted triazolyl groups.

In another embodiment of this invention R$^5$ is a substituted triazolyl-thiazolyl- group wherein said thiazolyl moiety is substituted with one F, and said triazolyl moiety is substituted on the nitrogen with a hydroxyl substituted alkyl group.

In another embodiment of this invention R$^5$ is a substituted triazolyl-thiazolyl- wherein said thiazolyl moiety is substituted with one F, and said triazolyl moiety is substituted on the nitrogen with a —CH$_2$CH$_2$OH group.

In another embodiment of this invention R$^5$ is a substituted triazolyl-thiazolyl- wherein said thiazolyl moiety is substituted with one F, and said triazolyl moiety is substituted on the nitrogen with an -alkylene-O-alkyl group.

In another embodiment of this invention R⁵ is a substituted triazolyl-thiazolyl- wherein said thiazolyl moiety is substituted with one F, and said triazolyl moiety is substituted on the nitrogen with a —CH₂CH₂OCH₃ group.

In another embodiment of this invention R⁵ is a substituted triazolyl-thiazolyl- wherein said thiazolyl moiety is substituted with halo, and said triazolyl moiety is unsubstituted.

In another embodiment of this invention R⁵ is a substituted triazolyl-thiazolyl- wherein said thiazolyl moiety is substituted with F, and said triazolyl moiety is unsubstituted.

In another embodiment of this invention R⁵ moiety is a substituted triazolyl-thiazolyl- wherein said thiazolyl moiety is substituted with alkoxy, and said triazolyl moiety is substituted as described in any of the above embodiments describing substituted triazolyl groups.

In another embodiment of this invention R⁵ is a substituted triazolyl-thiazolyl- wherein said thiazolyl moiety is substituted with —OCH₃, and said triazolyl moiety is substituted as described in any one of the above embodiments describing substituted triazolyl groups.

In another embodiment of this invention R⁵ is a substituted triazolyl-thiazolyl- group wherein said thiazolyl moiety is substituted with one —OCH₃, and said triazolyl moiety is substituted on the nitrogen with a hydroxyl substituted alkyl group.

In another embodiment of this invention R⁵ is a substituted triazolyl-thiazolyl- wherein said thiazolyl moiety is substituted with one —OCH₃, and said triazolyl moiety is substituted on the nitrogen with a —CH₂CH₂OH group.

In another embodiment of this invention R⁵ is a substituted triazolyl-thiazolyl- wherein said thiazolyl moiety is substituted with one —OCH₃, and said triazolyl moiety is substituted on the nitrogen with an -alkylene-O-alkyl group, and the alkylene moiety of said -alkylene-O-alkyl group is not —CH₂— (i.e., the alkylene moiety is 2 or more carbons in length).

In another embodiment of this invention R⁵ is a substituted triazolyl-thiazolyl- wherein said thiazolyl moiety is substituted with one —OCH₃, and said triazolyl moiety is substituted on the nitrogen with a —CH₂CH₂OCH₃ group.

In another embodiment of this invention R⁵ is a substituted triazolyl-thiazolyl- wherein said thiazolyl moiety is substituted with alkoxy, and said triazolyl moiety is unsubstituted.

In another embodiment of this invention R⁵ is a substituted triazolyl-thiazolyl- wherein said thiazolyl moiety is substituted with —OCH₃, and said triazolyl moiety is unsubstituted.

In another embodiment of this invention R⁵ is a substituted triazolyl-thiazolyl- wherein said thiazolyl moiety is substituted with an alkylamino, and said triazolyl moiety is substituted as described in any of the above embodiments describing triazolyl groups.

In another embodiment of this invention R⁵ is a substituted triazolyl-thiazolyl- wherein said thiazolyl moiety is substituted with a dialkylamino, and said triazolyl moiety is substituted as described in any of the above embodiments describing substituted triazolyl groups.

In another embodiment of this invention R⁵ is a substituted triazolyl-thiazolyl- wherein said thiazolyl moiety is substituted with an alkylamino, and said triazolyl moiety is unsubstituted.

In another embodiment of this invention R⁵ is a substituted triazolyl-thiazolyl- wherein said thiazolyl moiety is substituted with a dialkylamino, and said triazolyl moiety is unsubstituted.

In another embodiment of this invention R⁵ is a substituted triazolyl-thiazolyl- wherein said triazolyl is substituted with 1 or 2 groups independently selected from the group consisting of: (a) hydroxyl substituted alkyl group (e.g., —CH₂COH(CH₃)₂, and —CH₂CH₂OH), (b) alkyl (e.g., —C₁-C₆alkyl, —C₁-C₄alkyl, —C₁-C₂alkyl, and —CH₃), —NH₂, and (c)-alkylene-O-alkyl (e.g., —CH₂CH₂OCH₃), provided that the alkylene moiety of said -alkylene-O-alkyl group is not —CH₂— (i.e., the alkylene moiety is 2 or more carbons in length) when said -alkylene-O-alkyl group is bound to the nitrogen of said triazolyl; and said thiazolyl is substituted with 1 group selected from the group consisting of: (a) alkyl (e.g., —C₁-C₆alkyl, or —C₁-C₄alkyl, or —C₁-C₂alkyl, or —CH₃), (b) halo (e.g., Cl, F, or Br), (c) alkylamino (e.g., C₁-C₆alkyl-NH—, or C₁-C₂alkyl-NH—, or CH₃—NH—, or CH₃CH₂—NH—), and (d) dialkylamino (e.g., (C₁-C₆ alkyl)₂-N— wherein each alkyl is independently selected, or (C₁-C₂alkyl)₂-N— wherein each alkyl is independently selected, or (CH₃)₂N—, or (CH₃CH₂)₂—N—, or (CH₃)(CH₃CH₂)N—).

In another embodiment of this invention R⁵ is

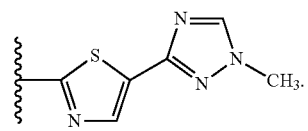 [SMILES: *c1ncc(-c2ncn(C)n2)s1]

In another embodiment of this invention R⁵ is pyridazinyl-thienyl-.

In another embodiment of this invention R⁵ is

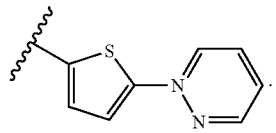

When the pyridazinyl moiety of R⁵ is substituted with alkyl, examples of the alkyl groups include, for example, —C₁-C₆alkyl, —C₁-C₄alkyl, —C₁-C₂alkyl, and —CH₃.

When the pyridazinyl moiety of R⁵ is substituted with halo atoms, examples of the halo atoms include, for example, Cl, F and Br. In one embodiment of this invention the halo on the pyridazinyl is F. In another embodiment of this invention the pyridazinyl is substituted with one F. When the pyridazinyl moiety is substituted with halos, the carbons adjacent to the nitrogens are not substituted with halos.

When the pyridazinyl moiety of R⁵ is substituted with an alkylamino group, examples of the alkylamino group include, for example, C₁-C₆alkyl-NH—, C₁-C₂alkyl-NH—, CH₃—NH—, and CH₃CH₂—NH—.

When the pyridazinyl moiety of R⁵ is substituted with a dialkylamino group, examples of the dialkylamino group include, for example, (C₁-C₆alkyl)₂-N— wherein each alkyl is independently selected, (C₁-C₂alkyl)₂-N— wherein each alkyl is independently selected, (CH₃)₂N—, (CH₃CH₂)₂—N—, and (CH₃)(CH₃CH₂)N—.

In another embodiment of this invention R⁵ is a substituted pyridazinyl-thienyl- wherein said pyridazinyl is substituted and said thienyl is unsubstituted.

In another embodiment of this invention R⁵ is a substituted pyridazinyl-thienyl- wherein said pyridazinyl is substituted with a =O group, and said thienyl is unsubstituted.

In another embodiment of this invention $R^5$ is a substituted pyridazinyl-thienyl- wherein said pyridazinyl is substituted with an alkyl group, and said thienyl is unsubstituted.

In another embodiment of this invention $R^5$ is a substituted pyridazinyl-thienyl- wherein said pyridazinyl is substituted with a methyl group, and said thienyl is unsubstituted.

In another embodiment of this invention $R^5$ is a substituted pyridazinyl-thienyl- wherein said pyridazinyl is substituted with a =O group, and with an alkyl group, and said thienyl is unsubstituted.

In another embodiment of this invention $R^5$ is a substituted pyridazinyl-thienyl- wherein said pyridazinyl is substituted with a =O group, and with a methyl group, and said thienyl is unsubstituted.

In another embodiment of this invention $R^5$ is a substituted pyridazinyl-thienyl- wherein said pyridazinyl is substituted with an amino group, and said thienyl is unsubstituted.

In another embodiment of this invention $R^5$ is a substituted pyridazinyl-thienyl- wherein said pyridazinyl is substituted with an alkylamino group, and said thienyl is unsubstituted.

In another embodiment of this invention $R^5$ is a substituted pyridazinyl-thienyl- wherein said pyridazinyl is substituted with a dialkylamino group, and said thienyl is unsubstituted.

In another embodiment of this invention $R^5$ is a substituted pyridazinyl-thienyl- wherein said pyridazinyl is substituted and said thienyl is substituted.

In another embodiment of this invention $R^5$ is a substituted pyridazinyl-thienyl- wherein said pyridazinyl is unsubstituted and said thienyl is substituted.

In another embodiment of this invention $R^5$ is a substituted pyridazinyl-thienyl- wherein said pyridazinyl is unsubstituted and said thienyl is substituted with 1 to 2 independently selected halos.

In another embodiment of this invention $R^5$ is a substituted pyridazinyl-thienyl- wherein said pyridazinyl is unsubstituted and said thienyl is substituted with 1 to 2 halos independently selected from the group consisting of: Br, Cl and F.

In another embodiment of this invention $R^5$ is a substituted pyridazinyl-thienyl- wherein said pyridazinyl is unsubstituted and said thienyl is substituted with 1 to 2 independently selected alkoxy groups.

In another embodiment of this invention $R^5$ is a substituted pyridazinyl-thienyl- wherein said pyridazinyl is unsubstituted and said thienyl is substituted with 1 to 2 —OCH$_3$ groups.

In another embodiment of this invention $R^5$ is a substituted pyridazinyl-thienyl- wherein said pyridazinyl is substituted as described in any one of the embodiments above describing substituted pyridazinyl groups, and said thienyl is substituted.

In another embodiment of this invention $R^5$ is a substituted pyridazinyl-thienyl- wherein said pyridazinyl is substituted as described in any one of the embodiments above describing substituted pyridazinyl groups, and said thienyl is substituted with 1 to 2 independently selected halos.

In another embodiment of this invention $R^5$ is a substituted pyridazinyl-thienyl- wherein said pyridazinyl is substituted as described in any one of the embodiments above describing substituted pyridazinyl groups, and said thienyl is substituted with 1 to 2 halos independently selected from the group consisting of: Br, Cl and F.

In another embodiment of this invention $R^5$ is a substituted pyridazinyl-thienyl- wherein said pyridazinyl is substituted as described in any one of the embodiments above describing substituted pyridazinyl groups, and said thienyl is substituted with 1 to 2 independently selected alkoxy groups.

In another embodiment of this invention $R^5$ is a substituted pyridazinyl-thienyl- wherein said pyridazinyl is substituted as described in any one of the embodiments above describing substituted pyridazinyl groups, and said thienyl is substituted with 1 to 2 —OCH$_3$ groups.

In another embodiment of this invention $R^5$ is a substituted pyridazinyl-thienyl- wherein said pyridazinyl is substituted with 1 or 2 groups independently selected from the group consisting of alkyl (e.g., methyl) and =O, and said thienyl is substituted with 1 to 2 groups independently selected from the group consisting of: alkoxy (e.g., —OCH$_3$), halo (e.g., Br, Cl and F).

In another embodiment of this invention $R^5$ is

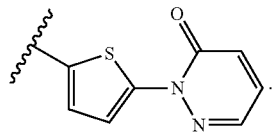 [SMILES: *c1ccc(-n2ncccc2=O)s1 ; "."]

In another embodiment of this invention $R^5$ is

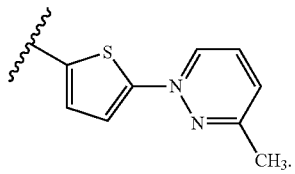

In another embodiment of this invention $R^5$ is

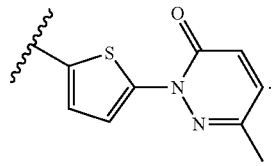 [SMILES: *c1ccc(-n2nc(C)ccc2=O)s1]

In another embodiment of this invention $R^5$ is a substituted triazolyl-phenyl- group wherein (a) said triazolyl moiety is optionally substituted on the nitrogen with a substituent selected from the group consisting of: —CH$_2$COH(CH$_3$)$_2$ and —CH$_2$CH$_2$OH, (b) said triazolyl moiety is optionally substituted on the nitrogen with an alkyl group, (c) said triazolyl moiety is optionally substituted on the nitrogen with an alkyl group, and on the carbon with an alkyl group, (d) said triazolyl moiety is optionally substituted on the nitrogen with a —CH$_3$ group, (e) said triazolyl moiety is optionally substituted on the nitrogen with one —CH$_3$ group, and on the carbon with one —CH$_3$ group, (f) said triazolyl moiety is optionally substituted on the carbon with a —NH$_2$ group, or (g) said triazolyl moiety is optionally substituted on the nitrogen with a —CH$_2$CH$_2$OCH$_3$ group; and wherein said phenyl moiety is optionally substituted with halo.

In another embodiment of this invention $R^5$ is a substituted triazolyl-phenyl- group wherein (a) said triazolyl moiety is optionally substituted on the nitrogen with a substituent selected from the group consisting of: —CH$_2$COH(CH$_3$)$_2$ and —CH$_2$CH$_2$OH, (b) said triazolyl moiety is optionally substituted on the nitrogen with an alkyl group, (c) said triazolyl moiety is optionally substituted on the nitrogen with an alkyl group, and on the carbon with an alkyl group, (d) said triazolyl moiety is optionally substituted on the nitrogen with a —CH$_3$ group, (e) said triazolyl moiety is optionally substituted on the nitrogen with one —CH$_3$ group, and on the carbon with one —CH$_3$ group, (f) said triazolyl moiety is optionally substituted on the carbon with a —NH$_2$ group, or (g) said triazolyl moiety is optionally substituted on the nitrogen with a —CH$_2$CH$_2$OCH$_3$ group; and wherein said phenyl moiety is substituted with halo.

In another embodiment of this invention R$^5$ is a substituted triazolyl-phenyl- group wherein (a) said triazolyl moiety is substituted on the nitrogen with a substituent selected from the group consisting of: —CH$_2$COH(CH$_3$)$_2$ and —CH$_2$CH$_2$OH, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —CH$_3$ group, (e) said triazolyl moiety is substituted on the nitrogen with one —CH$_3$ group, and on the carbon with one —CH$_3$ group, (f) said triazolyl moiety is substituted on the carbon with a —NH$_2$ group, or (g) said triazolyl moiety is substituted on the nitrogen with a —CH$_2$CH$_2$OCH$_3$ group; and wherein said phenyl moiety is optionally substituted with halo.

In another embodiment of this invention R$^5$ is a substituted triazolyl-phenyl- group wherein (a) said triazolyl moiety is substituted on the nitrogen with a substituent selected from the group consisting of: —CH$_2$COH(CH$_3$)$_2$ and —CH$_2$CH$_2$OH, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —CH$_3$ group, (e) said triazolyl moiety is substituted on the nitrogen with one —CH$_3$ group, and on the carbon with one —CH$_3$ group, (f) said triazolyl moiety is substituted on the carbon with a —NH$_2$ group, or (g) said triazolyl moiety is substituted on the nitrogen with a —CH$_2$CH$_2$OCH$_3$ group; and wherein said phenyl moiety is substituted with halo.

In another embodiment of this invention R$^5$ is a substituted triazolyl-phenyl- group wherein (a) said triazolyl moiety is substituted on the nitrogen with a substituent selected from the group consisting of: —CH$_2$COH(CH$_3$)$_2$ and —CH$_2$CH$_2$OH, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —CH$_3$ group, (e) said triazolyl moiety is substituted on the nitrogen with one —CH$_3$ group, and on the carbon with one —CH$_3$ group, (f) said triazolyl moiety is substituted on the carbon with a —NH$_2$ group, or (g) said triazolyl moiety is substituted on the nitrogen with a —CH$_2$CH$_2$OCH$_3$ group; and wherein said phenyl moiety is unsubstituted.

In another embodiment of this invention R$^5$ is a substituted triazolyl-phenyl- group wherein (a) said triazolyl moiety is optionally substituted on the nitrogen with a substituent selected from the group consisting of: —CH$_2$COH(CH$_3$)$_2$ and —CH$_2$CH$_2$OH, (b) said triazolyl moiety is optionally substituted on the nitrogen with an alkyl group, (c) said triazolyl moiety is optionally substituted on the nitrogen with an alkyl group, and on the carbon with an alkyl group, (d) said triazolyl moiety is optionally substituted on the nitrogen with a —CH$_3$ group, (e) said triazolyl moiety is optionally substituted on the nitrogen with one —CH$_3$ group, and on the carbon with one —CH$_3$ group, (f) said triazolyl moiety is optionally substituted on the carbon with a —NH$_2$ group, or (g) said triazolyl moiety is optionally substituted on the nitrogen with a —CH$_2$CH$_2$OCH$_3$ group; and wherein said phenyl moiety is optionally substituted with alkoxy.

In another embodiment of this invention R$^5$ is a substituted triazolyl-phenyl- group wherein (a) said triazolyl moiety is optionally substituted on the nitrogen with a substituent selected from the group consisting of: —CH$_2$COH(CH$_3$)$_2$ and —CH$_2$CH$_2$OH, (b) said triazolyl moiety is optionally substituted on the nitrogen with an alkyl group, (c) said triazolyl moiety is optionally substituted on the nitrogen with an alkyl group, and on the carbon with an alkyl group, (d) said triazolyl moiety is optionally substituted on the nitrogen with a —CH$_3$ group, (e) said triazolyl moiety is optionally substituted on the nitrogen with one —CH$_3$ group, and on the carbon with one —CH$_3$ group, (f) said triazolyl moiety is optionally substituted on the carbon with a —NH$_2$ group, or (g) said triazolyl moiety is optionally substituted on the nitrogen with a —CH$_2$CH$_2$OCH$_3$ group; and wherein said phenyl moiety is substituted with alkoxy.

In another embodiment of this invention R$^5$ is a substituted triazolyl-phenyl- group wherein (a) said triazolyl moiety is substituted on the nitrogen with a substituent selected from the group consisting of: —CH$_2$COH(CH$_3$)$_2$ and —CH$_2$CH$_2$OH, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —CH$_3$ group, (e) said triazolyl moiety is substituted on the nitrogen with one —CH$_3$ group, and on the carbon with one —CH$_3$ group, (f) said triazolyl moiety is substituted on the carbon with a —NH$_2$ group, or (g) said triazolyl moiety is substituted on the nitrogen with a —CH$_2$CH$_2$OCH$_3$ group; and wherein said phenyl moiety is optionally substituted with alkoxy.

In another embodiment of this invention R$^5$ is a substituted triazolyl-phenyl- group wherein (a) said triazolyl moiety is substituted on the nitrogen with a substituent selected from the group consisting of: —CH$_2$COH(CH$_3$)$_2$ and —CH$_2$CH$_2$OH, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —CH$_3$ group, (e) said triazolyl moiety is substituted on the nitrogen with one —CH$_3$ group, and on the carbon with one —CH$_3$ group, (f) said triazolyl moiety is substituted on the carbon with a —NH$_2$ group, or (g) said triazolyl moiety is substituted on the nitrogen with a —CH$_2$CH$_2$OCH$_3$ group; and wherein said phenyl moiety is substituted with alkoxy.

In another embodiment of this invention R$^5$ is a substituted triazolyl-thienyl- group wherein (a) said triazolyl moiety is optionally substituted on the nitrogen with a substituent selected from the group consisting of: —CH$_2$COH(CH$_3$)$_2$ and —CH$_2$CH$_2$OH, (b) said triazolyl moiety is optionally substituted on the nitrogen with an alkyl group, (c) said triazolyl moiety is optionally substituted on the nitrogen with an alkyl group, and on the carbon with an alkyl group, (d) said triazolyl moiety is optionally substituted on the nitrogen with a —CH$_3$ group, (e) said triazolyl moiety is optionally substituted on the nitrogen with one —CH$_3$ group, and on the carbon with one —CH$_3$ group, (f) said triazolyl moiety is optionally substituted on the carbon with a —NH$_2$ group, or (g) said triazolyl moiety is optionally substituted on the nitrogen with a —CH$_2$CH$_2$OCH$_3$ group; and wherein said thienyl moiety is optionally substituted with halo.

In another embodiment of this invention R$^5$ is a substituted triazolyl-thienyl- group wherein (a) said triazolyl moiety is optionally substituted on the nitrogen with a substituent selected from the group consisting of: —CH$_2$COH(CH$_3$)$_2$ and —CH$_2$CH$_2$OH, (b) said triazolyl moiety is optionally substituted on the nitrogen with an alkyl group, (c) said triazolyl moiety is optionally substituted on the nitrogen with an alkyl group, and on the carbon with an alkyl group, (d) said triazolyl moiety is optionally substituted on the nitrogen with a —$CH_3$ group, (e) said triazolyl moiety is optionally substituted on the nitrogen with one —$CH_3$ group, and on the carbon with one —$CH_3$ group, (f) said triazolyl moiety is optionally substituted on the carbon with a —$NH_2$ group, or (g) said triazolyl moiety is optionally substituted on the nitrogen with a —$CH_2CH_2OCH_3$ group; and wherein said thienyl moiety is substituted with halo.

In another embodiment of this invention $R^5$ is a substituted triazolyl-thienyl- group wherein (a) said triazolyl moiety is substituted on the nitrogen with a substituent selected from the group consisting of: —$CH_2COH(CH_3)_2$ and —$CH_2CH_2OH$, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —$CH_3$ group, (e) said triazolyl moiety is substituted on the nitrogen with one —$CH_3$ group, and on the carbon with one —$CH_3$ group, (f) said triazolyl moiety is substituted on the carbon with a —$NH_2$ group, or (g) said triazolyl moiety is substituted on the nitrogen with a —$CH_2CH_2OCH_3$ group; and wherein said thienyl moiety is optionally substituted with halo.

In another embodiment of this invention $R^5$ is a substituted triazolyl-thienyl- group wherein (a) said triazolyl moiety is substituted on the nitrogen with a substituent selected from the group consisting of: —$CH_2COH(CH_3)_2$ and —$CH_2CH_2OH$, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —$CH_3$ group, (e) said triazolyl moiety is substituted on the nitrogen with one —$CH_3$ group, and on the carbon with one —$CH_3$ group, (f) said triazolyl moiety is substituted on the carbon with a —$NH_2$ group, or (g) said triazolyl moiety is substituted on the nitrogen with a —$CH_2CH_2OCH_3$ group; and wherein said thienyl moiety is substituted with halo.

In another embodiment of this invention $R^5$ is a substituted triazolyl-thienyl- group wherein (a) said triazolyl moiety is substituted on the nitrogen with a substituent selected from the group consisting of: —$CH_2COH(CH_3)_2$ and —$CH_2CH_2OH$, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —$CH_3$ group, (e) said triazolyl moiety is substituted on the nitrogen with one —$CH_3$ group, and on the carbon with one —$CH_3$ group, (f) said triazolyl moiety is substituted on the carbon with a —$NH_2$ group, or (g) said triazolyl moiety is substituted on the nitrogen with a —$CH_2CH_2OCH_3$ group; and wherein said thienyl moiety is unsubstituted.

In another embodiment of this invention $R^5$ is a substituted triazolyl-thienyl- group wherein (a) said triazolyl moiety is optionally substituted on the nitrogen with a substituent selected from the group consisting of: —$CH_2COH(CH_3)_2$, and —$CH_2CH_2OH$, (b) said triazolyl moiety is optionally substituted on the nitrogen with an alkyl group, (c) said triazolyl moiety is optionally substituted on the nitrogen with an alkyl group, and on the carbon with an alkyl group, (d) said triazolyl moiety is optionally substituted on the nitrogen with a —$CH_3$ group, (e) said triazolyl moiety is optionally substituted on the nitrogen with one —$CH_3$ group, and on the carbon with one —$CH_3$ group, (f) said triazolyl moiety is optionally substituted on the carbon with a —$NH_2$ group, or (g) said triazolyl moiety is optionally substituted on the nitrogen with a —$CH_2CH_2OCH_3$ group; and wherein said thienyl moiety is optionally substituted with alkoxy.

In another embodiment of this invention $R^5$ is a substituted triazolyl-thienyl- group wherein (a) said triazolyl moiety is optionally substituted on the nitrogen with a substituent selected from the group consisting of: —$CH_2COH(CH_3)_2$ and —$CH_2CH_2OH$, (b) said triazolyl moiety is optionally substituted on the nitrogen with an alkyl group, (c) said triazolyl moiety is optionally substituted on the nitrogen with an alkyl group, and on the carbon with an alkyl group, (d) said triazolyl moiety is optionally substituted on the nitrogen with a —$CH_3$ group, (e) said triazolyl moiety is optionally substituted on the nitrogen with one —$CH_3$ group, and on the carbon with one —$CH_3$ group, (f) said triazolyl moiety is optionally substituted on the carbon with a —$NH_2$ group, or (g) said triazolyl moiety is optionally substituted on the nitrogen with a —$CH_2CH_2OCH_3$ group; and wherein said thienyl moiety is substituted with alkoxy.

In another embodiment of this invention $R^5$ is a substituted triazolyl-thienyl- group wherein (a) said triazolyl moiety is substituted on the nitrogen with a substituent selected from the group consisting of: —$CH_2COH(CH_3)_2$ and —$CH_2CH_2OH$, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —$CH_3$ group, (e) said triazolyl moiety is substituted on the nitrogen with one —$CH_3$ group, and on the carbon with one —$CH_3$ group, (f) said triazolyl moiety is substituted on the carbon with a —$NH_2$ group, or (g) said triazolyl moiety is substituted on the nitrogen with a —$CH_2CH_2OCH_3$ group; and wherein said thienyl moiety is optionally substituted with alkoxy.

In another embodiment of this invention $R^5$ is a substituted triazolyl-thienyl- group wherein (a) said triazolyl moiety is substituted on the nitrogen with a substituent selected from the group consisting of: —$CH_2COH(CH_3)_2$, and —$CH_2CH_2OH$, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —$CH_3$ group, (e) said triazolyl moiety is substituted on the nitrogen with one —$CH_3$ group, and on the carbon with one —$CH_3$ group, (f) said triazolyl moiety is substituted on the carbon with a —$NH_2$ group, or (g) said triazolyl moiety is substituted on the nitrogen with a —$CH_2CH_2OCH_3$ group; and wherein said thienyl moiety is substituted with alkoxy.

Other embodiments of the invention are described below. The embodiments have been numbered for ease of reference.

Embodiment No. 1 is directed to compounds of formula 1.0 wherein $R^2$ is a —O—$(C_1-C_2)$alkyl group, and $R^1$ is substituted pyridyl.

Embodiment No. 2 is directed to compounds of formula 1.0 wherein $R^2$ is a —O—$(C_1-C_2)$alkyl group, and $R^1$ is pyridyl substituted with one substituent.

Embodiment No. 3 is directed to compounds of formula 1.0 wherein $R^2$ is a —O—$(C_1-C_2)$alkyl group, and $R^1$ is selected from the group consisting of:

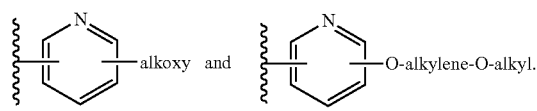

Embodiment No. 4 is directed to compounds of formula 1.0 wherein $R^2$ is a —O—$(C_1$-$C_2)$alkyl group, and $R^1$ is:

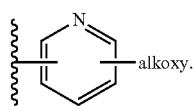

Embodiment No. 5 is directed to compounds of formula 1.0 wherein $R^2$ is a —O—$(C_1$-$C_2)$alkyl group, and $R^1$ is:

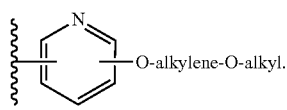

Embodiment No. 6 is directed to compounds of formula 1.0 wherein $R^2$ is a —O—$(C_1$-$C_2)$alkyl group, and $R^1$ is:

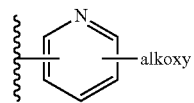

wherein said alkoxy group is —OCH($CH_3)_2$.

Embodiment No. 7 is directed to compounds of formula 1.0 wherein, $R^2$ is a —O—$(C_1$-$C_2)$alkyl group, and $R^1$ is:

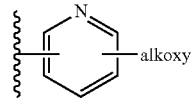

wherein said alkoxy group is —OC$_2$H$_5$.

Embodiment No. 8 is directed to compounds of formula 1.0 wherein $R^2$ is a —O—$(C_1$-$C_2)$alkyl group, and $R^1$ is:

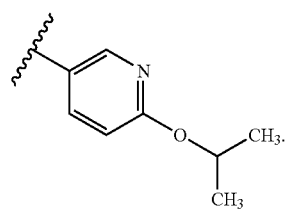 [SMILES: *c1ccc(OC(C)C)nc1]

Embodiment No. 9 is directed to compounds of formula 1.0 wherein $R^2$ is a —O—$(C_1$-$C_2)$alkyl group, and $R^1$ is:

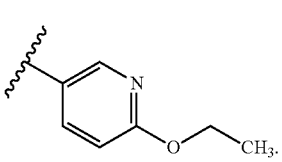

Embodiment No. 10 is directed to compounds of formula 1.0 wherein z is 1, $R^2$ is a —O—$(C_1$-$C_2)$alkyl group, and $R^1$ is:

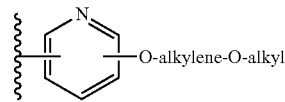

wherein said —O-alkylene-O-alkyl group is —OCH$_2$CH$_2$OCH$_3$.

Embodiment No. 11 is directed to compounds of formula 1.0 wherein $R^2$ is a —O—$(C_1$-$C_2)$alkyl group, and $R^1$ is:

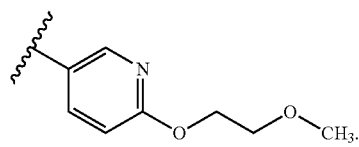 [SMILES: *c1ccc(OCCOC)nc1]

Embodiment No. 12 is directed to compounds of formula 1.0 wherein $R^2$ is —OCH$_3$, and $R^1$ is substituted pyridyl.

Embodiment No. 13 is directed to compounds of formula 1.0 wherein $R^2$ is —OCH$_3$, and $R^1$ is pyridyl substituted with one substituent.

Embodiment No. 14 is directed to compounds of formula 1.0 wherein $R^2$ is —OCH$_3$, and $R^1$ is selected from the group consisting of:

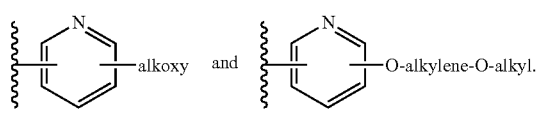

Embodiment No. 15 is directed to compounds of formula 1.0 wherein $R^2$ is —OCH$_3$, and $R^1$ is:

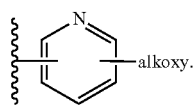

Embodiment No. 16 is directed to compounds of formula 1.0 wherein $R^2$ is —OCH$_3$, and $R^1$ is:

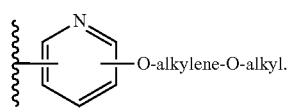

Embodiment No. 17 is directed to compounds of formula 1.0 wherein $R^2$ is —OCH$_3$, and $R^1$ is:

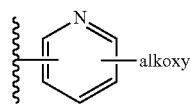

wherein said alkoxy group is —OCH(CH$_3$)$_2$.

Embodiment No. 18 is directed to compounds of formula 1.0 wherein R$^2$ is —OCH$_3$, and R$^1$ is:

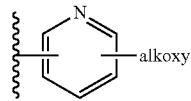

wherein said alkoxy group is —OC$_2$H$_5$.

Embodiment No. 19 is directed to compounds of formula 1.0 wherein R$^2$ is —OCH$_3$, and R$^1$ is:

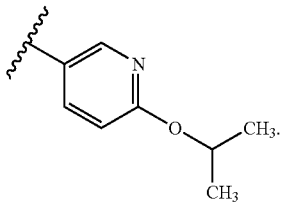 [SMILES: *c1ccc(OC(C)C)nc1]

Embodiment No. 20 is directed to compounds of formula 1.0 wherein R$^2$ is —OCH$_3$, and R$^1$ is:

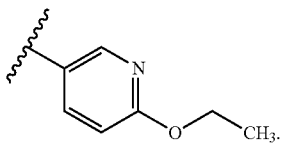

Embodiment No. 21 is directed to compounds of formula 1.0 wherein R$^2$ is —OCH$_3$, and R$^1$ is:

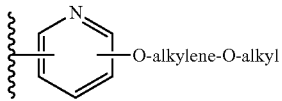

wherein said —O-alkylene-O-alkyl group is —OCH$_2$CH$_2$OCH$_3$.

Embodiment No. 22 is directed to compounds of formula 1.0 wherein R$^2$ is —OCH$_3$, and R$^1$ is:

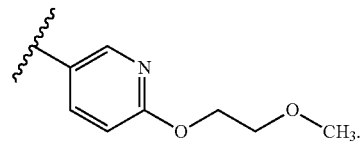

Embodiment No. 23 is directed to compounds of formula 1.0 wherein R$^2$ is a —S—(C$_1$-C$_2$)alkyl group, and R$^1$ is substituted pyridyl.

Embodiment No. 24 is directed to compounds of formula 1.0 wherein R$^2$ is a —S—(C$_1$-C$_2$)alkyl group, and R$^1$ is pyridyl substituted with one substituent.

Embodiment No. 25 is directed to compounds of formula 1.0 wherein R$^2$ is a —S—(C$_1$-C$_2$)alkyl group, and R$^1$ is selected from the group consisting of:

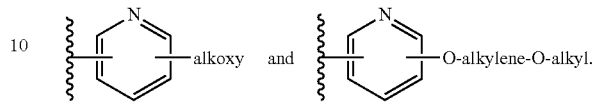

Embodiment No. 26 is directed to compounds of formula 1.0 wherein R$^2$ is a —S—(C$_1$-C$_2$)alkyl group, and R$^1$ is:

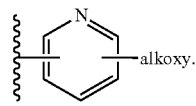

Embodiment No. 27 is directed to compounds of formula 1.0 wherein R$^2$ is a —S—(C$_1$-C$_2$)alkyl group, and R$^1$ is:

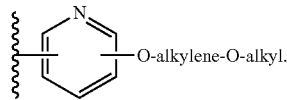

Embodiment No. 28 is directed to compounds of formula 1.0 wherein R$^2$ is a —S—(C$_1$-C$_2$)alkyl group, and R$^1$ is:

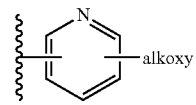

wherein said alkoxy group is —OCH(CH$_3$)$_2$.

Embodiment No. 29 is directed to compounds of formula 1.0 wherein R$^2$ is a —S—(C$_1$-C$_2$)alkyl group, and R$^1$ is:

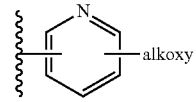

wherein said alkoxy group is —OC$_2$H$_5$.

Embodiment No. 30 is directed to compounds of formula 1.0 wherein R$^2$ is a —S—(C$_1$-C$_2$)alkyl group, and R$^1$ is:

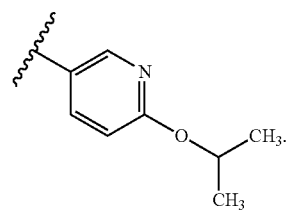 [SMILES: *c1ccc(OC(C)C)nc1]

Embodiment No. 31 is directed to compounds of formula 1.0 wherein R$^2$ is a —S—(C$_1$-C$_2$)alkyl group, and R$^1$ is:

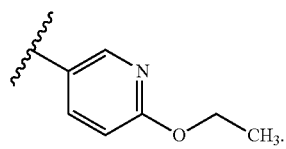

Embodiment No. 32 is directed to compounds of formula 1.0 wherein $R^2$ is a —S—$(C_1$-$C_2)$alkyl group, and $R^1$ is:

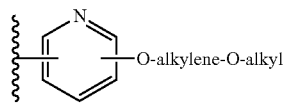

wherein said —O-alkylene-O-alkyl group is —OCH$_2$CH$_2$OCH$_3$.

Embodiment No. 33 is directed to compounds of formula 1.0 wherein $R^2$ is a —S—$(C_1$-$C_2)$alkyl group, and $R^1$ is:

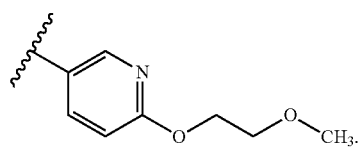 [SMILES: *c1ccc(OCCOC)nc1]

Embodiment No. 34 is directed to compounds of formula 1.0 wherein $R^2$ is —SCH$_3$, and $R^1$ is substituted pyridyl.

Embodiment No. 35 is directed to compounds of formula 1.0 wherein $R^2$ is —SCH$_3$, and $R^1$ is pyridyl substituted with one substituent.

Embodiment No. 36 is directed to compounds of formula 1.0 wherein $R^2$ is —SCH$_3$, and $R^1$ is selected from the group consisting of:

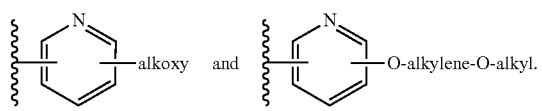

Embodiment No. 37 is directed to compounds of formula 1.0 wherein $R^2$ is —SCH$_3$, and $R^1$ is:

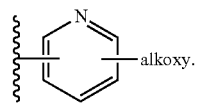

Embodiment No. 38 is directed to compounds of formula 1.0 wherein $R^2$ is —SCH$_3$, and $R^1$ is:

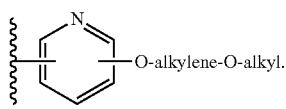

Embodiment No. 39 is directed to compounds of formula 1.0 wherein $R^2$ is —SCH$_3$, and $R^1$ is:

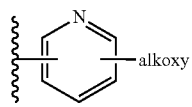

wherein said alkoxy group is —OCH(CH$_3$)$_2$.

Embodiment No. 40 is directed to compounds of formula 1.0 wherein $R^2$ is —SCH$_3$, and $R^1$ is:

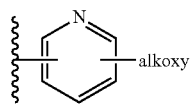

wherein said alkoxy group is —OC$_2$H$_5$.

Embodiment No. 41 is directed to compounds of formula 1.0 wherein $R^2$ is —SCH$_3$, and $R^1$ is:

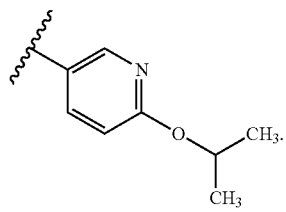 [SMILES: *c1ccc(OC(C)C)nc1]

Embodiment No. 42 is directed to compounds of formula 1.0 wherein $R^2$ is —SCH$_3$, and $R^1$ is:

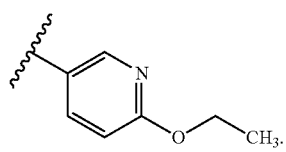

Embodiment No. 43 is directed to compounds of formula 1.0 wherein $R^2$ is —SCH$_3$, and $R^1$ is:

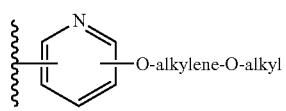

wherein said —O-alkylene-O-alkyl group is —OCH$_2$CH$_2$OCH$_3$.

Embodiment No. 44 is directed to compounds of formula 1.0 wherein $R^2$ is —SCH$_3$, and $R^1$ is:

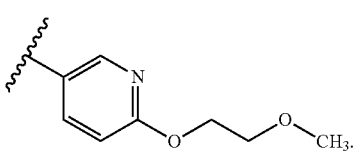 [SMILES: *c1ccc(OCCOC)nc1]

Embodiment No. 45 is directed to compounds of formula 1.0 having the formula 1.1:

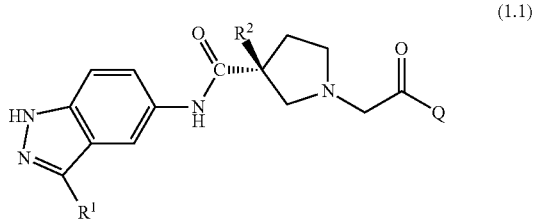

(1.1)

Embodiment No. 46 is directed to any one of Embodiment Numbers 1 to 44 wherein the compound of formula 1.0 is a compound of formula 1.1.

Other embodiments of the invention directed to the $R^5$ substituent are described below. The language "as described in any one of Embodiment Numbers 1 to 46" means that the embodiment being described is applicable to each one of Embodiment Numbers 1 to 46. For example, another embodiment of this invention is directed to compounds described in Embodiment No. 1 wherein $R^5$ is as described in any one of the paragraphs below. In another example, another embodiment of this invention is directed to the compounds described in Embodiment No. 2 wherein $R^5$ is as described in any one of the paragraphs below, etc.

Thus, other embodiments of this invention are directed to compounds of formula 1.0 as described in any one of Embodiment Numbers 1 to 46 wherein $R^5$ is a substituted triazolyl-phenyl- wherein the triazolyl moiety is substituted with one or two alkyl groups selected from the group consisting of: —$C_1$-$C_6$alkyl, —$C_1$-$C_4$alkyl, —$C_1$-$C_2$alkyl, and —$CH_3$.

Other embodiments of this invention are directed to compounds of formula 1.0 as described in any one of Embodiment Numbers 1 to 46 wherein $R^5$ is a substituted triazolyl-phenyl- wherein the triazolyl moiety is substituted with one or two alkyl groups selected from the group consisting of: —$C_1$-$C_4$alkyl, —$C_1$-$C_2$alkyl, and —$CH_3$. Other embodiments of this invention are directed to compounds of formula 1.0 as described in any one of Embodiment Numbers 1 to 46 wherein $R^5$ is a substituted triazolyl-phenyl- wherein the triazolyl moiety is substituted with one or two —$CH_3$ groups.

Other embodiments of this invention are directed to compounds of formula 1.0 as described in any one of Embodiment Numbers 1 to 46 wherein $R^5$ is a substituted triazolyl-phenyl- wherein the triazolyl moiety is substituted on the nitrogen with an alkyl group selected from the group consisting of: —$C_1$-$C_4$alkyl, —$C_1$-$C_2$alkyl, and —$CH_3$. Other embodiments of this invention are directed to compounds of formula 1.0 as described in any one of Embodiment Numbers 1 to 46 wherein $R^5$ is a substituted triazolyl-phenyl- wherein the triazolyl moiety is substituted on the nitrogen with —$CH_3$ group.

Other embodiments of this invention are directed to compounds of formula 1.0 as described in any one of Embodiment Numbers 1 to 46 wherein $R^5$ is a substituted triazolyl-phenyl- wherein the triazolyl moiety is substituted on the nitrogen with an -alkylene-O-alkyl group selected from the group consisting of: —$C_2$-$C_4$alkylene-O—$C_1$-$C_6$alkyl, —$C_2$alkylene-O—$C_1$-$C_2$alkyl, —$C_2$-$C_4$alkylene-O—$CH_3$, and —$CH_2CH_2OCH_3$.

Other embodiments of this invention are directed to compounds of formula 1.0 as described in any one of Embodiment Numbers 1 to 46 wherein $R^5$ is a substituted triazolyl-phenyl- wherein the triazolyl moiety is substituted on the nitrogen with an -alkylene-O-alkyl group selected from the group consisting of: —$C_2$alkylene-O—$C_1$-$C_2$alkyl, and —$CH_2CH_2OCH_3$. Other embodiments of this invention are directed to compounds of formula 1.0 as described in any one of Embodiment Numbers 1 to 46 wherein $R^5$ is a substituted triazolyl-phenyl- wherein the triazolyl moiety is substituted on the nitrogen with —$CH_2CH_2OCH_3$.

Other embodiments of this invention are directed to compounds of formula 1.0 as described in any one of Embodiment Numbers 1 to 46 wherein $R^5$ is a substituted triazolyl-phenyl- wherein the triazolyl moiety is substituted on the nitrogen with a hydroxy substituted alkyl group selected from the group consisting of: hydroxy substituted —$C_1$-$C_4$alkyl, hydroxy substituted —$C_1$-$C_2$alkyl, and hydroxy substituted —$CH_3$.

Other embodiments of this invention are directed to compounds of formula 1.0 as described in any one of Embodiment Numbers 1 to 46 wherein $R^5$ is a substituted triazolyl-phenyl- wherein the triazolyl moiety is substituted on the nitrogen with a hydroxy substituted alkyl group selected from the group consisting of: $CH_2COH(CH_3)_2$, and —$CH_2CH_2OH$.

Other embodiments of this invention are directed to compounds of formula 1.0 as described in any one of Embodiment Numbers 1 to 46 wherein the optional halo substituents for the phenyl moiety of $R^5$ are independently selected from the group consisting of: Cl, F and Br.

Other embodiments of this invention are directed to compounds of formula 1.0 as described in any one of Embodiment Numbers 1 to 46 wherein the optional halo substituents for the phenyl moiety of $R^5$ are F.

Other embodiments of this invention are directed to compounds of formula 1.0 as described in any one of Embodiment Numbers 1 to 46 wherein the optional halo substituent for the phenyl moiety of $R^5$ is one F.

Other embodiments of this invention are directed to compounds of formula 1.0 as described in any one of Embodiment Numbers 1 to 46 wherein $R^5$ is a substituted triazolyl-phenyl- group wherein (a) said triazolyl moiety is optionally substituted on the nitrogen with a substituent selected from the group consisting of: —$CH_2COH(CH_3)_2$ and —$CH_2CH_2OH$, (b) said triazolyl moiety is optionally substituted on the nitrogen with an alkyl group, (c) said triazolyl moiety is optionally substituted on the nitrogen with an alkyl group, and on the carbon with an alkyl group, (d) said triazolyl moiety is optionally substituted on the nitrogen with a —$CH_3$ group, (e) said triazolyl moiety is optionally substituted on the nitrogen with one —$CH_3$ group, and on the carbon with one —$CH_3$ group, (f) said triazolyl moiety is optionally substituted on the carbon with a —$NH_2$ group, or (g) said triazolyl moiety is optionally substituted on the nitrogen with a —$CH_2CH_2OCH_3$ group; and wherein said phenyl moiety is optionally substituted with halo (e.g., one halo, such as for example, F).

Other embodiments of this invention are directed to compounds of formula 1.0 as described in any one of Embodiment Numbers 1 to 46 wherein $R^5$ is a substituted triazolyl-phenyl- group wherein (a) said triazolyl moiety is optionally substituted on the nitrogen with a substituent selected from the group consisting of: —$CH_2COH(CH_3)_2$ and —$CH_2CH_2OH$, (b) said triazolyl moiety is optionally substituted on the nitrogen with an alkyl group, (c) said triazolyl moiety is optionally substituted on the nitrogen with an alkyl group, and on the carbon with an alkyl group, (d) said triazolyl moiety is optionally substituted on the nitrogen with a —$CH_3$ group, (e) said triazolyl moiety is optionally substituted on the nitrogen with one —$CH_3$ group, and on the carbon with one —$CH_3$ group, (f) said triazolyl moiety is optionally substituted on the carbon with a —$NH_2$ group, or (g) said triazolyl moiety is optionally substituted on the nitrogen with a —CH₂CH₂OCH₃ group; and wherein said phenyl moiety is substituted with halo (e.g., one halo, such as for example, F).

Other embodiments of this invention are directed to compounds of formula 1.0 as described in any one of Embodiment Numbers 1 to 46 wherein $R^5$ is a substituted triazolyl-phenyl-group wherein (a) said triazolyl moiety is substituted on the nitrogen with a substituent selected from the group consisting of: —CH₂COH(CH₃)₂ and —CH₂CH₂OH, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —CH₃ group, (e) said triazolyl moiety is substituted on the nitrogen with one —CH₃ group, and on the carbon with one —CH₃ group, (f) said triazolyl moiety is substituted on the carbon with a —NH₂ group, or (g) said triazolyl moiety is substituted on the nitrogen with a—CH₂CH₂OCH₃ group; and wherein said phenyl moiety is optionally substituted with halo (e.g., one halo, such as for example, F).

Other embodiments of this invention are directed to compounds of formula 1.0 as described in any one of Embodiment Numbers 1 to 46 wherein $R^5$ is a substituted triazolyl-phenyl-group wherein (a) said triazolyl moiety is substituted on the nitrogen with a substituent selected from the group consisting of: —CH₂COH(CH₃)₂ and —CH₂CH₂OH, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —CH₃ group, (e) said triazolyl moiety is substituted on the nitrogen with one —CH₃ group, and on the carbon with one —CH₃ group, (f) said triazolyl moiety is substituted on the carbon with a —NH₂ group, or (g) said triazolyl moiety is substituted on the nitrogen with a —CH₂CH₂OCH₃ group; and wherein said phenyl moiety is substituted with halo (e.g., one halo, such as for example, F).

Other embodiments of this invention are directed to compounds of formula 1.0 as described in any one of Embodiment Numbers 1 to 46 wherein the optional substituents for the phenyl moiety of $R^5$ are independently selected from the group consisting of: alkoxy.

Other embodiments of this invention are directed to compounds of formula 1.0 as described in any one of Embodiment Numbers 1 to 46 wherein the optional substituents for the phenyl moiety of $R^5$ are —OCH₃.

Other embodiments of this invention are directed to compounds of formula 1.0 as described in any one of Embodiment Numbers 1 to 46 wherein the optional substituent for the phenyl moiety of $R^5$ is one —OCH₃.

Other embodiments of this invention are directed to compounds of formula 1.0 as described in any one of Embodiment Numbers 1 to 46 wherein $R^5$ is a substituted triazolyl-phenyl-group wherein (a) said triazolyl moiety is optionally substituted on the nitrogen with a substituent selected from the group consisting of: —CH₂COH(CH₃)₂, and —CH₂CH₂OH, (b) said triazolyl moiety is optionally substituted on the nitrogen with an alkyl group, (c) said triazolyl moiety is optionally substituted on the nitrogen with an alkyl group, and on the carbon with an alkyl group, (d) said triazolyl moiety is optionally substituted on the nitrogen with a —CH₃ group, (e) said triazolyl moiety is optionally substituted on the nitrogen with one —CH₃ group, and on the carbon with one —CH₃ group, (f) said triazolyl moiety is optionally substituted on the carbon with a —NH₂ group, or (g) said triazolyl moiety is optionally substituted on the nitrogen with a —CH₂CH₂OCH₃ group; and wherein said phenyl moiety is optionally substituted with alkoxy (e.g., one —OCH₃).

Other embodiments of this invention are directed to compounds of formula 1.0 as described in any one of Embodiment Numbers 1 to 46 wherein $R^5$ is a substituted triazolyl-phenyl-group wherein (a) said triazolyl moiety is optionally substituted on the nitrogen with a substituent selected from the group consisting of: —CH₂COH(CH₃)₂, and —CH₂CH₂OH, (b) said triazolyl moiety is optionally substituted on the nitrogen with an alkyl group, (c) said triazolyl moiety is optionally substituted on the nitrogen with an alkyl group, and on the carbon with an alkyl group, (d) said triazolyl moiety is optionally substituted on the nitrogen with a —CH₃ group, (e) said triazolyl moiety is optionally substituted on the nitrogen with one —CH₃ group, and on the carbon with one —CH₃ group, (f) said triazolyl moiety is optionally substituted on the carbon with a —NH₂ group, or (g) said triazolyl moiety is optionally substituted on the nitrogen with a —CH₂CH₂OCH₃ group; and wherein said phenyl moiety is substituted with alkoxy (e.g., one —OCH₃).

Other embodiments of this invention are directed to compounds of formula 1.0 as described in any one of Embodiment Numbers 1 to 46 wherein $R^5$ is a substituted triazolyl-phenyl-group wherein (a) said triazolyl moiety is substituted on the nitrogen with a substituent selected from the group consisting of: —CH₂COH(CH₃)₂, and —CH₂CH₂OH, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —CH₃ group, (e) said triazolyl moiety is substituted on the nitrogen with one —CH₃ group, and on the carbon with one —CH₃ group, (f) said triazolyl moiety is substituted on the carbon with a —NH₂ group, or (g) said triazolyl moiety is substituted on the nitrogen with a—CH₂CH₂OCH₃ group; and wherein said phenyl moiety is optionally substituted with alkoxy (e.g., one —OCH₃).

Other embodiments of this invention are directed to compounds of formula 1.0 as described in any one of Embodiment Numbers 1 to 46 wherein $R^5$ is a substituted triazolyl-phenyl-group wherein (a) said triazolyl moiety is substituted on the nitrogen with a substituent selected from the group consisting of: —CH₂COH(CH₃)₂, and —CH₂CH₂OH, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —CH₃ group, (e) said triazolyl moiety is substituted on the nitrogen with one —CH₃ group, and on the carbon with one —CH₃ group, (f) said triazolyl moiety is substituted on the carbon with a —NH₂ group, or (g) said triazolyl moiety is substituted on the nitrogen with a —CH$_2$CH$_2$OCH$_3$ group; and wherein said phenyl moiety is unsubstituted.

Other embodiments of this invention are directed to compounds of formula 1.0 as described in any one of Embodiment Numbers 1 to 46 wherein said substituted R$^5$ moiety is a substituted triazolyl-phenyl group wherein said triazolyl moiety is substituted with: (a) one substituent selected from the group consisting of: —CH$_2$COH(CH$_3$)$_2$, and —CH$_2$CH$_2$OH, (b) one alkyl group, (c) two alkyl groups, (d) one —CH$_3$ group, (e) two —CH$_3$ groups, (f) one —NH$_2$ group, or (g) one —CH$_2$CH$_2$OCH$_3$ group.

Other embodiments of this invention are directed to compounds of formula 1.0 as described in any one of Embodiment Numbers 1 to 46 wherein R$^5$ is a substituted triazolyl-thienyl- wherein the triazolyl moiety is substituted with one or two alkyl groups selected from the group consisting of: —C$_1$-C$_6$alkyl, —C$_1$-C$_4$alkyl, —C$_1$-C$_2$alkyl, and —CH$_3$.

Other embodiments of this invention are directed to compounds of formula 1.0 as described in any one of Embodiment Numbers 1 to 46 wherein R$^5$ is a substituted triazolyl-thienyl- wherein the triazolyl moiety is substituted with one or two alkyl groups selected from the group consisting of: —C$_1$-C$_4$alkyl, —C$_1$-C$_2$alkyl, and —CH$_3$. Other embodiments of this invention are directed to compounds of formula 1.0 as described in any one of Embodiment Numbers 1 to 46 wherein R$^5$ is a substituted triazolyl-thienyl- wherein the triazolyl moiety is substituted with one or two —CH$_3$ groups.

Other embodiments of this invention are directed to compounds of formula 1.0 as described in any one of Embodiment Numbers 1 to 46 wherein R$^5$ is a substituted triazolyl-thienyl- wherein the triazolyl moiety is substituted on the nitrogen with an alkyl group selected from the group consisting of: —C$_1$-C$_4$alkyl, —C$_1$-C$_2$alkyl, and —CH$_3$. Other embodiments of this invention are directed to compounds of formula 1.0 as described in any one of Embodiment Numbers 1 to 46 wherein R$^5$ is a substituted triazolyl-thienyl- wherein the triazolyl moiety is substituted on the nitrogen with —CH$_3$.

Other embodiments of this invention are directed to compounds of formula 1.0 as described in any one of Embodiment Numbers 1 to 46 wherein R$^5$ is a substituted triazolyl-thienyl- wherein the triazolyl moiety is substituted on the nitrogen with an -alkylene-O-alkyl group selected from the group consisting of: —C$_2$-C$_4$alkylene-O—C$_1$-C$_6$alkyl, —C$_2$alkylene-O—C$_1$-C$_2$alkyl, —C$_2$-C$_4$alkylene-O—CH$_3$, and —CH$_2$CH$_2$OCH$_3$.

Other embodiments of this invention are directed to compounds of formula 1.0 as described in any one of Embodiment Numbers 1 to 46 wherein R$^5$ is a substituted triazolyl-thienyl- wherein the triazolyl moiety is substituted on the nitrogen with an -alkylene-O-alkyl group selected from the group consisting of: —C$_2$alkylene-O—C$_1$-C$_2$alkyl, and —CH$_2$CH$_2$OCH$_3$. Other embodiments of this invention are directed to compounds of formula 1.0 as described in any one of Embodiment Numbers 1 to 46 wherein R$^5$ is a substituted triazolyl-thienyl- wherein the triazolyl moiety is substituted on the nitrogen with —CH$_2$CH$_2$OCH$_3$.

Other embodiments of this invention are directed to compounds of formula 1.0 as described in any one of Embodiment Numbers 1 to 46 wherein R$^5$ is a substituted triazolyl-thienyl- wherein the triazolyl moiety is substituted on the nitrogen with a hydroxy substituted alkyl group selected from the group consisting of: hydroxy substituted —C$_1$-C$_4$alkyl, hydroxy substituted —C$_1$-C$_2$alkyl, and hydroxy substituted —CH$_3$.

Other embodiments of this invention are directed to compounds of formula 1.0 as described in any one of Embodiment Numbers 1 to 46 wherein R$^5$ is a substituted triazolyl-thienyl- wherein the triazolyl moiety is substituted on the nitrogen with a hydroxy substituted alkyl group selected from the group consisting of: CH$_2$COH(CH$_3$)$_2$, and —CH$_2$CH$_2$OH.

Other embodiments of this invention are directed to compounds of formula 1.0 as described in any one of Embodiment Numbers 1 to 46 wherein the optional halo substituents for the thienyl moiety of R$^5$ are independently selected from the group consisting of: Cl, F and Br.

Other embodiments of this invention are directed to compounds of formula 1.0 as described in any one of Embodiment Numbers 1 to 46 wherein the optional halo substituents for the thienyl moiety of R$^5$ are F.

Other embodiments of this invention are directed to compounds of formula 1.0 as described in any one of Embodiment Numbers 1 to 46 wherein the optional halo substituent for the thienyl moiety of R$^5$ is one F.

Other embodiments of this invention are directed to compounds of formula 1.0 as described in any one of Embodiment Numbers 1 to 46 wherein R$^5$ is a substituted triazolyl-thienyl- group wherein (a) said triazolyl moiety is optionally substituted on the nitrogen with a substituent selected from the group consisting of: —CH$_2$COH(CH$_3$)$_2$, and —CH$_2$CH$_2$OH, (b) said triazolyl moiety is optionally substituted on the nitrogen with an alkyl group, (c) said triazolyl moiety is optionally substituted on the nitrogen with an alkyl group, and on the carbon with an alkyl group, (d) said triazolyl moiety is optionally substituted on the nitrogen with a —CH$_3$ group, (e) said triazolyl moiety is optionally substituted on the nitrogen with one —CH$_3$ group, and on the carbon with one —CH$_3$ group, (f) said triazolyl moiety is optionally substituted on the carbon with a —NH$_2$ group, or (g) said triazolyl moiety is optionally substituted on the nitrogen with a —CH$_2$CH$_2$OCH$_3$ group; and wherein said thienyl moiety is optionally substituted with halo (e.g., one halo, such as for example, F).

Other embodiments of this invention are directed to compounds of formula 1.0 as described in any one of Embodiment Numbers 1 to 46 wherein R$^5$ is a substituted triazolyl-thienyl- group wherein (a) said triazolyl moiety is optionally substituted on the nitrogen with a substituent selected from the group consisting of: —CH$_2$COH(CH$_3$)$_2$, —CH$_2$CH$_2$OH, (b) said triazolyl moiety is optionally substituted on the nitrogen with an alkyl group, (c) said triazolyl moiety is optionally substituted on the nitrogen with an alkyl group, and on the carbon with an alkyl group, (d) said triazolyl moiety is optionally substituted on the nitrogen with a —CH$_3$ group, (e) said triazolyl moiety is optionally substituted on the nitrogen with one —CH$_3$ group, and on the carbon with one —CH$_3$ group, (f) said triazolyl moiety is optionally substituted on the carbon with a —NH$_2$ group, or (g) said triazolyl moiety is optionally substituted on the nitrogen with a —CH$_2$CH$_2$OCH$_3$ group; and wherein said thienyl moiety is substituted with halo (e.g., one halo, such as for example, F).

Other embodiments of this invention are directed to compounds of formula 1.0 as described in any one of Embodiment Numbers 1 to 46 wherein R$^5$ is a substituted triazolyl-thienyl- group wherein (a) said triazolyl moiety is substituted on the nitrogen with a substituent selected from the group consisting of: —CH$_2$COH(CH$_3$)$_2$, and —CH$_2$CH$_2$OH, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —CH$_3$ group, (e) said triazolyl moiety is substituted on the nitrogen with one —CH$_3$ group, and on the carbon with one —CH$_3$ group, (f) said triazolyl moiety is substituted on the carbon with a —NH$_2$ group, or (g) said triazolyl moiety is substituted on the nitrogen with a —$CH_2CH_2OCH_3$ group; and wherein said thienyl moiety is optionally substituted with halo (e.g., one halo, such as for example, F).

Other embodiments of this invention are directed to compounds of formula 1.0 as described in any one of Embodiment Numbers 1 to 46 wherein $R^5$ is a substituted triazolyl-thienyl-group wherein (a) said triazolyl moiety is substituted on the nitrogen with a substituent selected from the group consisting of: —$CH_2COH(CH_3)_2$, and —$CH_2CH_2OH$, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —$CH_3$ group, (e) said triazolyl moiety is substituted on the nitrogen with one —$CH_3$ group, and on the carbon with one —$CH_3$ group, (f) said triazolyl moiety is substituted on the carbon with a —$NH_2$ group, or (g) said triazolyl moiety is substituted on the nitrogen with a—$CH_2CH_2OCH_3$ group; and wherein said thienyl moiety is substituted with halo (e.g., one halo, such as for example, F).

Other embodiments of this invention are directed to compounds of formula 1.0 as described in any one of Embodiment Numbers 1 to 46 wherein $R^5$ is a substituted triazolyl-thienyl-group wherein (a) said triazolyl moiety is substituted on the nitrogen with a substituent selected from the group consisting of: —$CH_2COH(CH_3)_2$, and —$CH_2CH_2OH$, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —$CH_3$ group, (e) said triazolyl moiety is substituted on the nitrogen with one —$CH_3$ group, and on the carbon with one —$CH_3$ group, (f) said triazolyl moiety is substituted on the carbon with a —$NH_2$ group, or (g) said triazolyl moiety is substituted on the nitrogen with a—$CH_2CH_2OCH_3$ group; and wherein said thienyl moiety is unsubstituted.

Other embodiments of this invention are directed to compounds of formula 1.0 as described in any one of Embodiment Numbers 1 to 46 wherein said substituted $R^5$ moiety is a substituted triazolyl-thienyl group wherein said triazolyl moiety is substituted with: (a) one substituent selected from the group consisting of: —$CH_2COH(CH_3)_2$, and —$CH_2CH_2OH$, (b) one alkyl group, (c) two alkyl groups, (d) one —$CH_3$ group, (e) two —$CH_3$ groups, (f) one —$NH_2$ group, or (g) one —$CH_2CH_2OCH_3$ group.

Other embodiments of this invention are directed to compounds of formula 1.0 as described in any one of Embodiment Numbers 1 to 46 wherein the optional substituents for the thienyl moiety of $R^5$ are independently selected from the group consisting of: alkoxy.

Other embodiments of this invention are directed to compounds of formula 1.0 as described in any one of Embodiment Numbers 1 to 46 wherein the optional substituents for the thienyl moiety of $R^5$ are —$OCH_3$.

Other embodiments of this invention are directed to compounds of formula 1.0 as described in any one of Embodiment Numbers 1 to 46 wherein the optional substituent for the thienyl moiety of $R^5$ is one —$OCH_3$.

Other embodiments of this invention are directed to compounds of formula 1.0 as described in any one of Embodiment Numbers 1 to 46 wherein $R^5$ is a substituted triazolyl-thienyl-group wherein (a) said triazolyl moiety is optionally substituted on the nitrogen with a substituent selected from the group consisting of: —$CH_2COH(CH_3)_2$, and —$CH_2CH_2OH$, (b) said triazolyl moiety is optionally substituted on the nitrogen with an alkyl group, (c) said triazolyl moiety is optionally substituted on the nitrogen with an alkyl group, and on the carbon with an alkyl group, (d) said triazolyl moiety is optionally substituted on the nitrogen with a —$CH_3$ group, (e) said triazolyl moiety is optionally substituted on the nitrogen with one —$CH_3$ group, and on the carbon with one —$CH_3$ group, (f) said triazolyl moiety is optionally substituted on the carbon with a —$NH_2$ group, or (g) said triazolyl moiety is optionally substituted on the nitrogen with a —$CH_2CH_2OCH_3$ group; and wherein said thienyl moiety is optionally substituted with alkoxy (e.g., one —$OCH_3$).

Other embodiments of this invention are directed to compounds of formula 1.0 as described in any one of Embodiment Numbers 1 to 46 wherein $R^5$ is a substituted triazolyl-thienyl-group wherein (a) said triazolyl moiety is optionally substituted on the nitrogen with a substituent selected from the group consisting of: —$CH_2COH(CH_3)_2$, and —$CH_2CH_2OH$, (b) said triazolyl moiety is optionally substituted on the nitrogen with an alkyl group, (c) said triazolyl moiety is optionally substituted on the nitrogen with an alkyl group, and on the carbon with an alkyl group, (d) said triazolyl moiety is optionally substituted on the nitrogen with a —$CH_3$ group, (e) said triazolyl moiety is optionally substituted on the nitrogen with one —$CH_3$ group, and on the carbon with one —$CH_3$ group, (f) said triazolyl moiety is optionally substituted on the carbon with a —$NH_2$ group, or (g) said triazolyl moiety is optionally substituted on the nitrogen with a —$CH_2CH_2OCH_3$ group; and wherein said thienyl moiety is substituted with alkoxy (e.g., one —$OCH_3$).

Other embodiments of this invention are directed to compounds of formula 1.0 as described in any one of Embodiment Numbers 1 to 46 wherein $R^5$ is a substituted triazolyl-thienyl-group wherein (a) said triazolyl moiety is substituted on the nitrogen with a substituent selected from the group consisting of: —$CH_2COH(CH_3)_2$, and —$CH_2CH_2OH$, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —$CH_3$ group, (e) said triazolyl moiety is substituted on the nitrogen with one —$CH_3$ group, and on the carbon with one —$CH_3$ group, (f) said triazolyl moiety is substituted on the carbon with a —$NH_2$ group, or (g) said triazolyl moiety is substituted on the nitrogen with a—$CH_2CH_2OCH_3$ group; and wherein said thienyl moiety is optionally substituted with alkoxy (e.g., one —$OCH_3$).

Other embodiments of this invention are directed to compounds of formula 1.0 as described in any one of Embodiment Numbers 1 to 46 wherein $R^5$ is a substituted triazolyl-thienyl-group wherein (a) said triazolyl moiety is substituted on the nitrogen with a substituent selected from the group consisting of: —$CH_2COH(CH_3)_2$, and —$CH_2CH_2OH$, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —$CH_3$ group, (e) said triazolyl moiety is substituted on the nitrogen with one —$CH_3$ group, and on the carbon with one —$CH_3$ group, (f) said triazolyl moiety is substituted on the carbon with a —$NH_2$ group, or (g) said triazolyl moiety is substituted on the nitrogen with a—$CH_2CH_2OCH_3$ group; and wherein said thienyl moiety is substituted with alkoxy (e.g., one —$OCH_3$).

Other embodiments of this invention are directed to compounds of formula 1.0 as described in any one of Embodiment Numbers 1 to 46 wherein $R^5$ is a substituted triazolyl-pyridyl-wherein the triazolyl moiety is substituted with one or two alkyl groups selected from the group consisting of: —$C_1$-$C_6$alkyl, —$C_1$-$C_4$alkyl, —$C_1$-$C_2$alkyl, and —$CH_3$.

Other embodiments of this invention are directed to compounds of formula 1.0 as described in any one of Embodiment Numbers 1 to 46 wherein $R^5$ is a substituted triazolyl-pyridyl- wherein the triazolyl moiety is substituted with one or two alkyl groups selected from the group consisting of: —$C_1$-$C_4$alkyl, —$C_1$-$C_2$alkyl, and —$CH_3$. Other embodiments of this invention are directed to compounds of formula 1.0 as described in any one of Embodiment Numbers 1 to 46 wherein $R^5$ is a substituted triazolyl-pyridyl- wherein the triazolyl moiety is substituted with one or two —$CH_3$ groups.

Other embodiments of this invention are directed to compounds of formula 1.0 as described in any one of Embodiment Numbers 1 to 46 wherein $R^5$ is a substituted triazolyl-pyridyl- wherein the triazolyl moiety is substituted on the nitrogen with an alkyl group selected from the group consisting of: —$C_1$-$C_4$alkyl, —$C_1$-$C_2$alkyl, and —$CH_3$. Other embodiments of this invention are directed to compounds of formula 1.0 as described in any one of Embodiment Numbers 1 to 46 wherein $R^5$ is a substituted triazolyl-pyridyl- wherein the triazolyl moiety is substituted on the nitrogen with —$CH_3$.

Other embodiments of this invention are directed to compounds of formula 1.0 as described in any one of Embodiment Numbers 1 to 46 wherein $R^5$ is a substituted triazolyl-pyridyl- wherein the triazolyl moiety is substituted on the nitrogen with an -alkylene-O-alkyl group selected from the group consisting of: —$C_2$-$C_4$alkylene-O—$C_1$-$C_6$alkyl, —$C_2$alkylene-O—$C_1$-$C_2$alkyl, —$C_2$-$C_4$alkylene-O—$CH_3$, and —$CH_2CH_2OCH_3$.

Other embodiments of this invention are directed to compounds of formula 1.0 as described in any one of Embodiment Numbers 1 to 46 wherein $R^5$ is a substituted triazolyl-pyridyl- wherein the triazolyl moiety is substituted on the nitrogen with an -alkylene-O-alkyl group selected from the group consisting of: —$C_2$alkylene-O—$C_1$-$C_2$alkyl, and —$CH_2CH_2OCH_3$. Other embodiments of this invention are directed to compounds of formula 1.0 as described in any one of Embodiment Numbers 1 to 46 wherein $R^5$ is a substituted triazolyl-pyridyl- wherein the triazolyl moiety is substituted on the nitrogen with —$CH_2CH_2OCH_3$.

Other embodiments of this invention are directed to compounds of formula 1.0 as described in any one of Embodiment Numbers 1 to 46 wherein $R^5$ is a substituted triazolyl-pyridyl- wherein the triazolyl moiety is substituted on the nitrogen with a hydroxy substituted alkyl group selected from the group consisting of: hydroxy substituted —$C_1$-$C_4$alkyl, hydroxy substituted —$C_1$-$C_2$alkyl, and hydroxy substituted —$CH_3$.

Other embodiments of this invention are directed to compounds of formula 1.0 as described in any one of Embodiment Numbers 1 to 46 wherein $R^5$ is a substituted triazolyl-pyridyl- wherein the triazolyl moiety is substituted on the nitrogen with a hydroxy substituted alkyl group selected from the group consisting of: $CH_2COH(CH_3)_2$, and —$CH_2CH_2OH$.

Other embodiments of this invention are directed to compounds of formula 1.0 as described in any one of Embodiment Numbers 1 to 46 wherein $R^5$ is a substituted triazolyl-pyridyl-group wherein (a) said triazolyl moiety is optionally substituted on the nitrogen with a substituent selected from the group consisting of: —$CH_2COH(CH_3)_2$, and —$CH_2CH_2OH$, (b) said triazolyl moiety is optionally substituted on the nitrogen with an alkyl group, (c) said triazolyl moiety is optionally substituted on the nitrogen with an alkyl group, and on the carbon with an alkyl group, (d) said triazolyl moiety is optionally substituted on the nitrogen with a —$CH_3$ group, (e) said triazolyl moiety is optionally substituted on the nitrogen with one —$CH_3$ group, and on the carbon with one —$CH_3$ group, (f) said triazolyl moiety is optionally substituted on the carbon with a —$NH_2$ group, or (g) said triazolyl moiety is optionally substituted on the nitrogen with a —$CH_2CH_2OCH_3$ group; and wherein said pyridyl moiety is unsubstitued.

Other embodiments of this invention are directed to compounds of formula 1.0 as described in any one of Embodiment Numbers 1 to 46 wherein $R^5$ is a substituted triazolyl-pyridyl-group wherein (a) said triazolyl moiety is substituted on the nitrogen with a substituent selected from the group consisting of: —$CH_2COH(CH_3)_2$, and —$CH_2CH_2OH$, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —$CH_3$ group, (e) said triazolyl moiety is substituted on the nitrogen with one —$CH_3$ group, and on the carbon with one —$CH_3$ group, (f) said triazolyl moiety is substituted on the carbon with a —$NH_2$ group, or (g) said triazolyl moiety is substituted on the nitrogen with a—$CH_2CH_2OCH_3$ group; and wherein said pyridyl moiety is unsubstitued.

Other embodiments of this invention are directed to compounds of formula 1.0 as described in any one of Embodiment Numbers 1 to 46 wherein $R^5$ is a substituted triazolyl-thiazolyl- wherein the triazolyl moiety is substituted with one or two alkyl groups selected from the group consisting of: —$C_1$-$C_6$alkyl, —$C_1$-$C_4$alkyl, —$C_1$-$C_2$alkyl, and —$CH_3$.

Other embodiments of this invention are directed to compounds of formula 1.0 as described in any one of Embodiment Numbers 1 to 46 wherein $R^5$ is a substituted triazolyl-thiazolyl- wherein the triazolyl moiety is substituted with one or two alkyl groups selected from the group consisting of: —$C_1$-$C_4$alkyl, —$C_1$-$C_2$alkyl, and —$CH_3$. Other embodiments of this invention are directed to compounds of formula 1.0 as described in any one of Embodiment Numbers 1 to 46 wherein $R^5$ is a substituted triazolyl-thiazolyl- wherein the triazolyl moiety is substituted with one or two —$CH_3$ groups.

Other embodiments of this invention are directed to compounds of formula 1.0 as described in any one of Embodiment Numbers 1 to 46 wherein $R^5$ is a substituted triazolyl-thiazolyl- wherein the triazolyl moiety is substituted on the nitrogen with an alkyl group selected from the group consisting of: —$C_1$-$C_4$alkyl, —$C_1$-$C_2$alkyl, and —$CH_3$. Other embodiments of this invention are directed to compounds of formula 1.0 as described in any one of Embodiment Numbers 1 to 46 wherein $R^5$ is a substituted triazolyl-thiazolyl- wherein the triazolyl moiety is substituted on the nitrogen with —$CH_3$.

Other embodiments of this invention are directed to compounds of formula 1.0 as described in any one of Embodiment Numbers 1 to 46 wherein $R^5$ is a substituted triazolyl-thiazolyl- wherein the triazolyl moiety is substituted on the nitrogen with an -alkylene-O-alkyl group selected from the group consisting of: —$C_2$-$C_4$alkylene-O—$C_1$-$C_6$alkyl, —$C_2$alkylene-O—$C_1$-$C_2$alkyl, —$C_2$-$C_4$alkylene-O—$CH_3$, and —$CH_2CH_2OCH_3$.

Other embodiments of this invention are directed to compounds of formula 1.0 as described in any one of Embodiment Numbers 1 to 46 wherein $R^5$ is a substituted triazolyl-thiazolyl- wherein the triazolyl moiety is substituted on the nitrogen with an -alkylene-O-alkyl group selected from the group consisting of: —$C_2$alkylene-O—$C_1$-$C_2$alkyl, and —$CH_2CH_2OCH_3$. Other embodiments of this invention are directed to compounds of formula 1.0 as described in any one of Embodiment Numbers 1 to 46 wherein $R^5$ is a substituted triazolyl-thiazolyl- wherein the triazolyl moiety is substituted on the nitrogen with —$CH_2CH_2OCH_3$.

Other embodiments of this invention are directed to compounds of formula 1.0 as described in any one of Embodiment Numbers 1 to 46 wherein $R^5$ is a substituted triazolyl-thiazolyl- wherein the triazolyl moiety is substituted on the nitrogen with a hydroxy substituted alkyl group selected from the group consisting of: hydroxy substituted —$C_1$-$C_4$alkyl, hydroxy substituted —$C_1$-$C_2$alkyl, and hydroxy substituted —$CH_3$.

Other embodiments of this invention are directed to compounds of formula 1.0 as described in any one of Embodiment Numbers 1 to 46 wherein $R^5$ is a substituted triazolyl-thiazolyl- wherein the triazolyl moiety is substituted on the nitrogen with a hydroxy substituted alkyl group selected from the group consisting of: $CH_2COH(CH_3)_2$, and —$CH_2CH_2OH$.

Other embodiments of this invention are directed to compounds of formula 1.0 as described in any one of Embodiment Numbers 1 to 46 wherein $R^5$ is a substituted triazolyl-thiazolyl- group wherein (a) said triazolyl moiety is optionally substituted on the nitrogen with a substituent selected from the group consisting of: —$CH_2COH(CH_3)_2$, and —$CH_2CH_2OH$, (b) said triazolyl moiety is optionally substituted on the nitrogen with an alkyl group, (c) said triazolyl moiety is optionally substituted on the nitrogen with an alkyl group, and on the carbon with an alkyl group, (d) said triazolyl moiety is optionally substituted on the nitrogen with a —$CH_3$ group, (e) said triazolyl moiety is optionally substituted on the nitrogen with one —$CH_3$ group, and on the carbon with one —$CH_3$ group, (f) said triazolyl moiety is optionally substituted on the carbon with a —$NH_2$ group, or (g) said triazolyl moiety is optionally substituted on the nitrogen with a —$CH_2CH_2OCH_3$ group; and wherein said thiazolyl moiety is unsubstitued.

Other embodiments of this invention are directed to compounds of formula 1.0 as described in any one of Embodiment Numbers 1 to 46 wherein $R^5$ is a substituted triazolyl-thiazolyl- group wherein (a) said triazolyl moiety is substituted on the nitrogen with a substituent selected from the group consisting of: —$CH_2COH(CH_3)_2$, and —$CH_2CH_2OH$, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —$CH_3$ group, (e) said triazolyl moiety is substituted on the nitrogen with one —$CH_3$ group, and on the carbon with one —$CH_3$ group, (f) said triazolyl moiety is substituted on the carbon with a —$NH_2$ group, or (g) said triazolyl moiety is substituted on the nitrogen with a—$CH_2CH_2OCH_3$ group; and wherein said thiazolyl moiety is unsubstitued.

Other embodiments of this invention are directed to compounds of formula 1.0 as described in any one of Embodiment Numbers 1 to 46 wherein $R^5$ is a substituted pyradizinyl-thienyl- wherein the pyridazinyl moiety is substituted with 1 or 2 groups independently selected from the group consisting of alkyl (e.g., methyl) and =O, and said thienyl moiety is unsubstituted.

Other embodiments of this invention are directed to compounds of formula 1.0 as described in any one of Embodiment Numbers 1 to 46 wherein $R^5$ is a substituted pyradizinyl-thienyl- wherein the pyridazinyl moiety is substituted with an =O moiety, or said pyridazinyl group is substituted with an alkyl (e.g., methyl), or said pyridazinyl is substituted with an =O moiety and an alkyl (e.g., methyl), and said thienyl moiety is unsubstituted.

Other embodiments of this invention are directed to compounds of formula 1.0 as described in any one of Embodiment Numbers 1 to 46 wherein $R^5$ is selected from the group consisting of:

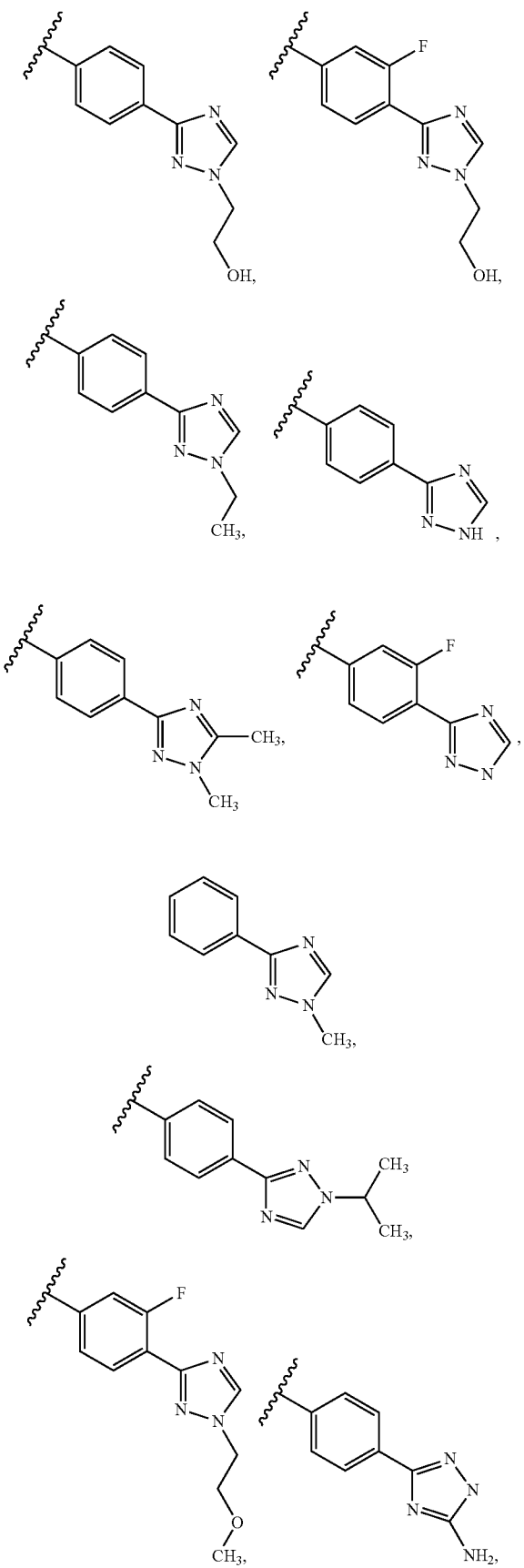

-continued
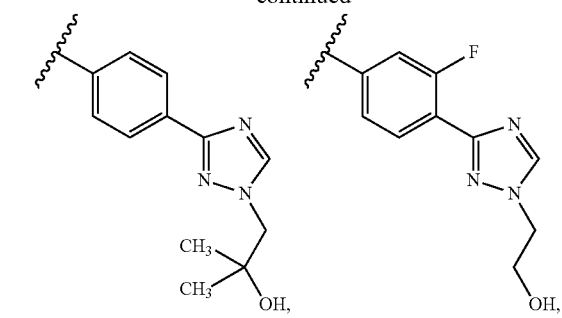
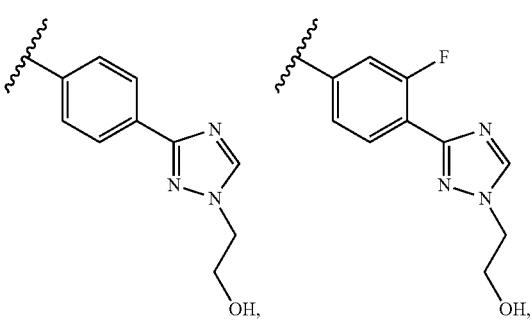
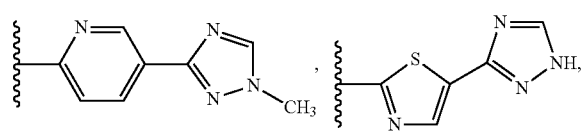
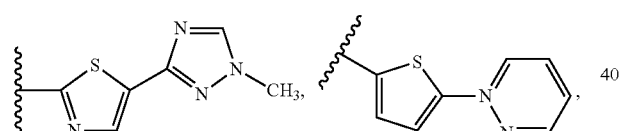
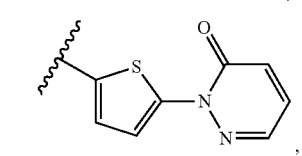, 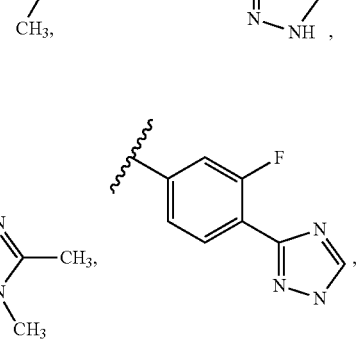
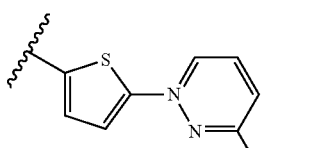
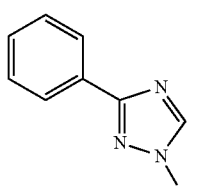
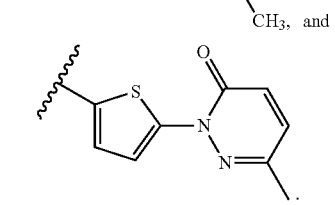
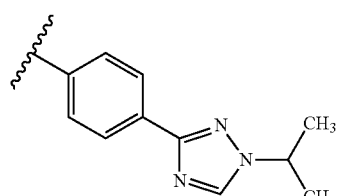
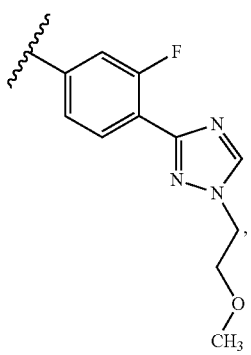
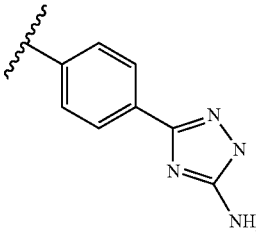
Other embodiments of this invention are directed to compounds of formula 1.0 as described in any one of Embodiment Numbers 1 to 46 wherein $R^5$ is selected from the group consisting of:

-continued
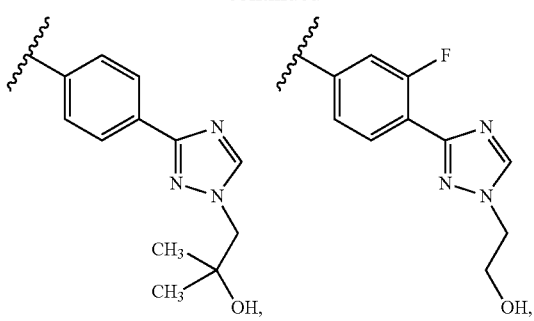
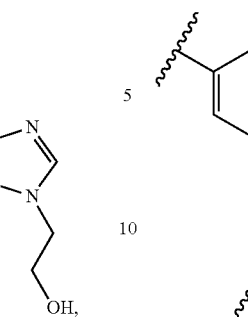
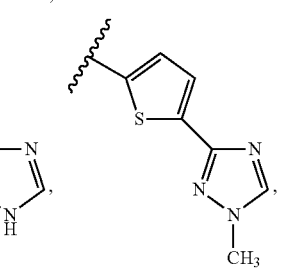
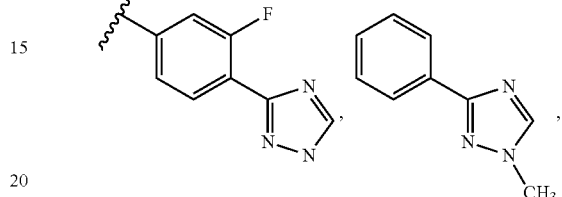
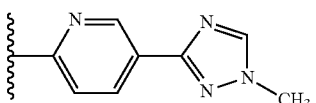
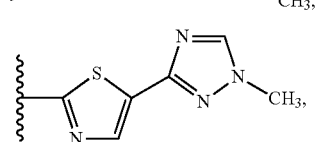
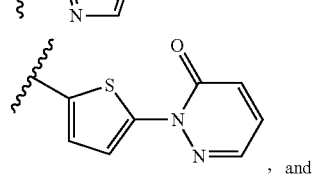
, and
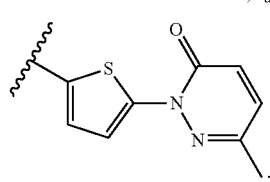
Other embodiments of this invention are directed to compounds of formula 1.0 as described in any one of Embodiment Numbers 1 to 46 wherein $R^5$ is selected from the group consisting of:
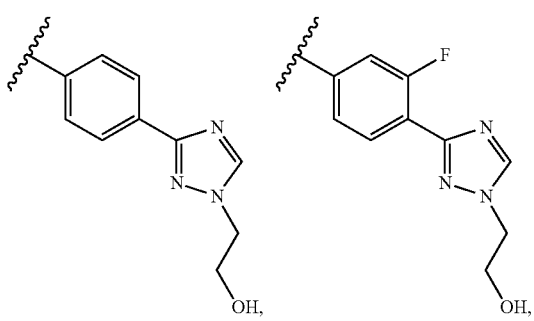
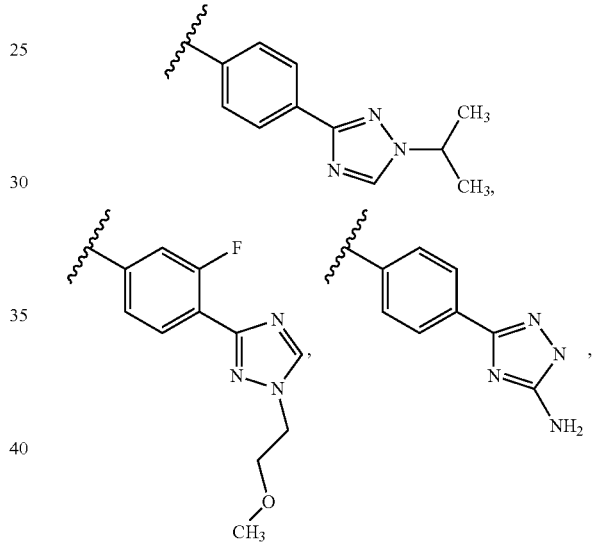
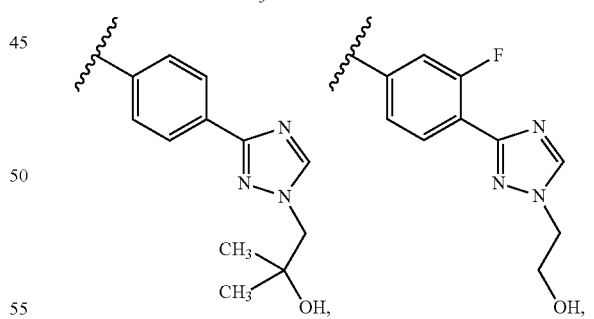
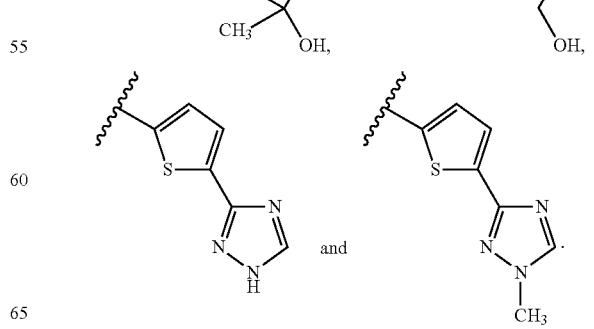

Other embodiments of this invention are directed to compounds of formula 1.0 as described in any one of Embodiment Numbers 1 to 46 wherein $R^5$ is selected from the group consisting of:

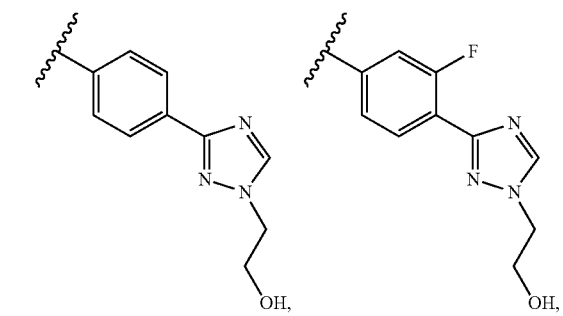

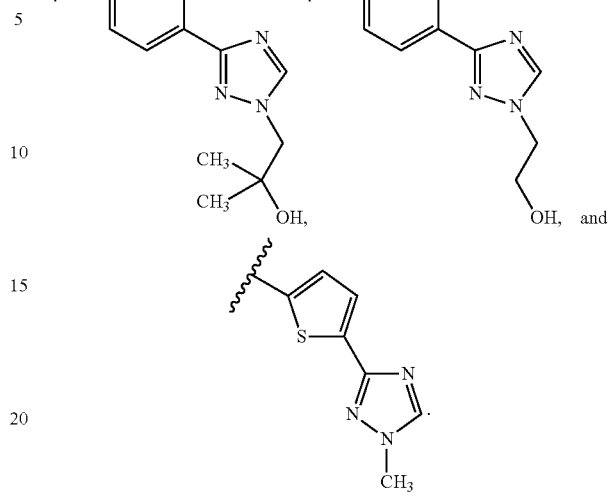

Other embodiments of this invention are directed to compounds of formula 1.1:

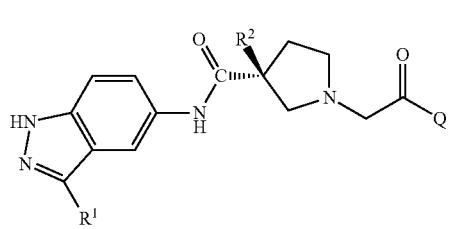

(1.1)

wherein:
$R^1$ and $R^2$ are as defined in any one of embodiment numbers 1 to 44,
Q is:

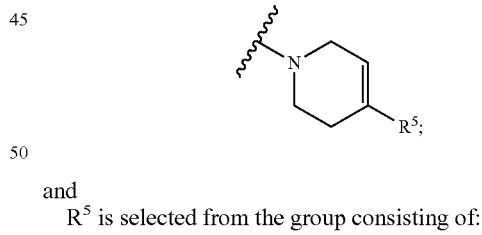

and
$R^5$ is selected from the group consisting of:

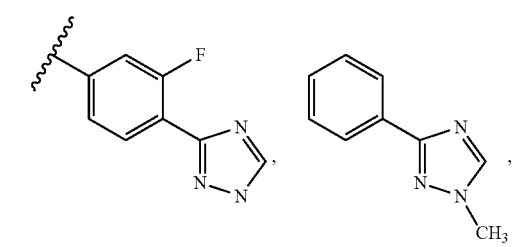

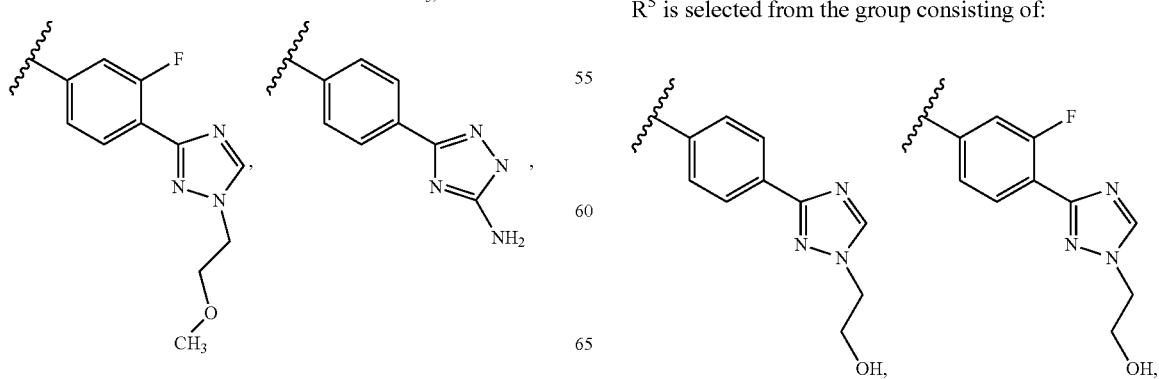

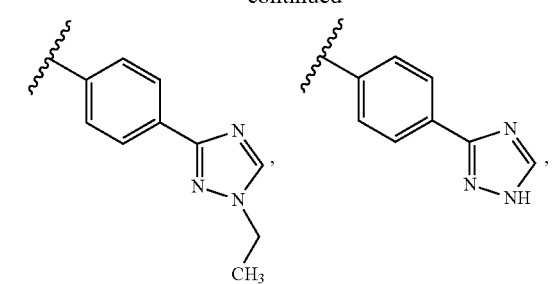
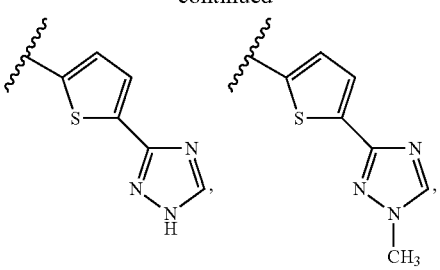
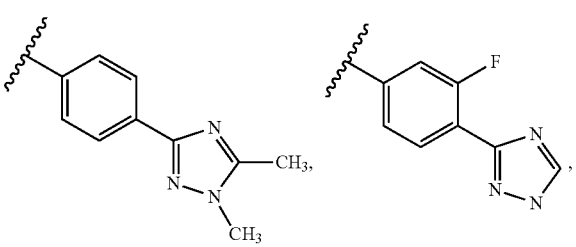
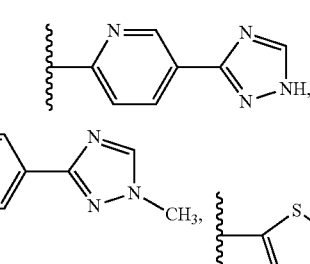
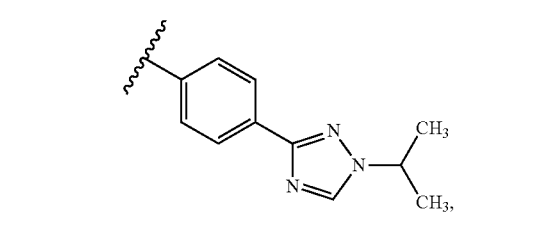
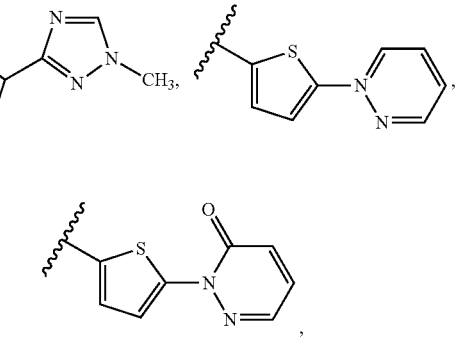
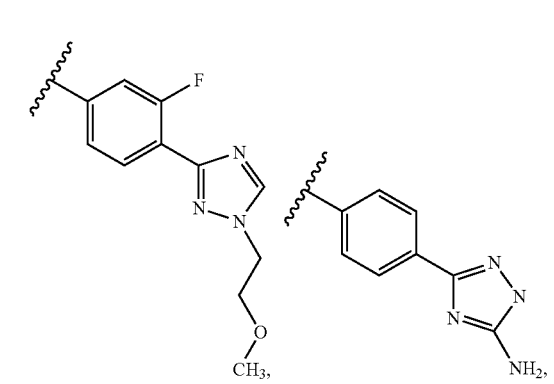
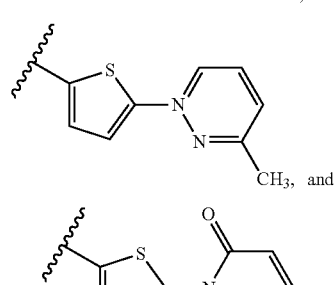
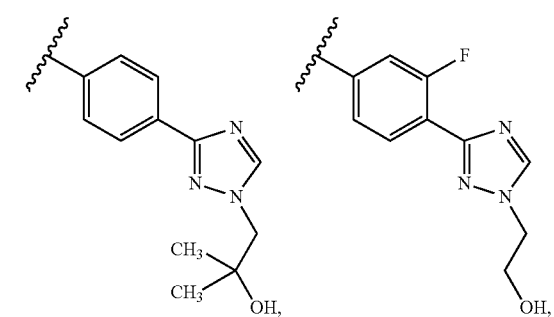
Other embodiments of this invention are directed to compounds of formula 1.1:
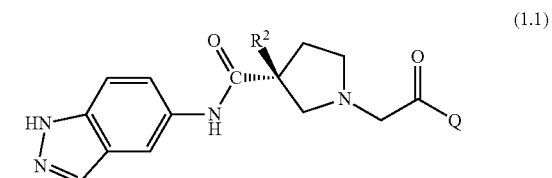
(1.1)

wherein:
$R^2$ is a —O—$(C_1-C_2)$alkyl group, and $R^1$ is:
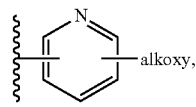
Q is:
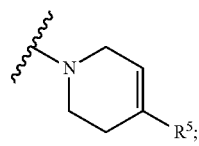
and
$R^5$ is selected from the group consisting of:
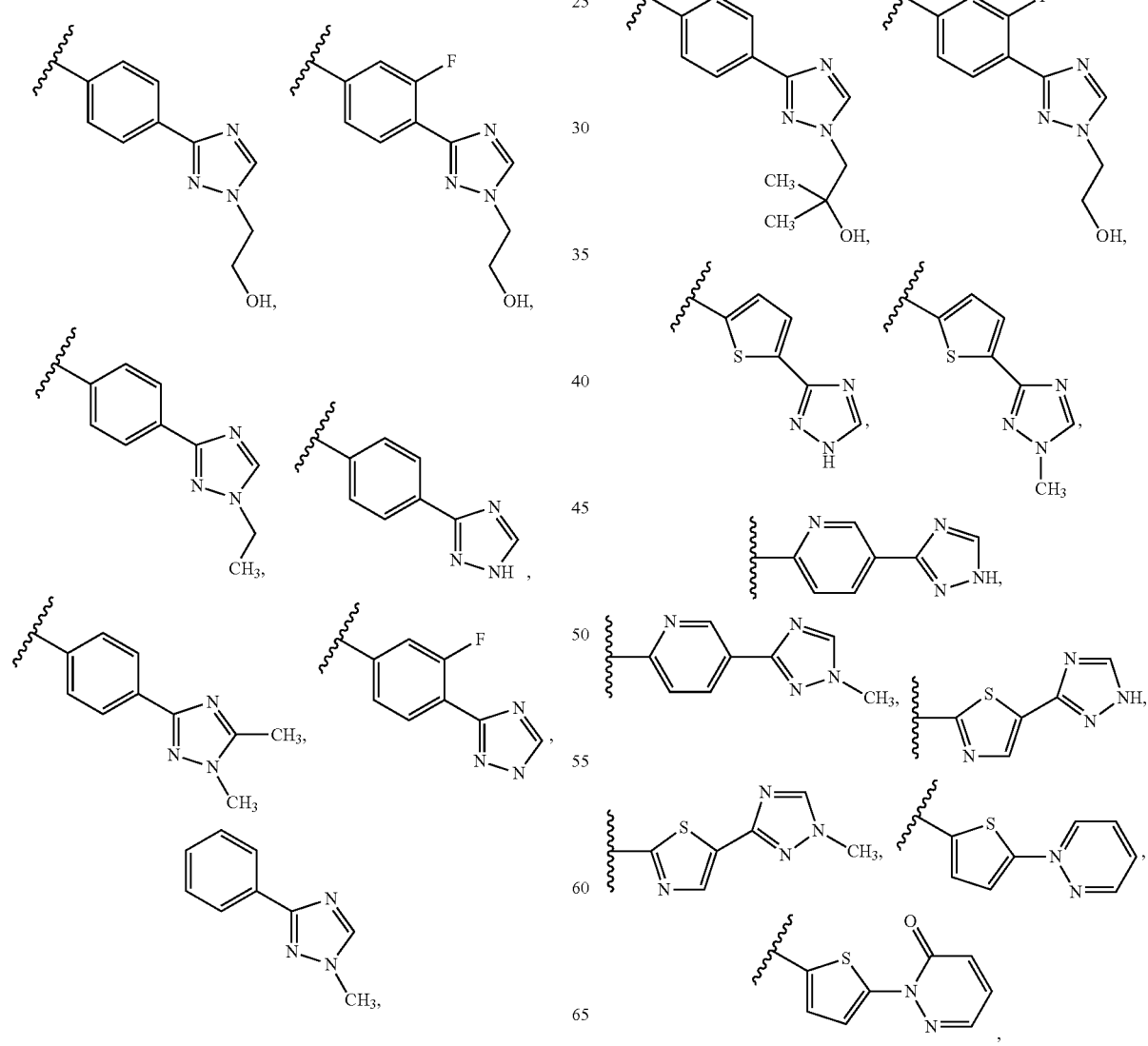

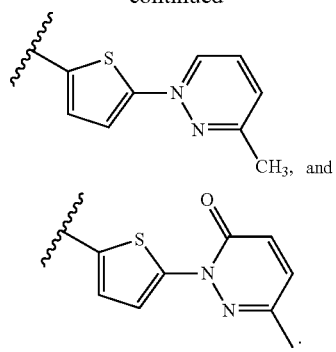
Other embodiments of this invention are directed to compounds of formula 1.1:
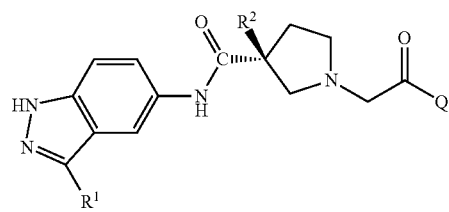
(1.1)
wherein:
R² is a —S—(C₁-C₂)alkyl group, and R¹ is:
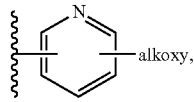
alkoxy,
Q is:
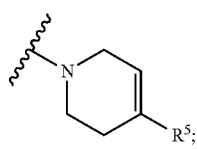
and
R⁵ is selected from the group consisting of:
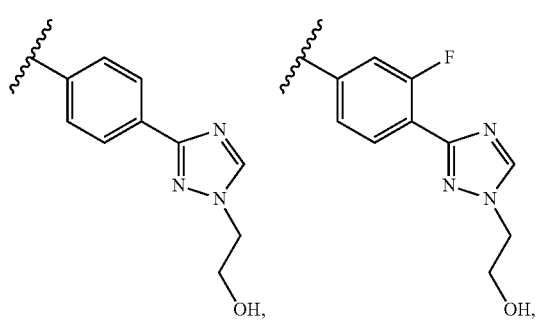
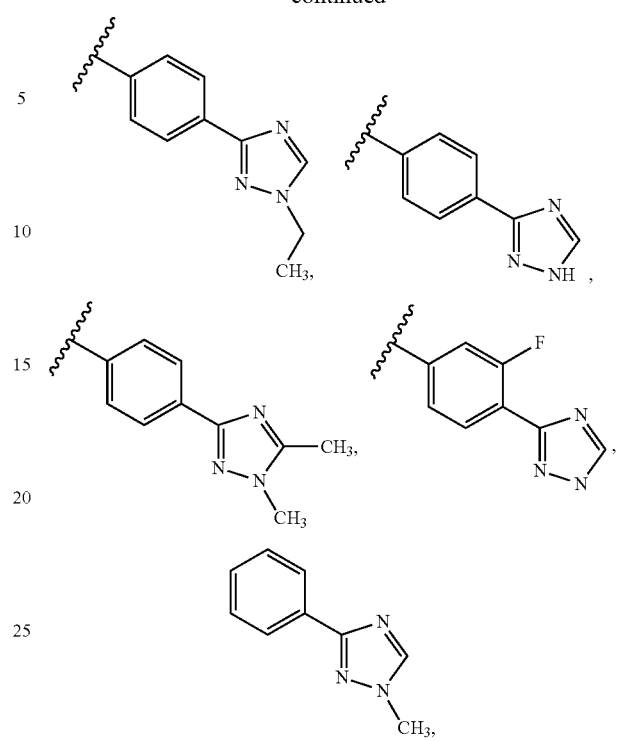
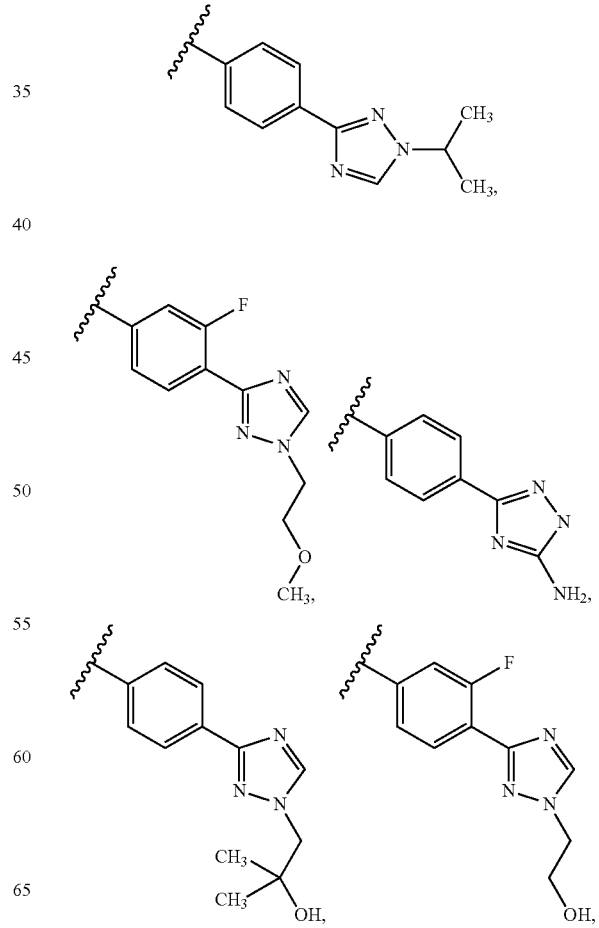

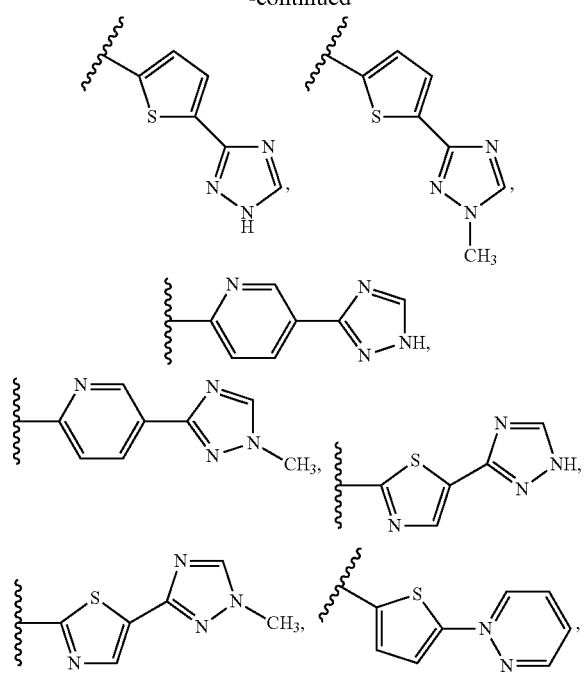
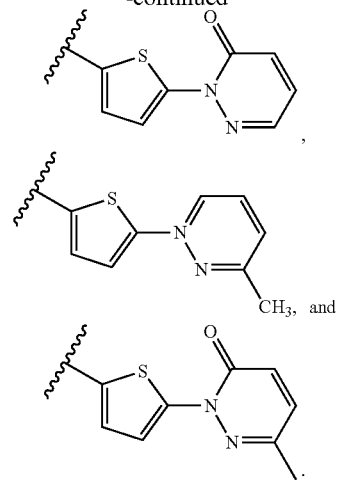
Other embodiments of this invention are directed to any one of the embodiments above (for example, any one of embodiment numbers 1 to 46, or any one of the embodiments following embodiment number 46) wherein one or more hydrogen atoms are deuterium.
Representative compounds of this invention include, but are not limited to:
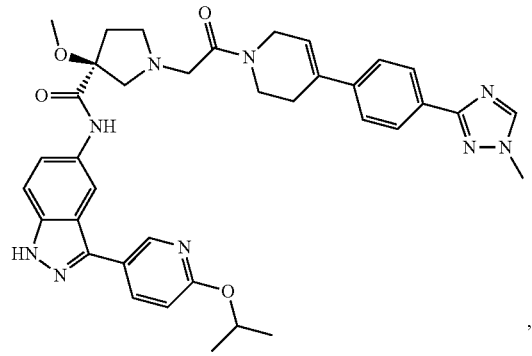
(A1)
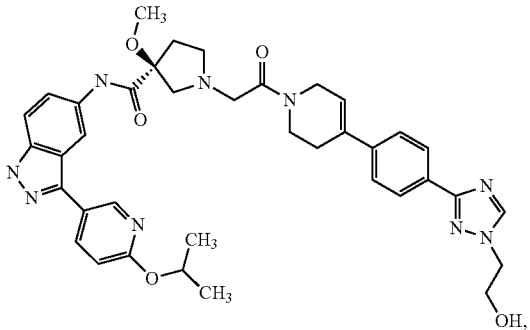
(A2)
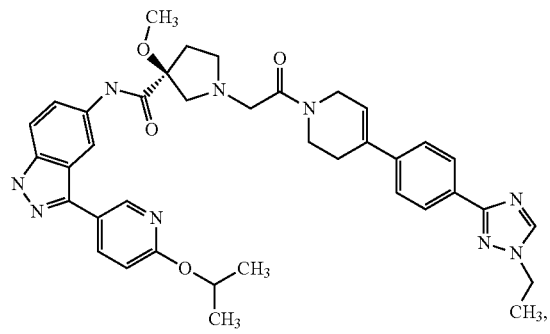
(A3)
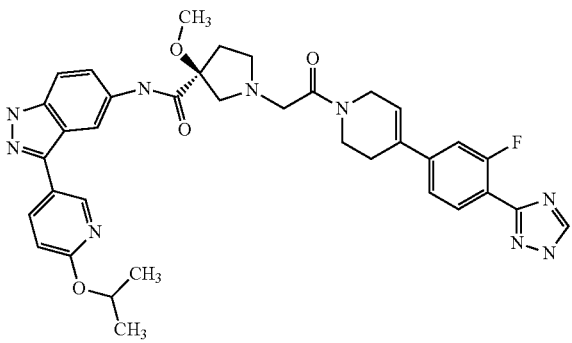
(A4)

-continued
(A5)
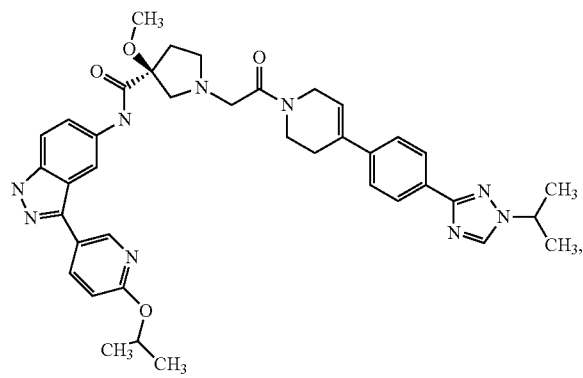
(A6)
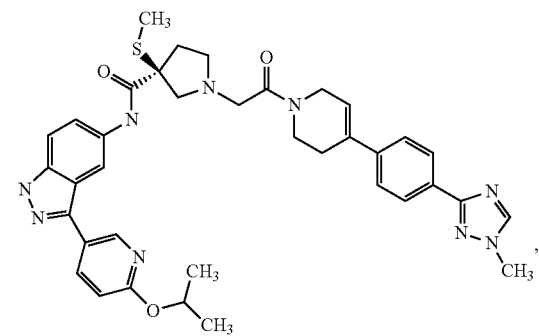
(A7)
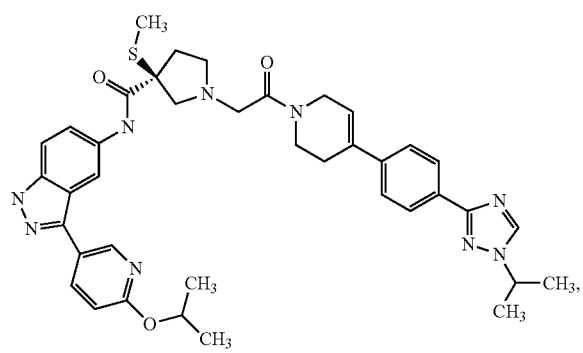
(A8)
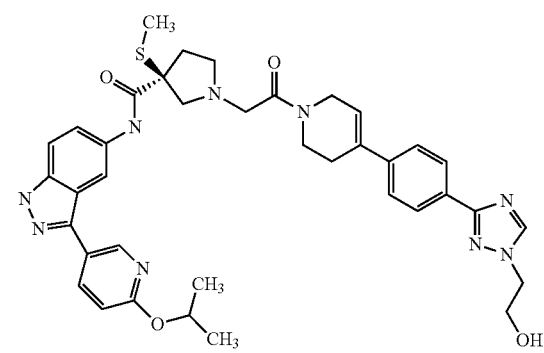
(A9)
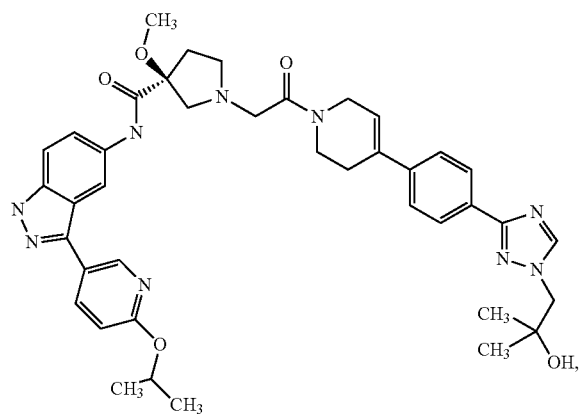
(A10)
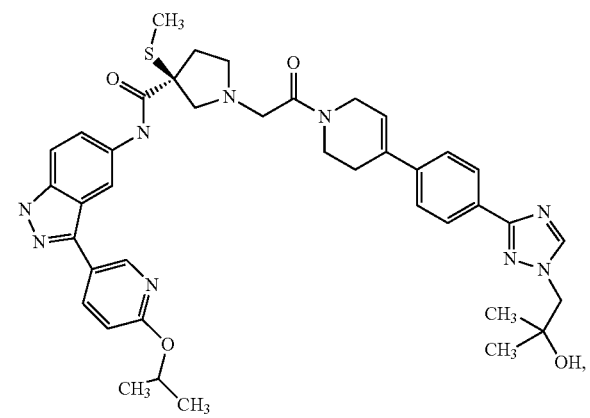
(A11)
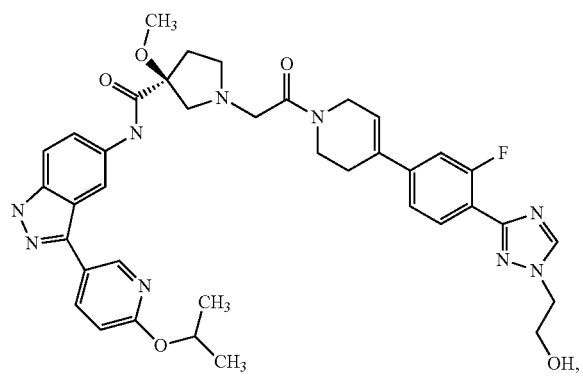
(A12)
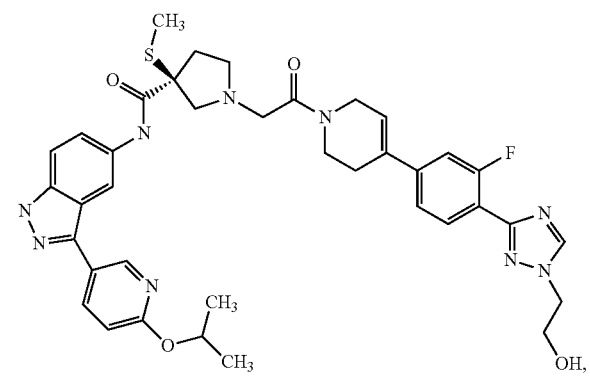

(A13)
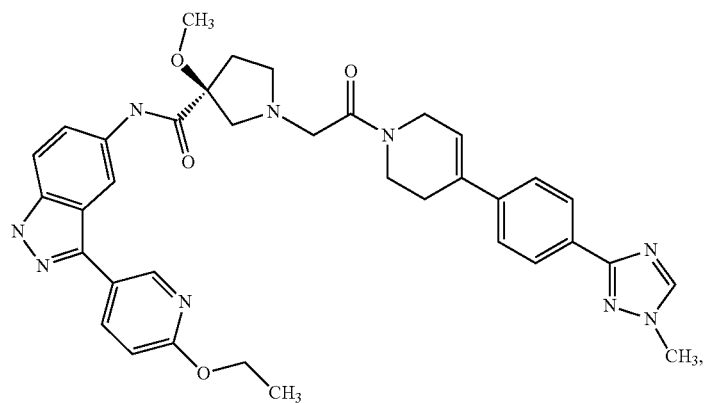
(A14)
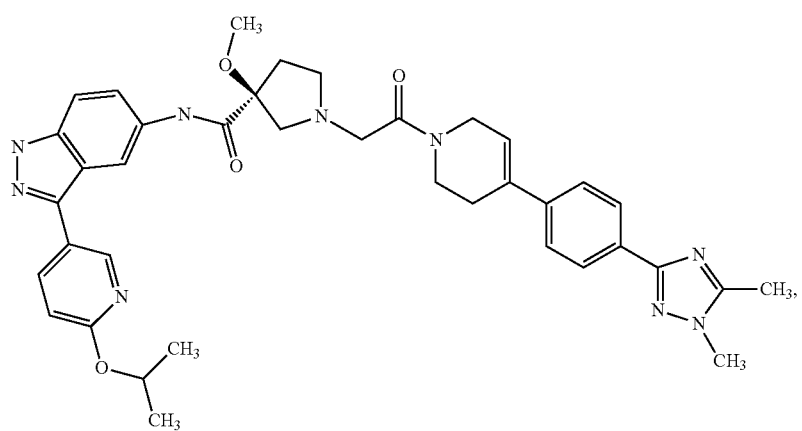
(A15)
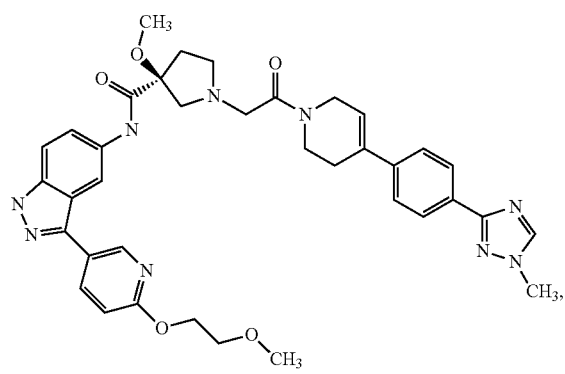
(A16)
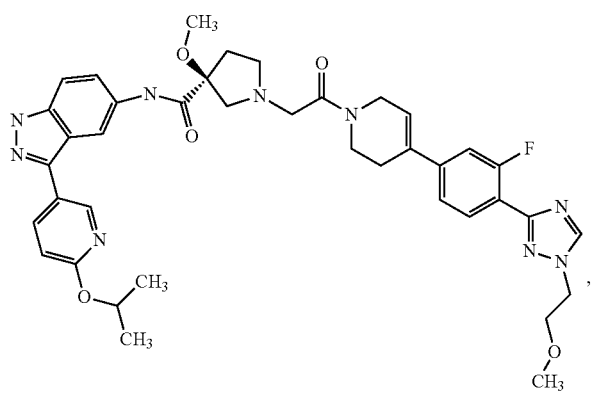

-continued
(A18)
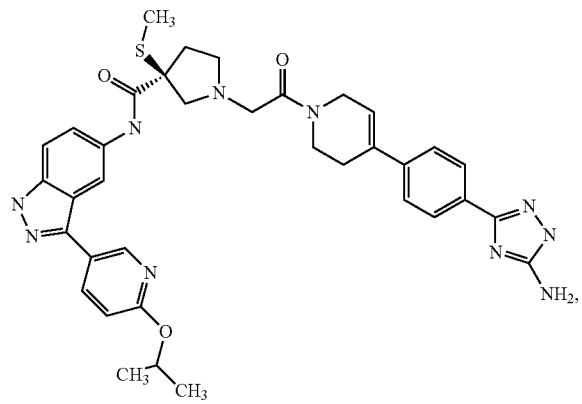
(A19)
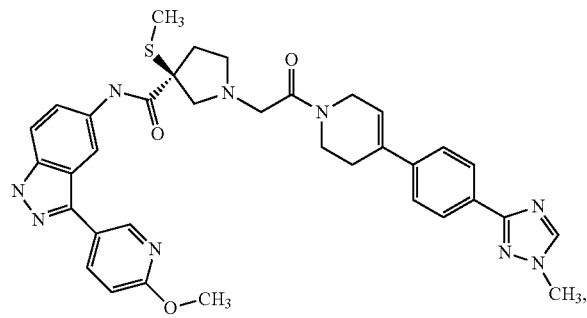
(A20)
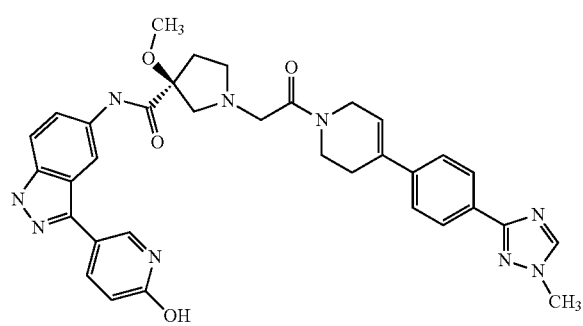
(A21)
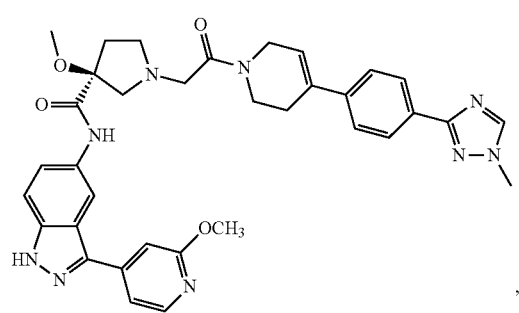
(A22)
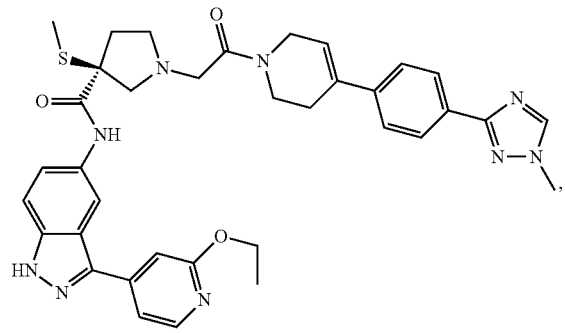
(A23)
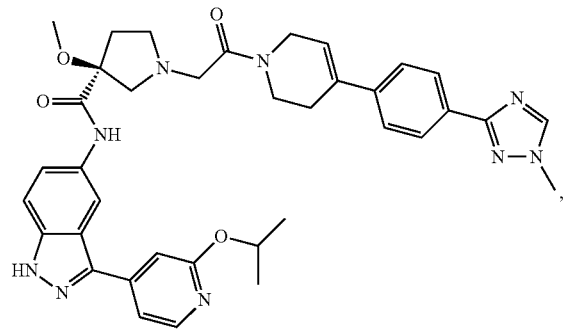
(A24)
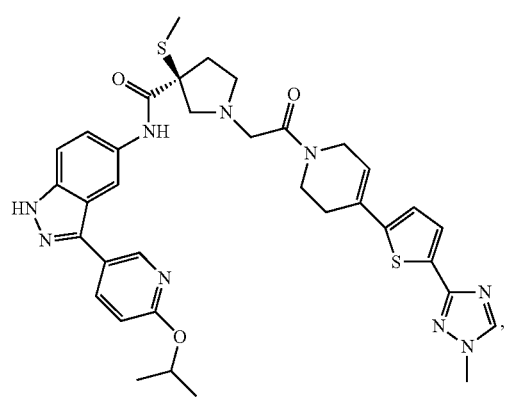
(A25)
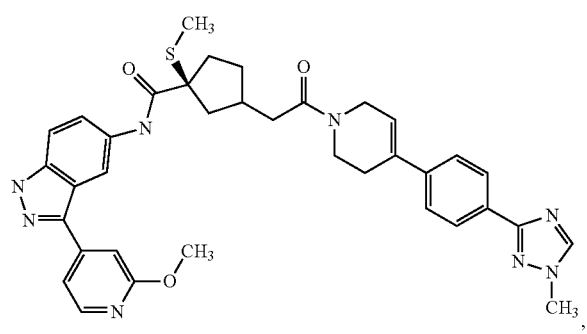

-continued
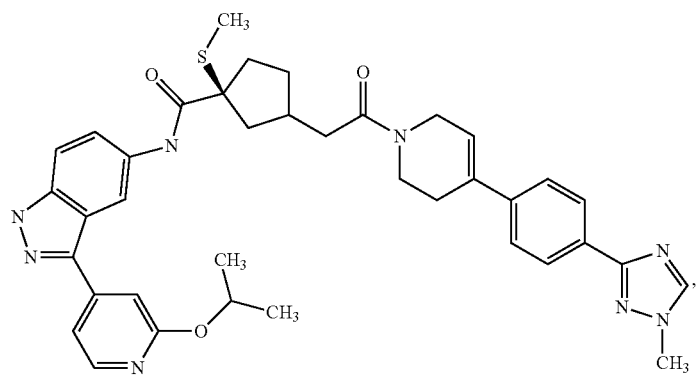
(A26)
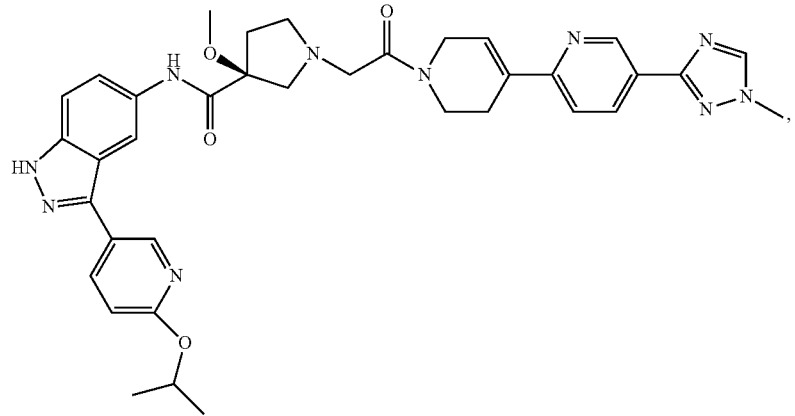
(A27)
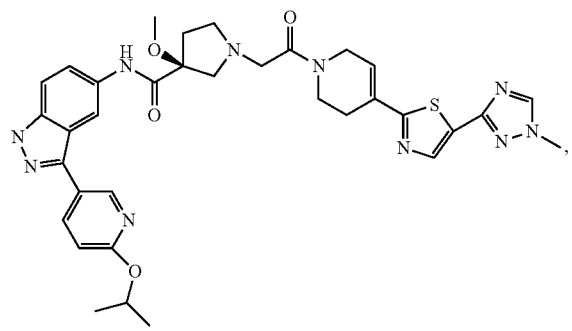
(A28)
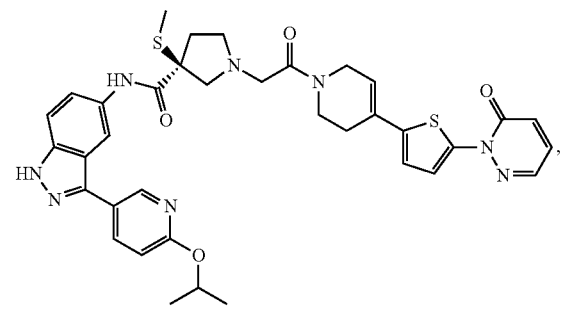
(A29)
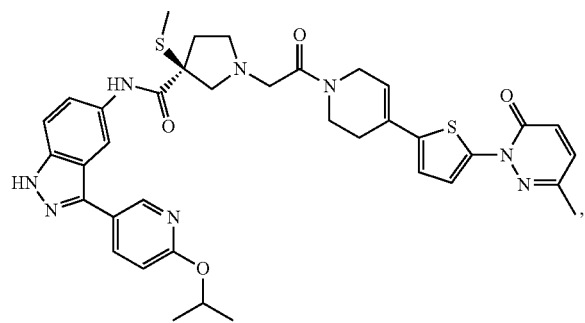
(A30)
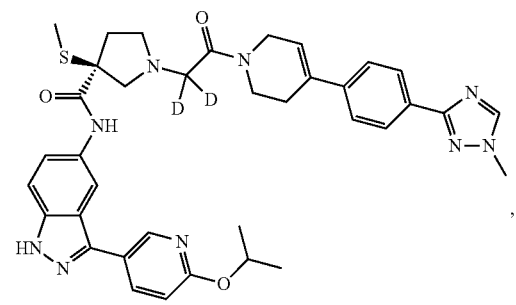
(A31)

(A32) 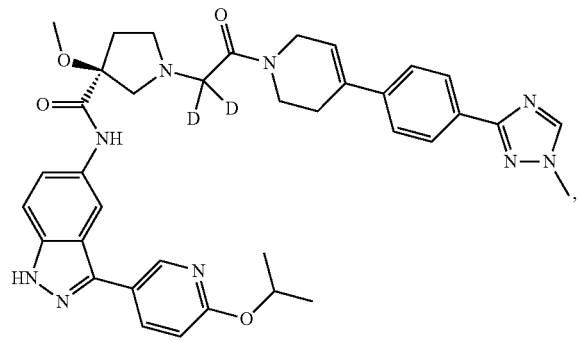
(A33) 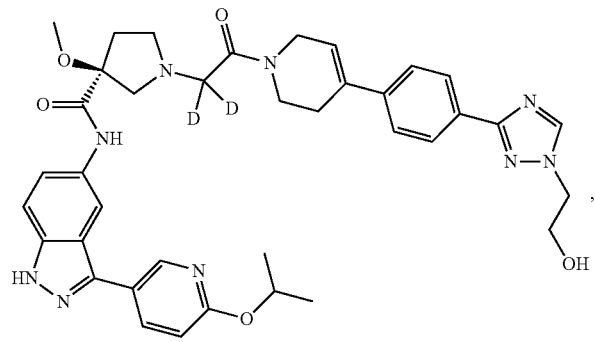
(A34) 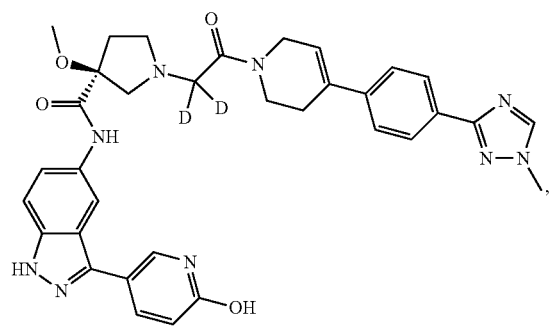
(A35) 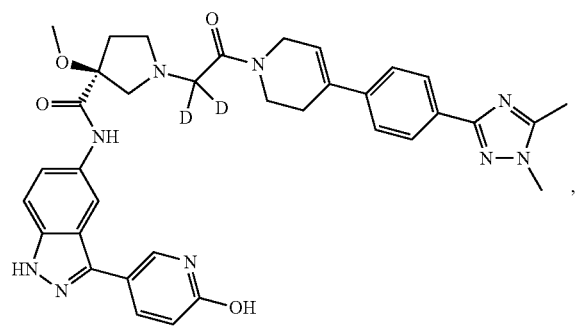
(A36) 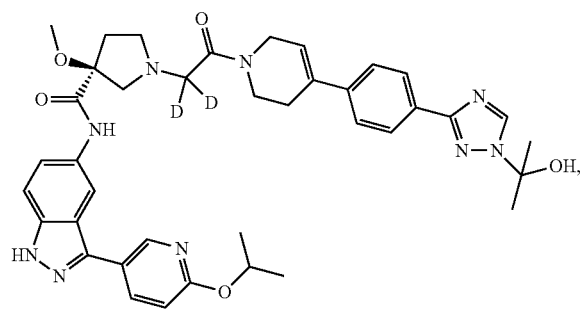
(A37) 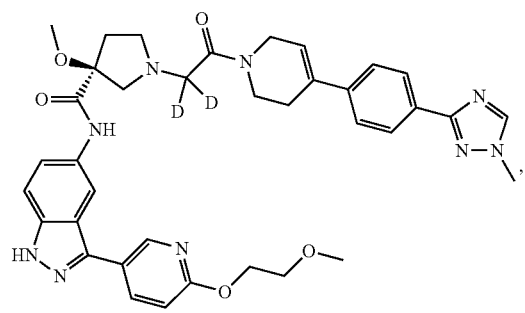
(A38) 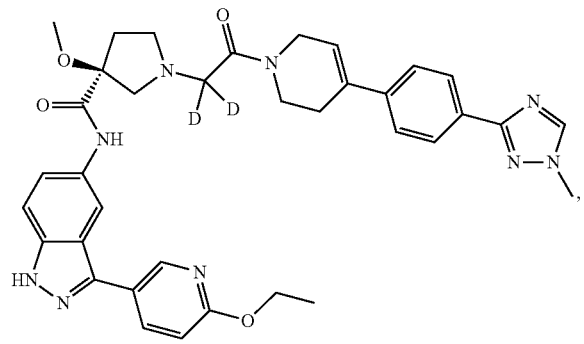
(A39) 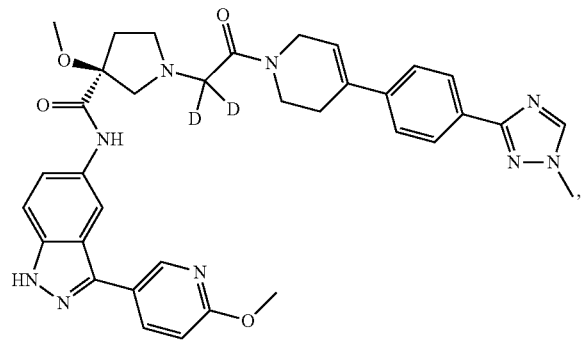

-continued
(A40)
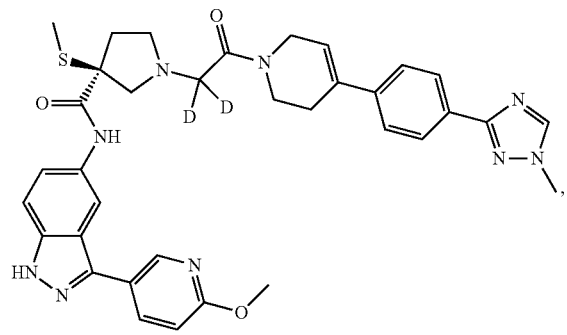
(A41)
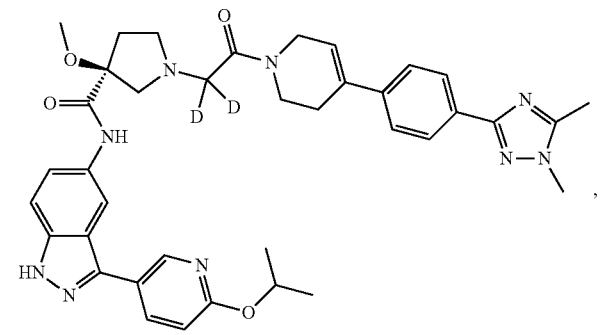
(A42)
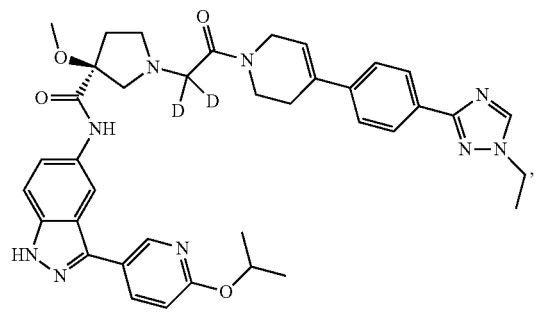
(A43)
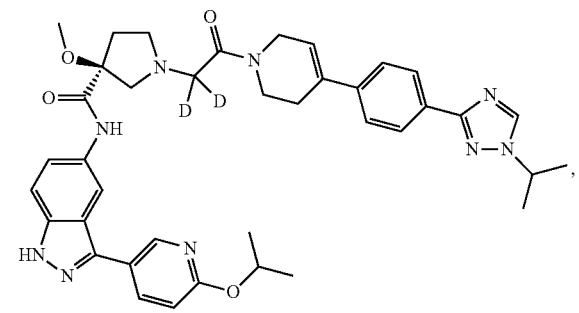
(A44)
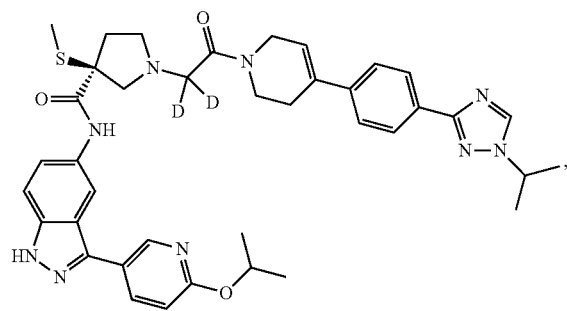
(A45)
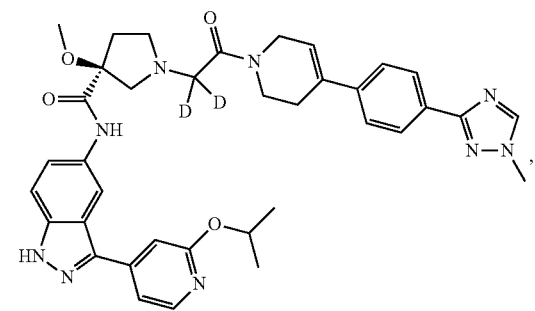
(A46)
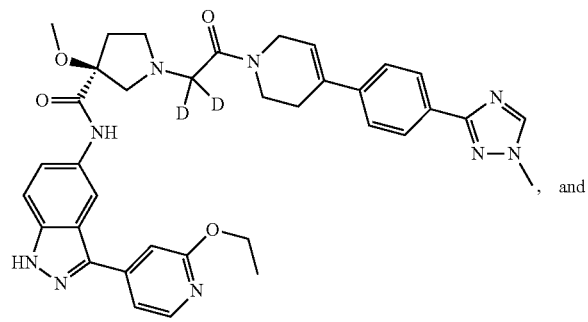, and
(A47)
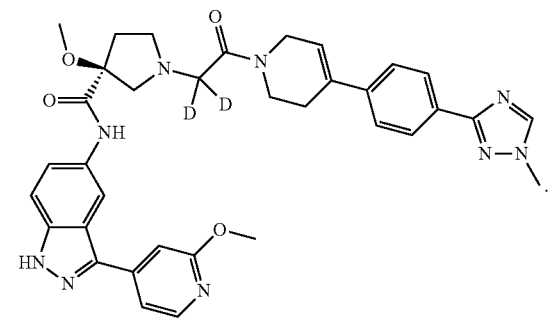.

Representative compounds of this invention include, but are not limited to:
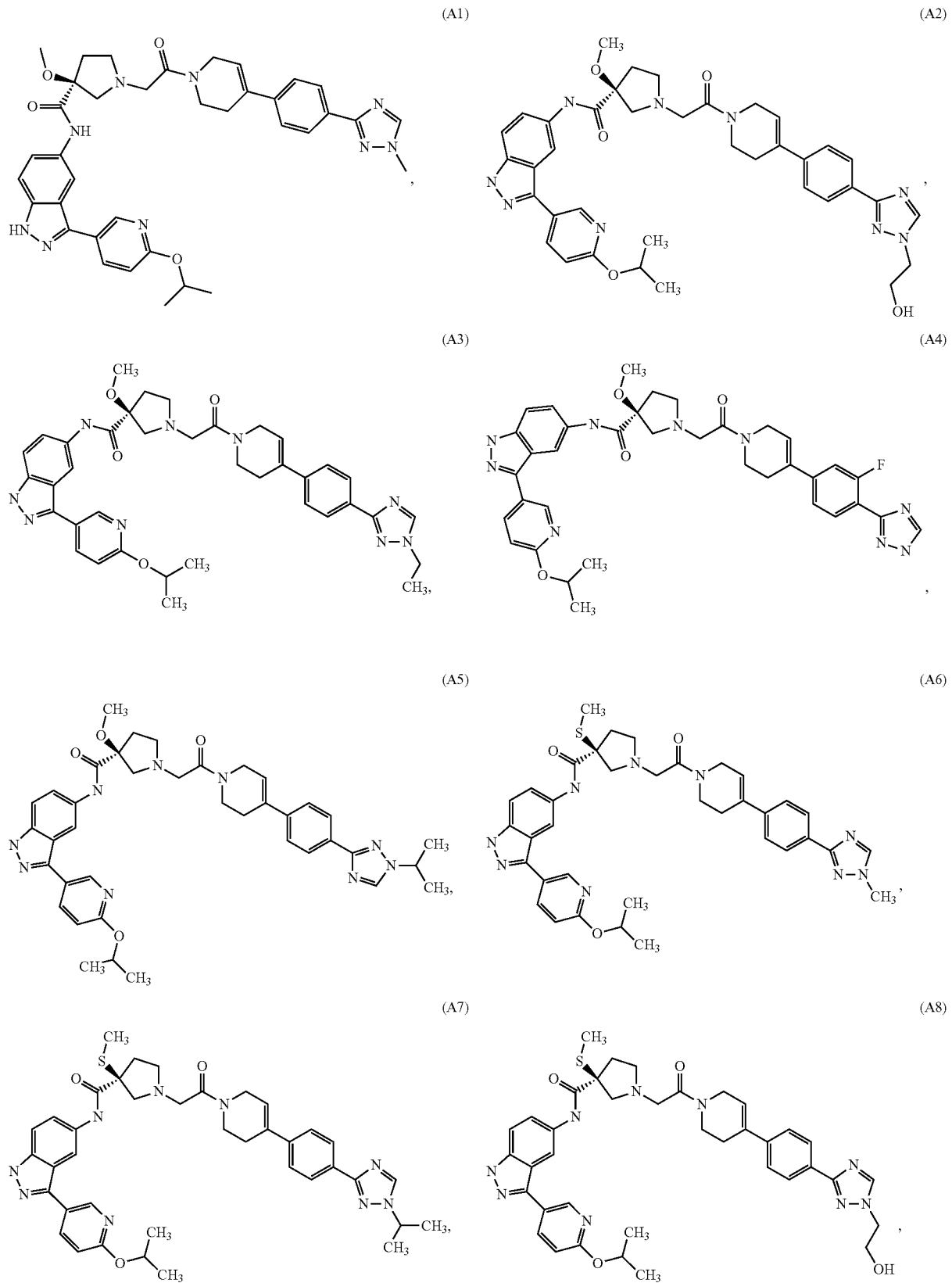

-continued
(A9)
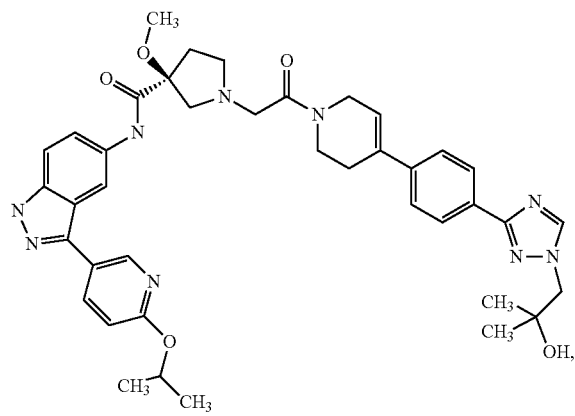
(A10)
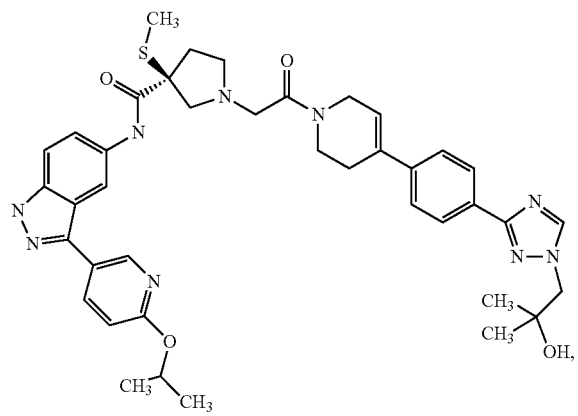
(A11)
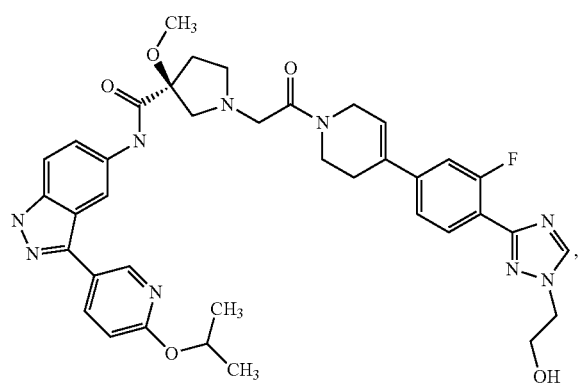
(A12)
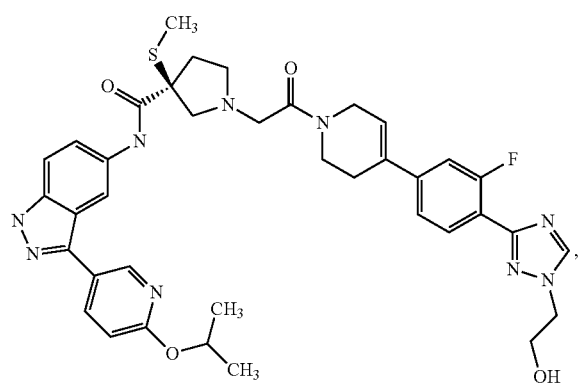
(A13)
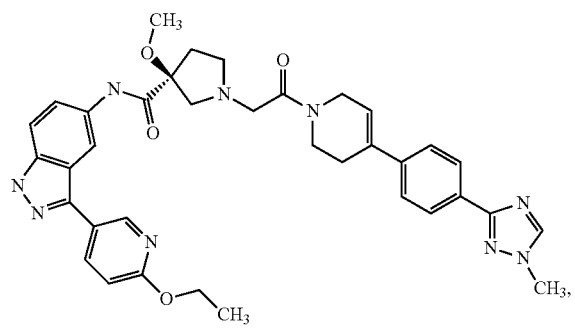
(A14)
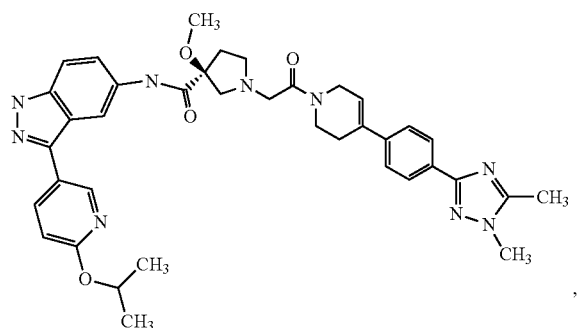
(A15)
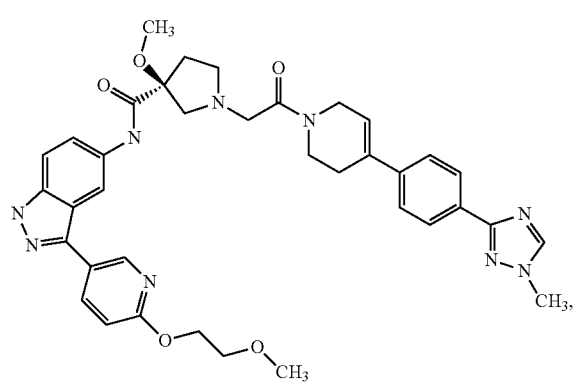
(A16)
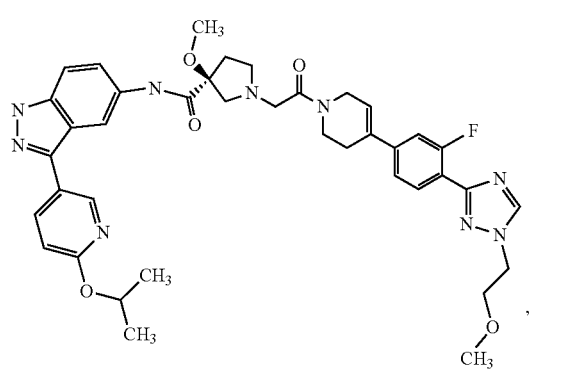

-continued
(A18)
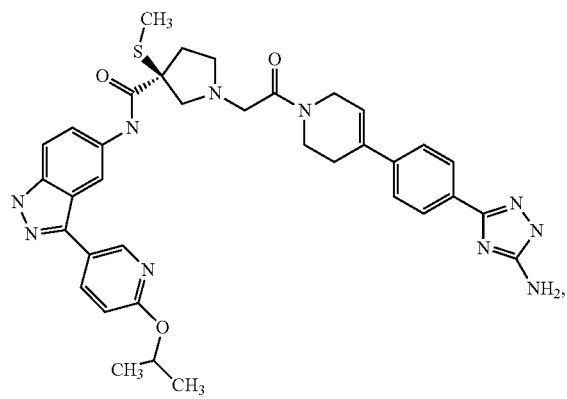
(A19)
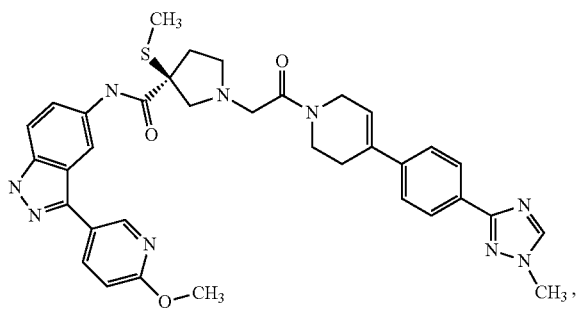
(A20)
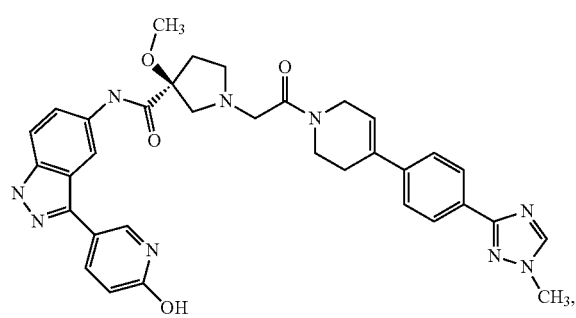
(A21)
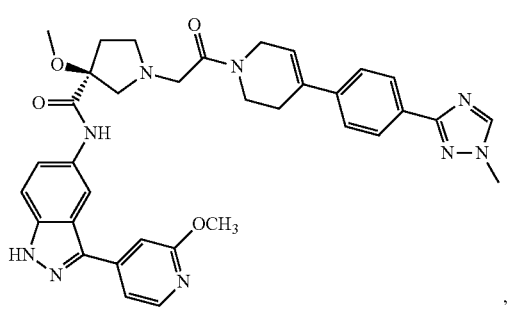
(A22)
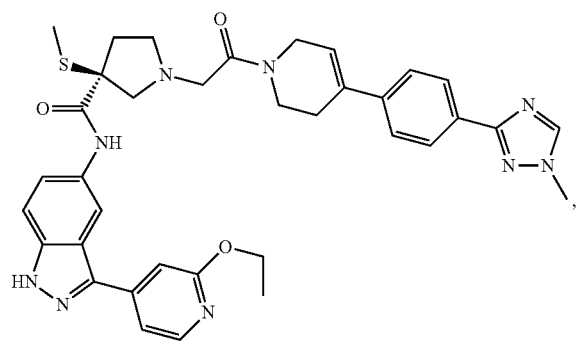
(A23)
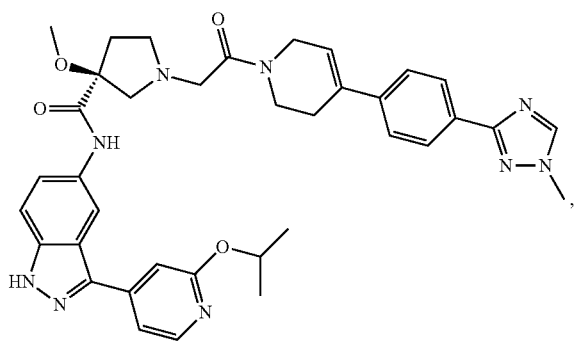
(A24)
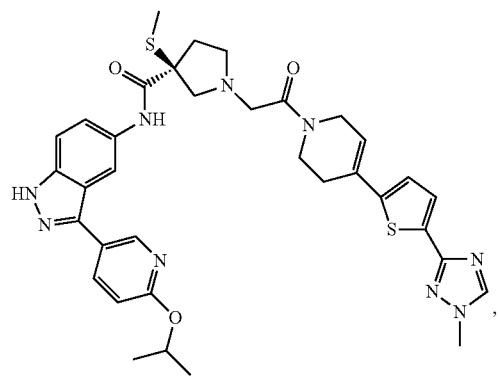
(A25)

(A26)
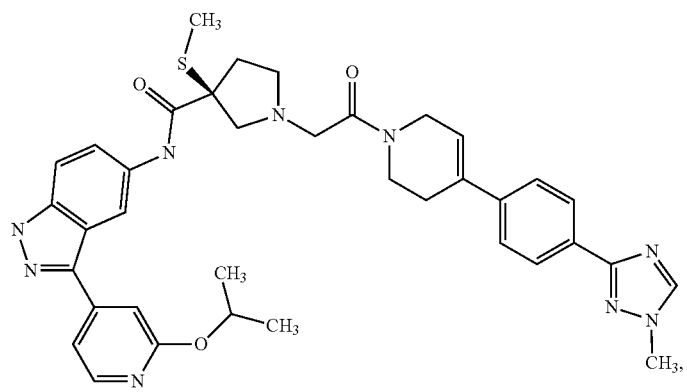
(A27)
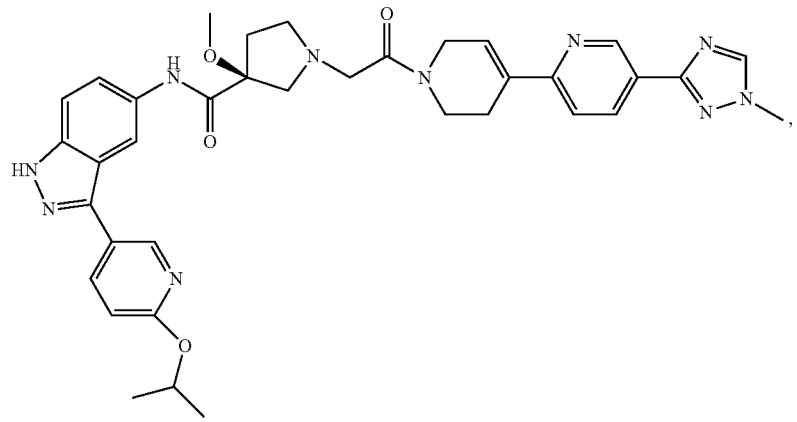
(A28)
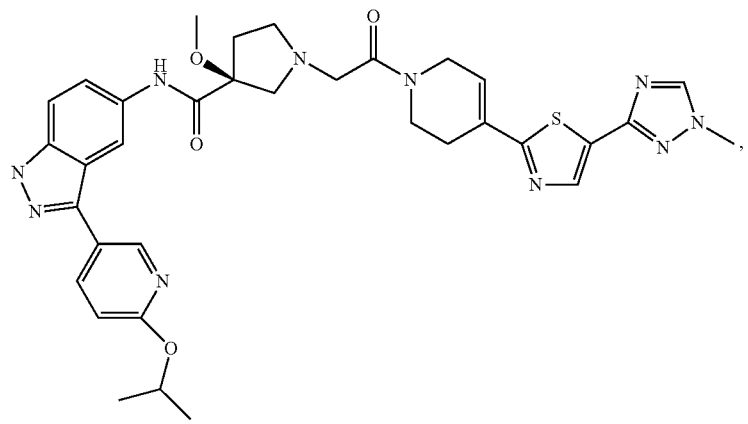
(A29)
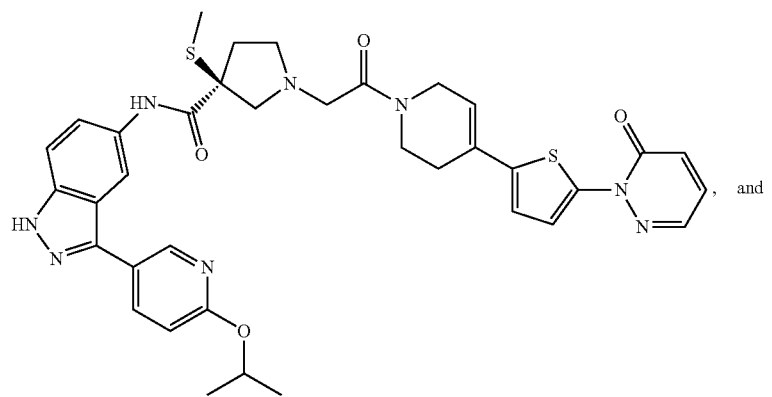
, and

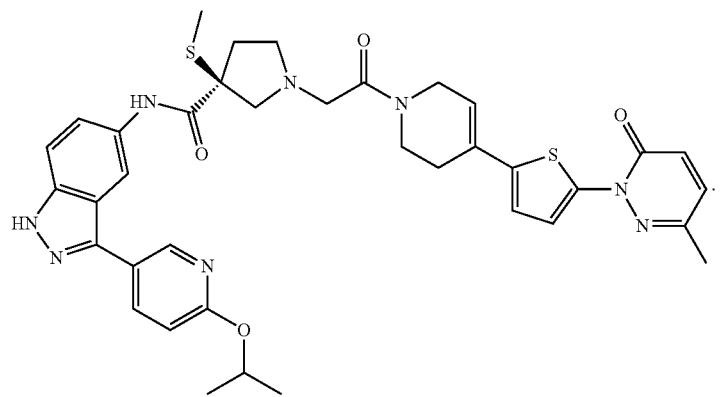
Representative compounds of this invention include, but are not limited to:
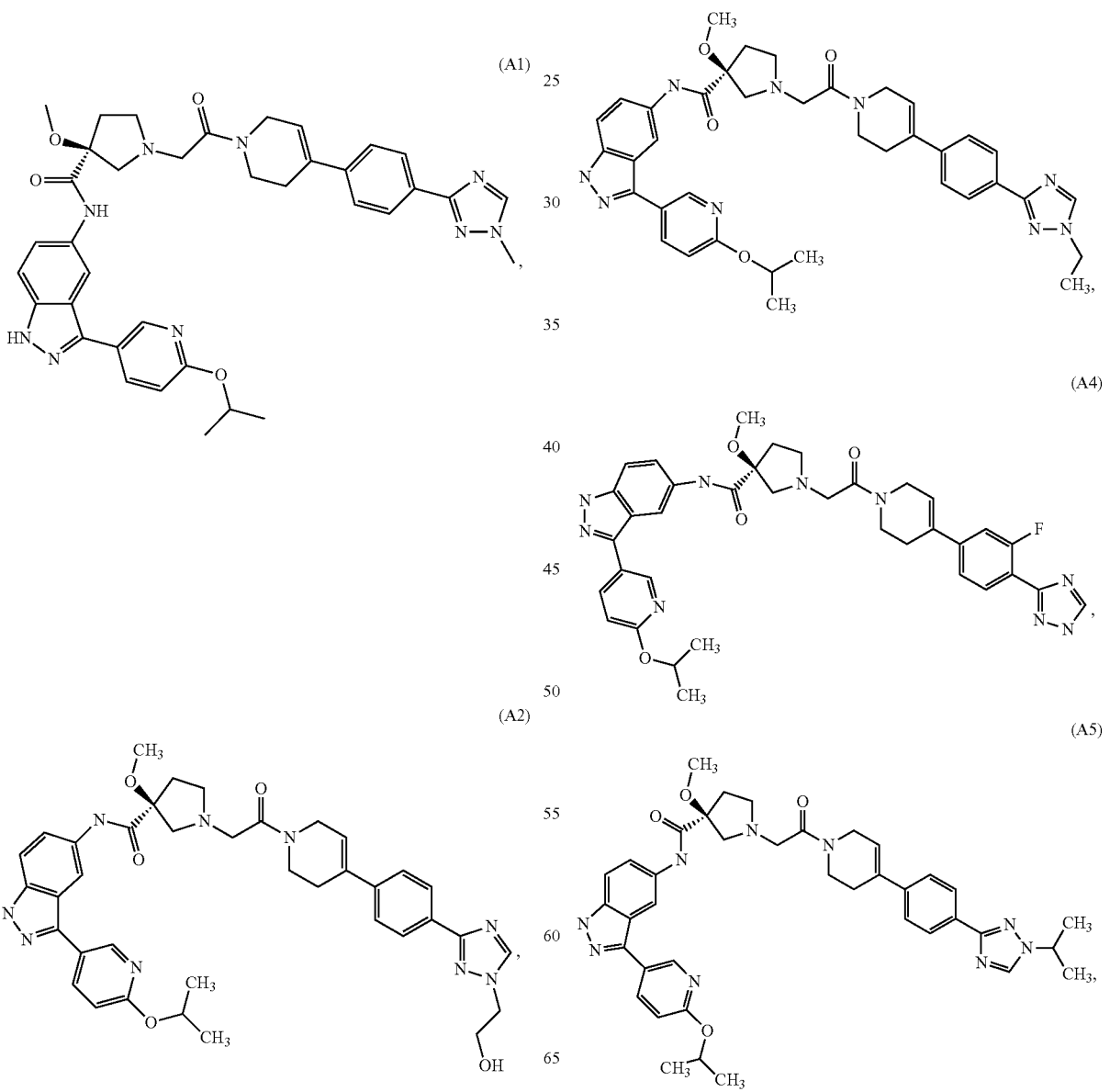

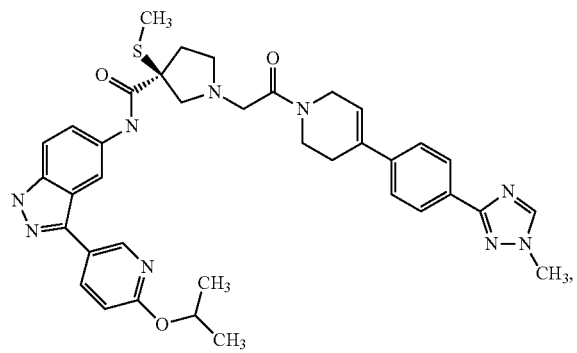
(A6)
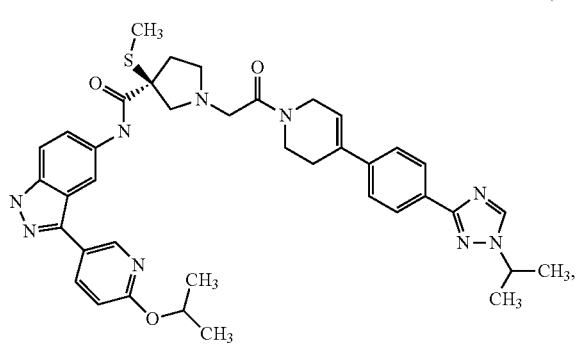
(A7)
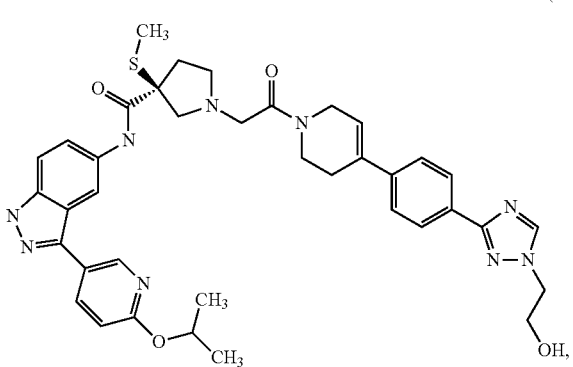
(A8)
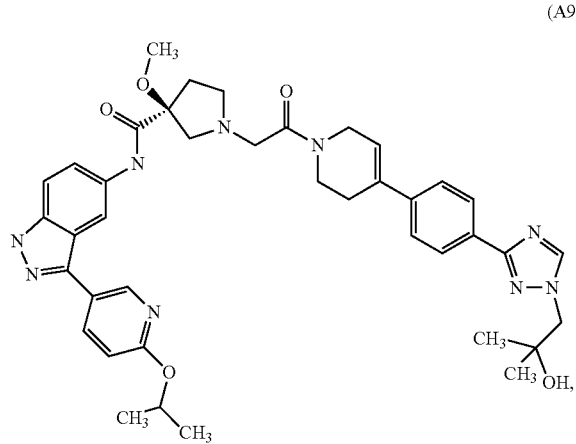
(A9)
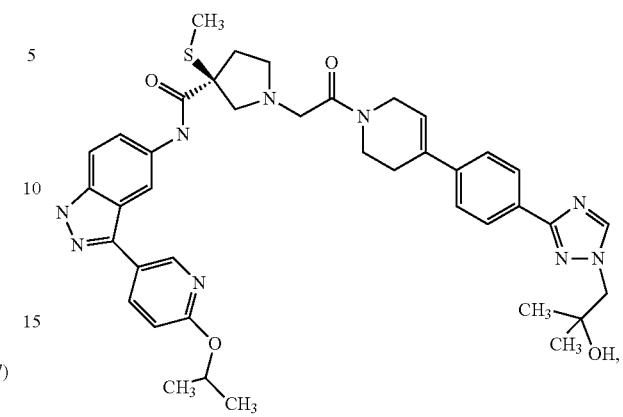
(A10)
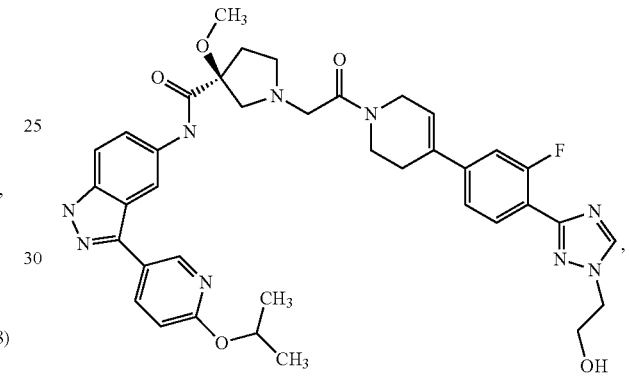
(A11)
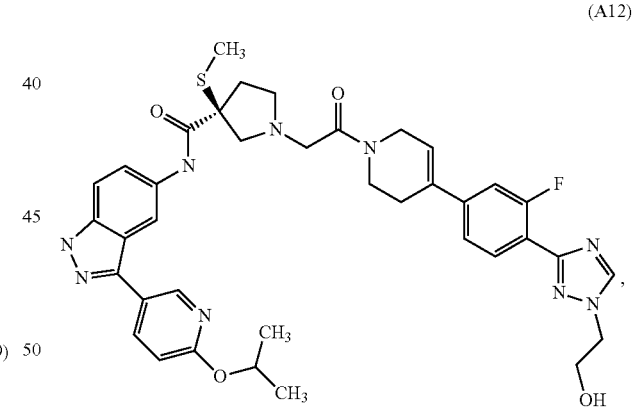
(A12)
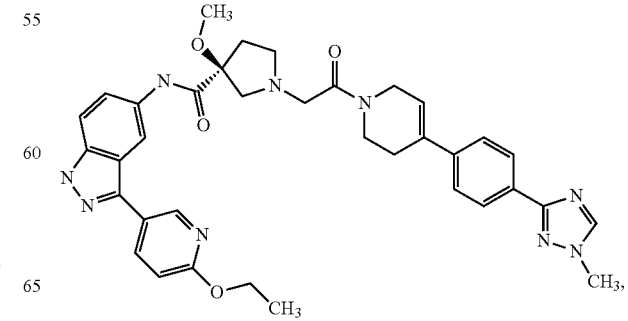
(A13)

99
-continued
(A14)
(A15)
(A16)
(A18)
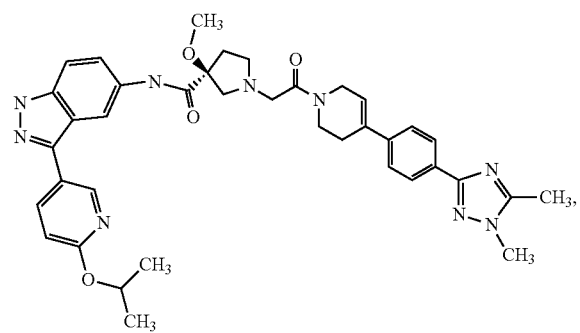
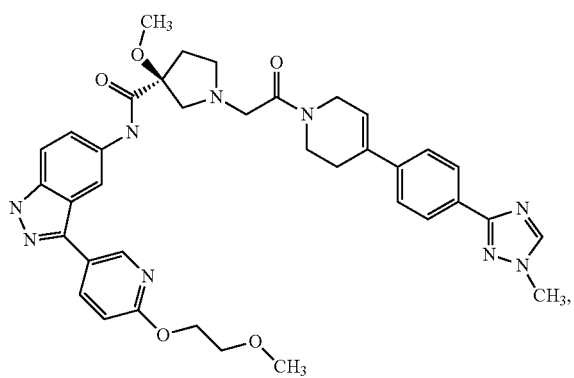
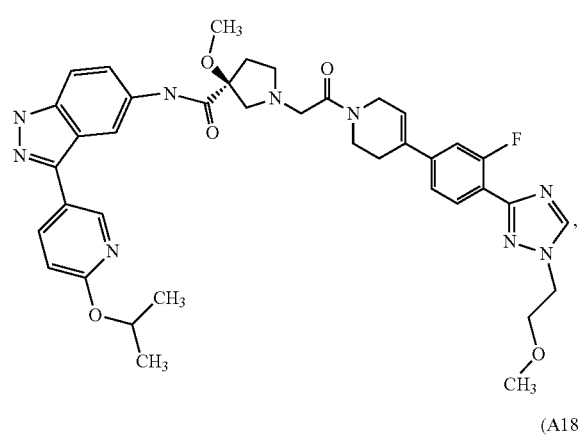
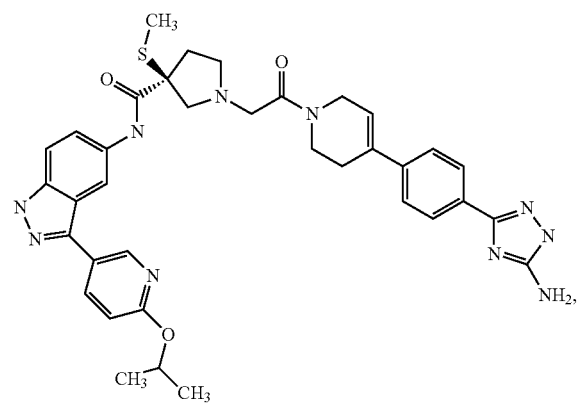
100
-continued
(A19)
(A20)
(A21)
(A22)
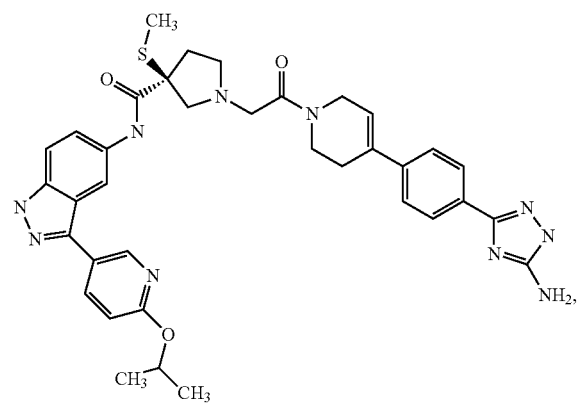

(A23)
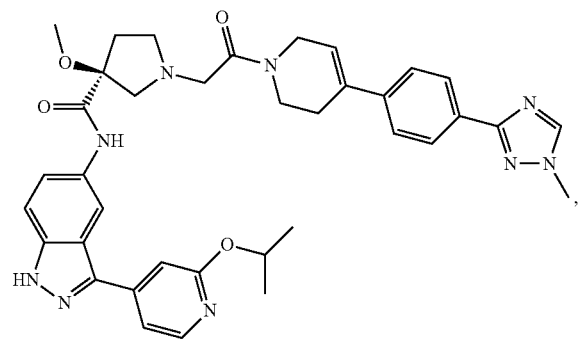
(A31)
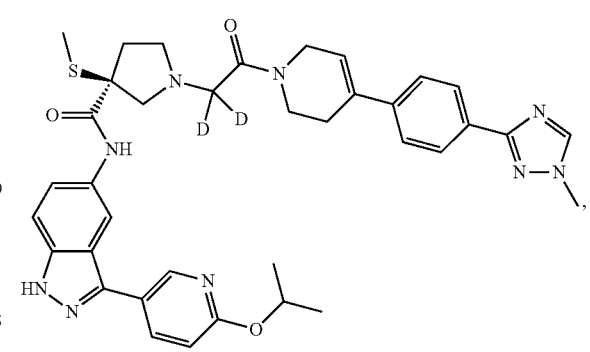
(A24)
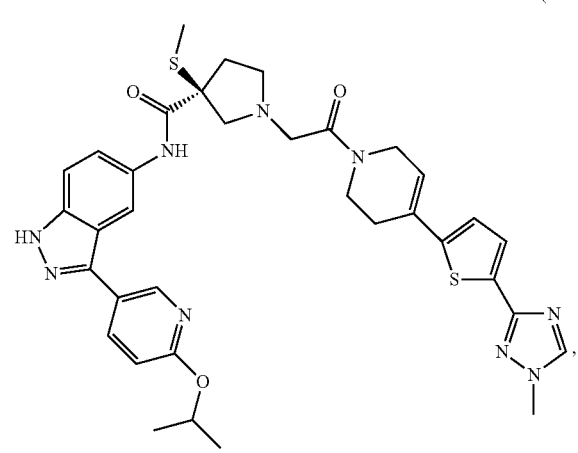
(A32)
(A25)
(A33)
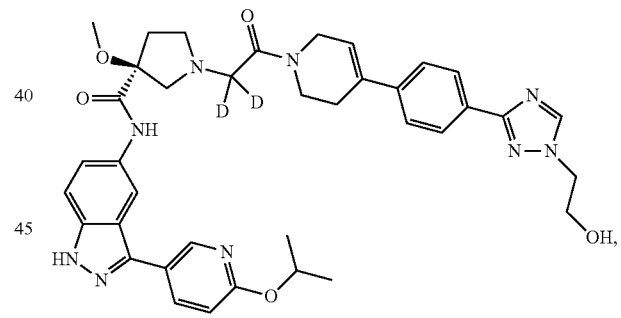
(A26)
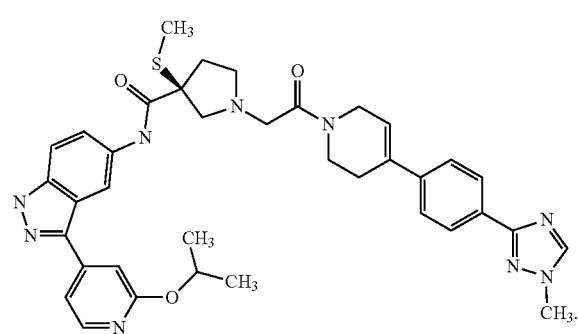
(A34)
Representative compounds of this invention wherein hydrogen has been replaced by deuterium include, but are not limited to:

103
(A35)
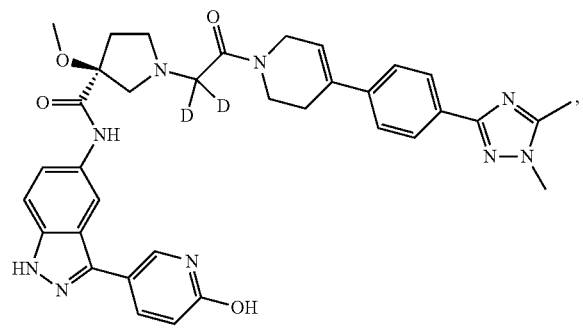
(A36)
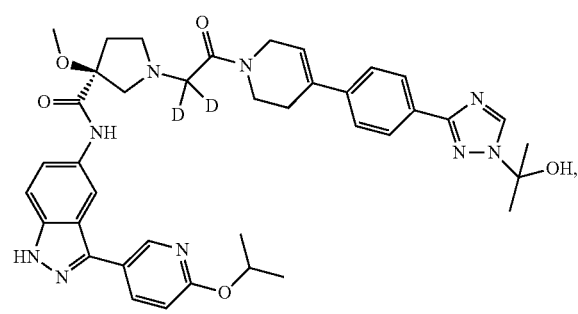
(A37)
(A38)
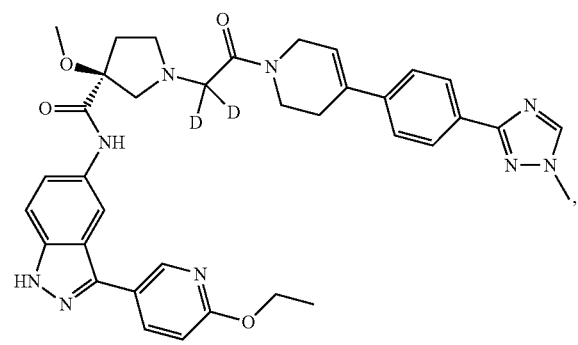
104
(A39)
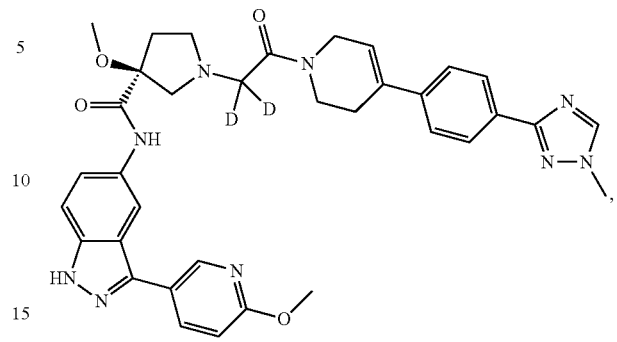
(A40)
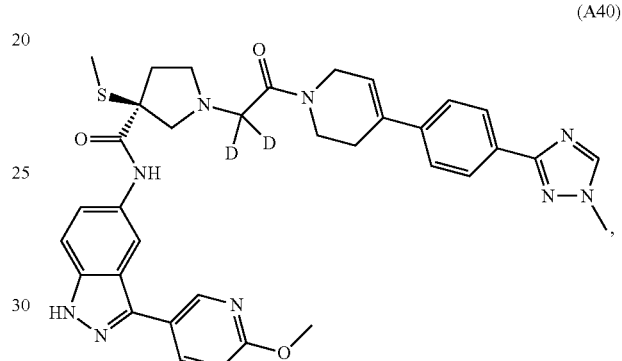
(A41)
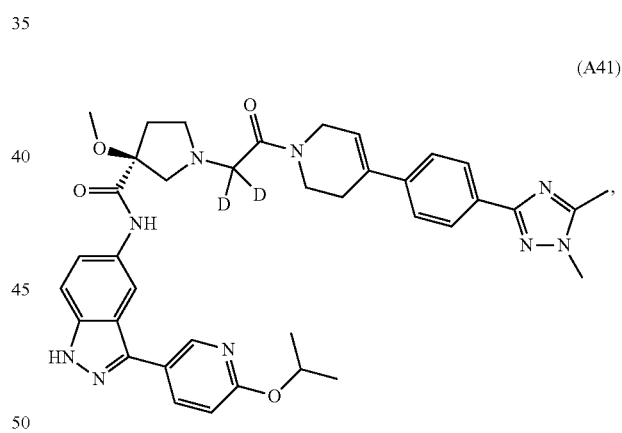
(A42)
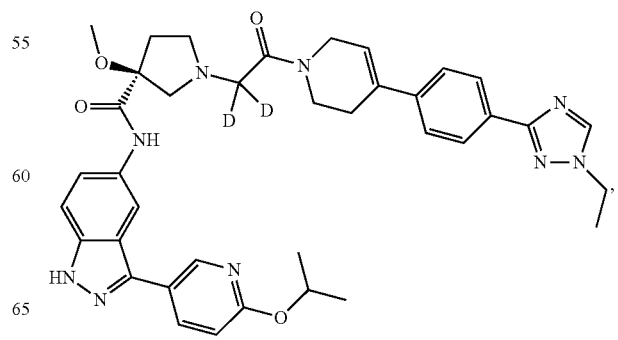

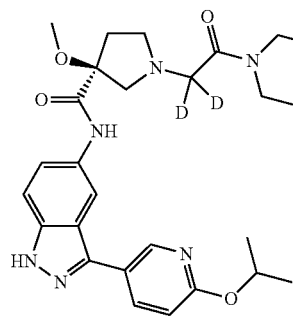
(A43)

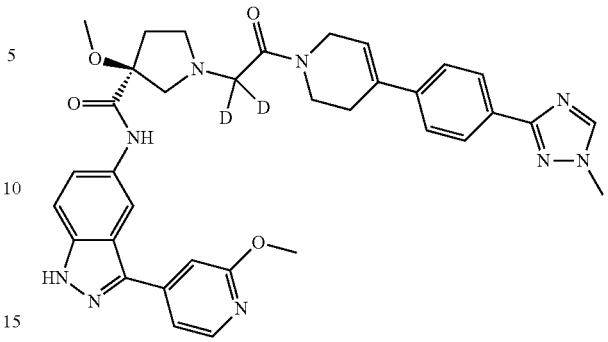
(A47)

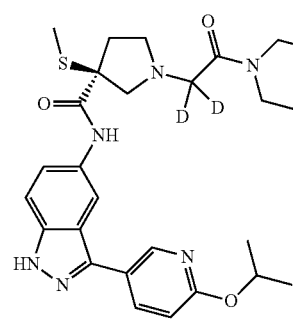
(A44)

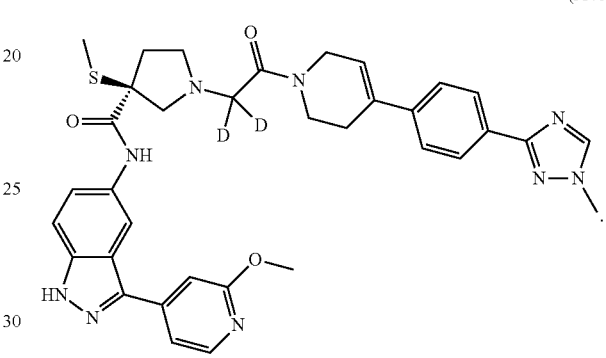
and
(A48)

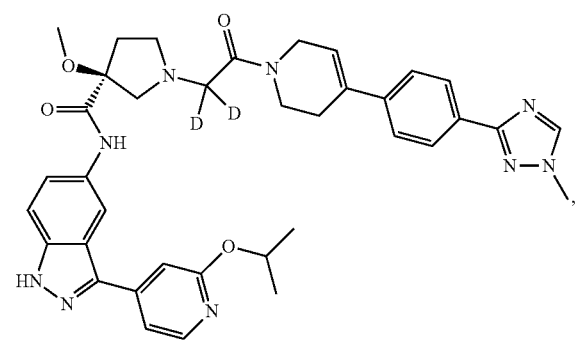
(A45)

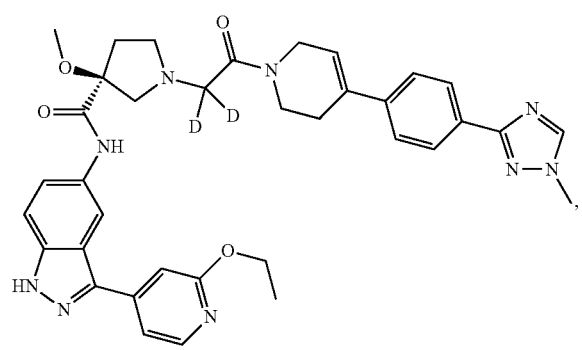
(A46)

Another embodiment of this invention is directed to compound A1.
Another embodiment of this invention is directed to compound A2.
Another embodiment of this invention is directed to compound A3.
Another embodiment of this invention is directed to compound A4.
Another embodiment of this invention is directed to compound A5.
Another embodiment of this invention is directed to compound A6.
Another embodiment of this invention is directed to compound A7.
Another embodiment of this invention is directed to compound A8.
Another embodiment of this invention is directed to compound A9.
Another embodiment of this invention is directed to compound A10.
Another embodiment of this invention is directed to compound A11.
Another embodiment of this invention is directed to compound A12.
Another embodiment of this invention is directed to compound A13.
Another embodiment of this invention is directed to compound A14.
Another embodiment of this invention is directed to compound A15.
Another embodiment of this invention is directed to compound A16.
Another embodiment of this invention is directed to compound A18.

Another embodiment of this invention is directed to compound A19.

Another embodiment of this invention is directed to compound A20.

Another embodiment of this invention is directed to compound A21.

Another embodiment of this invention is directed to compound A22.

Another embodiment of this invention is directed to compound A23.

Another embodiment of this invention is directed to compound A24.

Another embodiment of this invention is directed to compound A25.

Another embodiment of this invention is directed to compound A26.

Another embodiment of this invention is directed to compound A27.

Another embodiment of this invention is directed to compound A28.

Another embodiment of this invention is directed to compound A29.

Another embodiment of this invention is directed to compound A30.

Another embodiment of this invention is directed to compound A31.

Another embodiment of this invention is directed to compound A32.

Another embodiment of this invention is directed to compound A33.

Another embodiment of this invention is directed to compound A34.

Another embodiment of this invention is directed to compound A35.

Another embodiment of this invention is directed to compound A36.

Another embodiment of this invention is directed to compound A37.

Another embodiment of this invention is directed to compound A38.

Another embodiment of this invention is directed to compound A39.

Another embodiment of this invention is directed to compound A40.

Another embodiment of this invention is directed to compound A41.

Another embodiment of this invention is directed to compound A42.

Another embodiment of this invention is directed to compound A43.

Another embodiment of this invention is directed to compound A44.

Another embodiment of this invention is directed to compound A45.

Another embodiment of this invention is directed to compound A46.

Another embodiment of this invention is directed to compound A47.

Another embodiment of this invention is directed to compound A48.

Another embodiment of this invention is directed to a pharmaceutically acceptable salt of compound A1.

Another embodiment of this invention is directed to a pharmaceutically acceptable salt of compound A2.

Another embodiment of this invention is directed to a pharmaceutically acceptable salt of compound A3.

Another embodiment of this invention is directed to a pharmaceutically acceptable salt of compound A4.

Another embodiment of this invention is directed to a pharmaceutically acceptable salt of compound A5.

Another embodiment of this invention is directed to a pharmaceutically acceptable salt of compound A6.

Another embodiment of this invention is directed to a pharmaceutically acceptable salt of compound A7.

Another embodiment of this invention is directed to a pharmaceutically acceptable salt of compound A8.

Another embodiment of this invention is directed to a pharmaceutically acceptable salt of compound A9.

Another embodiment of this invention is directed to a pharmaceutically acceptable salt of compound A10.

Another embodiment of this invention is directed to a pharmaceutically acceptable salt of compound A11.

Another embodiment of this invention is directed to a pharmaceutically acceptable salt of compound A12.

Another embodiment of this invention is directed to a pharmaceutically acceptable salt of compound A13.

Another embodiment of this invention is directed to a pharmaceutically acceptable salt of compound A14.

Another embodiment of this invention is directed to a pharmaceutically acceptable salt of compound A15.

Another embodiment of this invention is directed to a pharmaceutically acceptable salt of compound A16.

Another embodiment of this invention is directed to a pharmaceutically acceptable salt of compound A18.

Another embodiment of this invention is directed to a pharmaceutically acceptable salt of compound A19.

Another embodiment of this invention is directed to a pharmaceutically acceptable salt of compound A20.

Another embodiment of this invention is directed to a pharmaceutically acceptable salt of compound A21.

Another embodiment of this invention is directed to a pharmaceutically acceptable salt of compound A22.

Another embodiment of this invention is directed to a pharmaceutically acceptable salt of compound A23.

Another embodiment of this invention is directed to a pharmaceutically acceptable salt of compound A24.

Another embodiment of this invention is directed to a pharmaceutically acceptable salt of compound A25.

Another embodiment of this invention is directed to a pharmaceutically acceptable salt of compound A26.

Another embodiment of this invention is directed to a pharmaceutically acceptable salt of compound A27.

Another embodiment of this invention is directed to a pharmaceutically acceptable salt of compound A28.

Another embodiment of this invention is directed to a pharmaceutically acceptable salt of compound A29.

Another embodiment of this invention is directed to a pharmaceutically acceptable salt of compound A30.

Another embodiment of this invention is directed to a pharmaceutically acceptable salt of compound A31.

Another embodiment of this invention is directed to a pharmaceutically acceptable salt of compound A32.

Another embodiment of this invention is directed to a pharmaceutically acceptable salt of compound A33.

Another embodiment of this invention is directed to a pharmaceutically acceptable salt of compound A34.

Another embodiment of this invention is directed to a pharmaceutically acceptable salt of compound A35.

Another embodiment of this invention is directed to a pharmaceutically acceptable salt of compound A36.

Another embodiment of this invention is directed to a pharmaceutically acceptable salt of compound A37.

Another embodiment of this invention is directed to a pharmaceutically acceptable salt of compound A38.

Another embodiment of this invention is directed to a pharmaceutically acceptable salt of compound A39.

Another embodiment of this invention is directed to a pharmaceutically acceptable salt of compound A40.

Another embodiment of this invention is directed to a pharmaceutically acceptable salt of compound A41.

Another embodiment of this invention is directed to a pharmaceutically acceptable salt of compound A42.

Another embodiment of this invention is directed to a pharmaceutically acceptable salt of compound A43.

Another embodiment of this invention is directed to a pharmaceutically acceptable salt of compound A44.

Another embodiment of this invention is directed to a pharmaceutically acceptable salt of compound A45.

Another embodiment of this invention is directed to a pharmaceutically acceptable salt of compound A46.

Another embodiment of this invention is directed to a pharmaceutically acceptable salt of compound A47.

Another embodiment of this invention is directed to a pharmaceutically acceptable salt of compound A48.

Another embodiment of this invention is directed to a solvate of compound A1.

Another embodiment of this invention is directed to a solvate of compound A2.

Another embodiment of this invention is directed to solvate of compound A3.

Another embodiment of this invention is directed to solvate of compound A4.

Another embodiment of this invention is directed to a solvate of compound A5.

Another embodiment of this invention is directed to a solvate of compound A6.

Another embodiment of this invention is directed to a solvate of compound A7.

Another embodiment of this invention is directed to a solvate of compound A8.

Another embodiment of this invention is directed to a solvate of compound A9.

Another embodiment of this invention is directed to a solvate of compound A10.

Another embodiment of this invention is directed to solvate of compound A11.

Another embodiment of this invention is directed to a solvate of compound A12.

Another embodiment of this invention is directed to a solvate of compound A13.

Another embodiment of this invention is directed to a solvate of compound A14.

Another embodiment of this invention is directed to a solvate of compound A15.

Another embodiment of this invention is directed to a solvate of compound A16.

Another embodiment of this invention is directed to a solvate of compound A18.

Another embodiment of this invention is directed to a solvate of compound A19.

Another embodiment of this invention is directed to a solvate of compound A20.

Another embodiment of this invention is directed to a solvate of compound A21

Another embodiment of this invention is directed to a solvate of compound A22.

Another embodiment of this invention is directed to a solvate of compound A23.

Another embodiment of this invention is directed to a solvate of compound A24.

Another embodiment of this invention is directed to a solvate of compound A25.

Another embodiment of this invention is directed to a solvate of compound A26.

Another embodiment of this invention is directed to a solvate of compound A27.

Another embodiment of this invention is directed to a solvate of compound A28.

Another embodiment of this invention is directed to a solvate of compound A29.

Another embodiment of this invention is directed to a solvate of compound A30.

Another embodiment of this invention is directed to a solvate of compound A31

Another embodiment of this invention is directed to a solvate of compound A32.

Another embodiment of this invention is directed to a solvate of compound A33.

Another embodiment of this invention is directed to a solvate of compound A34.

Another embodiment of this invention is directed to a solvate of compound A35.

Another embodiment of this invention is directed to a solvate of compound A36.

Another embodiment of this invention is directed to a solvate of compound A37.

Another embodiment of this invention is directed to a solvate of compound A38.

Another embodiment of this invention is directed to a solvate of compound A39.

Another embodiment of this invention is directed to a solvate of compound A40.

Another embodiment of this invention is directed to a solvate of compound A41

Another embodiment of this invention is directed to a solvate of compound A42.

Another embodiment of this invention is directed to a solvate of compound A43.

Another embodiment of this invention is directed to a solvate of compound A44.

Another embodiment of this invention is directed to a solvate of compound A45.

Another embodiment of this invention is directed to a solvate of compound A46.

Another embodiment of this invention is directed to a solvate of compound A47.

Another embodiment of this invention is directed to a solvate of compound A48.

Other embodiments of this invention are directed to any one of the embodiments of formula 1.0 wherein the compound is in pure and isolated form.

Other embodiments of this invention are directed to any one of the embodiments of formula 1.0 wherein the compound is in pure form.

Other embodiments of this invention are directed to any one of the embodiments of formula 1.0 wherein the compound is in isolated form.

Other embodiments of this invention are directed to any one of the compounds of A1 to A16 and A18 to A48 in pure and isolated form.

Other embodiments of this invention are directed to any one of the compounds of A1 to A16 and A18 to A30 in pure and isolated form.

Other embodiments of this invention are directed to any one of the compounds of A1 to A16 and A18 to A26 in pure and isolated form.

Other embodiments of this invention are directed to any one of the compounds of A31 to A48 in pure and isolated form.

Other embodiments of this invention are directed to any one of the compounds of A1 to A16 and A18 to A48 in pure form.

Other embodiments of this invention are directed to any one of the compounds of A1 to A16 and A18 to A30 in pure form.

Other embodiments of this invention are directed to any one of the compounds of A1 to A16 and A18 to A26 in pure form.

Other embodiments of this invention are directed to any one of the compounds of A31 to A48 in pure.

Other embodiments of this invention are directed to any one of the compounds of A1 to A16 and A18 to A48 in isolated form.

Other embodiments of this invention are directed to any one of the compounds of A1 to A16 and A18 to A30 in isolated form.

Other embodiments of this invention are directed to any one of the compounds of A1 to A16 and A18 to A26 in isolated form.

Other embodiments of this invention are directed to any one of the compounds of A31 to A48 in isolated form.

Another embodiment of this invention is directed to a pharmaceutical composition comprising an effective amount of at least one compound (e.g., 1, 2 or 3, or 1 or 2, or 1, and usually 1) of formula 1.0 (preferably of formula 1.1) and a pharmaceutically acceptable carrier.

Another embodiment of this invention is directed to a pharmaceutical composition comprising an effective amount of a compound of formula 1.0 (preferably of formula 1.1) and a pharmaceutically acceptable carrier.

Another embodiment of this invention is directed to a pharmaceutical composition comprising an effective amount of at least one compound (e.g., 1, 2 or 3, or 1 or 2, or 1, and usually 1) selected from the group consisting of: A1 to A16 and A18 to A48, and a pharmaceutically acceptable carrier.

Another embodiment of this invention is directed to a pharmaceutical composition comprising an effective amount of at least one compound (e.g., 1, 2 or 3, or 1 or 2, or 1, and usually 1) selected from the group consisting of: A1 to A16 and A18 to A30, and a pharmaceutically acceptable carrier.

Another embodiment of this invention is directed to a pharmaceutical composition comprising an effective amount of at least one compound (e.g., 1, 2 or 3, or 1 or 2, or 1, and usually 1) selected from the group consisting of: A1 to A16 and A18 to A26, and a pharmaceutically acceptable carrier.

Another embodiment of this invention is directed to a pharmaceutical composition comprising an effective amount of at least one compound (e.g., 1, 2 or 3, or 1 or 2, or 1, and usually 1) selected from the group consisting of: A31 to A48, and a pharmaceutically acceptable carrier.

Another embodiment of this invention is directed to a pharmaceutical composition comprising an effective amount of a compound selected from the group consisting of: A1 to A16 and A18 to A48, and a pharmaceutically acceptable carrier.

Another embodiment of this invention is directed to a pharmaceutical composition comprising an effective amount of a compound selected from the group consisting of: A1 to A16 and A18 to A30, and a pharmaceutically acceptable carrier.

Another embodiment of this invention is directed to a pharmaceutical composition comprising an effective amount of a compound selected from the group consisting of: A1 to A16 and A18 to A26, and a pharmaceutically acceptable carrier.

Another embodiment of this invention is directed to a pharmaceutical composition comprising an effective amount of a compound selected from the group consisting of: A31 to A48, and a pharmaceutically acceptable carrier.

Another embodiment of this invention is directed to a pharmaceutical composition comprising an effective amount of at least one compound (e.g., 1, 2 or 3, or 1 or 2, or 1, and usually 1) of formula 1.0 (preferably of formula 1.1), at least one (e.g., 1, 2 or 3, or 1 or 2, or 1, and usually 1) other active pharmaceutically active ingredient, and a pharmaceutically acceptable carrier.

Another embodiment of this invention is directed to a pharmaceutical composition comprising an effective amount of a compound of formula 1.0 (preferably of formula 1.1), another active pharmaceutically active ingredient, and a pharmaceutically acceptable carrier.

Another embodiment of this invention is directed to a pharmaceutical composition comprising an effective amount of at least one compound (e.g., 1, 2 or 3, or 1 or 2, or 1, and usually 1) selected from the group consisting of: A1 to A16 and A18 to A48, at least one (e.g., 1, 2 or 3, or 1 or 2, or 1, and usually 1) other active pharmaceutically active ingredient, and a pharmaceutically acceptable carrier.

Another embodiment of this invention is directed to a pharmaceutical composition comprising an effective amount of at least one compound (e.g., 1, 2 or 3, or 1 or 2, or 1, and usually 1) selected from the group consisting of: A1 to A16 and A18 to A30, at least one (e.g., 1, 2 or 3, or 1 or 2, or 1, and usually 1) other active pharmaceutically active ingredient, and a pharmaceutically acceptable carrier.

Another embodiment of this invention is directed to a pharmaceutical composition comprising an effective amount of at least one compound (e.g., 1, 2 or 3, or 1 or 2, or 1, and usually 1) selected from the group consisting of: A1 to A16 and A18 to A26, at least one (e.g., 1, 2 or 3, or 1 or 2, or 1, and usually 1) other active pharmaceutically active ingredient, and a pharmaceutically acceptable carrier.

Another embodiment of this invention is directed to a pharmaceutical composition comprising an effective amount of at least one compound (e.g., 1, 2 or 3, or 1 or 2, or 1, and usually 1) selected from the group consisting of: A31 to A48, at least one (e.g., 1, 2 or 3, or 1 or 2, or 1, and usually 1) other active pharmaceutically active ingredient, and a pharmaceutically acceptable carrier.

Another embodiment of this invention is directed to a pharmaceutical composition comprising an effective amount of a compound selected from the group consisting of: A1 to A16 and A18 to A48, another active pharmaceutically active ingredient, and a pharmaceutically acceptable carrier.

Another embodiment of this invention is directed to a pharmaceutical composition comprising an effective amount of a compound selected from the group consisting of: A1 to A16 and A18 to A30, another active pharmaceutically active ingredient, and a pharmaceutically acceptable carrier.

Another embodiment of this invention is directed to a pharmaceutical composition comprising an effective amount of a compound selected from the group consisting of: A1 to A16 and A18 to A26, another active pharmaceutically active ingredient, and a pharmaceutically acceptable carrier.

Another embodiment of this invention is directed to a pharmaceutical composition comprising an effective amount of a compound selected from the group consisting of: A31 to A48, another active pharmaceutically active ingredient, and a pharmaceutically acceptable carrier.

Another embodiment of this invention is directed to a pharmaceutical composition comprising an effective amount of at least one compound (e.g., 1, 2 or 3, or 1 or 2, or 1, and usually 1) of formula 1.0 (preferably of formula 1.1), at least one (e.g., 1, 2 or 3, or 1 or 2, or 1, and usually 1) chemotherapeutic agent, and a pharmaceutically acceptable carrier.

Another embodiment of this invention is directed to a pharmaceutical composition comprising an effective amount of a compound of formula 1.0 (preferably of formula 1.1), a chemotherapeutic agent, and a pharmaceutically acceptable carrier.

Another embodiment of this invention is directed to a pharmaceutical composition comprising an effective amount of at least one compound (e.g., 1, 2 or 3, or 1 or 2, or 1, and usually 1) selected from the group consisting of: A1 to A16 and A18 to A48, at least one (e.g., 1, 2 or 3, or 1 or 2, or 1, and usually 1) chemotherapeutic agent, and a pharmaceutically acceptable carrier.

Another embodiment of this invention is directed to a pharmaceutical composition comprising an effective amount of at least one compound (e.g., 1, 2 or 3, or 1 or 2, or 1, and usually 1) selected from the group consisting of: A1 to A16 and A18 to A30, at least one (e.g., 1, 2 or 3, or 1 or 2, or 1, and usually 1) chemotherapeutic agent, and a pharmaceutically acceptable carrier.

Another embodiment of this invention is directed to a pharmaceutical composition comprising an effective amount of at least one compound (e.g., 1, 2 or 3, or 1 or 2, or 1, and usually 1) selected from the group consisting of: A1 to A16 and A18 to A26, at least one (e.g., 1, 2 or 3, or 1 or 2, or 1, and usually 1) chemotherapeutic agent, and a pharmaceutically acceptable carrier.

Another embodiment of this invention is directed to a pharmaceutical composition comprising an effective amount of at least one compound (e.g., 1, 2 or 3, or 1 or 2, or 1, and usually 1) selected from the group consisting of: A31 to A48, at least one (e.g., 1, 2 or 3, or 1 or 2, or 1, and usually 1) chemotherapeutic agent, and a pharmaceutically acceptable carrier.

Another embodiment of this invention is directed to a pharmaceutical composition comprising an effective amount of a compound selected from the group consisting of: A1 to A16 and A18 to A48, a chemotherapeutic agent, and a pharmaceutically acceptable carrier.

Another embodiment of this invention is directed to a pharmaceutical composition comprising an effective amount of a compound selected from the group consisting of: A1 to A16 and A18 to A30, a chemotherapeutic agent, and a pharmaceutically acceptable carrier.

Another embodiment of this invention is directed to a pharmaceutical composition comprising an effective amount of a compound selected from the group consisting of: A1 to A16 and A18 to A26, a chemotherapeutic agent, and a pharmaceutically acceptable carrier.

Another embodiment of this invention is directed to a pharmaceutical composition comprising an effective amount of a compound selected from the group consisting of: A31 to A48, a chemotherapeutic agent, and a pharmaceutically acceptable carrier.

Another embodiment of this invention is directed to a method of treating cancer in a patient in need of such treatment, said method comprising administering to said patient an effective amount of at least one (1, 2 or 3, or 1 or 2, or 1, and usually 1) compound of formula 1.0 (preferably of formula 1.6).

Another embodiment of this invention is directed to a method of treating cancer in a patient in need of such treatment, said method comprising administering to said patient an effective amount of one compound of formula 1.0 (preferably of formula 1.6).

Another embodiment of this invention is directed to a method of treating cancer in a patient in need of such treatment, said method comprising administering to said patient an effective amount of at least one (1, 2 or 3, or 1 or 2, or 1, and usually 1) compound of A1 to A16 and A18 to A48.

Another embodiment of this invention is directed to a method of treating cancer in a patient in need of such treatment, said method comprising administering to said patient an effective amount of at least one (1, 2 or 3, or 1 or 2, or 1, and usually 1) compound of A1 to A16 and A18 to A30.

Another embodiment of this invention is directed to a method of treating cancer in a patient in need of such treatment, said method comprising administering to said patient an effective amount of at least one (1, 2 or 3, or 1 or 2, or 1, and usually 1) compound of A1 to A16 and A18 to A26.

Another embodiment of this invention is directed to a method of treating cancer in a patient in need of such treatment, said method comprising administering to said patient an effective amount of at least one (1, 2 or 3, or 1 or 2, or 1, and usually 1) compound of A31 to A48.

Another embodiment of this invention is directed to a method of treating cancer in a patient in need of such treatment, said method comprising administering to said patient an effective amount of one compound of A1 to A16 and A18 to A48.

Another embodiment of this invention is directed to a method of treating cancer in a patient in need of such treatment, said method comprising administering to said patient an effective amount of one compound of A1 to A16 and A18 to A30.

Another embodiment of this invention is directed to a method of treating cancer in a patient in need of such treatment, said method comprising administering to said patient an effective amount of one compound of A1 to A16 and A18 to A26.

Another embodiment of this invention is directed to a method of treating cancer in a patient in need of such treatment, said method comprising administering to said patient an effective amount of one compound of A31 to A48.

Another embodiment of this invention is directed to a method of treating cancer in a patient in need of such treatment, said method comprising administering to said patient an effective amount of at least one (1, 2 or 3, or 1 or 2, or 1, and usually 1) compound of formula 1.0, and an effective amount of at least one (1, 2 or 3, or 1 or 2, or 1, and usually 1) chemotherapeutic agent.

Another embodiment of this invention is directed to a method of treating cancer in a patient in need of such treatment, said method comprising administering to said patient an effective amount of one compound of formula 1.0, and an effective amount of at least one (1, 2 or 3, or 1 or 2, or 1, and usually 1) chemotherapeutic agent.

Another embodiment of this invention is directed to a method of treating cancer in a patient in need of such treatment, said method comprising administering to said patient an effective amount of at least one (1, 2 or 3, or 1 or 2, or 1, and usually 1) compound of A1 to A16 and A18 to A48, and an effective amount of at least one (1, 2 or 3, or 1 or 2, or 1, and usually 1) chemotherapeutic agent.

Another embodiment of this invention is directed to a method of treating cancer in a patient in need of such treatment, said method comprising administering to said patient an effective amount of at least one (1, 2 or 3, or 1 or 2, or 1, and usually 1) compound of A1 to A16 and A18 to A30, and an effective amount of at least one (1, 2 or 3, or 1 or 2, or 1, and usually 1) chemotherapeutic agent.

Another embodiment of this invention is directed to a method of treating cancer in a patient in need of such treatment, said method comprising administering to said patient an effective amount of at least one (1, 2 or 3, or 1 or 2, or 1, and usually 1) compound of A1 to A16 and A18 to A26, and an effective amount of at least one (1, 2 or 3, or 1 or 2, or 1, and usually 1) chemotherapeutic agent.

Another embodiment of this invention is directed to a method of treating cancer in a patient in need of such treatment, said method comprising administering to said patient an effective amount of at least one (1, 2 or 3, or 1 or 2, or 1, and usually 1) compound of A31 to A48, and an effective amount of at least one (1, 2 or 3, or 1 or 2, or 1, and usually 1) chemotherapeutic agent.

Another embodiment of this invention is directed to a method of treating cancer in a patient in need of such treatment, said method comprising administering to said patient an effective amount of one compound of A1 to A16 and A18 to A48, and an effective amount of at least one (1, 2 or 3, or 1 or 2, or 1, and usually 1) chemotherapeutic agent.

Another embodiment of this invention is directed to a method of treating cancer in a patient in need of such treatment, said method comprising administering to said patient an effective amount of one compound of A1 to A16 and A18 to A30, and an effective amount of at least one (1, 2 or 3, or 1 or 2, or 1, and usually 1) chemotherapeutic agent.

Another embodiment of this invention is directed to a method of treating cancer in a patient in need of such treatment, said method comprising administering to said patient an effective amount of one compound of A1 to A16 and A18 to A26, and an effective amount of at least one (1, 2 or 3, or 1 or 2, or 1, and usually 1) chemotherapeutic agent.

Another embodiment of this invention is directed to a method of treating cancer in a patient in need of such treatment, said method comprising administering to said patient an effective amount of one compound of A31 to A48, and an effective amount of at least one (1, 2 or 3, or 1 or 2, or 1, and usually 1) chemotherapeutic agent.

The compounds of this invention inhibit the activity of ERK1 and ERK2 Thus, this invention further provides a method of inhibiting ERK in mammals, especially humans, by the administration of an effective amount (e.g., a therapeutically effective amount) of one or more (e.g., one) compounds of this invention. The administration of the compounds of this invention to patients, to inhibit ERK1 and/or ERK2, is useful in the treatment of cancer.

In any of the methods of treating cancer described herein, unless stated otherwise, the methods can optionally include the administration of an effective amount of one or more (e.g., 1, 2 or 3, or 1 or 2, or 1) chemotherapeutic agents. The chemotherapeutic agents can be administered currently or sequentially with the compounds of this invention.

The methods of treating cancer described herein include methods wherein a combination of drugs (i.e., compounds, or pharmaceutically active ingredients, or pharmaceutical compositions) are used (i.e., the methods of treating cancer of this invention include combination therapies). Those skilled in the art will appreciate that the drugs are generally administered individually as a pharmaceutical composition. The use of a pharmaceutical composition comprising more than one drug is within the scope of this invention.

In any of the methods of treating cancer described herein, unless stated otherwise, the methods can optionally include the administration of an effective amount of radiation therapy. For radiation therapy, 7-radiation is preferred.

Examples of cancers which may be treated by the methods of this invention include, but are not limited to: (A) lung cancer (e.g., lung adenocarcinoma and non small cell lung cancer), (B) pancreatic cancers (e.g., pancreatic carcinoma such as, for example, exocrine pancreatic carcinoma), (C) colon cancers (e.g., colorectal carcinomas, such as, for example, colon adenocarcinoma and colon adenoma), (D) myeloid leukemias (for example, acute myelogenous leukemia (AML), CML, and CMML), (E) thyroid cancer, (F) myelodysplastic syndrome (MDS), (G) bladder carcinoma, (H) epidermal carcinoma, (I) melanoma, (J) breast cancer, (K) prostate cancer, (L) head and neck cancers (e.g., squamous cell cancer of the head and neck), (M) ovarian cancer, (N) brain cancers (e.g., gliomas, such as glioma blastoma multiforme), (O) cancers of mesenchymal origin (e.g., fibrosarcomas and rhabdomyosarcomas), (P) sarcomas, (Q) tetracarcinomas, (R) nuroblastomas, (S) kidney carcinomas, (T) hepatomas, (U) non-Hodgkin's lymphoma, (V) multiple myeloma, and (W) anaplastic thyroid carcinoma.

Thus, another embodiment of this invention is directed to a method for treating lung cancer, pancreatic cancer, colon cancer (e.g., colorectal cancer), myeloid leukemias (e.g., AML, CML, and CMML), thyroid cancer, myelodysplastic syndrome (MDS), bladder carcinoma, epidermal carcinoma, melanoma, breast cancer, prostate cancer, head and neck cancers (e.g., squamous cell cancer of the head and neck), ovarian cancer, brain cancers (e.g., gliomas, such as glioma blastoma multiforme), cancers of mesenchymal origin (e.g., fibrosarcomas and rhabdomyosarcomas), sarcomas, tetracarcinomas, nuroblastomas, kidney carcinomas, hepatomas, non-Hodgkin's lymphoma, multiple myeloma, or anaplastic thyroid carcinoma, in a patient in need of such treatment, said method comprising administering to said patient an effective amount of at least one (e.g., 1, 2 or 3, 1 or 2, and usually 1) compound of formula 1.0.

Another embodiment of this invention is directed to a method for treating lung cancer, pancreatic cancer, colon cancer (e.g., colorectal cancer), myeloid leukemias (e.g., AML, CML, and CMML), thyroid cancer, myelodysplastic syndrome (MDS), bladder carcinoma, epidermal carcinoma, melanoma, breast cancer, prostate cancer, head and neck cancers (e.g., squamous cell cancer of the head and neck), ovarian cancer, brain cancers (e.g., gliomas, such as glioma blastoma multiforme), cancers of mesenchymal origin (e.g., fibrosarcomas and rhabdomyosarcomas), sarcomas, tetracarcinomas, nuroblastomas, kidney carcinomas, hepatomas, non-Hodgkin's lymphoma, multiple myeloma, or anaplastic thyroid carcinoma in a patient in need of such treatment, said method comprising administering to said patient an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

Another embodiment of this invention is directed to a method for treating lung cancer, pancreatic cancer, colon cancer (e.g., colorectal cancer), myeloid leukemias (e.g., AML, CML, and CMML), thyroid cancer, myelodysplastic syndrome (MDS), bladder carcinoma, epidermal carcinoma, melanoma, breast cancer, prostate cancer, head and neck cancers (e.g., squamous cell cancer of the head and neck), ovarian cancer, brain cancers (e.g., gliomas, such as glioma blastoma multiforme), cancers of mesenchymal origin (e.g., fibrosarcomas and rhabdomyosarcomas), sarcomas, tetracarcinomas, nuroblastomas, kidney carcinomas, hepatomas, non-Hodgkin's lymphoma, multiple myeloma, or anaplastic thyroid carcinoma in a patient in need of such treatment, said method comprising administering to said patient an effective amount of a pharmaceutical composition comprising an effective amount of at least one (e.g., 1, 2 or 3, 1 or 2, and usually 1) compound of formula 1.0.

Another embodiment of this invention is directed to a method for treating lung cancer, pancreatic cancer, colon cancer (e.g., colorectal cancer), myeloid leukemias (e.g., AML, CML, and CMML), thyroid cancer, myelodysplastic syndrome (MDS), bladder carcinoma, epidermal carcinoma, melanoma, breast cancer, prostate cancer, head and neck cancers (e.g., squamous cell cancer of the head and neck), ovarian cancer, brain cancers (e.g., gliomas, such as glioma blastoma multiforme), cancers of mesenchymal origin (e.g., fibrosarcomas and rhabdomyosarcomas), sarcomas, tetracarcinomas, nuroblastomas, kidney carcinomas, hepatomas, non-Hodgkin's lymphoma, multiple myeloma, or anaplastic thyroid carcinoma in a patient in need of such treatment, said method comprising administering to said patient an effective amount of a pharmaceutical composition comprising an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

Another embodiment of this invention is directed to a method for treating cancer in a patient in need of such treatment, said method comprising administering to said patient an effective amount of at least one (e.g., 1, 2 or 3, 1 or 2, and usually 1) compound of formula 1.0, wherein said cancer is selected from the group consisting of: melanoma, pancreatic cancer, thyroid cancer, colorectal cancer, lung cancer, breast cancer, and ovarian cancer.

Another embodiment of this invention is directed to a method for treating cancer in a patient in need of such treatment, said method comprising administering to said patient an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent wherein said cancer is selected from the group consisting of: melanoma, pancreatic cancer, thyroid cancer, colorectal cancer, lung cancer, breast cancer, and ovarian cancer.

Another embodiment of this invention is directed to a method for treating cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0, wherein said cancer is selected from the group consisting of: melanoma, pancreatic cancer, thyroid cancer, colorectal cancer, lung cancer, breast cancer, and ovarian cancer.

Another embodiment of this invention is directed to a method for treating cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent wherein said cancer is selected from the group consisting of: melanoma, pancreatic cancer, thyroid cancer, colorectal cancer, lung cancer, breast cancer, and ovarian cancer.

Another embodiment of this invention is directed to a method for treating melanoma in a patient in need of such treatment, said method comprising administering to said patient an effective amount of at least one (e.g., 1, 2 or 3, 1 or 2, and usually 1) compound of formula 1.0.

Another embodiment of this invention is directed to a method for treating melanoma in a patient in need of such treatment, said method comprising administering to said patient an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

Another embodiment of this invention is directed to a method for treating melanoma in a patient in need of such treatment, said method comprising administering to said patient an effective amount of a pharmaceutical composition comprising an effective amount of at least one (e.g., 1, 2 or 3, 1 or 2, and usually 1) compound of formula 1.0.

Another embodiment of this invention is directed to a method for treating melanoma in a patient in need of such treatment, said method comprising administering to said patient an effective amount of a pharmaceutical composition comprising an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

Another embodiment of this invention is directed to a method for treating pancreatic cancer in a patient in need of such treatment, said method comprising administering to said patient an effective amount of at least one (e.g., 1, 2 or 3, 1 or 2, and usually 1) compound of formula 1.0.

Another embodiment of this invention is directed to a method for treating pancreatic cancer in a patient in need of such treatment, said method comprising administering to said patient an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

Another embodiment of this invention is directed to a method for treating pancreatic cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0.

Another embodiment of this invention is directed to a method for treating pancreatic cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

Another embodiment of this invention is directed to a method for treating thyroid cancer in a patient in need of such treatment, said method comprising administering to said patient an effective amount of at least one (e.g., 1, 2 or 3, 1 or 2, and usually 1) compound of formula 1.0.

Another embodiment of this invention is directed to a method for treating thyroid cancer in a patient in need of such treatment, said method comprising administering to said patient an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

Another embodiment of this invention is directed to a method for treating thyroid cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0.

Another embodiment of this invention is directed to a method for treating thyroid cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

Another embodiment of this invention is directed to a method for treating colorectal cancer in a patient in need of such treatment, said method comprising administering to said patient an effective amount of at least one (e.g., 1, 2 or 3, 1 or 2, and usually 1) compound of formula 1.0.

Another embodiment of this invention is directed to a method for treating colorectal cancer in a patient in need of such treatment, said method comprising administering to said patient an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

Another embodiment of this invention is directed to a method for treating colorectal cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0.

Another embodiment of this invention is directed to a method for treating colorectal cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

Another embodiment of this invention is directed to a method for treating lung cancer in a patient in need of such treatment, said method comprising administering to said patient an effective amount of at least one (e.g., 1, 2 or 3, 1 or 2, and usually 1) compound of formula 1.0.

Another embodiment of this invention is directed to a method for treating lung cancer in a patient in need of such treatment, said method comprising administering to said patient an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

Another embodiment of this invention is directed to a method for treating lung cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0.

Another embodiment of this invention is directed to a method for treating lung cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

Another embodiment of this invention is directed to a method for treating breast cancer in a patient in need of such treatment, said method comprising administering to said patient an effective amount of at least one (e.g., 1, 2 or 3, 1 or 2, and usually 1) compound of formula 1.0.

Another embodiment of this invention is directed to a method for treating breast cancer in a patient in need of such treatment, said method comprising administering to said patient an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

Another embodiment of this invention is directed to a method for treating breast cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0.

Another embodiment of this invention is directed to a method for treating breast cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

Another embodiment of this invention is directed to a method for treating ovarian cancer in a patient in need of such treatment, said method comprising administering to said patient an effective amount of at least one (e.g., 1, 2 or 3, 1 or 2, and usually 1) compound of formula 1.0.

This invention also provides a method for treating ovarian cancer in a patient in need of such treatment, said method comprising administering to said patient an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

Another embodiment of this invention is directed to a method for treating ovarian cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0.

Another embodiment of this invention is directed to a method for treating ovarian cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

Other embodiments of this invention are directed to methods of treating breast cancer (i.e., post-menopausal and pre-menopausal breast cancer, e.g., hormone-dependent breast cancer) in a patient in need of such treatment, said treatment comprising the administration of an effective amount of at least one (e.g., 1, 2 or 3, 1 or 2, and usually 1) compound of formula 1.0 in combination with hormonal therapies (i.e., antihormonal agents).

Other embodiments of this invention are directed to methods of treating breast cancer (i.e., post-menopausal and pre-menopausal breast cancer, e.g., hormone-dependent breast cancer) in a patient in need of such treatment, said treatment comprising the administration of an effective amount of a pharmaceutical composition comprising an effective amount of at least one (e.g., 1, 2 or 3, 1 or 2, and usually 1) compound of formula 1.0 in combination with hormonal therapies (i.e., antihormonal agents).

Other embodiments of this invention are directed to methods of treating breast cancer (i.e., post-menopausal and pre-menopausal breast cancer, e.g., hormone-dependent breast cancer) in a patient in need of such treatment, said treatment comprising the administration of an effective amount of at least one (e.g., 1, 2 or 3, 1 or 2, and usually 1) compound of formula 1.0 in combination with hormonal therapies (i.e., antihormonal agents), and in combination with an effective amount of at least one (e.g., 1, 2 or 3, 1 or 2, or 1) chemotherapeutic agent.

Other embodiments of this invention are directed to methods of treating breast cancer (i.e., post-menopausal and pre-menopausal breast cancer, e.g., hormone-dependent breast cancer) in a patient in need of such treatment, said treatment comprising the administration of an effective amount of a pharmaceutical composition comprising an effective amount of at least one (e.g., 1, 2 or 3, 1 or 2, and usually 1) compound of formula 1.0 in combination with hormonal therapies (i.e., antihormonal agents), and in combination with an effective amount of at least one (e.g., 1, 2 or 3, 1 or 2, or 1) chemotherapeutic agent.

The methods of treating breast cancer described herein include the treatment of hormone-dependent metastatic and advanced breast cancer, adjuvant therapy for hormone-dependent primary and early breast cancer, the treatment of ductal carcinoma in situ, and the treatment of inflammatory breast cancer in situ.

The methods of treating hormone-dependent breast cancer can also be used to prevent breast cancer in patients having a high risk of developing breast cancer.

Thus, other embodiment of this invention are directed to methods of preventing breast cancer (i.e., post-menopausal and premenopausal breast cancer, e.g., hormone-dependent breast cancer) in a patient in need of such treatment, said treatment comprising the administration of an effective amount of at least one (e.g., 1, 2 or 3, 1 or 2, and usually 1) compound of formula 1.0 in combination with hormonal therapies (i.e., antihormonal agents).

Other embodiments of this invention are directed to methods of preventing breast cancer (i.e., post-menopausal and premenopausal breast cancer, e.g., hormone-dependent breast cancer) in a patient in need of such treatment, said treatment comprising the administration of an effective amount of a pharmaceutical composition comprising an effective amount of at least one (e.g., 1, 2 or 3, 1 or 2, and usually 1) compound of formula 1.0 in combination with hormonal therapies (i.e., antihormonal agents).

Other embodiments of this invention are directed to methods of preventing breast cancer (i.e., post-menopausal and premenopausal breast cancer, e.g., hormone-dependent breast cancer) in a patient in need of such treatment, said treatment comprising the administration of an effective amount of at least one (e.g., 1, 2 or 3, 1 or 2, and usually 1) compound of formula 1.0 in combination with hormonal therapies (i.e., antihormonal agents), and in combination with an effective amount of at least one (e.g., 1, 2 or 3, 1 or 2, or 1) chemotherapeutic agent.

Other embodiments of this invention are directed to methods of preventing breast cancer (i.e., post-menopausal and premenopausal breast cancer, e.g., hormone-dependent breast cancer) in a patient in need of such treatment, said treatment comprising the administration of an effective amount of a pharmaceutical composition comprising an effective amount of at least one (e.g., 1, 2 or 3, 1 or 2, and usually 1) compound of formula 1.0 in combination with hormonal therapies (i.e., antihormonal agents), and in combination with an effective amount of at least one (e.g., 1, 2 or 3, 1 or 2, or 1) chemotherapeutic agent.

Another embodiment of this invention is directed to a method for treating brain cancer (e.g., glioma, such as glioma blastoma multiforme) in a patient in need of such treatment, said method comprising administering to said patient an effective amount of at least one (e.g., 1, 2 or 3, 1 or 2, and usually 1) compound of formula 1.0.

Another embodiment of this invention is directed to a method for treating brain cancer (e.g., glioma, such as glioma blastoma multiforme) in a patient in need of such treatment, said method comprising administering to said patient an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

Another embodiment of this invention is directed to a method for treating brain cancer (e.g., glioma, such as glioma blastoma multiforme) a in a patient in need of such treatment, said method comprising administering to said patient an effective amount of a pharmaceutical composition comprising an effective amount of at least one (e.g., 1, 2 or 3, 1 or 2, and usually 1) compound of formula 1.0.

Another embodiment of this invention is directed to a method for treating brain cancer (e.g., glioma, such as glioma blastoma multiforme) in a patient in need of such treatment, said method comprising administering to said patient an effective amount of a pharmaceutical composition comprising an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

Another embodiment of this invention is directed to a method for treating brain cancer (e.g., glioma, such as glioma blastoma multiforme) in a patient in need of such treatment, said method comprising administering to said patient an effective amount of at least one (e.g., 1, 2 or 3, 1 or 2, and usually 1) compound of formula 1.0, in combination with an effective amount of a chemotherapeutic agent wherein said chemotherapeutic agent is temozolomide.

Another embodiment of this invention is directed to a method for treating brain cancer (e.g., glioma, such as glioma blastoma multiforme) in a patient in need of such treatment, said method comprising administering to said patient an effective amount of a pharmaceutical composition comprising an effective amount of at least one (e.g., 1, 2 or 3, 1 or 2, and usually 1) compound of formula 1.0, in combination with an effective amount of a chemotherapeutic agent, wherein said chemotherapeutic agent is temozolomide.

Another embodiment of this invention is directed to a method for treating prostate cancer in a patient in need of such treatment, said method comprising administering to said patient an effective amount of at least one (e.g., 1, 2 or 3, 1 or 2, and usually 1) compound of formula 1.0.

Another embodiment of this invention is directed to a method for treating prostate cancer in a patient in need of such treatment, said method comprising administering to said patient an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

Another embodiment of this invention is directed to a method for treating prostate cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0.

Another embodiment of this invention is directed to a method for treating prostate cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

Another embodiment of this invention is directed to a method for treating myelodysplastic syndrome in a patient in need of such treatment, said method comprising administering to said patient an effective amount of at least one (e.g., 1, 2 or 3, 1 or 2, and usually 1) compound of formula 1.0.

Another embodiment of this invention is directed to a method for treating myelodysplastic syndrome in a patient in need of such treatment, said method comprising administering to said patient an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

Another embodiment of this invention is directed to a method for treating myelodysplastic syndrome in a patient in need of such treatment, said method comprising administering to said patient an effective amount of a pharmaceutical composition comprising an effective amount of at least one (e.g., 1, 2 or 3, 1 or 2, and usually 1) compound of formula 1.0.

Another embodiment of this invention is directed to a method for treating myelodysplastic syndrome in a patient in need of such treatment, said method comprising administering to said patient an effective amount of a pharmaceutical composition comprising an effective amount of at least one (e.g., 1, 2 or 3, 1 or 2, and usually 1) compound of formula I, in combination with an effective amount of at least one (e.g., 1, 2 or 3, 1 or 2, or 1) chemotherapeutic agent.

Another embodiment of this invention is directed to a method for treating myeloid leukemias in a patient in need of such treatment, said method comprising administering to said patient an effective amount of at least one (e.g., 1, 2 or 3, 1 or 2, and usually 1) compound of formula 1.0.

Another embodiment of this invention is directed to a method for treating myeloid leukemias in a patient in need of such treatment, said method comprising administering to said patient an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

Another embodiment of this invention is directed to a method for treating myeloid leukemias in a patient in need of such treatment, said method comprising administering to said patient an effective amount of a pharmaceutical composition comprising an effective amount of at least one (e.g., 1, 2 or 3, 1 or 2, and usually 1) compound of formula 1.0.

Another embodiment of this invention is directed to a method for treating myeloid leukemias in a patient in need of such treatment, said method comprising administering to said patient an effective amount of a pharmaceutical composition comprising an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

Another embodiment of this invention is directed to a method for treating acute myelogenous leukemia (AML) in a patient in need of such treatment, said method comprising administering to said patient an effective amount of at least one (e.g., 1, 2 or 3, 1 or 2, and usually 1) compound of formula 1.0.

Another embodiment of this invention is directed to a method for treating acute myelogenous leukemia (AML) in a patient in need of such treatment, said method comprising administering to said patient an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

Another embodiment of this invention is directed to a method for treating acute myelogenous leukemia (AML) in a patient in need of such treatment, said method comprising administering to said patient an effective amount of a pharmaceutical composition comprising an effective amount of at least one (e.g., 1, 2 or 3, 1 or 2, and usually 1) compound of formula 1.0.

Another embodiment of this invention is directed to a method for treating acute myelogenous leukemia (AML) in a patient in need of such treatment, said method comprising administering to said patient an effective amount of a pharmaceutical composition comprising an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

Another embodiment of this invention is directed to a method for treating chronic myelomonocytic leukemia (CMML) in a patient in need of such treatment, said method comprising administering to said patient an effective amount of at least one (e.g., 1, 2 or 3, 1 or 2, and usually 1) compound of formula 1.0.

Another embodiment of this invention is directed to a method for treating chronic myelomonocytic leukemia (CMML) in a patient in need of such treatment, said method comprising administering to said patient an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

Another embodiment of this invention is directed to a method for treating chronic myelomonocytic leukemia (CMML) in a patient in need of such treatment, said method comprising administering to said patient an effective amount of a pharmaceutical composition comprising an effective amount of at least one (e.g., 1, 2 or 3, 1 or 2, and usually 1) compound of formula 1.0.

Another embodiment of this invention is directed to a method for treating chronic myelomonocytic leukemia (CMML) in a patient in need of such treatment, said method comprising administering to said patient an effective amount of a pharmaceutical composition comprising an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

Another embodiment of this invention is directed to a method for treating chronic myelogenous leukemia (chronic myeloid leukemia, CML) in a patient in need of such treatment, said method comprising administering to said patient an effective amount of at least one (e.g., 1, 2 or 3, 1 or 2, and usually 1) compound of formula 1.0.

Another embodiment of this invention is directed to a method for treating chronic myelogenous leukemia (chronic myeloid leukemia, CML) in a patient in need of such treatment, said method comprising administering to said patient an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

Another embodiment of this invention is directed to a method for treating chronic myelogenous leukemia (chronic myeloid leukemia, CML) in a patient in need of such treatment, said method comprising administering to said patient an effective amount of a pharmaceutical composition comprising an effective amount of at least one (e.g., 1, 2 or 3, 1 or 2, and usually 1) compound of formula 1.0.

Another embodiment of this invention is directed to a method for treating chronic myelogenous leukemia (chronic myeloid leukemia, CML) in a patient in need of such treatment, said method comprising administering to said patient an effective amount of a pharmaceutical composition comprising an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

Another embodiment of this invention is directed to a method for treating myeloid leukemias in a patient in need of such treatment, said method comprising administering to said patient an effective amount of at least one (e.g., 1, 2 or 3, 1 or 2, and usually 1) compound of formula 1.0.

Another embodiment of this invention is directed to a method for treating myeloid leukemias in a patient in need of such treatment, said method comprising administering to said patient an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

Another embodiment of this invention is directed to a method for treating myeloid leukemias in a patient in need of such treatment, said method comprising administering to said patient an effective amount of a pharmaceutical composition comprising an effective amount of at least one (e.g., 1, 2 or 3, 1 or 2, and usually 1) compound of formula 1.0.

Another embodiment of this invention is directed to a method for treating myeloid leukemias in a patient in need of such treatment, said method comprising administering to said patient an effective amount of a pharmaceutical composition comprising an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

Another embodiment of this invention is directed to a method for treating bladder cancer in a patient in need of such treatment, said method comprising administering to said patient an effective amount of at least one (e.g., 1, 2 or 3, 1 or 2, and usually 1) compound of formula 1.0.

Another embodiment of this invention is directed to a method for treating bladder cancer in a patient in need of such treatment, said method comprising administering to said patient an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

Another embodiment of this invention is directed to a method for treating bladder cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0.

Another embodiment of this invention is directed to a method for treating bladder cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

Another embodiment of this invention is directed to a method for treating non-Hodgkin's lymphoma in a patient in need of such treatment, said method comprising administering to said patient an effective amount of at least one (e.g., 1, 2 or 3, 1 or 2, and usually 1) compound of formula 1.0.

Another embodiment of this invention is directed to a method for treating non-Hodgkin's lymphoma in a patient in need of such treatment, said method comprising administering to said patient an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

Another embodiment of this invention is directed to a method for treating non-Hodgkin's lymphoma in a patient in need of such treatment, said method comprising administering to said patient an effective amount of a pharmaceutical composition comprising an effective amount of at least one (e.g., 1, 2 or 3, 1 or 2, and usually 1) compound of formula 1.0.

Another embodiment of this invention is directed to a method for treating non-Hodgkin's lymphoma in a patient in need of such treatment, said method comprising administering to said patient an effective amount of a pharmaceutical composition comprising an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

Another embodiment of this invention is directed to a method for treating multiple myeloma in a patient in need of such treatment, said method comprising administering to said patient an effective amount of at least one (e.g., 1, 2 or 3, 1 or 2, and usually 1) compound of formula 1.0.

Another embodiment of this invention is directed to a method for treating multiple myeloma in a patient in need of such treatment, said method comprising administering to said patient an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

Another embodiment of this invention is directed to a method for treating multiple myeloma in a patient in need of such treatment, said method comprising administering to said patient an effective amount of a pharmaceutical composition comprising an effective amount of at least one (e.g., 1, 2 or 3, 1 or 2, and usually 1) compound of formula 1.0.

Another embodiment of this invention is directed to a method for treating multiple myeloma in a patient in need of such treatment, said method comprising administering to said patient an effective amount of a pharmaceutical composition comprising an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

Chemotherapeutic agents (antineoplastic agent) include but are not limited to: microtubule affecting agents, alkylating agents, antimetabolites, natural products and their derivatives, hormones and steroids (including synthetic analogs), and synthetics.

Examples of alkylating agents (including nitrogen mustards, ethylenimine derivatives, alkyl sulfonates, nitrosoureas and triazenes) include: Uracil mustard, Chlormethine, Cyclophosphamide (Cytoxan®), Ifosfamide, Melphalan, Chlorambucil, Pipobroman, Triethylene-melamine, Triethylenethiophosphoramine, Busulfan, Carmustine, Lomustine, Streptozocin, Dacarbazine, and Temozolomide.

Examples of antimetabolites (including folic acid antagonists, pyrimidine analogs, purine analogs and adenosine deaminase inhibitors) include: Methotrexate, 5-Fluorouracil, Floxuridine, Cytarabine, 6-Mercaptopurine, 6-Thioguanine, Fludarabine phosphate, Pentostatine, and Gemcitabine.

Examples of natural products and their derivatives (including vinca alkaloids, antitumor antibiotics, enzymes, lymphokines and epipodophyllotoxins) include: Vinblastine, Vincristine, Vindesine, Bleomycin, Dactinomycin, Daunorubicin, Doxorubicin, Epirubicin, Idarubicin, Paclitaxel (paclitaxel is a microtubule affecting agent and is commercially available as Taxon, Paclitaxel derivatives (e.g. taxotere), Mithramycin, Deoxyco-formycin, Mitomycin-C, L-Asparaginase, Interferons (especially IFN-a), Etoposide, and Teniposide.

Examples of hormones and steroids (including synthetic analogs) include: 17α-Ethinylestradiol, Diethylstilbestrol, Testosterone, Prednisone, Fluoxymesterone, Dromostanolone propionate, Testolactone, Megestrolacetate, Tamoxifen, Methylprednisolone, Methyl-testosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, and Zoladex.

Examples of synthetics (including inorganic complexes such as platinum coordination complexes): Cisplatin, Carboplatin, Hydroxyurea, Amsacrine, Procarbazine, Mitotane, Mitoxantrone, Levamisole, and Hexamethylmelamine.

Examples of other chemotherapeutics include: Navelbene, CPT-11, Anastrazole, Letrazole, Capecitabinbe, Reloxafine, and Droloxafine.

A microtubule affecting agent (e.g., paclitaxel, a paclitaxel derivative or a paclitaxel-like compound), as used herein, is a compound that interferes with cellular mitosis, i.e., having an anti-mitotic effect, by affecting microtubule formation and/or action. Such agents can be, for instance, microtubule stabilizing agents or agents which disrupt microtubule formation.

Microtubule affecting agents, useful in the methods of this invention, are well known to those skilled in the art and include, but are not limited to: Allocolchicine (NSC 406042), Halichondrin B (NSC 609395), Colchicine (NSC 757), Colchicine derivatives (e.g., NSC 33410), Dolastatin 10 (NSC 376128), Maytansine (NSC 153858), Rhizoxin (NSC 332598), Paclitaxel (Taxol®, NSC 125973), Paclitaxel derivatives (e.g., Taxotere, NSC 608832), Thiocolchicine (NSC 361792), Trityl Cysteine (NSC 83265), Vinblastine Sulfate (NSC 49842), Vincristine Sulfate (NSC 67574), Epothilone A, Epothilone, Discodermolide (see Service, (1996) Science, 274:2009), Estramustine, Nocodazole, MAP4, and the like. Examples of such agents are described in, for example, Bulinski (1997) J. Cell Sci. 110:3055-3064, Panda (1997) Proc. Natl. Acad. Sci. USA 94:10560-10564, Muhlradt (1997) Cancer Res. 57:3344-3346, Nicolaou (1997) Nature 387:268-272, Vasquez (1997) Mol. Biol. Cell. 8:973-985, and Panda (1996) J. Biol. Chem. 271:29807-29812.

Chemotherapeutic agents with paclitaxel-like activity include, but are not limited to, paclitaxel and paclitaxel derivatives (paclitaxel-like compounds) and analogues. Paclitaxel and its derivatives (e.g. Taxol and Taxotere) are available commercially. In addition, methods of making paclitaxel and paclitaxel derivatives and analogues are well known to those of skill in the art (see, e.g., U.S. Pat. Nos. 5,569,729; 5,565,478; 5,530,020; 5,527,924; 5,508,447; 5,489,589; 5,488,116; 5,484,809; 5,478,854; 5,478,736; 5,475,120; 5,468,769; 5,461,169; 5,440,057; 5,422,364; 5,411,984; 5,405,972; and 5,296,506).

More specifically, the term "paclitaxel" as used herein refers to the drug commercially available as Taxol® (NSC number: 125973). Taxol® inhibits eukaryotic cell replication by enhancing polymerization of tubulin moieties into stabilized microtubule bundles that are unable to reorganize into the proper structures for mitosis. Of the many available chemotherapeutic drugs, paclitaxel has generated interest because of its efficacy in clinical trials against drug-refractory tumors, including ovarian and mammary gland tumors (Hawkins (1992) Oncology, 6: 17-23, Horwitz (1992) Trends Pharmacol. Sci. 13: 134-146, Rowinsky (1990) J. Natl. Canc. Inst. 82: 1247-1259).

Additional microtubule affecting agents can be assessed using one of many such assays known in the art, e.g., a semiautomated assay which measures the tubulin-polymerizing activity of paclitaxel analogs in combination with a cellular assay to measure the potential of these compounds to block cells in mitosis (see Lopes (1997) Cancer Chemother. Pharmacol. 41:37-47).

Generally, activity of a test compound is determined by contacting a cell with that compound and determining whether or not the cell cycle is disrupted, in particular, through the inhibition of a mitotic event. Such inhibition may be mediated by disruption of the mitotic apparatus, e.g., disruption of normal spindle formation. Cells in which mitosis is interrupted may be characterized by altered morphology (e.g., microtubule compaction, increased chromosome number, etc.).

Compounds with possible tubulin polymerization activity can be screened in vitro. For example, the compounds are screened against cultured WR21 cells (derived from line 69-2 wap-ras mice) for inhibition of proliferation and/or for altered cellular morphology, in particular for microtubule compaction. In vivo screening of positive-testing compounds can then be performed using nude mice bearing the WR21 tumor cells. Detailed protocols for this screening method are described by Porter (1995) Lab. Anim. Sci., 45(2):145-150.

Other methods of screening compounds for desired activity are well known to those of skill in the art. Typically such assays involve assays for inhibition of microtubule assembly and/or disassembly. Assays for microtubule assembly are described, for example, by Gaskin et al. (1974) J. Molec. Biol., 89: 737-758. U.S. Pat. No. 5,569,720 also provides in vitro and in vivo assays for compounds with paclitaxel-like activity.

Thus, in the methods of this invention wherein at least one chemotherapeutic agent is used, examples of said chemotherapeutic agents include those selected from the group consisting of: microtubule affecting agents, alkylating agents, antimetabolites, natural products and their derivatives, hormones and steroids (including synthetic analogs), and synthetics.

In the methods of this invention wherein at least one chemotherapeutic agent is used, examples of said chemotherapeutic agents also include: (1) taxanes, (2) platinum coordinator compounds, (3) epidermal growth factor (EGF) inhibitors that are antibodies, (4) EGF inhibitors that are small molecules, (5) vascular endolithial growth factor (VEGF) inhibitors that are antibodies, (6) VEGF kinase inhibitors that are small molecules, (7) estrogen receptor antagonists or selective estrogen receptor modulators (SERMs), (8) anti-tumor nucleoside derivatives, (9) epothilones, (10) topoisomerase inhibitors, (11) vinca alkaloids, (12) antibodies that are inhibitors of αVβ3 integrins, (13) folate antagonists, (14) ribonucleotide reductase inhibitors, (15) anthracyclines, (16) biologics; (17) inhibitors of angiogenesis and/or suppressors of tumor necrosis factor alpha (TNF-alpha) such as thalidomide (or related imid), (18) Bcr/abl kinase inhibitors, (19) MEK1 and/or MEK 2 inhibitors that are small molecules, (20) IGF-1 and IGF-2 inhibitors that are small molecules, (21) small molecule inhibitors of RAF and BRAF kinases, (22) small molecule inhibitors of cell cycle dependent kinases such as CDK1, CDK2, CDK4 and CDK6, (23) alkylating agents, and (24) farnesyl protein transferase inhibitors (also know as FPT inhibitors or FTI (i.e., farnesyl transfer inhibitors)).

In the methods of this invention wherein at least one chemotherapeutic agent is used, examples of such chemotherapeutic agents include:

(1) taxanes such as paclitaxel (TAXOL®) and/or docetaxel (Taxotere®);

(2) platinum coordinator compounds, such as, for example, carboplatin, cisplatin and oxaliplatin (e.g. Eloxatin);

(3) EGF inhibitors that are antibodies, such as: HER2 antibodies (such as, for example trastuzumab (Herceptin®), Genentech, Inc.), Cetuximab (Erbitux, IMC-C225, ImClone Systems), EMD 72000 (Merck KGaA), anti-EFGR monoclonal antibody ABX (Abgenix), TheraCIM-h-R3 (Center of Molecular Immunology), monoclonal antibody 425 (Merck KGaA), monoclonal antibody ICR-62 (ICR, Sutton, England); Herzyme (Elan Pharmaceutical Technologies and Ribozyme Pharmaceuticals), PKI 166 (Novartis), EKB 569 (Wyeth-Ayerst), GW 572016 (GlaxoSmithKline), CI 1033 (Pfizer Global Research and Development), trastuzmab-maytansinoid conjugate (Genentech, Inc.), mitumomab (Imclone Systems and Merck KGaA) and Melvax II (Imclone Systems and Merck KgaA);

(4) EGF inhibitors that are small molecules, such as, Tarceva™ (OSI-774, OSI Pharmaceuticals, Inc.), and Iressa (ZD 1839, Astra Zeneca);

(5) VEGF inhibitors that are antibodies such as: bevacizumab (Genentech, Inc.), and IMC-1C11 (ImClone Systems), DC 101 (a KDR VEGF Receptor 2 from ImClone Systems);

(6) VEGF kinase inhibitors that are small molecules such as SU 5416 (from Sugen, Inc), SU 6688 (from Sugen, Inc.), Bay 43-9006 (a dual VEGF and bRAF inhibitor from Bayer Pharmaceuticals and Onyx Pharmaceuticals);

(7) estrogen receptor antagonists or selective estrogen receptor modulators (SERMs), such as tamoxifen, idoxifene, raloxifene, trans-2,3-dihydroraloxifene, levormeloxifene, droloxifene, MDL 103,323, and acolbifene (Schering Corp.);

(8) anti-tumor nucleoside derivatives such as 5-fluorouracil, gemcitabine, capecitabine, cytarabine (Ara-C), fludarabine (F-Ara-A), decitabine, and chlorodeoxyadenosine (Cda, 2-Cda);

(9) epothilones such as BMS-247550 (Bristol-Myers Squibb), and EP0906 (Novartis Pharmaceuticals);

(10) topoisomerase inhibitors such as topotecan (Glaxo SmithKline), and Camptosar (Pharmacia);

(11) vinca alkaloids, such as, navelbine (Anvar and Fabre, France), vincristine and vinblastine;

(12) antibodies that are inhibitors of αVβ3 integrins, such as, LM-609 (see, Clinical Cancer Research, Vol. 6, page 3056-3061, August 2000, the disclosure of which is incorporated herein by reference thereto);

(13) folate antagonists, such as Methotrexate (MTX), and Premetrexed (Alimta);

(14) ribonucleotide reductase inhibitors, such as Hydroxyurea (HU);

(15) anthracyclines, such as Daunorubicin, Doxorubicin (Adriamycin), and Idarubicin;

(16) biologics, such as interferon (e.g., Intron-A and Roferon), pegylated interferon (e.g., Peg-Intron and Pegasys), and Rituximab (Rituxan, antibody used for the treatment of non-Hodgkin's lymphoma);

(17) thalidomide (or related imid);

(18) Bcr/abl kinase inhibitors, such as, for example Gleevec (STI-571), AMN-17, ONO12380, SU11248 (Sunitinib) and BMS-354825

(19) MEK1 and/or MEK2 inhibitors, such as PD0325901 and Arry-142886 (AZD6244);

(20) IGF-1 and IGF-2 inhibitors that are small molecules, such as, for example, NVP-AEW541;

(21) small molecule inhibitors of RAF and BRAF kinases, such as, for example, BAY 43-9006 (Sorafenib);

(22) small molecule inhibitors of cell cycle dependent kinases such as CDK1, CDK2, CDK4 and CDK6, such as, for example, CYC202, BMS387032, and Flavopiridol;

(23) alkylating agents, such as, for example, Temodar® brand of temozolornide;

(24) farnesyl protein transferase inhibitors, such as, for example:

(a) Sarasar® brand of Ionifarnib (i.e., 4-[2-[4-(3,10-dibromo-8-chloro-6,11-dihydro-5H-benzo[5,6]cyclohepta[1,2-b]hyridin-11-yl)-1-piperidinyl)-2-oxoethyl]-1-piperidinecarboxamide, see for example, U.S. Pat. No. 5,874,442 issued Feb. 23, 1999, and U.S. Pat. No. 6,632,455 issued Oct. 14, 2003 the disclosures of each being incorporated herein by reference thereto), (b) Zarnestra® brand of tipifarnib (i.e., (R)-6-amino[(4-chlorophenyl)(1-methyl-1H-imidazol-5-yl)methyl]-4-(3-chlorophenyl)-1-methyl-2(1H)-quinolinone, see for example, WO 97/16443 published May 9, 1997 and U.S. Pat. No. 5,968,952 issued Oct. 19, 1999, the disclosures of each being incorporated herein by reference thereto), and (c) Bristol-Myers Squibb 214662:

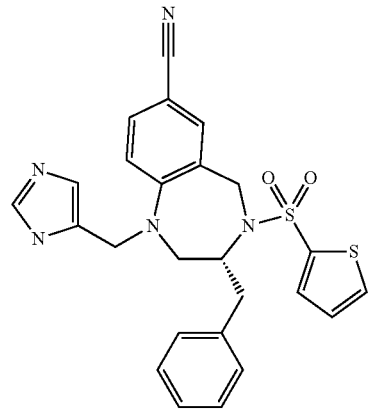 [SMILES: N#Cc1ccc2c(c1)CN(S(=O)(=O)c1cccs1)[C@H](Cc1ccccc1)CN2Cc1cnc[nH]1]

(see WO97/30992 published Aug. 28, 1997, U.S. Pat. No. 6,011,029 issued Jan. 4, 2000, and U.S. Pat. No. 6,455,523, the disclosures of each being incorporated herein by reference thereto).

The Bcr/abl kinase inhibitors, EGF receptor inhibitors, and HER-2 antibodies (EGF receptor inhibitors that are antibodies) described above are also known as signal transduction inhibitors. Therefore, chemotherapeutic agents, as used herein, include signal transduction inhibitors.

Typical signal transduction inhibitors, that are chemotherapeutic agents, include but are not limited to: (i) Bcr/abl kinase inhibitors such as, for example, STI 571 (Gleevec), (ii) Epidermal growth factor (EGF) receptor inhibitor such as, for example, Kinase inhibitors (Iressa, OSI-774) and antibodies (Imclone: C225 [Goldstein et al. (1995), Clin Cancer Res. 1:1311-1318], and Abgenix: ABX-EGF) and (iii) HER-2/neu receptor inhibitors such as, for example, Herceptin® (trastuzumab).

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA), the Physician's Desk Reference, 56th Edition, 2002 (published by Medical Economics company, Inc. Montvale, N.J. 07645-1742), the Physician's Desk Reference, 57th Edition, 2003 (published by Thompson PDR, Montvale, N.J. 07645-1742); and the Physician's Desk Reference, 60th Edition, 2006 (published by Thompson P D R, Montvale, N.J. 07645-1742); the disclosures of which are incorporated herein by reference thereto.

For example, the compound of formula 1.0 (e.g., a pharmaceutical composition comprising the compound of formula 1.0); can be administered orally (e.g., as a capsule), and the chemotherapeutic agents can be administered intravenously, usually as an IV solution. The use of a pharmaceutical composition comprising more than one drug is within the scope of this invention.

The compound of formula 1.0 and the chemotherapeutic agents are administered in therapeutically effective dosages to obtain clinically acceptable results, e.g., reduction or elimination of symptoms or of the tumor. Thus, the compound of formula 1.0 and chemotherapeutic agents can be administered concurrently or consecutively in a treatment protocol. The administration of the chemotherapeutic agents can be made according to treatment protocols already known in the art.

In general when more than one chemotherapeutic agent is used in the methods of this invention, the chemotherapeutic agents are administered on the same day either concurrently or consecutively in their standard dosage form. For example, the chemotherapeutic agents are usually administered intravenously, preferably by an IV drip using IV solutions well known in the art (e.g., isotonic saline (0.9% NaCl) or dextrose solution (e.g., 5% dextrose)).

When two or more chemotherapeutic agents are used, the chemotherapeutic agents are generally administered on the same day; however, those skilled in the art will appreciate that the chemotherapeutic agents can be administered on different days and in different weeks. The skilled clinician can administer the chemotherapeutic agents according to their recommended dosage schedule from the manufacturer of the agent and can adjust the schedule according to the needs of the patient, e.g., based on the patient's response to the treatment. For example, when gemcitabine is used in combination with a platinum coordinator compound, such as, for example, cisplatin, to treat lung cancer, both the gemcitabine and the cisplatin are given on the same day on day one of the treatment cycle, and then gemcitabine is given alone on day 8 and given alone again on day 15

The compounds of this invention and chemotherapeutic agents can be administered in a treatment protocol that usually lasts one to seven weeks, and is repeated typically from 6 to 12 times. Generally the treatment protocol can last one to four weeks. Treatment protocols of one to three weeks can also be used. A treatment protocol of one to two weeks can also be used. During this treatment protocol or cycle the compounds of this invention can be administered daily while the chemotherapeutic agents can be administered one or more times a week. Generally, a compound of this invention can be administered daily (i.e., once per day), and in one embodiment twice per day, and the chemotherapeutic agent is administered once a week or once every three weeks. For example, the taxanes (e.g., Paclitaxel (e.g., Taxol®) or Docetaxel (e.g., Taxotere®)) can be administered once a week or once every three weeks.

However, those skilled in the art will appreciate that treatment protocols can be varied according to the needs of the patient. Thus, the combination of compounds (drugs) used in the methods of this invention can be administered in variations of the protocols described above. For example, the compounds of this invention can be administered discontinuously rather than continuously during the treatment cycle. Thus, for example, during the treatment cycle the compounds of this invention can be administered daily for a week and then discontinued for a week, with this administration repeating during the treatment cycle. Or the compounds of this invention can be administered daily for two weeks and discontinued for a week, with this administration repeating during the treatment cycle. Thus, the compounds of this invention can be administered daily for one or more weeks during the cycle and discontinued for one or more weeks during the cycle, with this pattern of administration repeating during the treatment cycle. This discontinuous treatment can also be based upon numbers of days rather than a full week. For example, daily dosing for 1 to 6 days, no dosing for 1 to 6 days, with this pattern repeating during the treatment protocol. The number of days (or weeks) wherein the compounds of this invention are not dosed do not have to equal the number of days (or weeks) wherein the compounds of this invention are dosed. Usually, if a discontinuous dosing protocol is used, the number of days or weeks that the compounds of this invention are dosed is at least equal or greater than the number of days or weeks that the compounds of this invention are not dosed.

The chemotherapeutic agent could be given by bolus or continuous infusion. The chemotherapeutic agent could be given daily to once every week, or once every two weeks, or once every three weeks, or once every four weeks during the treatment cycle. If administered daily during a treatment cycle, this daily dosing can be discontinuous over the number of weeks of the treatment cycle. For example, dosed for a week (or a number of days), no dosing for a week (or a number of days, with the pattern repeating during the treatment cycle.

The compounds of this invention can be administered orally, preferably as a solid dosage form, and in one embodiment as a capsule, and while the total therapeutically effective daily dose can be administered in one to four, or one to two divided doses per day, generally, the therapeutically effective dose is given once or twice a day, and in one embodiment twice a day. The compounds of this invention can be administered in an amount of about 50 to about 400 mg once per day, and can be administered in an amount of about 50 to about 300 mg once per day. The compounds of this invention are generally administered in an amount of about 50 to about 350 mg twice a day, usually 50 mg to about 200 mg twice a day, and in one embodiment about 75 mg to about 125 mg administered twice a day, and in another embodiment about 100 mg administered twice a day.

If the patient is responding, or is stable, after completion of the therapy cycle, the therapy cycle can be repeated according to the judgment of the skilled clinician. Upon completion of the therapy cycles, the patient can be continued on the compounds of this invention at the same dose that was administered in the treatment protocol, or, if the dose was less than 200 mg twice a day, the dose can be raised to 200 mg twice a day. This maintenance dose can be continued until the patient progresses or can no longer tolerate the dose (in which case the dose can be reduced and the patient can be continued on the reduced dose).

The chemotherapeutic agents, used with the compounds of this invention, are administered in their normally prescribed dosages during the treatment cycle (i.e., the chemotherapeutic agents are administered according to the standard of practice for the administration of these drugs). For example: (a) about 30 to about 300 mg/m$^2$ for the taxanes; (b) about 30 to about 100 mg/m$^2$ for Cisplatin; (c) AUC of about 2 to about 8 for Carboplatin; (d) about 2 to about 4 mg/m$^2$ for EGF inhibitors that are antibodies; (e) about 50 to about 500 mg/m² for EGF inhibitors that are small molecules; (f) about 1 to about 10 mg/m² for VEGF kinase inhibitors that are antibodies; (g) about 50 to about 2400 mg/m² for VEGF inhibitors that are small molecules; (h) about 1 to about 20 mg for SERMs; (i) about 500 to about 1250 mg/m² for the anti-tumor nucleosides 5-Fluorouracil, Gemcitabine and Capecitabine; (j) for the anti-tumor nucleoside Cytarabine (Ara-C) 100-200 mg/m²/day for 7 to 10 days every 3 to 4 weeks, and high doses for refractory leukemia and lymphoma, i.e., 1 to 3 gm/m² for one hour every 12 hours for 4-8 doses every 3 to four weeks; (k) for the anti-tumor nucleoside Fludarabine (F-ara-A) 10-25 mg/m²/day every 3 to 4 weeks; (l) for the anti-tumor nucleoside Decitabine 30 to 75 mg/m² for three days every 6 weeks for a maximum of 8 cycles; (m) for the anti-tumor nucleoside Chlorodeoxyadenosine (CdA, 2-CdA) 0.05-0.1 mg/kg/day as continuous infusion for up to 7 days every 3 to 4 weeks; (n) about 1 to about 100 mg/m² for epothilones; (o) about 1 to about 350 mg/m² for topoisomerase inhibitors; (p) about 1 to about 50 mg/m² for vinca alkaloids; (q) for the folate antagonist Methotrexate (MTX) 20-60 mg/m² by oral, IV or IM every 3 to 4 weeks, the intermediate dose regimen is 80-250 mg/m² IV over 60 minutes every 3 to 4 weeks, and the high dose regimen is 250-1000 mg/m² IV given with leucovorin every 3 to 4 weeks; (r) for the folate antagonist Premetrexed (Alimta) 300-600 mg/m² (10 minutes IV infusion day 1) every 3 weeks; (s) for the ribonucleotide reductase inhibitor Hydroxyurea (HU) 20-50 mg/kg/day (as needed to bring blood cell counts down); (t) the platinum coordinator compound Oxaliplatin (Eloxatin) 50-100 mg/m² every 3 to 4 weeks (preferably used for solid tumors such as non-small cell lung cancer, colorectal cancer and ovarian cancer); (u) for the anthracycline daunorubicin 10-50 mg/m²/day IV for 3-5 days every 3 to 4 weeks; (v) for the anthracycline Doxorubicin (Adriamycin) 50-100 mg/m² IV continuous infusion over 1-4 days every 3 to 4 weeks, or 10-40 mg/m² IV weekly; (w) for the anthracycline Idarubicin 10-30 mg/m² daily for 1-3 days as a slow IV infusion over 10-20 minutes every 3 to 4 weeks; (x) for the biologic interferon (Intron-A, Roferon) 5 to 20 million IU three times per week; (y) for the biologic pegylated interferon (Peg-intron, Pegasys) 3 to 4 micrograms/kg/day chronic sub cutaneous (until relapse or loss of activity); (z) for the biologic Rituximab (Rituxan) (antibody used for non-Hodgkin's lymphoma) 200-400 mg/m² IV weekly over 4-8 weeks for 6 months; (aa) for the alkylating agent temozolomide 75 mg/m² to 250 mg/m², for example, 150 mg/m², or for example, 200 mg/m², such as 200 mg/m² for 5 days; and (bb) for the MEK1 and/or MEK2 inhibitor PD0325901, 15 mg to 30 mg, for example, 15 mg daily for 21 days every 4 weeks.

Gleevec can be used orally in an amount of about 200 to about 800 mg/day.

Thalidomide (and related imids) can be used orally in amounts of about 200 to about 800 mg/day, and can be contiuously dosed or used until releapse or toxicity. See for example Mitsiades et al., "Apoptotic signaling induced by immunomodulatory thalidomide analogs in human multiple myeloma cells; therapeutic implications", Blood, 99(12):4525-30, Jun. 15, 2002, the disclosure of which is incorporated herein by reference thereto.

The FPT inhibitor Sarasar® (brand of Ionifarnib) can be administered orally (e.g., capsule) in amounts of about 50 to about 200 mg given twice a day, or in amounts of about 75 to about 125 mg given twice a day, or in amounts of about 100 to about 200 mg given twice a day, or in an amount of about 100 mg given twice a day.

Paclitaxel (e.g., Taxol®), for example, can be administered once per week in an amount of about 50 to about 100 mg/m² and in another example about 60 to about 80 mg/m². In another example Paclitaxel (e.g., Taxol®) can be administered once every three weeks in an amount of about 150 to about 250 mg/m² and in another example about 175 to about 225 mg/m².

In another example, Docetaxel (e.g., Taxotere®) can be administered once per week in an amount of about 10 to about 45 mg/m². In another example Docetaxel (e.g., Taxotere®) can be administered once every three weeks in an amount of about 50 to about 100 mg/m².

In another example Cisplatin can be administered once per week in an amount of about 20 to about 40 mg/m². In another example Cisplatin can be administered once every three weeks in an amount of about 60 to about 100 mg/m².

In another example Carboplatin can be administered once per week in an amount to provide an AUC of about 2 to about 3. In another example Carboplatin can be administered once every three weeks in an amount to provide an AUC of about 5 to about 8.

Other embodiments of this invention are directed to any one of the method of treating cancer embodiments wherein the compounds of formula 1.0 and the chemotherapeutic agents are administered as a pharmaceutical composition comprising an effective amount of the compounds of formula 1.0, an effective amount of the chemotherapeutic agents, and a pharmaceutically acceptable carrier.

Other embodiments of this invention are directed to any one of the method of treating cancer embodiments wherein a chemotherapeutic agent is used wherein the chemotherapeutic agent is selected from the group consisting of: paclitaxel, docetaxel, carboplatin, cisplatin, gemcitabine, tamoxifen, Herceptin, Cetuximab, Tarceva, Iressa, bevacizumab, navelbine, IMC-1C11, SU5416 and SU6688.

Other embodiments of this invention are directed to any one of the method of treating cancer embodiments wherein a chemotherapeutic agent is used wherein the chemotherapeutic agent is selected from the group consisting of: paclitaxel, docetaxel, carboplatin, cisplatin, navelbine, gemcitabine, and Herceptin.

Other embodiments of this invention are directed to any one of the method of treating cancer embodiments wherein a chemotherapeutic agent is used wherein the chemotherapeutic agent is selected from the group consisting of: Cyclophasphamide, 5-Fluorouracil, Temozolomide, Vincristine, Cisplatin, Carboplatin, and Gemcitabine.

Other embodiments of this invention are directed to any one of the method of treating cancer embodiments wherein a chemotherapeutic agent is used wherein the chemotherapeutic agent is selected from the group consisting of: Gemcitabine, Cisplatin and Carboplatin.

This invention also provides a method of treating cancer in a patient in need of such treatment, said treatment comprising administering to said patient a therapeutically effective amount at least one (e.g., 1, 2 or 3, or 1 or 2, or 1, and usually 1) compound of formula 1.0, and therapeutically effective amounts of at least one (e.g., 1, 2 or 3, or 1 or 2, or 2, or 1) chemotherapeutic agent selected from the group consisting of: (1) taxanes, (2) platinum coordinator compounds, (3) epidermal growth factor (EGF) inhibitors that are antibodies, (4) EGF inhibitors that are small molecules, (5) vascular endolithial growth factor (VEGF) inhibitors that are antibodies, (6) VEGF kinase inhibitors that are small molecules, (7) estrogen receptor antagonists or selective estrogen receptor modulators (SERMs), (8) anti-tumor nucleoside derivatives, (9) epothilones, (10) topoisomerase inhibitors, (11) vinca alkaloids, (12) antibodies that are inhibitors of αVβ3 integrins, (13) folate antagonists, (14) ribonucleotide reductase inhibitors, (15) anthracyclines, (16) biologics; (17) inhibitors of angiogenesis and/or suppressors of tumor necrosis factor alpha (TNF-alpha) such as thalidomide (or related imid), (18) Bcr/abl kinase inhibitors, (19) MEK1 and/or MEK 2 inhibitors that are small molecules, (20) IGF-1 and IGF-2 inhibitors that are small molecules, (21) small molecule inhibitors of RAF and BRAF kinases, (22) small molecule inhibitors of cell cycle dependent kinases such as CDK1, CDK2, CDK4 and CDK6, (23) alkylating agents, and (24) farnesyl protein transferase inhibitors (also know as FPT inhibitors or FTI (i.e., farnesyl transfer inhibitors)).

This invention also provides a method of treating cancer in a patient in need of such treatment, said treatment comprising administering to said patient a therapeutically effective amount at least one (e.g., 1, 2 or 3, or 1 or 2, or 1, and usually 1) compound of formula 1.0, and therapeutically effective amounts of at least two (e.g., 2 or 3, or 2, and usually 2) different antineoplastic agents selected from the group consisting of: (1) taxanes, (2) platinum coordinator compounds, (3) epidermal growth factor (EGF) inhibitors that are antibodies, (4) EGF inhibitors that are small molecules, (5) vascular endolithial growth factor (VEGF) inhibitors that are antibodies, (6) VEGF kinase inhibitors that are small molecules, (7) estrogen receptor antagonists or selective estrogen receptor modulators (SERMs), (8) anti-tumor nucleoside derivatives, (9) epothilones, (10) topoisomerase inhibitors, (11) vinca alkaloids, (12) antibodies that are inhibitors of αVβ3 integrins, (13) folate antagonists, (14) ribonucleotide reductase inhibitors, (15) anthracyclines, (16) biologics; (17) inhibitors of angiogenesis and/or suppressors of tumor necrosis factor alpha (TNF-alpha) such as thalidomide (or related imid), (18) Bcr/abl kinase inhibitors, (19) MEK1 and/or MEK 2 inhibitors that are small molecules, (20) IGF-1 and IGF-2 inhibitors that are small molecules, (21) small molecule inhibitors of RAF and BRAF kinases, (22) small molecule inhibitors of cell cycle dependent kinases such as CDK1, CDK2, CDK4 and CDK6, (23) alkylating agents, and (24) farnesyl protein transferase inhibitors (also know as FPT inhibitors or FTI (i.e., farnesyl transfer inhibitors)).

This invention also provides a method of treating cancer in a patient in need of such treatment, said method comprising administering to said patient therapeutically effective amounts at least one (e.g., 1, 2 or 3, or 1 or 2, or 1, and usually 1) compound of formula 1.0, and an antineoplastic agent selected from the group consisting of: (1) EGF inhibitors that are antibodies, (2) EGF inhibitors that are small molecules, (3) VEGF inhibitors that are antibodies, and (4) VEGF inhibitors that are small molecules. Radiation therapy can also be used in conjunction with this above combination therapy, i.e., the above method using a combination of compounds of the invention and antineoplastic agent can also comprise the administration of a therapeutically effect amount of radiation.

This invention also provides a method of treating leukemias (e.g., acute myeloid leukemia (AML), and chronic myeloid leukemia (CML)) in a patient in need of such treatment, said method comprising administering to said patient therapeutically effective amounts at least one (e.g., 1, 2 or 3, or 1 or 2, or 1, and usually 1) compound of formula 1.0, and: (1) Gleevec and interferon to treat CML; (2) Gleevec and pegylated interferon to treat CML; (3) Gleevec to treat CML; (4) an anti-tumor nucleoside derivative (e.g., Ara-C) to treat AML; or (5) an anti-tumor nucleoside derivative (e.g., Ara-C) in combination with an anthracycline to treat AML.

This invention also provides a method of treating non-Hodgkin's lymphoma in a patient in need of such treatment, said method comprising administering therapeutically effective amounts at least one (e.g., 1, 2 or 3, or 1 or 2, or 1, and usually 1) compound of formula 1.0 and: (1) a biologic (e.g., Rituxan); (2) a biologic (e.g., Rituxan) and an anti-tumor nucleoside derivative (e.g., Fludarabine); or (3) Genasense (antisense to BCL-2).

This invention also provides a method of treating multiple myeloma in a patient in need of such treatment, said method comprising administering to said patient therapeutically effective amounts of at least one (e.g., 1, 2 or 3, or 1 or 2, or 1, and usually 1) compound of formula 1.0 and: (1) a proteosome inhibitor (e.g., PS-341 from Millenium); or (2) Thalidomide (or related imid).

This invention also provides a method of treating cancer in a patient in need of such treatment, said method comprising administering to said patient therapeutically effective amounts of: (a) at least one (e.g., 1, 2 or 3, or 1 or 2, or 1, and usually 1) compound of formula 1.0, and (b) at least one (e.g., 1, 2 or 3, or 1 or 2, or 2, or 1) antineoplastic agent selected from the group consisting of: (1) taxanes, (2) platinum coordinator compounds, (3) EGF inhibitors that are antibodies, (4) EGF inhibitors that are small molecules, (5) VEGF inhibitors that are antibodies, (6) VEGF kinase inhibitors that are small molecules, (7) estrogen receptor antagonists or selective estrogen receptor modulators, (8) anti-tumor nucleoside derivatives, (9) epothilones, (10) topoisomerase inhibitors, (11) vinca alkaloids, and (12) antibodies that are inhibitors of αVβ3 integrins.

This invention also provides a method of treating non small cell lung cancer in a patient in need of such treatment, said method comprising administering to said patient therapeutically effective amounts of: (a) at least one (e.g., 1, 2 or 3, or 1 or 2, or 1, and usually 1) compound of formula 1.0, and (b) at least one (e.g., 1, 2 or 3, or 1 or 2, or 2, or 1) antineoplastic agent selected from the group consisting of: (1) taxanes, (2) platinum coordinator compounds, (3) EGF inhibitors that are antibodies, (4) EGF inhibitors that are small molecules, (5) VEGF inhibitors that are antibodies, (6) VEGF kinase inhibitors that are small molecules, (7) estrogen receptor antagonists or selective estrogen receptor modulators, (8) anti-tumor nucleoside derivatives, (9) epothilones, (10) topoisomerase inhibitors, (11) vinca alkaloids, and (12) antibodies that are inhibitors of αVβ3 integrins.

This invention also provides a method of treating non small cell lung cancer in a patient in need of such treatment, said method comprising administering to said patient therapeutically effective amounts of: (a) at least one (e.g., 1, 2 or 3, or 1 or 2, or 1, and usually 1) compound of formula 1.0, and (b) at least one (e.g., 1, 2 or 3, or 1 or 2, or 2, or 1) antineoplastic agent selected from the group consisting of: (1) taxanes, (2) platinum coordinator compounds, (3) anti-tumor nucleoside derivatives, (4) topoisomerase inhibitors, and (5) vinca alkaloids.

This invention also provides a method of treating non small cell lung cancer in a patient in need of such treatment, said method comprising administering therapeutically effective amounts of: (a) at least one (e.g., 1, 2 or 3, or 1 or 2, or 1, and usually 1) compound of formula 1.0, (b) carboplatin, and (c) paclitaxel.

This invention also provides a method of treating non small cell lung cancer in a patient in need of such treatment, said method comprising administering to said patient therapeutically effective amounts of: (a) at least one (e.g., 1, 2 or 3, or 1 or 2, or 1, and usually 1) compound of formula 1.0, (b) cisplatin, and (c) gemcitabine.

This invention also provides a method of treating non small cell lung cancer in a patient in need of such treatment, said method comprising administering therapeutically effective amounts of: (a) at least one (e.g., 1, 2 or 3, or 1 or 2, or 1, and usually 1) compound of formula 1.0, (b) carboplatin, and (c) gemcitabine.

This invention also provides a method of treating non small cell lung cancer in a patient in need of such treatment, said method comprising administering therapeutically effective amounts of: (a) at least one (e.g., 1, 2 or 3, or 1 or 2, or 1, and usually 1) compound of formula 1.0, (b) Carboplatin, and (c) Docetaxel.

This invention also provides a method of treating cancer in a patient in need of such treatment, said method comprising administering therapeutically effective amounts of: (a) at least one (e.g., 1, 2 or 3, or 1 or 2, or 1, and usually 1) compound of formula 1.0, and (b) an antineoplastic agent selected from the group consisting of: (1) EGF inhibitors that are antibodies, (2) EGF inhibitors that are small molecules, (3) VEGF inhibitors that are antibodies, (4) VEGF kinase inhibitors that are small molecules.

This invention also provides a method of treating squamous cell cancer of the head and neck, in a patient in need of such treatment, said method comprising administering to said patient therapeutically effective amounts of: (a) at least one (e.g., 1, 2 or 3, or 1 or 2, or 1, and usually 1) compound of formula 1.0, and (b) at least one (e.g., 1, 2 or 3, or 1 or 2, or 2, or 1) antineoplastic agent selected from the group consisting of: (1) taxanes, and (2) platinum coordinator compounds.

This invention also provides a method of treating squamous cell cancer of the head and neck, in a patient in need of such treatment, said method comprising administering to said patient therapeutically effective amounts of: (a) at least one (e.g., 1, 2 or 3, or 1 or 2, or 1, and usually 1) compound of formula 1.0, and (b) at least one (e.g., 1, 2 or 3, or 1 or 2, or 2, or 1) antineoplastic agent selected from the group consisting of: (1) taxanes, (2) platinum coordinator compounds, and (3) anti-tumor nucleoside derivatives (e.g., 5-Fluorouracil).

This invention also provides a method of treating CML in a patient in need of such treatment, said method comprising administering therapeutically effective amounts of: (a) at least one (e.g., 1, 2 or 3, or 1 or 2, or 1, and usually 1) compound of formula 1.0, (b) Gleevec, and (c) interferon (e.g., Intron-A).

This invention also provides a method of treating CML in a patient in need of such treatment comprising administering therapeutically effective amounts of: (a) at least one (e.g., 1, 2 or 3, or 1 or 2, or 1, and usually 1) compound of formula 1.0, (b) Gleevec; and (c) pegylated interferon (e.g., Peg-Intron, and Pegasys).

This invention also provides a method of treating CML in a patient in need of such treatment comprising administering therapeutically effective amounts of: (a) at least one (e.g., 1, 2 or 3, or 1 or 2, or 1, and usually 1) compound of formula 1.0 and (b) Gleevec.

This invention also provides a method of treating CMML in a patient in need of such treatment, said method comprising administering to said patient therapeutically effective amounts of at least one (e.g., 1, 2 or 3, or 1 or 2, or 1, and usually 1) compound of formula 1.0.

This invention also provides a method of treating AML in a patient in need of such treatment, said method comprising administering to said patient therapeutically effective amounts of: (a) at least one (e.g., 1, 2 or 3, or 1 or 2, or 1, and usually 1) compound of formula 1.0, and (b) an anti-tumor nucleoside derivative (e.g., Cytarabine (i.e., Ara-C)).

This invention also provides a method of treating AML in a patient in need of such treatment, said method comprising administering to said patient therapeutically effective amounts of: (a) at least one (e.g., 1, 2 or 3, or 1 or 2, or 1, and usually 1) compound of formula 1.0, (b) an anti-tumor nucleoside derivative (e.g., Cytarabine (i.e., Ara-C)), and (c) an anthracycline.

This invention also provides a method of treating non-Hodgkin's lymphoma in a patient in need of such treatment, said method comprising administering to said patient therapeutically effective amounts of: (a) at least one (e.g., 1, 2 or 3, or 1 or 2, or 1, and usually 1) compound of formula 1.0, and (b) Rituximab (Rituxan).

This invention also provides a method of treating non-Hodgkin's lymphoma in a patient in need of such treatment, said method comprising administering to said patient therapeutically effective amounts of: (a) at least one (e.g., 1, 2 or 3, or 1 or 2, or 1, and usually 1) compound of formula 1.0, (b) Rituximab (Rituxan), and (c) an anti-tumor nucleoside derivative (e.g., Fludarabine (i.e., F-ara-A).

This invention also provides a method of treating non-Hodgkin's lymphoma in a patient in need of such treatment, said method comprising administering to said patient therapeutically effective amounts of: (a) at least one (e.g., 1, 2 or 3, or 1 or 2, or 1, and usually 1) compound of formula 1.0, and (b) Genasense (antisense to BCL-2).

This invention also provides a method of treating multiple myeloma in a patient in need of such treatment, said method comprising administering therapeutically effective amounts of: (a) at least one (e.g., 1, 2 or 3, or 1 or 2, or 1, and usually 1) compound of formula 1.0, and (b) a proteosome inhibitor (e.g., PS-341 (Millenium)).

This invention also provides a method of treating multiple myeloma in a patient in need of such treatment, said method comprising administering to said patient therapeutically effective amounts of: (a) at least one (e.g., 1, 2 or 3, or 1 or 2, or 1, and usually 1) compound of formula 1.0, and (b) Thalidomide or related imid.

This invention also provides a method of treating multiple myeloma in a patient in need of such treatment, said method comprising administering therapeutically effective amounts of: (a) at least one (e.g., 1, 2 or 3, or 1 or 2, or 1, and usually 1) compound of formula 1.0, and (b) Thalidomide.

This invention is also directed to the methods of treating cancer described herein, particularly those described above, wherein in addition to the administration of the compound of formula 1.0 and antineoplastic agents, radiation therapy is also administered prior to, during, or after the treatment cycle.

This invention also provides a method for treating cancer (e.g., lung cancer, prostate cancer and myeloid leukemias) in a patient in need of such treatment, said method comprising administering to said patient (1) an effective amount of at least one (e.g., 1, 2 or 3, or 1 or 2, or 1, and usually 1) compound of formula 1.0, in combination with (2) at least one (e.g., 1, 2 or 3, or 1 or 2, or 2, or 1) antineoplastic agent, microtubule affecting agent and/or radiation therapy.

This invention also provides a method of treating cancer in a patient in need of such treatment, said method comprising administering to said patient an effective amount of at least one (e.g., 1, 2 or 3, or 1 or 2, or 1, and usually 1) compound of formula 1.0 in combination with an effective amount of at least one (e.g., 1, 2 or 3, or 1 or 2, or 1, and usually 1) signal transduction inhibitor.

Thus, in one example (e.g., treating non small cell lung cancer): (1) the compound of formula 1.0 is administered in an amount of about 50 mg to about 200 mg twice a day, and in another example about 75 mg to about 125 mg administered twice a day, and in yet another example about 100 mg administered twice a day, (2) Paclitaxel (e.g., Taxol® is administered once per week in an amount of about 50 to about 100 mg/m², and in another example about 60 to about 80 mg/m², and (3) Carboplatin is administered once per week in an amount to provide an AUC of about 2 to about 3.

In another example (e.g., treating non small cell lung cancer): (1) the compound of formula 1.0 is administered in an amount of about 50 mg to about 200 mg twice a day, and in another example about 75 mg to about 125 mg administered twice a day, and yet in another example about 100 mg administered twice a day, (2) Paclitaxel (e.g., Taxol® is administered once per week in an amount of about 50 to about 100 mg/m², and in another example about 60 to about 80 mg/m², and (3) Cisplatin is administered once per week in an amount of about 20 to about 40 mg/m².

In another example (e.g., treating non small cell lung cancer): (1) the compound of formula 1.0 is administered in an amount of about 50 mg to about 200 mg twice a day, and in another example about 75 mg to about 125 mg administered twice a day, and in yet another example about 100 mg administered twice a day, (2) Docetaxel (e.g., Taxotere®) is administered once per week in an amount of about 10 to about 45 mg/m², and (3) Carboplatin is administered once per week in an amount to provide an AUC of about 2 to about 3.

In another example (e.g., treating non small cell lung cancer): (1) the compound of formula 1.0 is administered in an amount of about 50 mg to about 200 mg twice a day, and in another example about 75 mg to about 125 mg administered twice a day, and in yet another example about 100 mg administered twice a day, (2) Docetaxel (e.g., Taxotere®) is administered once per week in an amount of about 10 to about 45 mg/m², and (3) Cisplatin is administered once per week in an amount of about 20 to about 40 mg/m².

In another example (e.g., treating non small cell lung cancer): (1) the compound of formula 1.0 is administered in an amount of about 50 mg to about 200 mg twice a day, and in another example about 75 mg to about 125 mg administered twice a day, and in yet another example about 100 mg administered twice a day, (2) Paclitaxel (e.g., Taxol® is administered once every three weeks in an amount of about 150 to about 250 mg/m², and in another example about 175 to about 225 mg/m², and in yet another example 175 mg/m², and (3) Carboplatin is administered once every three weeks in an amount to provide an AUC of about 5 to about 8, and in another example 6.

In another example of treating non small cell lung cancer: (1) the compound of formula 1.0 is administered in an amount of 100 mg administered twice a day, (2) Paclitaxel (e.g., Taxol® is administered once every three weeks in an amount of 175 mg/m², and (3) Carboplatin is administered once every three weeks in an amount to provide an AUC of 6.

In another example (e.g., treating non small cell lung cancer): (1) the compound of formula 1.0 is administered in an amount of about 50 mg to about 200 mg twice a day, and in another example about 75 mg to about 125 mg administered twice a day, and in yet another example about 100 mg administered twice a day, (2) Paclitaxel (e.g., Taxol® is administered once every three weeks in an amount of about 150 to about 250 mg/m², and in another example about 175 to about 225 mg/m², and (3) Cisplatin is administered once every three weeks in an amount of about 60 to about 100 mg/m².

In another example (e.g., treating non small cell lung cancer): (1) the compound of formula 1.0 is administered in an amount of about 50 mg to about 200 mg twice a day, and in another example about 75 mg to about 125 mg administered twice a day, and in yet another example about 100 mg administered twice a day, (2) Docetaxel (e.g., Taxotere® is administered once every three weeks in an amount of about 50 to about 100 mg/m², and (3) Carboplatin is administered once every three weeks in an amount to provide an AUC of about 5 to about 8.

In another example (e.g., treating non small cell lung cancer): (1) the compound of formula 1.0 is administered in an amount of about 50 mg to about 200 mg twice a day, in another example about 75 mg to about 125 mg administered twice a day, and in yet another example about 100 mg administered twice a day, (2) Docetaxel (e.g., Taxotere® is administered once every three weeks in an amount of about 50 to about 100 mg/m², and (3) Cisplatin is administered once every three weeks in an amount of about 60 to about 100 mg/m².

In another example for treating non small cell lung cancer using the compounds of formula 1.0, Docetaxel and Carboplatin: (1) the compound of formula 1.0 is administered in an amount of about 50 mg to about 200 mg twice a day, and in another example about 75 mg to about 125 mg administered twice a day, and in yet another example about 100 mg administered twice a day, (2) Docetaxel (e.g., Taxotere® is administered once every three weeks in an amount of about 75 mg/m², and (3) Carboplatin is administered once every three weeks in an amount to provide an AUC of about 6.

In another example of the treatments of non-small cell lung cancer described above the Docetaxel (e.g., Taxotere®) and Cisplatin, the Docetaxel (e.g., Taxotere®) and Carboplatin, the Paclitaxel (e.g., Taxol®) and Carboplatin, or the Paclitaxel (e.g., Taxol®) and Cisplatin are administered on the same day.

In another example (e.g., CML): (1) the compound of formula 1.0 is administered in an amount of about 100 mg to about 200 mg administered twice a day, (2) Gleevec is administered in an amount of about 400 to about 800 mg/day orally, and (3) interferon (Intron-A) is administered in an amount of about 5 to about 20 million IU three times per week.

In another example (e.g., CML): (1) the compound of formula 1.0 is administered in an amount of about 100 mg to about 200 mg administered twice a day, (2) Gleevec is administered in an amount of about 400 to about 800 mg/day orally, and (3) pegylated interferon (Peg-Intron or Pegasys) is administered in an amount of about 3 to about 6 micrograms/kg/day.

In another example (e.g., non-Hodgkin's lymphoma): (1) the compound of formula 1.0 is administered in an amount of about 50 mg to about 200 mg twice a day, and in another example about 75 mg to about 125 mg administered twice a day, and in yet another example about 100 mg administered twice a day, and (2) Genasense (antisense to BCL-2) is administered as a continuous IV infusion at a dose of about 2 to about 5 mg/kg/day (e.g., 3 mg/kg/day) for 5 to 7 days every 3 to 4 weeks.

In another example (e.g., multiple myeloma): (1) the compound of formula 1.0 is administered in an amount of about 50 mg to about 200 mg twice a day, and in another example about 75 mg to about 125 mg administered twice a day, and in yet another example about 100 mg administered twice a day, and (2) the proteosome inhibitor (e.g., PS-341—Millenium) is administered in an amount of about 1.5 mg/m² twice weekly for two consecutive weeks with a one week rest period.

In another example (e.g., multiple myeloma): (1) the compound of formula 1.0 is administered in an amount of about 50 mg to about 200 mg twice a day, and in another example about 75 mg to about 125 mg administered twice a day, and in yet another example about 100 mg administered twice a day, and (2) the Thalidomide (or related imid) is administered orally in an amount of about 200 to about 800 mg/day, with dosing being continuous until relapse or toxicity.

In one embodiment of the methods of treating cancer of this invention, the chemotherapeutic agents are selected from the group consisting of: paclitaxel, docetaxel, carboplatin, cisplatin, gemcitabine, tamoxifen, Herceptin, Cetuximab, Tarceva, Iressa, bevacizumab, navelbine, IMC-1C11, SU5416 and SU6688.

In another embodiment of the methods of treating cancer of this invention, the chemotherapeutic agents are selected from the group consisting of: paclitaxel, docetaxel, carboplatin, cisplatin, navelbine, gemcitabine, and Herceptin.

Thus, one embodiment of this invention is directed to a method of treating cancer comprising administering to a patient in need of such treatment therapeutically effective amounts of the compound of formula 1.0, a taxane, and a platinum coordination compound.

Another embodiment of this invention is directed to a method of treating cancer comprising administering to a patient in need of such treatment therapeutically effective amounts of the compound of formula 1.0, a taxane, and a platinum coordination compound, wherein said compound of formula 1.0 is administered every day, said taxane is administered once per week per cycle, and said platinum coordinator compound is administered once per week per cycle. In another embodiment the treatment is for one to four weeks per cycle.

Another embodiment of this invention is directed to a method of treating cancer comprising administering to a patient in need of such treatment therapeutically effective amounts of the compound of formula 1.0, a taxane, and a platinum coordination compound, wherein said compound of formula 1.0 is administered every day, said taxane is administered once every three weeks per cycle, and said platinum coordinator compound is administered once every three weeks per cycle. In another embodiment the treatment is for one to three weeks per cycle.

Another embodiment of this invention is directed to a method of treating cancer comprising administering to a patient in need of such treatment therapeutically effective amounts of the compound of formula 1.0, paclitaxel, and carboplatin. In another embodiment, said compound of formula 1.0 is administered every day, said paclitaxel is administered once per week per cycle, and said carboplatin is administered once per week per cycle. In another embodiment the treatment is for one to four weeks per cycle.

Another embodiment of this invention is directed to a method of treating cancer comprising administering to a patient in need of such treatment therapeutically effective amounts of the compound of formula 1.0, paclitaxel, and carboplatin. In another embodiment, said compound of formula 1.0 is administered every day, said paclitaxel is administered once every three weeks per cycle, and said carboplatin is administered once every three weeks per cycle. In another embodiment the treatment is for one to three weeks per cycle.

Another embodiment of this invention is directed to a method for treating non small cell lung cancer in a patient in need of such treatment comprising administering daily a therapeutically effective amount of the compound of formula 1.0, administering a therapeutically effective amount of carboplatin once a week per cycle, and administering a therapeutically effective amount of paclitaxel once a week per cycle, wherein the treatment is given for one to four weeks per cycle. In another embodiment said compound of formula 1.0 is administered twice per day. In another embodiment said carboplatin and said paclitaxel are administered on the same day, and in another embodiment said carboplatin and said paclitaxel are administered consecutively, and in another embodiment said carboplatin is administered after said paclitaxel.

Another embodiment of this invention is directed to a method for treating non small cell lung cancer in a patient in need of such treatment comprising administering daily a therapeutically effective amount of a compound of formula 1.0, administering a therapeutically effective amount of carboplatin once every three weeks per cycle, and administering a therapeutically effective amount of paclitaxel once every three weeks per cycle, wherein the treatment is given for one to three weeks. In another embodiment compound of formula 1.0 is administered twice per day. In another embodiment said carboplatin and said paclitaxel are administered on the same day, and in another embodiment said carboplatin and said paclitaxel are administered consecutively, and in another embodiment said carboplatin is administered after said paclitaxel.

Another embodiment of this invention is directed to a method for treating non small cell lung cancer in a patient in need of such treatment comprising administering about 50 to about 200 mg of a compound of formula 1.0 twice a day, administering carboplatin once per week per cycle in an amount to provide an AUC of about 2 to about 8 (and in another embodiment about 2 to about 3), and administering once per week per cycle about 60 to about 300 mg/m$^2$ (and in another embodiment about 50 to 100 mg/m$^2$, and in yet another embodiment about 60 to about 80 mg/m$^2$) of paclitaxel, wherein the treatment is given for one to four weeks per cycle. In another embodiment said compound of formula 1.0 is administered in amount of about 75 to about 125 mg twice a day, and in another embodiment about 100 mg twice a day. In another embodiment said carboplatin and said paclitaxel are administered on the same day, and in another embodiment said carboplatin and said paclitaxel are administered consecutively, and in another embodiment said carboplatin is administered after said paclitaxel.

In another embodiment, this invention is directed to a method for treating non small cell lung cancer in a patient in need of such treatment comprising administering about 50 to about 200 mg of a compound of formula 1.0 twice a day, administering carboplatin once every three weeks per cycle in an amount to provide an AUC of about 2 to about 8 (in another embodiment about 5 to about 8, and in another embodiment 6), and administering once every three weeks per cycle about 150 to about 250 mg/m$^2$ (and in another embodiment about 175 to about 225 mg/m$^2$, and in another embodiment 175 mg/m$^2$) of paclitaxel, wherein the treatment is given for one to three weeks. In another embodiment said compound of formula 1.0 is administered in an amount of about 75 to about 125 mg twice a day, and in another embodiment about 100 mg twice a day. In another embodiment said carboplatin and said paclitaxel are administered on the same day, and in another embodiment said carboplatin and said paclitaxel are administered consecutively, and in another embodiment said carboplatin is administered after said paclitaxel.

Other embodiments of this invention are directed to methods of treating cancer as described in the above embodiments (i.e., the embodiments directed to treating cancer and to treating non small cell lung cancer with a taxane and platinum coordinator compound) except that in place of paclitaxel and carboplatin the taxanes and platinum coordinator compounds used together in the methods are: (1) docetaxel (Taxotere®) and cisplatin; (2) paclitaxel and cisplatin; and (3) docetaxel and carboplatin. In another embodiment of the methods of this invention cisplatin is used in amounts of about 30 to about 100 mg/m². In another embodiment of the methods of this invention docetaxel is used in amounts of about 30 to about 100 mg/m².

In another embodiment this invention is directed to a method of treating cancer comprising administering to a patient in need of such treatment therapeutically effective amounts of a compound of formula 1.0, a taxane, and an EGF inhibitor that is an antibody. In another embodiment the taxane used is paclitaxel, and the EGF inhibitor is a HER2 antibody (in one embodiment Herceptin) or Cetuximab, and in another embodiment Herceptin is used. The length of treatment, and the amounts and administration of said compound of formula 1.0 and the taxane are as described in the embodiments above. The EGF inhibitor that is an antibody is administered once a week per cycle, and in another embodiment is administered on the same day as the taxane, and in another embodiment is administered consecutively with the taxane. For example, Herceptin is administered in a loading dose of about 3 to about 5 mg/m² (in another embodiment about 4 mg/m²), and then is administered in a maintenance dose of about 2 mg/m² once per week per cycle for the remainder of the treatment cycle (usually the cycle is 1 to 4 weeks). In one embodiment the cancer treated is breast cancer.

In another embodiment this invention is directed to a method of treating cancer comprising administering to a patient in need of such treatment therapeutically effective amounts of: (1) a compound of formula 1.0, (2) a taxane, and (3) an antineoplastic agent selected from the group consisting of: (a) an EGF inhibitor that is a small molecule, (b) a VEGF inhibitor that is an antibody, and (c) a VEGF kinase inhibitor that is a small molecule. In another embodiment, the taxane paclitaxel or docetaxel is used. In another embodiment the antineoplastic agent is selected from the group consisting of: tarceva, Iressa, bevacizumab, SU5416, SU6688 and BAY 43-9006. The length of treatment, and the amounts and administration of said compound of formula 1.0 and the taxane are as described in the embodiments above. The VEGF kinase inhibitor that is an antibody is usually given once per week per cycle. The EGF and VEGF inhibitors that are small molecules are usually given daily per cycle. In another embodiment, the VEGF inhibitor that is an antibody is given on the same day as the taxane, and in another embodiment is administered concurrently with the taxane. In another embodiment, when the EGF inhibitor that is a small molecule or the VEGF inhibitor that is a small molecule is administered on the same day as the taxane, the administration is concurrently with the taxane. The EGF or VEGF kinase inhibitor is generally administered in an amount of about 10 to about 500 mg/m².

In another embodiment this invention is directed to a method of treating cancer comprising administering to a patient in need of such treatment therapeutically effective amounts of a compound of formula 1.0, an anti-tumor nucleoside derivative, and a platinum coordination compound.

Another embodiment of this invention is directed to a method of treating cancer comprising administering to a patient in need of such treatment therapeutically effective amounts of a compound of formula 1.0, an anti-tumor nucleoside derivative, and a platinum coordination compound, wherein said compound of formula 1.0 is administered every day, said anti-tumor nucleoside derivative is administered once per week per cycle, and said platinum coordinator compound is administered once per week per cycle. Although the treatment can be for one to four weeks per cycle, in one embodiment the treatment is for one to seven weeks per cycle.

Another embodiment of this invention is directed to a method of treating cancer comprising administering to a patient in need of such treatment therapeutically effective amounts of a compound of formula 1.0, an anti-tumor nucleoside derivative, and a platinum coordination compound, wherein said compound of formula 1.0 is administered every day, said an anti-tumor nucleoside derivative is administered once per week per cycle, and said platinum coordinator compound is administered once every three weeks per cycle. Although the treatment can be for one to four weeks per cycle, in one embodiment the treatment is for one to seven weeks per cycle.

Another embodiment of this invention is directed to a method of treating cancer comprising administering to a patient in need of such treatment therapeutically effective amounts of a compound of formula 1.0, gemcitabine, and cisplatin. In another embodiment, said compound of formula 1.0 is administered every day, said gemcitabine is administered once per week per cycle, and said cisplatin is administered once per week per cycle. In one embodiment the treatment is for one to seven weeks per cycle.

Another embodiment of this invention is directed to a method of treating cancer comprising administering to a patient in need of such treatment therapeutically effective amounts of a compound of formula 1.0, gemcitabine, and cisplatin. In another embodiment, said compound of formula 1.0 is administered every day, said gemcitabine is administered once per week per cycle, and said cisplatin is administered once every three weeks per cycle. In another embodiment the treatment is for one to seven weeks.

Another embodiment of this invention is directed to a method of treating cancer comprising administering to a patient in need of such treatment therapeutically effective amounts of a compound of formula 1.0, gemcitabine, and carboplatin. In another embodiment said compound of formula 1.0 is administered every day, said gemcitabine is administered once per week per cycle, and said carboplatin is administered once per week per cycle. In another embodiment the treatment is for one to seven weeks per cycle.

Another embodiment of this invention is directed to a method of treating cancer comprising administering to a patient in need of such treatment therapeutically effective amounts of a compound of formula 1.0, gemcitabine, and carboplatin. In another embodiment said compound of formula 1.0 is administered every day, said gemcitabine is administered once per week per cycle, and said carboplatin is administered once every three weeks per cycle. In another embodiment the treatment is for one to seven weeks per cycle.

In the above embodiments using gemcitabine, the compound of formula 1.0 and the platinum coordinator compound are administered as described above for the embodiments using taxanes. Gemcitabine is administered in an amount of about 500 to about 1250 mg/m². In one embodiment the gemcitabine is administered on the same day as the platinum coordinator compound, and in another embodiment consecutively with the platinum coordinator compound, and in another embodiment the gemcitabine is administered after the platinum coordinator compound.

Another embodiment of this invention is directed to a method of treating cancer in a patient in need of such treatment comprising administering to said patient a compound of formula 1.0 and an antineoplastic agent selected from: (1) EGF inhibitors that are antibodies, (2) EGF inhibitors that are small molecules, (3) VEGF inhibitors that are antibodies, and (4) VEGF kinase inhibitors that are small molecules all as described above. The treatment is for one to seven weeks per cycle, and generally for one to four weeks per cycle. The compound of formula 1.0 is administered in the same manner as described above for the other embodiments of this invention. The small molecule antineoplastic agents are usually administered daily, and the antibody antineoplastic agents are usually administered once per week per cycle. In one embodiment the antineoplastic agents are selected from the group consisting of: Herceptin, Cetuximab, Tarceva, Iressa, bevacizumab, IMC-1C11, SU5416, SU6688 and BAY 43-9006.

In the embodiments of this invention wherein a platinum coordinator compound is used as well as at least one other antineoplastic agent, and these drugs are administered consecutively, the platinum coordinator compound is generally administered after the other antineoplastic agents have been administered.

Other embodiments of this invention include the administration of a therapeutically effective amount of radiation to the patient in addition to the administration of a compound of formula 1.0 and antineoplastic agents in the embodiments described above. Radiation is administered according to techniques and protocols well know to those skilled in the art.

Another embodiment of this invention is directed to a pharmaceutical composition comprising at least two different chemotherapeutic agents and a pharmaceutically acceptable carrier for intravenous administration. Preferably the pharmaceutically acceptable carrier is an isotonic saline solution (0.9% NaCl) or a dextrose solution (e.g., 5% dextrose).

Another embodiment of this invention is directed to a pharmaceutical composition comprising a compound of formula 1.0 and at least two different antineoplastic agents and a pharmaceutically acceptable carrier for intravenous administration. Preferably the pharmaceutically acceptable carrier is an isotonic saline solution (0.9% NaCl) or a dextrose solution (e.g., 5% dextrose).

Another embodiment of this invention is directed to a pharmaceutical composition comprising a compound of formula 1.0 and at least one antineoplastic agent and a pharmaceutically acceptable carrier for intravenous administration. Preferably the pharmaceutically acceptable carrier is an isotonic saline solution (0.9% NaCl) or a dextrose solution (e.g., 5% dextrose).

Other embodiments of this invention are directed to the use of a combination of at least one (e.g., one) compound of formula 1.0 and drugs for the treatment of breast cancer, i.e., this invention is directed to a combination therapy for the treatment of breast cancer. Those skilled in the art will appreciate that the compounds of formula 1.0 and drugs are generally administered as individual pharmaceutical compositions. The use of a pharmaceutical composition comprising more than one drug is within the scope of this invention.

Thus, another embodiment of this invention is directed to a method of treating (or preventing) breast cancer (i.e., postmenopausal and premenopausal breast cancer, e.g., hormone-dependent breast cancer) in a patient in need of such treatment comprising administering to said patient a therapeutically effective amount of at least one (e.g., one) compound of formula 1.0 and a therapeutically effective amount of at least one antihormonal agent selected from the group consisting of: (a) aromatase inhibitors, (b) antiestrogens, and (c) LHRH analogues; and said treatment optionally including the administration of at least one chemotherapeutic agent.

The compound of formula 1.0 is preferably administered orally, and in one embodiment is administered in capsule form.

Examples of aromatase inhibitors include but are not limited to: Anastrozole (e.g., Arimidex), Letrozole (e.g., Femara), Exemestane (Aromasin), Fadrozole and Formestane (e.g., Lentaron).

Examples of antiestrogens include but are not limited to: Tamoxifen (e.g., Nolvadex), Fulvestrant (e.g., Faslodex), Raloxifene (e.g., Evista), and Acolbifene.

Examples of LHRH analogues include but are not limited to: Goserelin (e.g., Zoladex) and Leuprolide (e.g., Leuprolide Acetate, such as Lupron or Lupron Depot).

Examples of chemotherapeutic agents include but are not limited to: Trastuzumab (e.g., Herceptin), Gefitinib (e.g., Iressa), Erlotinib (e.g., Erlotinib HCl, such as Tarceva), Bevacizumab (e.g., Avastin), Cetuximab (e.g., Erbitux), and Bortezomib (e.g., Velcade).

Preferably, when more than one antihormonal agent is used, each agent is selected from a different category of agent. For example, one agent is an aromatase inhibitor (e.g., Anastrozole, Letrozole, or Exemestane) and one agent is an antiestrogen (e.g., Tamoxifen or Fulvestrant).

Another embodiment of this invention is directed to a method of treating or preventing breast cancer in a patient in need of such treatment wherein said treatment comprises administering a therapeutically effective amount of at least one (e.g., one) compound of formula 1.0 and at least one antihormonal agent selected from the group consisting of: (a) aromatase inhibitors, (b) antiestrogens, and (c) LHRH analogues; and administering an effective amount of at least one chemotherapeutic agent.

Another embodiment of this invention is directed to a method of treating or preventing breast cancer in a patient in need of such treatment wherein said treatment comprises administering a therapeutically effective amount of at least one (e.g., one) compound of formula 1.0 and at least one antihormonal agent selected from the group consisting of: (a) aromatase inhibitors, (b) antiestrogens, and (c) LHRH analogues.

Another embodiment of this invention is directed to a method of treating or preventing breast cancer in a patient in need of such treatment wherein said treatment comprises administering a therapeutically effective amount of at least one (e.g., one) compound of formula 1.0 and at least one antihormonal agent selected from the group consisting of: (a) aromatase inhibitors, and (b) antiestrogens.

Another embodiment of this invention is directed to a method of treating or preventing breast cancer in a patient in need of such treatment wherein said treatment comprises administering a therapeutically effective amount of at least one (e.g., one) compound of formula 1.0, at least one antihormonal agent selected from the group consisting of: (a) aromatase inhibitors and (b) antiestrogens; and at least one chemotherapeutic agent.

Another embodiment of this invention is directed to a method of treating or preventing breast cancer in a patient in need of such treatment wherein said treatment comprises administering a therapeutically effective amount of at least one (e.g., one) compound of formula 1.0 and at least one aromatase inhibitor.

Another embodiment of this invention is directed to a method of treating or preventing breast cancer in a patient in need of such treatment wherein said treatment comprises administering a therapeutically effective amount of at least one (e.g., one) compound of formula 1.0, at least one aromatase inhibitor, and at least one chemotherapeutic agent.

Another embodiment of this invention is directed to a method of treating or preventing breast cancer in a patient in need of such treatment wherein said treatment comprises administering a therapeutically effective amount of: (1) at least one (e.g., one) compound of formula 1.0; and (2) at least one antihormonal agent selected from the group consisting of: (a) aromatase inhibitors that are selected from the group consisting of Anastrozole, Letrozole, Exemestane, Fadrozole and Formestane, (b) antiestrogens that are selected from the group consisting of: Tamoxifen, Fulvestrant, Raloxifene, and Acolbifene, and (c) LHRH analogues that are selected from the group consisting of: Goserelin and Leuprolide; and administering an effective amount of at least one chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of: (1) at least one (e.g., one) compound of formula 1.0; and (2) at least one antihormonal agent selected from the group consisting of: (a) aromatase inhibitors that are selected from the group consisting of Anastrozole, Letrozole, Exemestane, Fadrozole and Formestane, (b) antiestrogens that are selected from the group consisting of: Tamoxifen, Fulvestrant, Raloxifene, and Acolbifene, and (c) LHRH analogues that are selected from the group consisting of: Goserelin and Leuprolide.

Another embodiment of this invention is directed to a method of treating or preventing breast cancer in a patient in need of such treatment wherein said treatment comprises administering a therapeutically effective amount of: (1) at least one (e.g., one) compound of formula 1.0; and (2) at least one antihormonal agent selected from the group consisting of: (a) aromatase inhibitors that are selected from the group consisting of Anastrozole, Letrozole, Exemestane, Fadrozole and Formestane, and (b) antiestrogens that are selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of: (1) at least one (e.g., one) compound of formula 1.0; and (2) at least one antihormonal agent selected from the group consisting of: (a) aromatase inhibitors that are selected from the group consisting of Anastrozole, Letrozole, Exemestane, Fadrozole and Formestane, (b) antiestrogens that are selected from the group consisting of: Tamoxifen, Fulvestrant, Raloxifene, and Acolbifene; and administering an effective amount of at least one chemotherapeutic agents are selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of: (1) at least one (e.g., one) compound of formula 1.0; and (2) at least one aromatase inhibitor selected from the group consisting of Anastrozole, Letrozole, Exemestane, Fadrozole and Formestane.

Another embodiment of this invention is directed to a method of treating or preventing breast cancer in a patient in need of such treatment wherein said treatment comprises administering a therapeutically effective amount of: (1) at least one (e.g., one) compound of formula 1.0; (2) at least one aromatase inhibitor that is selected from the group consisting of Anastrozole, Letrozole, Exemestane, Fadrozole and Formestane; and (3) administering an effective amount of at least one chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of: (1) at least one (e.g., one) compound of formula 1.0; (2) at least one aromatase inhibitor; and (3) at least one LHRH analogue.

Another embodiment of this invention is directed to a method of treating or preventing breast cancer in a patient in need of such treatment wherein said treatment comprises administering a therapeutically effective amount of: (1) at least one (e.g., one) compound of formula 1.0; (2) at least one antiestrogen; and (3) at least one LHRH analogue.

Another embodiment of this invention is directed to a method of treating or preventing breast cancer in a patient in need of such treatment wherein said treatment comprises administering a therapeutically effective amount of: (1) at least one (e.g., one) compound of formula 1.0; (2) at least one aromatase inhibitor that is selected from the group consisting of Anastrozole, Letrozole, Exemestane, Fadrozole and Formestane; and (3) at least one LHRH analogue that is selected from the group consisting of: Goserelin and Leuprolide.

Another embodiment of this invention is directed to a method of treating or preventing breast cancer in a patient in need of such treatment wherein said treatment comprises administering a therapeutically effective amount of: (1) at least one (e.g., one) compound of formula 1.0; (2) at least one antiestrogen that is selected from the group consisting of: Tamoxifen, Fulvestrant, Raloxifene, and Acolbifene; and (3) at least one LHRH analogue that is selected from the group consisting of: Goserelin and Leuprolide.

Another embodiment of this invention is directed to a method of treating or preventing breast cancer in a patient in need of such treatment wherein said treatment comprises administering a therapeutically effective amount of at least one (e.g., one) compound of formula 1.0 and Anastrozole.

Another embodiment of this invention is directed to a method of treating or preventing breast cancer in a patient in need of such treatment wherein said treatment comprises administering a therapeutically effective amount of at least one (e.g., one) compound of formula 1.0 and Letrazole.

Another embodiment of this invention is directed to a method of treating or preventing breast cancer in a patient in need of such treatment wherein said treatment comprises administering a therapeutically effective amount of at least one (e.g., one) compound of formula 1.0 and Exemestane.

Another embodiment of this invention is directed to a method of treating or preventing breast cancer in a patient in need of such treatment wherein said treatment comprises administering a therapeutically effective amount of at least one (e.g., one) compound of formula 1.0 and Fadrozole.

Another embodiment of this invention is directed to a method of treating or preventing breast cancer in a patient in need of such treatment wherein said treatment comprises administering a therapeutically effective amount of at least one (e.g., one) compound of formula 1.0 and Formestane.

Another embodiment of this invention is directed to a method of treating or preventing breast cancer in a patient in need of such treatment wherein said treatment comprises administering a therapeutically effective amount of at least one (e.g., one) compound of formula 1.0 and Tamoxifen.

Another embodiment of this invention is directed to a method of treating or preventing breast cancer in a patient in need of such treatment wherein said treatment comprises administering a therapeutically effective amount of at least one (e.g., one) compound of formula 1.0 Fulvestrant.

Another embodiment of this invention is directed to a method of treating or preventing breast cancer in a patient in need of such treatment wherein said treatment comprises administering a therapeutically effective amount of at least one (e.g., one) compound of formula 1.0 and Raloxifene.

Another embodiment of this invention is directed to a method of treating or preventing breast cancer in a patient in need of such treatment wherein said treatment comprises administering a therapeutically effective amount of at least one (e.g., one) compound of formula 1.0 and Acolbifene.

Another embodiment of this invention is directed to a method of treating or preventing breast cancer in a patient in need of such treatment wherein said treatment comprises administering a therapeutically effective amount of at least one (e.g., one) compound of formula 1.0 and Goserelin.

Another embodiment of this invention is directed to a method of treating or preventing breast cancer in a patient in need of such treatment wherein said treatment comprises administering a therapeutically effective amount of at least one (e.g., one) compound of formula 1.0 and Leuprolide.

Another embodiment of this invention is directed to a method of treating or preventing breast cancer in a patient in need of such treatment wherein said treatment comprises administering a therapeutically effective amount of at least one (e.g., one) compound of formula 1.0, Anastrozole, and an antiestrogen selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of at least one (e.g., one) compound of formula 1.0, Letrozole, and an antiestrogen selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of at least one (e.g., one) compound of formula 1.0, Exemestane, and an antiestrogen selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of at least one (e.g., one) compound of formula 1.0, Fadrozole, and an antiestrogen selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of at least one (e.g., one) compound of formula 1.0, Formestane, and an antiestrogen selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of at least one (e.g., one) compound of formula 1.0, Anastrozole, and Tamoxifen.

Another embodiment of this invention is directed to a method of treating or preventing breast cancer in a patient in need of such treatment wherein said treatment comprises administering a therapeutically effective amount of at least one (e.g., one) compound of formula 1.0, Letrozole, and Tamoxifen.

Another embodiment of this invention is directed to a method of treating or preventing breast cancer in a patient in need of such treatment wherein said treatment comprises administering a therapeutically effective amount of at least one (e.g., one) compound of formula 1.0, Exemestane, and Tamoxifen.

Another embodiment of this invention is directed to a method of treating or preventing breast cancer in a patient in need of such treatment wherein said treatment comprises administering a therapeutically effective amount of at least one (e.g., one) compound of formula 1.0, Fadrozole, and Tamoxifen.

Another embodiment of this invention is directed to a method of treating or preventing breast cancer in a patient in need of such treatment wherein said treatment comprises administering a therapeutically effective amount of at least one (e.g., one) compound of formula 1.0, Formestane, and Tamoxifen.

Another embodiment of this invention is directed to a method of treating or preventing breast cancer in a patient in need of such treatment wherein said treatment comprises administering a therapeutically effective amount of at least one (e.g., one) compound of formula 1.0, Anastrozole, and Fulvestrant.

Another embodiment of this invention is directed to a method of treating or preventing breast cancer in a patient in need of such treatment wherein said treatment comprises administering a therapeutically effective amount of at least one (e.g., one) compound of formula 1.0, Letrozole, and Fulvestrant.

Another embodiment of this invention is directed to a method of treating or preventing breast cancer in a patient in need of such treatment wherein said treatment comprises administering a therapeutically effective amount of at least one (e.g., one) compound of formula 1.0, Exemestane, and Fulvestrant.

Another embodiment of this invention is directed to a method of treating or preventing breast cancer in a patient in need of such treatment wherein said treatment comprises administering a therapeutically effective amount of at least one (e.g., one) compound of formula 1.0, Fadrozole, and Fulvestrant.

Another embodiment of this invention is directed to a method of treating or preventing breast cancer in a patient in need of such treatment wherein said treatment comprises administering a therapeutically effective amount of at least one (e.g., one) compound of formula 1.0, Formestane, and Fulvestrant.

Another embodiment of this invention is directed to a method of treating or preventing breast cancer in a patient in need of such treatment wherein said treatment comprises administering a therapeutically effective amount of at least one (e.g., one) compound of formula 1.0, Anastrozole, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Letrozole, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Exemestane, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Fadrozole, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Formestane, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Raloxifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Goserelin, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Leuprolein, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Anastrozole, an antiestrogen selected from the group consisting of: Tamoxifen, Fulvestrant, Raloxifene, and Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Letrozole, an antiestrogen selected from the group consisting of: Tamoxifen, Fulvestrant, Raloxifene, and Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Exemestane, an antiestrogen selected from the group consisting of: Tamoxifen, Fulvestrant, Raloxifene, and Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Fadrozole, an antiestrogen selected from the group consisting of: Tamoxifen, Fulvestrant, Raloxifene, and Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Formestane, an antiestrogen selected from the group consisting of: Tamoxifen, Fulvestrant, Raloxifene, and Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Anastrozole, Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Letrozole, Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Exemestane, Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Fadrozole, Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Formestane, Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Anastrozole, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Letrozole, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Exemestane, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Fadrozole, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Formestane, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Goserelin and Tamoxifen.

Another embodiment of this invention is directed to a method of treating or preventing breast cancer in a patient in need of such treatment wherein said treatment comprises administering a therapeutically effective amount of at least one (e.g., one) compound of formula 1.0, Goserelin, and Fulvestrant.

Another embodiment of this invention is directed to a method of treating or preventing breast cancer in a patient in need of such treatment wherein said treatment comprises administering a therapeutically effective amount of at least one (e.g., one) compound of formula 1.0, Goserelin, and Raloxifene.

Another embodiment of this invention is directed to a method of treating or preventing breast cancer in a patient in need of such treatment wherein said treatment comprises administering a therapeutically effective amount of at least one (e.g., one) compound of formula 1.0, Goserelin and Acolbifene.

Another embodiment of this invention is directed to a method of treating or preventing breast cancer in a patient in need of such treatment wherein said treatment comprises administering a therapeutically effective amount of at least one (e.g., one) compound of formula 1.0, Leuprolide, and Tamoxifen.

Another embodiment of this invention is directed to a method of treating or preventing breast cancer in a patient in need of such treatment wherein said treatment comprises administering a therapeutically effective amount of at least one (e.g., one) compound of formula 1.0, Leuprolide, and Fulvestrant.

Another embodiment of this invention is directed to a method of treating or preventing breast cancer in a patient in need of such treatment wherein said treatment comprises administering a therapeutically effective amount of at least one (e.g., one) compound of formula 1.0, Leuprolide, and Raloxifene.

Another embodiment of this invention is directed to a method of treating or preventing breast cancer in a patient in need of such treatment wherein said treatment comprises administering a therapeutically effective amount of at least one (e.g., one) compound of formula 1.0, Leuprolide and Acolbifene.

Another embodiment of this invention is directed to a method of treating or preventing breast cancer in a patient in need of such treatment wherein said treatment comprises administering a therapeutically effective amount of at least one (e.g., one) compound of formula 1.0, Goserelin and Anastrozole.

Another embodiment of this invention is directed to a method of treating or preventing breast cancer in a patient in need of such treatment wherein said treatment comprises administering a therapeutically effective amount of at least one (e.g., one) compound of formula 1.0, Goserelin and Letrozole.

Another embodiment of this invention is directed to a method of treating or preventing breast cancer in a patient in need of such treatment wherein said treatment comprises administering a therapeutically effective amount of at least one (e.g., one) compound of formula 1.0, Goserelin and Exemestane.

Another embodiment of this invention is directed to a method of treating or preventing breast cancer in a patient in need of such treatment wherein said treatment comprises administering a therapeutically effective amount of at least one (e.g., one) compound of formula 1.0, Goserelin and Fadrozole.

Another embodiment of this invention is directed to a method of treating or preventing breast cancer in a patient in need of such treatment wherein said treatment comprises administering a therapeutically effective amount of at least one (e.g., one) compound of formula 1.0, Goserelin and Formestane.

Another embodiment of this invention is directed to a method of treating or preventing breast cancer in a patient in need of such treatment wherein said treatment comprises administering a therapeutically effective amount of at least one (e.g., one) compound of formula 1.0, Leuprolide and Anastrozole.

Another embodiment of this invention is directed to a method of treating or preventing breast cancer in a patient in need of such treatment wherein said treatment comprises administering a therapeutically effective amount of at least one (e.g., one) compound of formula 1.0, Leuprolide and Letrozole.

Another embodiment of this invention is directed to a method of treating or preventing breast cancer in a patient in need of such treatment wherein said treatment comprises administering a therapeutically effective amount of at least one (e.g., one) compound of formula 1.0, Leuprolide and Exemestane.

Another embodiment of this invention is directed to a method of treating or preventing breast cancer in a patient in need of such treatment wherein said treatment comprises administering a therapeutically effective amount of at least one (e.g., one) compound of formula 1.0, Leuprolide and Fadrozole.

Another embodiment of this invention is directed to a method of treating or preventing breast cancer in a patient in need of such treatment wherein said treatment comprises administering a therapeutically effective amount of at least one (e.g., one) compound of formula 1.0, Leuprolide and Formestane.

Another embodiment of this invention is directed to the treatment or prevention of breast cancer in a patient in need of such treatment, said treatment comprising the administration of a therapeutically effective amount of at least one (e.g., one) compound of formula 1.0 and Anastrozole.

Another embodiment of this invention is directed to the treatment or prevention of breast cancer in a patient in need of such treatment, said treatment comprising the administration of a therapeutically effective amount of at least one (e.g., one) compound of formula 1.0 and Letrozole.

Another embodiment of this invention is directed to the treatment or prevention of breast cancer in a patient in need of such treatment, said treatment comprising the administration of a therapeutically effective amount of at least one (e.g., one) compound of formula 1.0 and Exemestane.

Another embodiment of this invention is directed to the treatment or prevention of breast cancer in a patient in need of such treatment, said treatment comprising the administration of a therapeutically effective amount of at least one (e.g., one) compound of formula 1.0 and Tamoxifen.

Another embodiment of this invention is directed to the treatment or prevention of breast cancer in a patient in need of such treatment, said treatment comprising the administration of a therapeutically effective amount of at least one (e.g., one) compound of formula 1.0 and Fulvestrant.

Another embodiment of this invention is directed to the treatment or prevention of breast cancer in a patient in need of such treatment, said treatment comprising the administration of a therapeutically effective amount of at least one (e.g., one) compound of formula 1.0, Anastrozole, and Fulvestrant.

Another embodiment of this invention is directed to the treatment or prevention of breast cancer in a patient in need of such treatment, said treatment comprising the administration of a therapeutically effective amount of at least one compound of formula 1.0 (e.g., one), Letrozole, and Fulvestrant.

Another embodiment of this invention is directed to the treatment or prevention of breast cancer in a patient in need of such treatment, said treatment comprising the administration of a therapeutically effective amount of at least one (e.g., one) compound of formula 1.0, Exemestane, and Fulvestrant.

Another embodiment of this invention is directed to the treatment or prevention of breast cancer in a patient in need of such treatment, said treatment comprising the administration of a therapeutically effective amount of at least one (e.g., one) compound of formula 1.0, Anastrozole, and Tamoxifen.

Another embodiment of this invention is directed to the treatment or prevention of breast cancer in a patient in need of such treatment, said treatment comprising the administration of a therapeutically effective amount of at least one (e.g., one) compound of formula 1.0, Letrozole, and Tamoxifen.

Another embodiment of this invention is directed to the treatment or prevention of breast cancer in a patient in need of such treatment, said treatment comprising the administration of a therapeutically effective amount of at least one (e.g., one) compound of formula 1.0, Exemestane, and Tamoxifen.

Other embodiments of this invention are directed to any of the above described embodiments for the treatment of Breast Cancer wherein the chemotherapeutic agent is Trastuzumab.

Other embodiments of this invention are directed to any of the above described embodiments for the treatment or prevention of Breast Cancer wherein the method is directed to the treatment of breast cancer.

The compound of formula 1.0, antihormonal agents and chemotherapeutic agents can be administered concurrently or sequentially.

The antihormonal agents and optional chemotherapeutic agents are administered according to their protocols, dosage amounts, and dosage forms that are well know to those skilled in the art (e.g., the Physician's Desk Reference or published literature). For example, for Tamoxifen, Fulvestrant, Raloxifene, Anastrozole, Letrozole, Exemestane, Leuprolide and Goserelin, see the Physician's Desk Reference, $57^{th}$ Edition, 2003, published by Thomas PDR at Montvale, N.J. 07645-1742, the disclosure of which is incorporated herein by reference thereto.

In general, in the embodiments directed to the methods of treating Breast Cancer: (1) the compound of formula 1.0 can be administered daily (e.g., once per day, and in one embodiment twice a day), (2) the aromatase inhibitors can be administered in accordance with the known protocol for the aromatase inhibitor used (e.g., once per day), (3) the antiestrogens can be administered in accordance with the known protocol for the antiestrogen used (e.g., from once a day to once a month), (4) the LHRH analogue can be administered in accordance with the known protocol for the LHRH analogue used (e.g., once a month to once every three months), and (5) the chemotherapeutic agent can be administered in accordance with the known protocol for the chemotherapeutic agent used (e.g., from once a day to once a week).

Radiation therapy, if administered in the above treatments for breast cancer, is generally administered according to known protocols before administration of the compound of formula 1.0, antihormonal agents and optional chemotherapeutic agents.

Treatment according to the methods of treating breast cancer is continuous (i.e., a continuous dosing schedule is followed). The treatment is continued until there is a complete response, or until the skilled clinician determines that the patient is not benefiting from the treatment (for example, when there is disease progression).

The continuous treatment protocol for breast cancer can be changed to a discontinuous treatment schedule if, in the judgment of the skilled clinician, the patient would benefit from a discontinuous treatment schedule with one or more of the administered drugs. For example, the compound of formula 1.0 can be given using a discontinous treatment schedule while the remaining drugs used in the treatment are given as described herein. An example of a discontinuous treatment protocol for the compound of formula 1.0 is a repeating cycle of three weeks with the compound of formula 1.0 followed by one week without the compound of formula 1.0.

After a complete response is achieved with the breast cancer treatment, maintenance therapy with the compound of formula 1.0 can be continued using the dosing described in the methods of this invention. Maintenance therapy can also include administration of the antihormonal agents using the dosing described in the methods of this invention. Maintenance therapy can just be with the antihormonal agents. For example, after a complete response is achieved, an aromatase inhibitor (e.g., Anastrozole, Letrozole or Exemestane) can be continued for up to five years. Or, for example, an antiestrogen, e.g., Tamoxifen, may be used for up to five years after a complete response is achieved. Or, for example, an antiestrogen (e.g., Tamoxifen) can be used for up to five years after a complete response is achieved followed by the use of an aromatase inhibitor (e.g., Anastrozole, Letrozole or Exemestane) for up to five years.

In the embodiments directed to the treatment of breast cancer described above, the compound of formula 1.0 is administered continuously in a total daily dose of about 100 mg to about 600 mg. Usually this amount is administered in divided doses, and in one embodiment this amount is administered twice a day. In one embodiment the compound of formula 1.0 is dosed twice a day in an amount of about 50 mg to about 300 mg per dose. In another embodiment the compound of formula 1.0 is dosed twice a day in an amount of about 100 mg to about 200 mg per dose. Examples include the compound of formula 1.0 being dosed twice a day at 100 mg per dose. Examples also include the compound of formula 1.0 being dosed twice a day at 200 mg per dose.

Anastrozole is administered p.o. and is dosed once a day in amounts of about 0.5 to about 10 mg per dose, and in one embodiment in an amount of about 1.0 mg per dose.

Letrozole is administered p.o. and is dosed once a day in amounts of about 1.0 to about 10 mg per dose, and in one embodiment in an amount of about 2.5 mg per dose.

Exemestane is administered p.o. and is dosed once a day in amounts of about 10 to about 50 mg per dose, and in one embodiment in an amount of about 25 mg per dose.

Fadrozole is administered p.o. and is dosed twice a day in amounts of about 0.5 to about 10 mg per dose, and in one embodiment in an amount of about 2.0 mg per dose.

Formestane is administered i.m. and is dosed once every two weeks in amounts of about 100 to about 500 mg per dose, and in one embodiment in an amount of about 250 mg per dose.

Tamoxifen is administered p.o. and is dosed once a day in amounts of about 10 to about 100 mg per dose, and in one embodiment in an amount of about 20 mg per dose.

Fulvestrant is administered i.m. and is dosed once a month in amounts of about 100 to about 1000 mg per dose, and in one embodiment in an amount of about 250 mg per dose.

Raloxifene is administered p.o. and is dosed once a day in amounts of about 10 to about 120 mg per dose, and in one embodiment in an amount of about 60 mg per dose.

Acolbifene is administered p.o. and is dosed once a day in amounts of about 5 to about 20 mg per dose, and in one embodiment in an amount of about 20 mg per dose Goserelin is administered s.c. and is dosed once a month, or once every three months, in amounts of about 2 to about 20 mg per dose, and in one embodiment in an amount of about 3.6 mg per dose when administered once a month, and in another embodiment in an amount of about 10.8 mg per dose when administered once every three months.

Leuprolide is administered s.c. and is dosed once a month, or once every three months, in amounts of about 2 to about 20 mg per dose, and in one embodiment in an amount of about 3.75 mg per dose when administered once a month, and in another embodiment in an amount of about 11.25 mg per dose when administered once every three months.

Trastuzumab is administered by i.v. and is dosed once a week in amounts of about 2 to about 20 mpk per dose, and in one embodiment in an amount of about 2 mpk per dose. Trastuzumab is generally initially administered in a loading dose that is generally twice the dose of the weekly dose. Thus, for example, a 4 mpk loading dose is administered and then dosing is 2 mpk per dose per week.

Gefitinib is administered p.o. and is dosed once a day in amounts of about 100 to about 1000 mg per dose, and in one embodiment in an amount of about 250 mg per dose.

Erlotinib is administered p.o. and is dosed once a day in amounts of about 100 to about 500 mg per dose, and in one embodiment in an amount of about 150 mg per dose.

Bevacizumab is administered i.v. and is dosed once every two weeks in amounts of about 2.5 to about 15 mg per kilogram of body weight per dose, and in one embodiment in an amount of about 10 mg per kilogram per dose.

Cetuximab is administered i.v. and is dosed once a week in amounts of about 200 to about 500 mg per meter squared dose, and in one embodiment in an amount of about 250 mg per meter squared per dose.

Bortezomib is administered i.v. and is dosed twice a week for 2 weeks followed by a 10 day rest period (21 day treatment cycle) for a maximum of 8 treatment cycles in amounts of about 1.0 to about 2.5 mg per meter squared per dose, and in one embodiment in an amount of about 1.3 mg per meter squared per dose.

Thus in one embodiment of this invention breast cancer is treated (or prevented) in a patient in need of such treatment wherein said treatment comprises administering to said patient: (1) the compound of formula 1.0 orally in an amount of about 50 mg to about 300 mg per dose wherein each dose is administered twice a day, and (2) Anastrozole p.o. in an amount of about 0.5 to about 10 mg per dose wherein each dose is given once a day.

In another embodiment of this invention breast cancer is treated (or prevented) in a patient in need of such treatment wherein said treatment comprises administering to said patient: (1) the compound of formula 1.0 orally in an amount of about 100 to 200 mg per dose, wherein each dose is administered twice a day, and (2) Anastrozole in an amount of about 1.0 mg per dose wherein each dose is given once a day.

In another embodiment of this invention breast cancer is treated (or prevented) in a patient in need of such treatment wherein said treatment comprises administering to said patient: (1) the compound of formula 1.0 orally in an amount of about 50 mg to about 300 mg per dose wherein each dose is administered twice a day, and (2) Letrozole p.o. in an amount of about 1.0 to about 10 mg per dose wherein each dose is given once a day.

In another embodiment of this invention breast cancer is treated (or prevented) in a patient in need of such treatment wherein said treatment comprises administering to said patient: (1) the compound of formula 1.0 orally in an amount of about 100 to 200 mg per dose, wherein each dose is administered twice a day, and (2) Letrozole p.o. in an amount of about 2.5 mg per dose wherein each dose is given once a day.

In another embodiment of this invention breast cancer is treated (or prevented) in a patient in need of such treatment wherein said treatment comprises administering to said patient: (1) the compound of formula 1.0 orally in an amount of about 50 mg to about 300 mg per dose wherein each dose is administered twice a day, and (2) Exemestane p.o. in an amount of about 10 to about 50 mg per dose wherein each dose is given once a day.

In another embodiment of this invention breast cancer is treated (or prevented) in a patient in need of such treatment wherein said treatment comprises administering to said patient: (1) the compound of formula 1.0 orally in an amount of about 100 to 200 mg per dose, wherein each dose is administered twice a day, and (2) Exemestane in an amount of about 25 mg per dose wherein each dose is given once a day.

In another embodiment of this invention breast cancer is treated (or prevented) in a patient in need of such treatment wherein said treatment comprises administering to said patient: (1) the compound of formula 1.0 orally in an amount of about 50 mg to about 300 mg per dose wherein each dose is administered twice a day, and (2) Fulvestrant i.m. in an amount of about 100 to about 1000 mg per dose wherein each dose is given once a month.

In another embodiment of this invention breast cancer is treated (or prevented) in a patient in need of such treatment wherein said treatment comprises administering to said patient: (1) the compound of formula 1.0 orally in an amount of about 100 to 200 mg per dose, wherein each dose is administered twice a day, and (2) Fulvestrant i.m. in an amount of about 250 mg per dose wherein each dose is given once a month.

In another embodiment of this invention breast cancer is treated (or prevented) in a patient in need of such treatment wherein said treatment comprises administering to said patient: (1) the compound of formula 1.0 p.o. in an amount of about 50 mg to about 300 mg per dose wherein each dose is administered twice a day, and (2) Tamoxifen p.o. in an amount of about 10 to about 100 mg per dose wherein each dose is given once a day.

In another embodiment of this invention breast cancer is treated (or prevented) in a patient in need of such treatment wherein said treatment comprises administering to said patient: (1) the compound of formula 1.0 p.o. in an amount of about 100 to 200 mg per dose, wherein each dose is administered twice a day, and (2) Tamoxifen p.o. in an amount of about 20 mg per dose wherein each dose is given once a day.

In other embodiments of the invention breast cancer is treated in a patient in need of such treatment wherein said treatment comprises the administration of the compound of formula 1.0, one of the aromatase inhibitors (e.g., Anastrozole, Letrozole, or Exemestane, and in one embodiment Anastrozole), and one of the antiestrogens (e.g., Fulvestrant or Tamoxifen), wherein the compound of formula 1.0, aromatase inhibitor and antiestrogen are administered in the dosages described above.

Thus, for example in another embodiment of this invention breast cancer is treated (or prevented) in a patient in need of such treatment wherein said treatment comprises administering to said patient: (1) the compound of formula 1.0 p.o. in an amount of about 50 mg to about 300 mg per dose wherein each dose is administered twice a day, (2) Anastrozole p.o. in an amount of about 0.5 to about 10 mg per dose wherein each dose is given once a day, and (3) Fulvestrant i.m. in an amount of about 100 to about 1000 mg per dose wherein each dose is given once a month.

In another embodiment of this invention breast cancer is treated (or prevented) in a patient in need of such treatment wherein said treatment comprises administering to said patient: (1) the compound of formula 1.0 p.o in an amount of about 100 to 200 mg per dose, wherein each dose is administered twice a day, (2) Anastrozole p.o. in an amount of about 1.0 mg per dose wherein each dose is given once a day, and (3) Fulvestrant i.m. in an amount of about 250 mg per dose wherein each dose is given once a month.

In another embodiment of this invention breast cancer is treated (or prevented) in a patient in need of such treatment wherein said treatment comprises administering to said patient: (1) the compound of formula 1.0 p.o. in an amount of about 50 mg to about 300 mg per dose wherein each dose is administered twice a day, (2) Letrozole p.o in an amount of about 1.0 to about 10 mg per dose wherein each dose is given once a day, and (3) Fulvestrant in an amount of about 100 to about 1000 mg per dose wherein each dose is given once a month.

In another embodiment of this invention breast cancer is treated (or prevented) in a patient in need of such treatment wherein said treatment comprises administering to said patient: (1) the compound of formula 1.0 p.o. in an amount of about 100 to 200 mg per dose, wherein each dose is administered twice a day, (2) Letrozole p.o. in an amount of about 2.5 mg per dose wherein each dose is given once a day, and (3) Fulvestrant i.m. in an amount of about 250 mg per dose wherein each dose is given once a month.

In another embodiment of this invention breast cancer is treated (or prevented) in a patient in need of such treatment wherein said treatment comprises administering to said patient: (1) the compound of formula 1.0 p.o. in an amount of about 50 mg to about 300 mg per dose wherein each dose is administered twice a day, (2) Exemestane p.o. in an amount of about 10 to about 50 mg per dose wherein each dose is given once a day, and (3) Fulvestrant i.m. in an amount of about 100 to about 1000 mg per dose wherein each dose is given once a month.

In another embodiment of this invention breast cancer is treated (or prevented) in a patient in need of such treatment wherein said treatment comprises administering to said patient: (1) the compound of formula 1.0 p.o. in an amount of about 100 to 200 mg per dose, wherein each dose is administered twice a day, (2) Exemestane p.o. in an amount of about 25 mg per dose wherein each dose is given once a day, and (3) Fulvestrant i.m. in an amount of about 250 mg per dose wherein each dose is given once a month.

In another embodiment of this invention breast cancer is treated (or prevented) in a patient in need of such treatment wherein said treatment comprises administering to said patient: (1) the compound of formula 1.0 p.o. in an amount of about 50 mg to about 300 mg per dose wherein each dose is administered twice a day, (2) Anastrozole p.o. in an amount of about 0.5 to about 10 mg per dose wherein each dose is given once a day, and (3) Tamoxifen p.o. in an amount of about 10 to about 100 mg per dose wherein each dose is given once a day.

In another embodiment of this invention breast cancer is treated (or prevented) in a patient in need of such treatment wherein said treatment comprises administering to said patient: (1) the compound of formula 1.0 p.o. in an amount of about 100 to 200 mg per dose, wherein each dose is administered twice a day, (2) Anastrozole p.o. in an amount of about 1.0 mg per dose wherein each dose is given once a day, and (3) Tamoxifen p.o. in an amount of about 20 mg per dose wherein each dose is given once a day.

In another embodiment of this invention breast cancer is treated (or prevented) in a patient in need of such treatment wherein said treatment comprises administering to said patient: (1) the compound of formula 1.0 p.o. in an amount of about 50 mg to about 300 mg per dose wherein each dose is administered twice a day, (2) Letrozole p.o. in an amount of about 1.0 to about 10 mg per dose wherein each dose is given once a day, and (3) Tamoxifen p.o. in an amount of about 10 to about 100 mg per dose wherein each dose is given once a day.

In another embodiment of this invention breast cancer is treated (or prevented) in a patient in need of such treatment wherein said treatment comprises administering to said patient: (1) the compound of formula 1.0 p.o. in an amount of about 100 to 200 mg per dose, wherein each dose is administered twice a day, (2) Letrozole p.o. in an amount of about 2.5 mg per dose wherein each dose is given once a day, and (3) Tamoxifen p.o. in an amount of about 20 mg per dose wherein each dose is given once a day.

In another embodiment of this invention breast cancer is treated (or prevented) in a patient in need of such treatment wherein said treatment comprises administering to said patient: (1) the compound of formula 1.0 p.o. in an amount of about 50 mg to about 300 mg per dose wherein each dose is administered twice a day, (2) Exemestane p.o. in an amount of about 10 to about 50 mg per dose wherein each dose is given once a day, and (3) Tamoxifen p.o. in an amount of about 10 to about 100 mg per dose wherein each dose is given once a day.

In another embodiment of this invention breast cancer is treated (or prevented) in a patient in need of such treatment wherein said treatment comprises administering to said patient: (1) the compound of formula 1.0 p.o. in an amount of about 100 to 200 mg per dose, wherein each dose is administered twice a day, (2) Exemestane p.o. in an amount of about 25 mg per dose wherein each dose is given once a day, and (3) Tamoxifen p.o. in an amount of about 20 mg per dose wherein each dose is given once a day.

Those skilled in the art will appreciate that when other combinations of antihormonal agents are used, the individual antihormonal agent is used in the amounts specified above for that individual antihormonal agent.

Other embodiments of the treatment of Breast Cancer are directed to the methods of treating Breast Cancer described above wherein the compound of formula 1.0 is dosed twice a day in an amount of about 100 mg per dose.

Other embodiments of the treatment of Breast Cancer are directed to the methods of treating Breast Cancer described above wherein the compound of formula 1.0 is dosed twice a day in an amount of about 200 mg per dose.

Other embodiments of the treatment of Breast Cancer are directed to the methods of treating Breast Cancer described above wherein a chemotherapeutic agent is administered in addition to the compound of formula 1.0 and antihormonal agent (or antihormonal agents). In these embodiments the dosage ranges of the compound of formula 1.0 and antihormonal agents are as those described above in the combination therapies, or those described above for the individual compound of formula I and antihormonal agents, and the dosages of the chemotherapeutic agents are those described above for the individual chemotherapeutic agent. The dosages for the chemotherapeutic agents are well known in the art.

Other embodiments of this invention are directed to pharmaceutical compositions comprising the compound of formula 1.0 and at least one antihormonal agent and a pharmaceutically acceptable carrier.

Other embodiments of this invention are directed to pharmaceutical compositions comprising the compound of formula 1.0, at least one antihormonal agent, at least one chemotherapeutic agent, and a pharmaceutically acceptable carrier.

Other embodiments of this invention are directed to pharmaceutical compositions comprising the compound of formula 1.0, at least one chemotherapeutic agent, and a pharmaceutically acceptable carrier.

Those skilled in the art will appreciate that the compounds (drugs) used in the methods of this invention are available to the skilled clinician in pharmaceutical compositions (dosage forms) from the manufacturer and are used in those compositions. So, the recitation of the compound or class of compounds in the above described methods can be replaced with a recitation of a pharmaceutical composition comprising the particular compound or class of compounds. For example, the embodiment directed to a method of treating cancer comprising administering to a patient in need of such treatment therapeutically effective amounts of the compound of formula 1.0, a taxane, and a platinum coordination compound, includes within its scope a method of treating cancer comprising administering to a patient in need of such treatment therapeutically effective amounts of a pharmaceutical composition comprising the compound of formula 1.0, a pharmaceutical composition comprising a taxane, and a pharmaceutical composition comprising a platinum coordination compound.

Those skilled in the art will recognize that the actual dosages and protocols for administration employed in the methods of this invention may be varied according to the judgment of the skilled clinician. The actual dosage employed may be varied depending upon the requirements of the patient and the severity of the condition being treated. Determination of the proper dosage for a particular situation is within the skill of the art. A determination to vary the dosages and protocols for administration may be made after the skilled clinician takes into account such factors as the patient's age, condition and size, as well as the severity of the cancer being treated and the response of the patient to the treatment.

The amount and frequency of administration of the compound of formula 1.0 and the chemotherapeutic agents will be regulated according to the judgment of the attending clinician (physician) considering such factors as age, condition and size of the patient as well as severity of the cancer being treated.

The chemotherapeutic agent can be administered according to therapeutic protocols well known in the art. It will be apparent to those skilled in the art that the administration of the chemotherapeutic agent can be varied depending on the cancer being treated and the known effects of the chemotherapeutic agent on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the cancer to the administered therapeutic agents.

The initial administration can be made according to established protocols known in the art, and then, based upon the observed effects, the dosage, modes of administration and times of administration can be modified by the skilled clinician.

The particular choice of chemotherapeutic agent will depend upon the diagnosis of the attending physicians and their judgement of the condition of the patient and the appropriate treatment protocol.

The determination of the order of administration, and the number of repetitions of administration of the chemotherapeutic agent during a treatment protocol, is well within the knowledge of the skilled physician after evaluation of the cancer being treated and the condition of the patient.

Thus, in accordance with experience and knowledge, the practicing physician can modify each protocol for the administration of an chemotherapeutic agent according to the individual patient's needs, as the treatment proceeds. All such modifications are within the scope of the present invention.

The particular choice of antihormonal agents, optional chemotherapeutic agents and optional radiation will depend upon the diagnosis of the attending physicians and their judgment of the condition of the patient and the appropriate treatment protocol.

The determination of the order of administration, and the number of repetitions of administration of the antihormonal agents, optional chemotherapeutic agents and optional radiation during a treatment protocol, is well within the knowledge of the skilled physician after evaluation of the breast cancer being treated and the condition of the patient.

Thus, in accordance with experience and knowledge, the practicing physician can modify each protocol for the administration of antihormonal agents, optional chemotherapeutic agents and optional radiation according to the individual patient's needs, as the treatment proceeds. All such modifications are within the scope of the present invention.

The attending clinician, in judging whether treatment is effective at the dosage administered, will consider the general well-being of the patient as well as more definite signs such as relief of cancer-related symptoms (e.g., pain, cough (for lung cancer), and shortness of breath (for lung cancer)), inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

The compounds of the invention can be made according to the processes described in US 2007/0191604 published Aug. 16, 2007, U.S. Ser. No. 11/810,282 filed Jun. 5, 2007, as well as the processes described below. The disclosures of US 2007/0191604 and U.S. Ser. No. 11/810,282 are incorporated herein by reference thereto.

The LCMS conditions are: (1) column: C-18 reverse phase, 5 um, 4.6×50 mm, (2) MS:PE Sciex API-150EX, and (3) HPLC: Shimadzu LC-10 ADvp, 1 ml/min, linear gradient 10% acetonitrile in water to 95% acetonitrile in water, both contain 0.05% TFA Example 1

Synthesis of 3-Methoxy-1-(2-{4-[4-(1-methyl-1H-[1,2,4]triazol-3-yl)-phenyl]-3,6-dihydro-2H-pyridin-1-yl}-2-oxo-ethyl)-pyrrolidine-3-carboxylic acid [3-(6-isopropoxy-pyridin-3-yl)-1H-indazol-5-yl]-amide

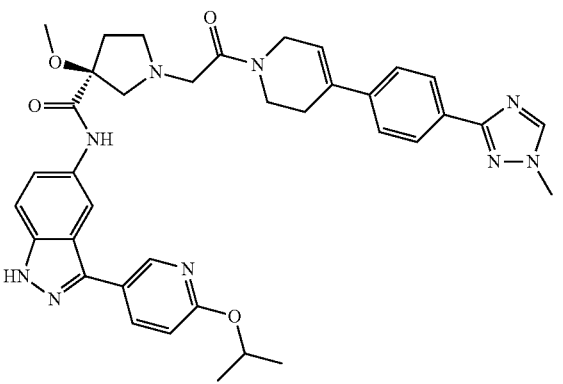

A1

Synthesis of 2-chloro-1-{4-[4-(1-methyl-1H-[1,2,4]triazol-3-yl)-phenyl]-3,6-dihydro-2H-pyridin-1-yl}-ethanone

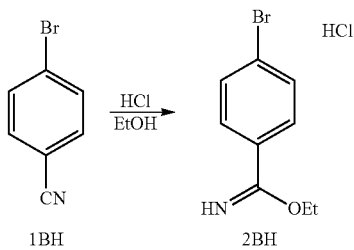 [SMILES: "EtOH" ; N#Cc1ccc(Br)cc1 ; Cl ; CCOC(=N)c1ccc(Br)cc1 ; Cl]

Step 1: Preparation of 4-bromo-benzimidic Acid Ethyl Ester

4-Bromo-benzonitrile (5 g) was suspended in absolute EtOH (100 ml) and cooled to 0-5° C. HCl gas was bubbled through, initially vigorously for several minutes and later slowly for 5 hours. The resulting solution was allowed to stir overnight. Most of solvent was removed and the precipitate was filtered, washed with EtOH twice and dried to afford compound 2BH (4.1 g) as white solid.

Step 2: Preparation of Compound 3BH

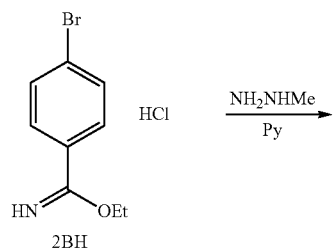

The 4-bromo-benzimidic acid ethyl ester (2.12 g, 8 mmols) was dissolved in pyridine (20 ml). Methylhydrazine (640 µl, 12 mmols) was added with stirring and the resulting mixture was allowed to stir overnight. The reaction mixture was concentrated under reduced pressure, and added ether, filtered, washed with ether three times and dried to provide the compound 3BH (2.2 g).

Step 3: Preparation of 3-(4-bromo-phenyl)-1-methyl-1H-[1,2,4]triazole

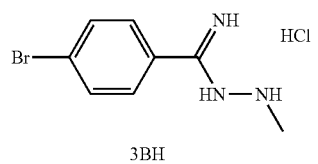

A mixture of compound 3BH (2.2 g) in formic acid (30 ml) was refluxed overnight and concentrated. The residue was treated with sat. NaHCO₃, and extracted with EtOAc three times. The combined organics were dried over MgSO₄. After concentration, compound 4BH was obtained as colorless crystals (1.39 g). (Note: it was found that the reaction can be done in just two hours. In large scale synthesis, use 10% NaOH to replace NaHCO₃).

Step 4: Preparation of 4-[4-(1-methyl-1H-[1,2,4]triazol-3-yl)-phenyl]-3,6-dihydro-2H-pyridine-1-carboxylic Acid tert-butyl Ester

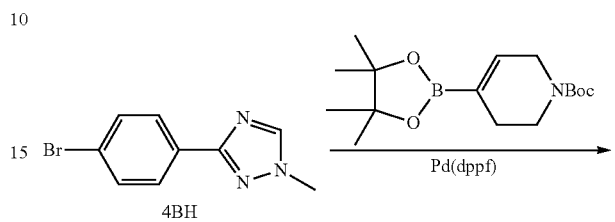

To a large pressure flask were charged compound 4BH (13.3 g, 55.9 mmols), 4-(4,4,5,5-tetramethyl-[1,3,2]dioxaborolan-2-yl)-3,6-dihydro-2H-pyridine-1-carboxylic acid tert-butyl ester (19 g, 61.5 mmols), [1,1'-bis(diphenylphosphino)ferrocene]dichloropalladium(II), complex with dichloromethane (1:1) (2.3 g, 2.8 mmols), K₂CO₃ (23.2 g, 168 mmols) and DME/water (5:1, 120 ml). The mixture was briefly degassed with Ar for ~0.5 minute, capped and stirred at 80C overnight. After cooling, the reaction mixture was diluted with EtOAc and brine. Organic layer was isolated, and dried (MgSO₄). After concentration, the residue was purified on silica gel. Elution with MeOH/EtOAc (0-10%) gave the desired product 5BH (13.9 g, 73%).

Step 5: Preparation of 4-[4-(1-methyl-1H-[1,2,4]triazol-3-yl)-phenyl]-1,2,3,6-tetrahydro-pyridine hydrochloride

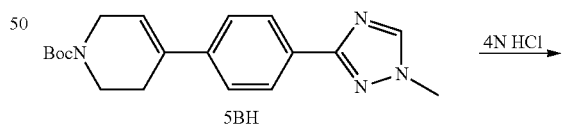

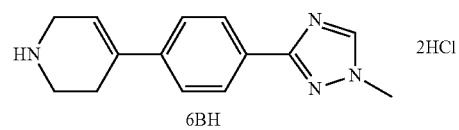

The Boc group can be removed by treating compound 5BH with 4N HCl in dioxane at rt for two hours. Removal of solvent under vacuum gave compound 6BH.

Step 6: Preparation of 2-chloro-1-{4-[4-(1-methyl-1H-[1,2,4]triazol-3-yl)-phenyl]-3,6-dihydro-2H-pyridin-1-yl}-ethanone

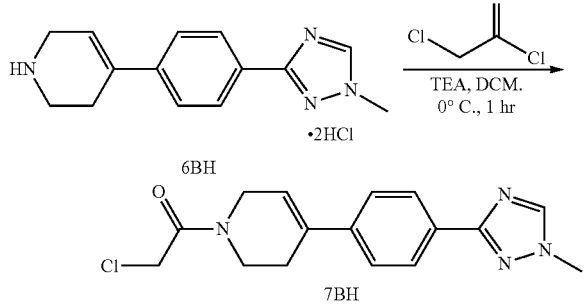

To a cold (0° C.) solution of 4-[4-(1-methyl-1H-[1,2,4]triazol-3-yl)-phenyl]-1,2,3,6-tetrahydro-pyridine 6BH (13.7 g, 44 mmol) in dichloromethane (450 ml) was added TEA (37 ml, 264 mmol) dropwise. After stirred at 0° C. for 10 min, chloroacetyl chloride (10.5 ml, 132 mmols) was added to the reaction mixture. The resulting mixture was stirred at 0° C. for 1 hr., and quenched with water (165 ml). The reaction mixture was diluted with dichloromethane (600 ml). The organic layer was separated and washed with brine, dried over $MgSO_4$. Reaction mixture was concentrated to ~50 ml, ether was added and the solid was filtered out to get the desired product 7BH (8.74 g).

Synthesis of 3-Methoxy-pyrrolidine-3-carboxylic acid methyl ester

Step 1: Preparation of Methyl α,α-dimethoxypropionate

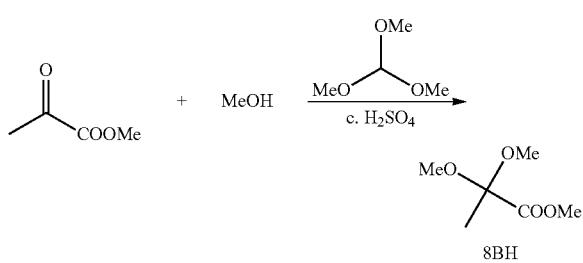

The procedure by Ernest Wenkert, et al. (JACS, 1983, 105, 2021-2029) was followed. A solution of methyl pyruvate (44 g), trimethyl orthoformate (62 ml), concentrated $H_2SO_4$ (0.2 ml) in MeOH (120 ml) was refluxed for 4 hours. In the next one hour period, solvent (about 80 ml) was distilled out. The reaction mixture was cooled to 10° C., poured into a KOH solution (1.2 g KOH in 600 ml water), and extracted with ether (3×). Combined ether extracts were washed with brine and dried ($MgSO_4$). After concentration, the residue was distilled under vacuum to provide the acetal (8BH) (40 g, 62%, 40-43C/1 torr).

Step 2: Preparation of 2-methoxyacrylate

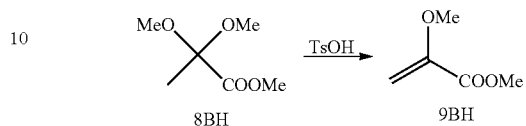

The procedure by Ernest Wenkert, et al. (JACS, 1983, 105, 2021-2029) was followed. To a one neck flask was charged α,α-dimethoxypropionate (8BH) (150 g) and Toluenesulfonic acid monohydrate (3 g) and a short path distillation head was attached. The mixture was heated at 140° C. (oil bath temperature) and methanol began to come out first. The product (76 g) of (9BH) was then distilled out later after oil bath temperature was raised over 190° C.

Step 3: Preparation of 1-benzyl-3-methoxy-pyrrolidine-3-carboxylic Acid Methyl Ester

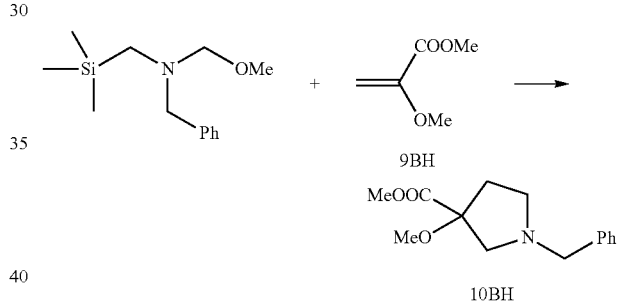

To a stirred solution of methyl 2-methoxyacrylate (20.8 g, 179 mmols) and N-(methoxymethyl)-N-(trimethylsilylmethyl)benzylamine (55 ml, 215 mmols) in dichloromethane (160 ml) was added at 0° C. a solution of trifluoroacetic acid (2 ml) in dichloromethane (10 ml). The resulting solution was warmed to room temperature and stirred overnight. After concentration, the crude product was purified by column chromatography on silica gel eluting with a solution of ethyl acetate/hexanes/$Et_3N$ (1000:3000:4 to 1000:1000:3) to give the title compound (10BH) (17.7 mg, 40%). (Note: adding $Et_3N$ is essential to ensure sharp separation.)

Step 4: Preparation of 3-methoxy-pyrrolidine-3-carboxylic Acid Methyl Ester Tartaric Acid Salt

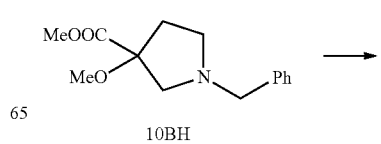

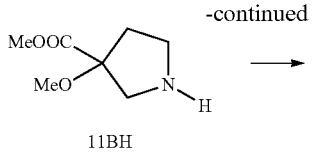

2.49 gm of 1-benzyl-3-methoxy-pyrrolidine-3-carboxylic acid methyl ester (10BH) was hydrogenated in ethanol using 10% Pd/C at 55 psi hydrogen for 24 hrs. Filtration of the Pd/C followed by evaporation of the ethanol 1.6 gm of crude debenzylated product (11BH). The crude product was dissolved in 95 ml of methanol and 1.35 gm of L-tartaric acid added. After 24 hrs, the crystals were filtered and re-crystallized from methanol to give 13.4 grams of title product (12BH).

Step 5: Preparation of 3-Methoxy-pyrrolidine-1,3-dicarboxylic acid 1-tert-butyl Ester

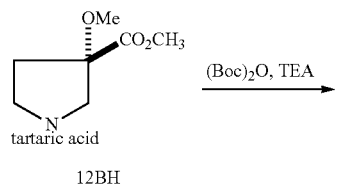

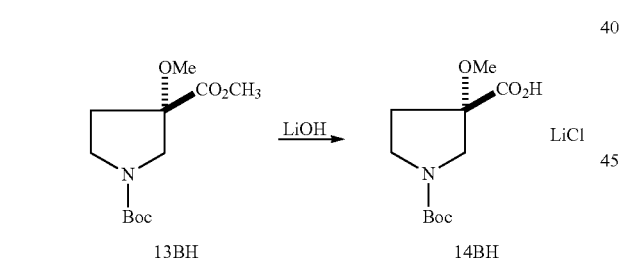

To a cold (0° C.) solution of 12BH (28 g, 90.52 mmol) in dry CH$_2$Cl$_2$ (250 mL) was added triethylamine (31.5 mL, 226.32 mmol, 2.5 equiv) followed by (Boc)$_2$O (25.7 g, 117.68 mmol, 1.3 equiv). The resulting mixture was stirred from 0° C. to rt for overnight then diluted with CH$_2$Cl$_2$, which was washed with saturated aqueous NaHCO$_3$ solution and brine, dried (MgSO$_4$) and concentrated. Chromatograph on silica gel (hexanes/ethyl acetate, 4:1) gave 13BH (23.5 mg, 90.52 mmol, 100%) as a colorless oil.

To a stirred solution of 13BH (23.5 mg, 90.52 mmol) in THF/MeOH (175 mL/175 mL) was added 135 mL of LiOH (1M in H$_2$O, 135 mmol, 1.5 equiv). The reaction mixture was stirred at rt for overnight, to which 135 mL of 1N HCl was added. The resulting mixture was stirred for additional 15 min and concentrated, azeotroped with dioxane (150 mL×3) to give 14BH (42.32 g) as a white solid, which can be used in the next step without further purification.

Alternatively compound 11BH can be prepared as follows:

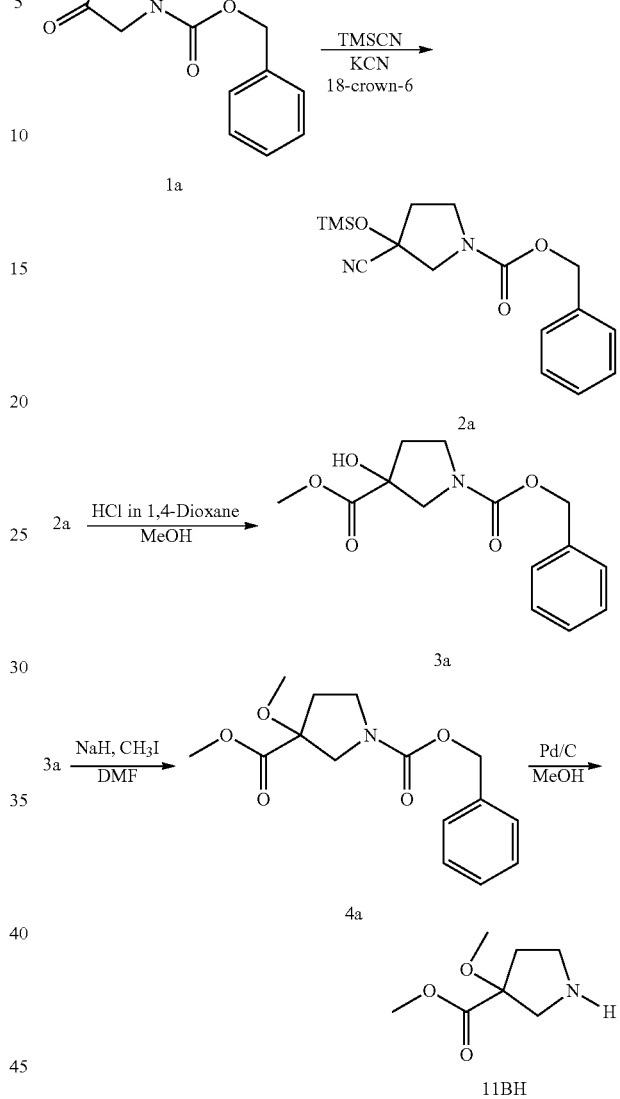

To an ice cold solution of 3-Oxo-pyrrolidine-1-carboxylic acid benzyl ester 1a (250 g, 1.14 mol) in 3.5 L anhydrous dichloromethane was added KCN (7.5 g, 0.12 mol), followed by 18-crown-6 (30 g, 0.11 mol), though not completely dissolved, was added TMSCN (183 mL, 1.37 mol) slowly over a period of 20 min. The reaction was stirred at ambient temperature for 1 overnight. A semi-saturated NaHCO$_3$ solution (2 L) was added at 15° C., stirred for 10 min and then the organic layer was separated, dried over magnesium sulfate, filtered and evaporated to give 3-Cyano-3-trimethylsilanyloxy-pyrrolidine-1-carboxylic acid benzyl ester 2a, 422 g (>100%).

3-Cyano-3-trimethylsilanyloxy-pyrrolidine-1-carboxylic acid benzyl ester 2a (422 g) in 4 L of anhydrous MeOH, was added 2.2 L of 4N HCl in dioxane. The reaction was refluxed for 13 h and stirred at ambient temperature for 1 overnight. Solvents were removed, suspended in 5 L of CH$_2$Cl$_2$, washed with 4+3 L of water, adjusted the pH to 6-7 with aq. NaHCO$_3$, dried over magnesium sulfate, filtered and evaporated to give 3-Hydroxy-pyrrolidine-1,3-dicarboxylic acid 1-benzyl ester 3-methyl ester 3a, 278 g (2 steps, 87%).

To a suspension of NaH (52 g, 1.3 mol) in 2.2 L of anhydrous DMF at 8° C., was added a solution of 3-Hydroxy-pyrrolidine-1,3-dicarboxylic acid 1-benzyl ester 3-methyl ester 3a (278 g, 1.0 mol) in 700 DMF, keeping the reaction temperature below 11° C. After complete addition (~20 min), ice bath was removed, stirred at 16-18° C. for 1 h, and then at ambient temperature for 1 h. Cooled back to 15° C., added MeI (81 mL, 1.3 mol) slowly. Reaction mixture was stirred at ambient temperature for 1 overnight. The reaction mixture was then poured in a cold water (4 L) and then extracted with Et$_2$O (6 L) and EtOAc (2 L), washed the organic later with water (5 L), brine (700 mL), dried over magnesium sulfate, filtered and evaporated to give crude 3-Methoxy-pyrrolidine-1,3-dicarboxylic acid 1-benzyl ester 3-methyl ester 4a 289 g (99% crude yield, contains mineral oil) (stirring/separation with pentane wash gave 4a, 268.2 g (92%).

3-Methoxy-pyrrolidine-1,3-dicarboxylic acid 1-benzyl ester 3-methyl ester 4a in MeOH (2200 mL), was added 14 g of 10% Pd/C (~50% in water). The reaction mixture was hydrogenated using H$_2$ at ~55 psi pressure (epen valve) for 1 overnight. The reaction mixture was filtered, dried to give 3-Methoxy-pyrrolidine-3-carboxylic acid methyl ester 11BH 126 g. (overall yield of 70% for 4 steps, no column purification).

Synthesis of 3-Methoxy-pyrrolidine-3-carboxylic Acid [3-(6-isopropoxy-pyridin-3-yl)-1H-indazol-5-yl]-amide

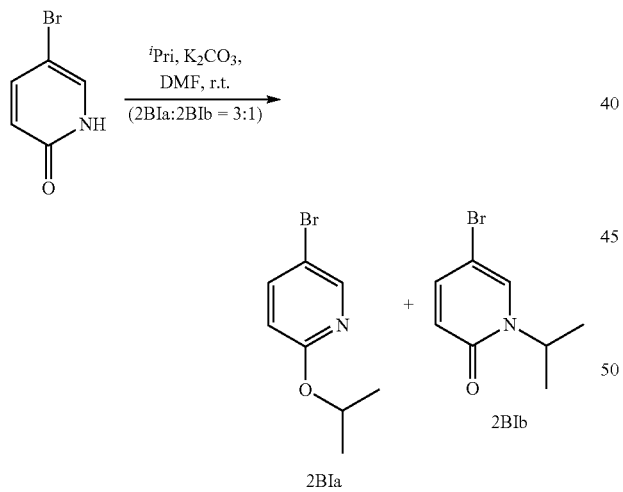

Step 1:

5-bromo-1H-pyridone 1BI (100 g, 0.58 mol), potassium carbonate (238 g, 1.73 mol) and 2-iodopropane (86 ml, 0.86 mol) were stirred in DMF (1 L) at r.t. for 1 day. The mixture were diluted with ethyl acetate and water, layers were separated. The separated organic layer was washed with water (×2), dried (MgSO$_4$) and filtered. Solvents were removed in vacuum and column purification [5% ethyl acetate in hexanes] gave first the less polar 5-isopropoxypyridine 2BIa (73 g, 59%) as colourless liquid. Continuous elution with [50% ethyl acetate in hexanes] gave the more polar 5-bromo-1-isopropylpyridone 2BIb as white solid (22 g, 18%).

Step 2

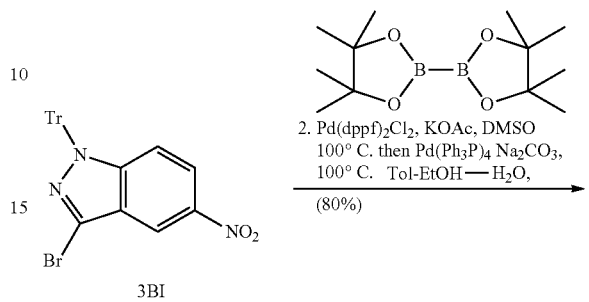

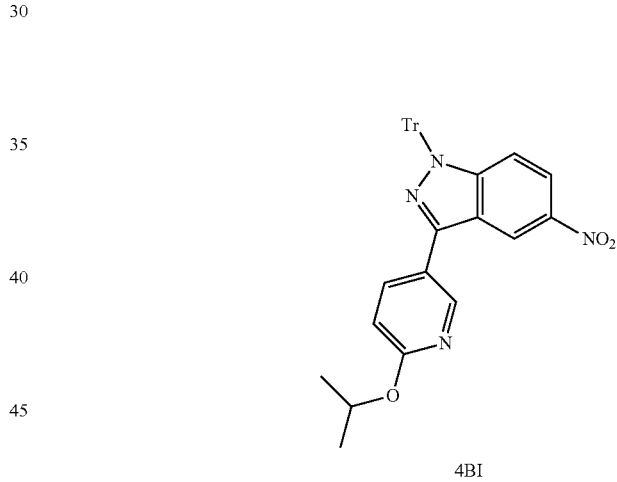

5-isopropoxypyridine 2BIa (10 g, 0.046 mol), bis(pinacolato)diboron (14.1 g, 0.056 mol), potassium acetate (13.6 g, 0.14 mol) and PdCl$_2$(dppf)$_2$·CH$_2$Cl$_2$ (3.78 g, 0.0046 mol) were weight into a 2-necked 1 L flask equipped with a water condenser. DMSO (100 ml) was added and the mixture was purged with nitrogen for 15 min. The mixture was heated at 100° C. under nitrogen for 2 hr. After being cooled to r.t., water (100 ml), toluene (100 ml), ethanol (100 ml), potassium carbonate (32 g, 0.23 mol) and bromoindazole 3BI (22.4 g, 0.046 mol) were added. The mixture were purged with nitrogen for 10 min at r.t. and Pd(Ph$_3$P)$_4$ (5.35 g, 0.0046 mol) was added. The final mixture were heated at 100° C. for 2 hr and cooled to r.t. Water and ethyl acetate were added. Solids were filtered through Celite. Layers were separated and the separated organic layer was washed with water (×2). The combined aqueous layers were back extracted with ethyl acetate (×1). The combined organic layers were dried (MgSO$_4$), filtered and solvents were removed in vacuum. Column purification [Hexanes-ethyl acetate=9:1 (v/v)] gave isopropoxy-indazole 4BI (20 g, 80%) as yellow solid.

Step 3

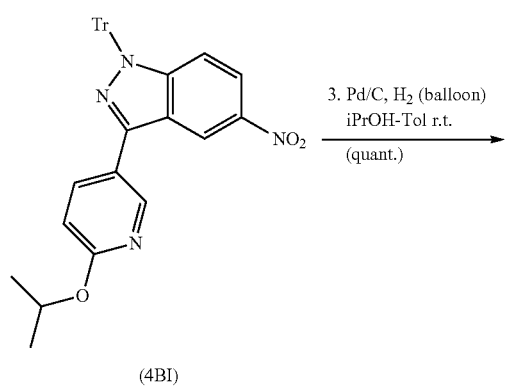

(4BI)

(5BI)

Isopropoxyindazole 4BI (20 g, 0.037 mol) and Pd/C (10%, 50% wet, 7.8 g, 0.0037 mol) were stirred in toluene (100 ml) and 2-propanol (200 ml) under H₂ (balloon) at r.t. for 1 day. The solid catalyst was filtered through Celite and solvents were removed in vacuum to give aminoindazole 5BI (quant.) as off-white solid.

Step 4

(5BI)

(7BI)

Aminoindazole 5BI (39 g, 0.076 mol) and pyrrolidinecarboxylic acid 14BH (32 g, 0.069 mol) were dissolved in DMF (300 ml) at r.t. HATU (29 g, 0.076 mol) followed by ⁱPr₂NEt (14.5 ml, 0.083 mol) were added. The mixture was stirred at r.t. overnight and was diluted with ethyl acetate and water. Layers were separated. The separated organic layer was washed with water (×2), dried (MgSO₄) and filtered. Concentration in vacuum followed by column purification [hexanes-ethyl acetate=4:1 (v/v)] gave crude 7BI as off-white foam.

Step 5

(7BI)

(8BI)

The crude 7BI was stirred in a mixture of dichloromethane (300 ml), trifluoroacetic acid (100 ml) and water (50 ml) at r.t. overnight. The mixture was cooled at 0° C. and quenched carefully with saturated aqueous sodium bicarbonate. Solvents were removed in vacuum. Dilute with water and ethyl acetate. Layers were separated and the separated aqueous layer was extracted with ethyl acetate (×3). The combined organic layers were dried ($MgSO_4$), filtered and solvents were removed in vacuum. Column purification [5 to 10% MeOH (7N ammonia) in dichloromethane] gave pyrrolidine 8BI (23 g, 84%) as off-white solid.

Alternatively:

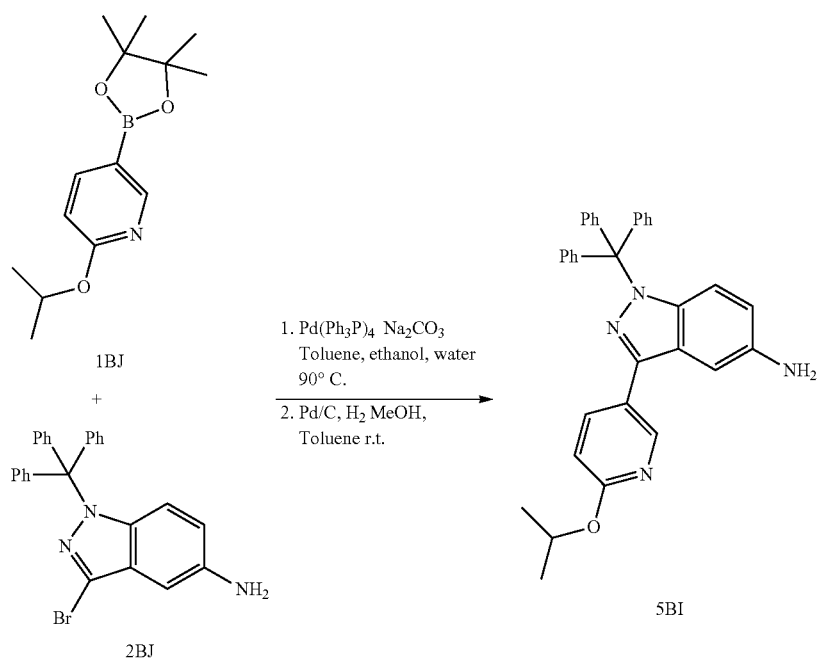

Boronate 1BJ (1.0 g, 3.80 mmol), bromoindazole 2BJ (1.84 g, 3.80 mmol), sodium bicarbonate (1.21 g, 11.4 mmol) were charged into a sealed-tube. Toluene (30 ml), ethanol (30 ml) and water (15 ml) were added. The slurry was purged with nitrogen for 15 min. and $Pd(Ph_3P)_4$ (439 mg, 0.38 mmol) was added in one portion. The mixture was heated in the sealed-tube at 90° C. overnight. After being cooled to r.t., water and ethyl acetate were added and the layers were separated. The separated organic layer was washed with water, dried ($MgSO_4$) and filtered. Solvents were removed in vacuum. The residue was dissolved in toluene (100 ml). Methanol (100 ml) followed with Pd/C (809 mg, 0.38 mmol, 50% wet) were added. The mixture was stirred under $H_2$ (balloon) overnight. The catalyst was filtered and solvents were removed in vacuum. Column purification [hexanes-ethyl acetate=2:1 (v/v)] gave aniline 5BI (1.2 g, 61%, 2 steps) as off-white solid.

Synthesis of 3-Methoxy-1-(2-{4-[4-(1-methyl-1H-[1,2,4]triazol-3-yl)-phenyl]-3,6-dihydro-2H-pyridin-1-yl}-2-oxo-ethyl)-pyrrolidine-3-carboxylic acid [3-(6-isopropoxy-pyridin-3-yl)-1H-indazol-5-yl]-amide

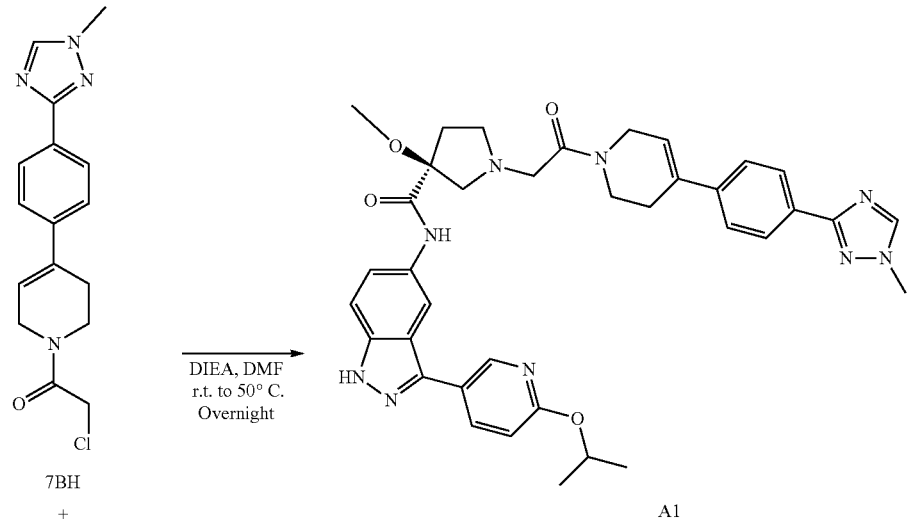

A mixture of compound 7BH (7.88 gm, 24.93 mmol), compound 8BI (9.86 gm, 24.93 mmol), and DIEA (26.1 ml, 149.62 mmol) in DMF (200 ml) was stirred at room temperature for 5 hr. Reaction was completed to about 89% based on the LCMS. It was then heated at 50° C. for overnight (16 hr.) LCMS shows the reaction is complete. DMF was removed under reduced pressure. The crude was dissolved in 700 ml of DCM and washed with 35 ml of water once. Aqueous layer was extracted with 20% MeOH/DCM (2×120 ml). The combined organic extracts were homogenized with MeOH and dried over MgSO$_4$. The solvent was removed and the crude was purified by column chromatography using 20% MeOH/EtOAc to get the desired product A1 as a yellow solid (70%). (LCMS M+1=674, ret. time=2.91 min.) $^1$H NMR (400 MHz, CD3OD): δ 8.67 (S, 1H), 8.42 (S, 1H), 8.35 (S, 1H), 8.15-8.19 (m, 1H), 7.94 (dd, 2H, J=8.4 & 10 Hz), 7.64 (m, 1H), 7.49 (m, 3H), 6.84 (m, 1H), 6.20 (d, 1H, J=11.2 Hz), 5.3 (m, 1H), 4.28 (s, 1H), 4.23 (m, 1H), 3.97 (s, 3H), 3.8 (m, 2H), 3.56 (d, 1H, 2.4 Hz), 3.52 (d, 1H, 6.4 Hz), 3.31 (s, 3H), 3.17 (t, 1H, J=10

Hz), 3.07 (t, 1H, J=12 Hz), 2.81 (m, 1H), 2.81 (m, 1H), 2.65 (s, 1H), 2.58 (s, 1H), 2.43 (m, 1H), 2.17 (m, 1H), 1.32 (d, 6H, J=6.4 Hz)

Example 2

Synthesis of 3-Methoxy-1-(2-{4-[4-(1-methyl-1H-[1,2,4]triazol-3-yl)-phenyl]-3,6-dihydro-2H-pyridin-1-yl}-2-oxo-ethyl)-pyrrolidine-3-carboxylic Acid [3-(6-hydroxy-pyridin-3-yl)-1H-indazol-5-yl]-amide

A20

The above compound (A20) was isolated from the decomposition of di-HCL salt of 3-Methoxy-1-(2-{4-[4-(1-methyl-1H-[1,2,4]triazol-3-yl)-phenyl]-3,6-dihydro-2H-pyridin-1-yl}-2-oxo-ethyl)-pyrrolidine-3-carboxylic acid [3-(6-isopropoxy-pyridin-3-yl)-1H-indazol-5-yl]-amide.

LCMS M+1 634, ret. time=2.28 min. $^1$H-NMR (400 MHz, DMSO-d$_6$): δ 13.09 (br, 1H), 11.84 (br, 1H), 10.02 (s, 1H), 8.51 (s, 1H), 8.37 (s, 1H), 8.02 (dd, 1H, J=9.5 Hz & 2.5 Hz), 7.95 (m, 2H), 7.82 (d, 1H, J=1.9 Hz), 7.71 (m, 1H), 7.51 (m, 3H), 6.52 (d, 1H, J=9.5 Hz), 6.27 (m, 1H), 4.08-4.34 (m, 2H), 3.92 (s, 3H), 3.70 (m, 2H), 3.49 (m, 2H), 3.24 (s, 3H), 3.16 (d, 1H, J=5.2 Hz), 2.84-3.13 (m, 3H), 2.55-2.76 (m, 2H), 2.36 (m, 1H), 2.05 (m, 1H).

Example 3

Synthesis of 1-(2-{4-[4-(1,5-Dimethyl-1H-[1,2,4]triazol-3-yl)-phenyl]-3,6-dihydro-2H-pyridin-1-yl}-2-oxo-ethyl)-3-methoxy-pyrrolidine-3-carboxylic acid [3-(6-isopropoxy-pyridin-3-yl)-1H-indazol-5-yl]-amide

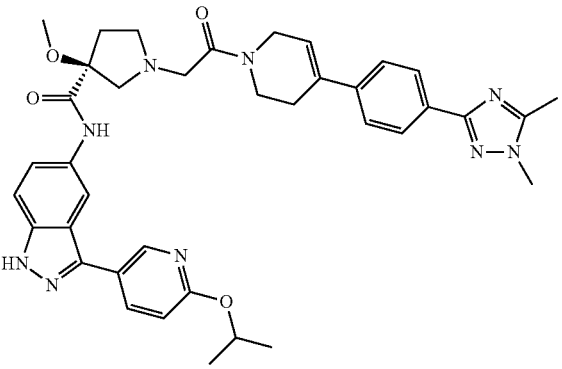

(A14)

Synthesis of (S)-1-(2-(4-(4-(1,5-dimethyl-1H-1,2,4-triazol-3-yl)phenyl)-5,6-dihydropyridin-1(2H)-yl)-2-oxoethyl)-N-(3-(6-isopropoxypyridin-3-yl)-1H-indazol-5-yl)-3-methoxypyrrolidine-3-carboxamide Step 1: Preparation of 3-(4-bromo-phenyl)-1,5-dimethyl-1H-[1,2,4]triazole

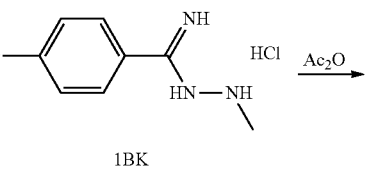

1BK

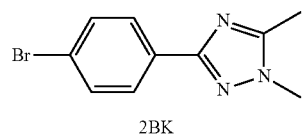

2BK

A mixture of 4-bromo-N'-methylbenzimidohydrazide hydrochloride 1 (1.7 g) (prepared according to a procedure in synthesis of Sch-1499895) in acetic anhydride (10 ml) was heated at 100° C. for 0.5 hour. After cooling and concentration under reduced pressure, the residue was dissolved in EtOAc, washed with saturated NaHCO$_3$ twice, brine and dried (MgSO$_4$). After evaporation of solvent, the residue was purified on silica gel. Elution with EtOAc gave 3-(4-bromophenyl)-1,5-dimethyl-1H-[1,2,4]-triazole 2BK (1.04 g).

Step 2: Preparation of tert-butyl 4-(4-(1,5-dimethyl-1H-1,2,4-triazol-3-yl)phenyl)-5,6-dihydropyridine-1(2H)-carboxylate

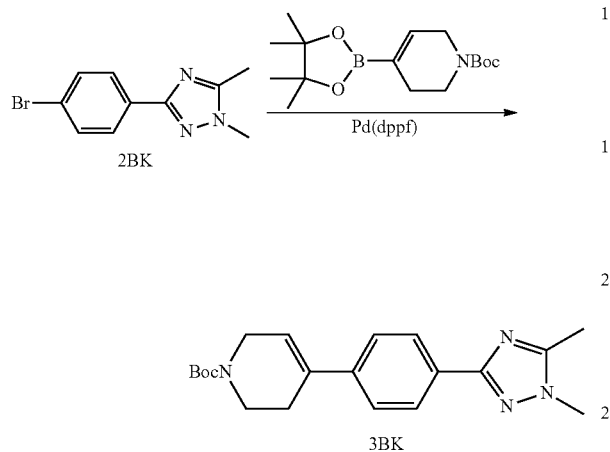

To a pressure tube were charged compound 2BK (252 mg, 1 mmol), 4-(4,4,5,5-tetramethyl-[1,3,2]dioxaborolan-2-yl)-3,6-dihydro-2H-pyridine-1-carboxylic acid tert-butyl ester (403 mg, 1.3 mmol), [1,1'-bis(diphenylphosphino)ferrocene]dichloropalladium(II), complex with dichloromethane (1:1) (41 mg, 0.05 mmol), K₂CO₃ (410 mg, 3 mmol) and DME/water (5:1, 6 ml). The mixture was briefly degassed with Ar for ~0.5 minute, capped and stirred at 100° C. overnight. After cooling, the reaction mixture was diluted with EtOAc and brine. Organic layer was isolated, and dried (MgSO₄). After concentration, the residue was purified on silica gel. Elution with MeOH/EtOAc (0-10%) gave the desired product 3BK (332 mg).

Step 3: Preparation of 4-(4-(1,5-dimethyl-1H-1,2,4-triazol-3-yl)phenyl)-1,2,3,6-tetrahydropyridine dihydrochloride

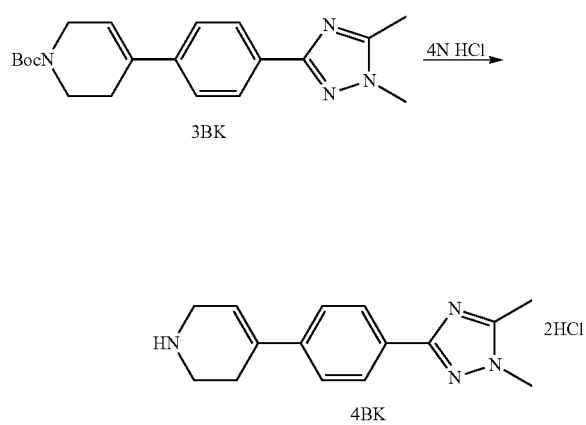

The Boc group can be removed by treating compound 3BK with 4N HCl in dioxane at rt for two hours. Removal of solvent under vacuum gave compound 4BK.

Step 4: Preparation of (5)-tert-butyl 2-(3-(3-(6-isopropoxypyridin-3-yl)-1H-indazol-5-ylcarbamoyl)-3-methoxypyrrolidin-1-yl)acetate

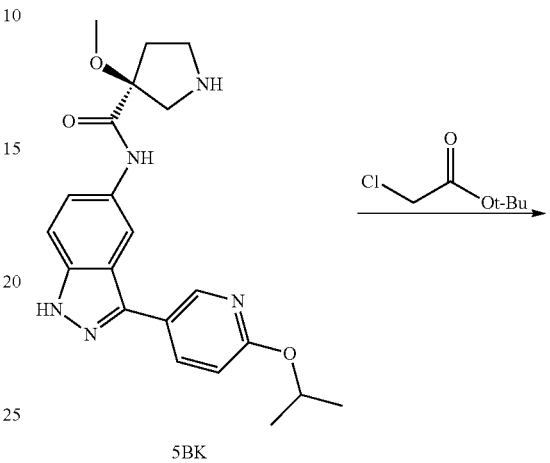

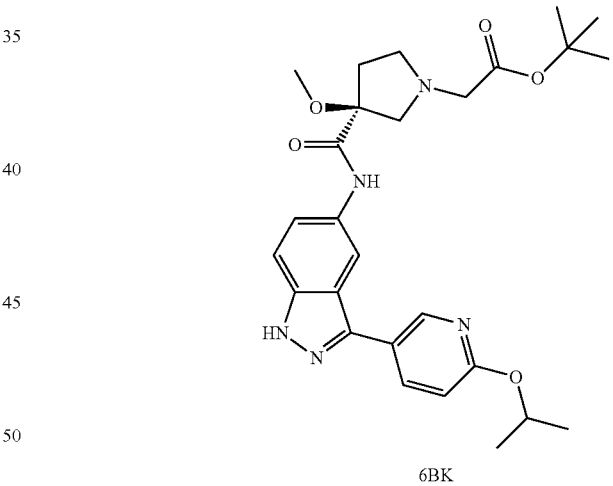

In a solution of compound 5BK (3.5 g, 6.6 mmol) (prepared according to a procedure in the synthesis of Sch-1499895) in acetonitrile (26 ml) was added DIEA (5.7 ml, 32.9 mmol). It was cooled to 0° C. and 0.47 ml (3.29 mmol) of tert-butyl chloroacetate was added dropwise. After stirring for 4 hr at 0° C., 0.47 ml (3.29 mmol) of tert-butyl chloroacetate was added again. It was stirred further for 1 hr at 0° C. and then warmed up to r.t. After stirring overnight at room temperature, it was dissolved in EtOAc (200 ml) and washed with NaHCO₃ (1×50 ml), water (1×50 ml) and brine (1×50 ml). The organic extracts were dried over MgSO₄ and the solvent was removed. The crude was purified by column chromatography using 20% MeOH/EtOAC to get the desired product 6BK (2.4 g).

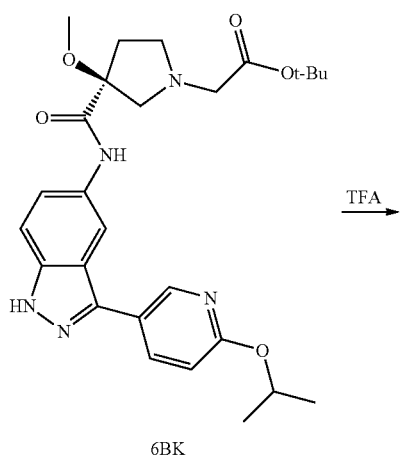

6BK

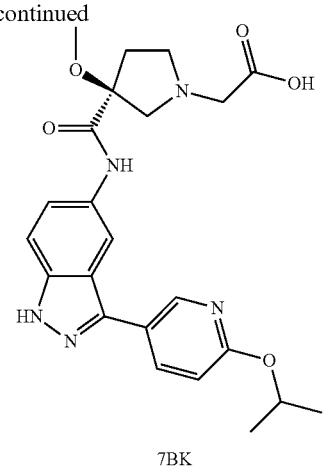

7BK

Compound 6BK (2.4 g) was treated with 40 ml of TFA for 45 minutes at room temperature. TFA was removed under reduced pressure and the solid was washed with ether to get the compound 7BK as a TFA salt (4.4 g, 95%).

Step 6: Preparation of (S)-1-(2-(4-(4-(1,5-dimethyl-1H-1,2,4-triazol-3-yl)phenyl)-5,6-dihydropyridin-1(2H)-yl)-2-oxoethyl)-N-(3-(6-isopropoxypyridin-3-yl)-1H-indazol-5-yl)-3-methoxypyrrolidine-3-carboxamide

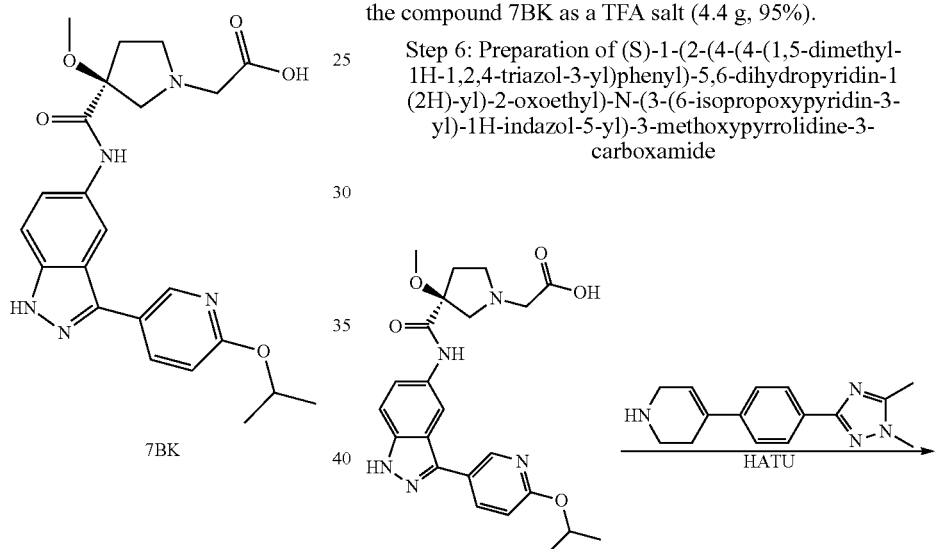

7BK (A14)

Step 5: Preparation of (S)-2-(3-(3-(6-isopropoxypyridin-3-yl)-1H-indazol-5-ylcarbamoyl)-3-methoxypyrrolidin-1-yl)acetic acid

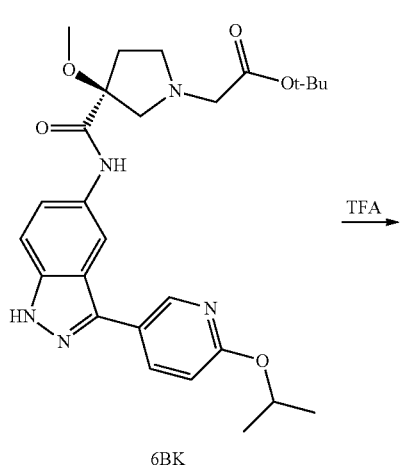

6BK

To a mixture of compound 7BK (0.12 mmol), HATU (46 mg, 0.12 mmol) in DMF (2 ml) was added compound 4BK (39 mg, 0.12 mmol) and DIEA (0.063 ml). The mixture was stirred for 20 minutes and directly purified by HPLC to give compound A14. Mass spectrum: LCMS M+1=690, retention time=3.25 minutes;

¹H NMR of A14 HCl salt (400 MHz, DMSO-d₆): δ 10.5 (br, 1H), 10.23 (d, J=17.6 Hz, 1H), 8.7 (m, 1H), 8.45 (d, J=1.2 Hz, 1H), 8.18 (m, 1H), 7.94 (m, 2H), 7.75 (dd, J=8.8, 2.0 Hz, 1H), 7.56 (m, 3H), 6.93 (m, 1H), 6.3 (m, 1H), 5.3 (m, 1H), 4.6-4.53 (m, 2H), 4.2-4.0 (m, 3H), 3.82 (s, 3H), 3.7-3.5 (m, 5H), 3.3 (s, 3H), 2.67-2.54 (m, 3H), 2.44 (s, 3H), 2.4 (m, 1H), 1.33 (d, J=6.4 Hz, 6H).

Example 4

Synthesis of 1-[2-(4-{3-Fluoro-4-[1-(2-methoxy-ethyl)-1H-[1,2,4]triazol-3-yl]-phenyl}-3,6-dihydro-2H-pyridin-1-yl)-2-oxo-ethyl]-3-methoxy-pyrrolidine-3-carboxylic acid [3-(6-isopropoxy-pyridin-3-yl)-1H-indazol-5-yl]-amide

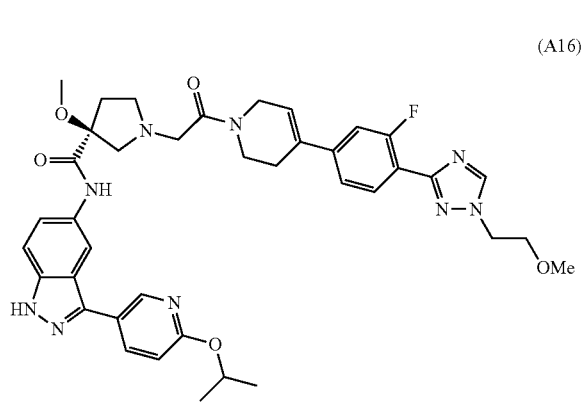 [SMILES: COCCn1cnc(-c2ccc(C3=CCN(C(=O)CN4CC[C@@](OC)(C(=O)Nc5ccc6[nH]nc(-c7ccc(OC(C)C)nc7)c6c5)C4)CC3)cc2F)n1]

(A16)

Synthesis of (S)-1-[2-(4-{3-fluoro-4-[1-(2-methoxy-ethyl)-1H-[1,2,4]triazol-3-yl]-phenyl}-3,6-dihydro-2H-pyridin-1-yl)-2-oxo-ethyl]-3-methoxy-pyrrolidine-3-carboxylic acid [3-(6-isopropoxy-pyridin-3-yl)-1H-indazol-5-yl]-amide Step 1: Preparation of 4-bromo-2-fluoro-benzamide

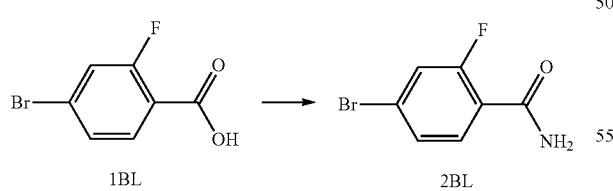

At 0° C., 1,1'-carbonyldiimidazole (8.8 g, 54.3 mmol) was added in portions to a stirred mixture of 4-bromo-2-fluorobenzoic acid (6 g, 27.3 mmol) in dichloromethane (100 ml). After 20 minutes, a clear solution was obtained. Ammonium hydroxide (28%, 30 ml) was added and the mixture was stirred overnight. Aqueous layer was isolated, extracted with dichloromethane twice. Combined organic extracts were washed with water, 1 N HCl twice, water, brine and dried (MgSO₄). Solvent was removed under vacuum, and the solid was washed with hexane to afford 4-bromo-2-fluoro-benzamide 2BL (5.56 g).

Step 2: Preparation of compound 3BL

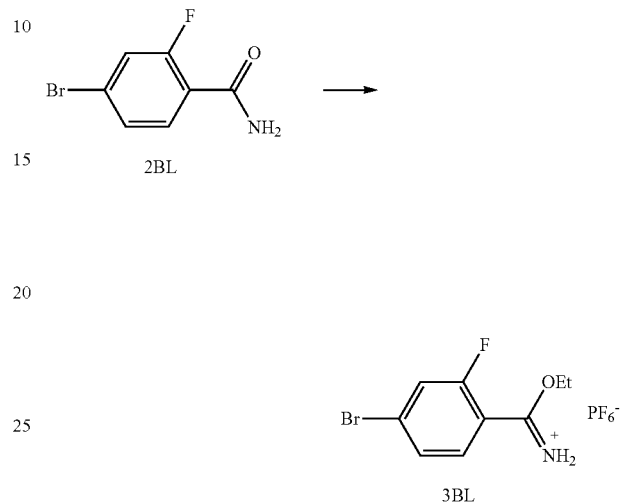

A mixture of compound 2BL (4.66 g, 21.48 mmol), Et₃OPF₆ (6.4 g, 25.77 mmol) in dichloroethane (86 ml) was refluxed for 1 hr. Solvent was removed under reduced pressure. The crude was cooled to 0° C., triturated with ether and filtered to give the desired product 3BL (7.5 g).

Step 3: Preparation of compound 4BL

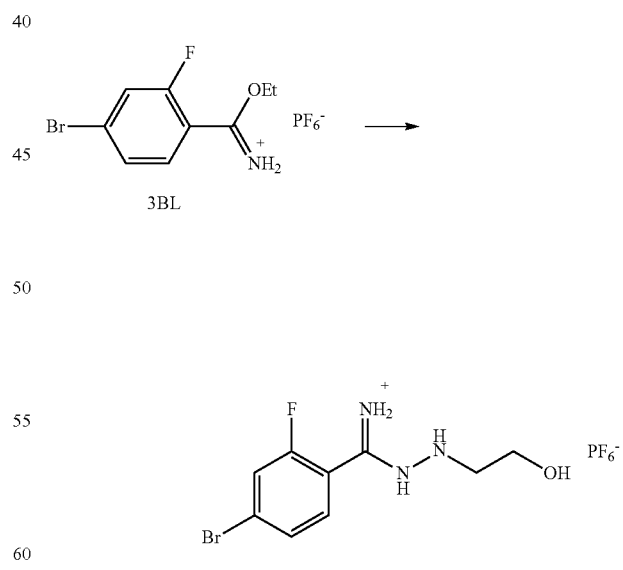

The compound 3BL (1.96 g) was dissolved in pyridine (10 ml). Hydroxyethylhydrazine (0.51 ml) was added with stirring and the resulting mixture was allowed to stir overnight. The reaction mixture was concentrated under reduced pres-

Step 4: Preparation of Compound 5BL

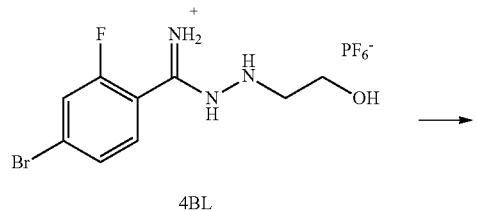

4BL

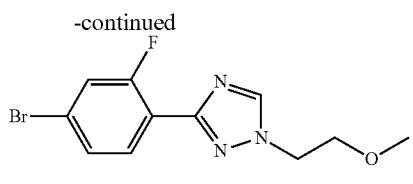

7BL

A solution of 5BL (429 mg, 1.5 mmol) in DMF (3 ml) was added with stirring into a flask containing NaH (60%, 66 mg, 1.65 mmol). After stirring for 30 minutes, MeI (0.103 ml, 1.65 mmol) was added slowly. After 30 minutes, the reaction mixture was diluted with EtOAc, washed with water three times, brine and dried (MgSO$_4$). After concentration, the residue was purified on silica gel. Elution with 10% MeOH/EtOAc gave compound 7BL (88 mg).

Step 6: Preparation of Compound A16

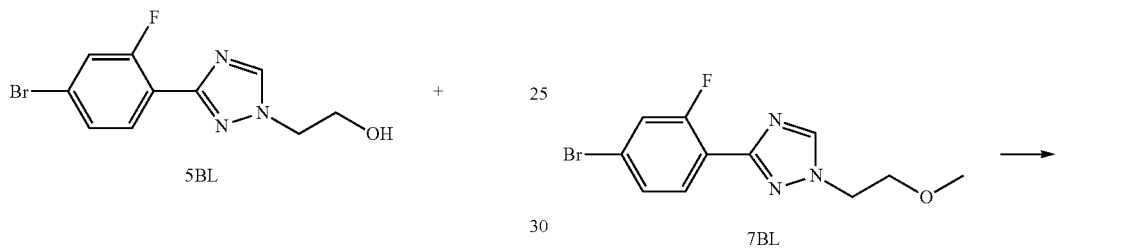

5BL

6BL

7BL

A mixture of the crude 4BL from the previous step in formic acid (30 ml) was refluxed overnight and concentrated under reduced pressure. The residue was treated with saturated NaHCO$_3$, and extracted with EtOAc three times. The combined organics were dried over MgSO$_4$. After concentration, compound residue was purified on silica gel. Elution with EtOAc gave compound 6BL (1.1 g), then 5BL (183 mg).

Compound 6BL can be easily converted to 5BL by aqueous basic hydrolysis.

Step 5: Preparation of compound 7BL

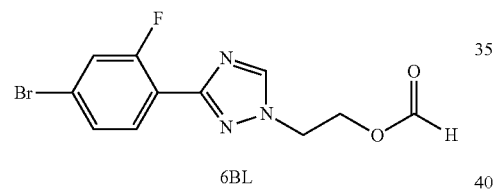

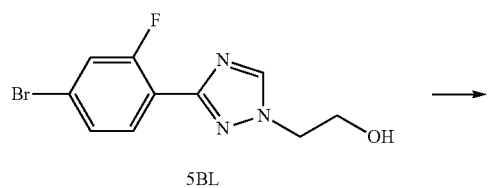

(A16)

Compound A16 was prepared from 7BL following procedures similar to those for the synthesis of (S)-1-(2-(4-(4-(1,5-dimethyl-1H-1,2,4-triazol-3-yl)phenyl)-5,6-dihydropyridin-1(2H)-yl)-2-oxoethyl)-N-(3-(6-isopropoxypyridin-3-yl)-1H-indazol-5-yl)-3-methoxypyrrolidine-3-carboxamide (A14, Example 3).

Mass spectrum: LCMS M+1=738, retention time 4 minutes.

$^1$H NMR of A16 HCl salt (400 MHz, DMSO-d$_6$): δ 10.45 (br, 1H), 10.23 (d, J=16.8 Hz, 1H), 8.7 (m, 1H), 8.6 (m, 1H), 8.46 (m, 1H), 8.18 (m, 1H), 8.0 (m, 1H), 7.74 (d, J=8 Hz, 1H), 7.57 (d, J=8 Hz, 1H), 7.42 (m, 1H), 6.93 (m, 1H), 6.43 (m, 1H), 5.3 (m, 1H), 4.6-4.5 (m, 2H), 4.41 (m, 2H), 4.21-4.01 (m, 4H), 3.8-3.6 (br, 7H), 3.33 (m, 3H), 3.25 (m, 2H), 2.67-2.54 (m, 3H), 2.4 (m, 1H), 1.33 (d, J=6.4 Hz, 6H).

Example 5

Synthesis of 1-(2-{4-[4-(1-Ethyl-1H-[1,2,4]triazol-3-yl)-phenyl]-3,6-dihydro-2H-pyridin-1-yl}-2-oxo-ethyl)-3-methoxy-pyrrolidine-3-carboxylic acid [3-(6-isopropoxy-pyridin-3-yl)-1H-indazol-5-yl]-amide

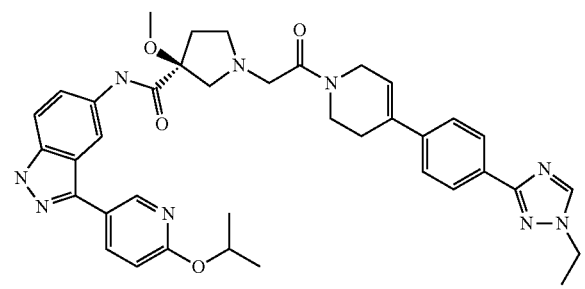

(A3)

Synthesis of 4-[4-(1-ethyl-1H-[1,2,4]triazol-3-yl)-phenyl]-1,2,3,6-tetrahydropyridine hydrochloride

Step 1: Preparation of 4-bromo-benzimidic Acid Ethyl Ester

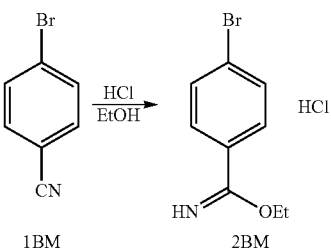 [SMILES: "EtOH" ; N#Cc1ccc(Br)cc1 ; Cl ; CCOC(=N)c1ccc(Br)cc1 ; Cl]

4-Bromo-benzonitrile (5 g) was suspended in absolute EtOH (100 ml) and cooled to 0-5° C. HCl gas was bubbled through, initially vigorously for several minutes and later slowly for 5 hours. The resulting solution was allowed to stir overnight. Most of solvent was removed and the precipitate was filtered, washed with EtOH twice and dried to afford compound 2BM (4.1 g) as white solid.

Step 2: Preparation of Compound 3BM

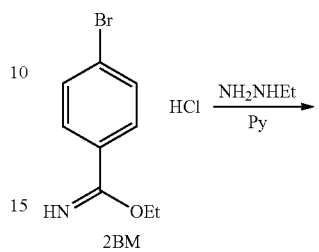

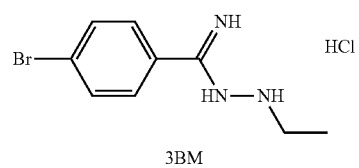

The 4-bromo-benzimidic acid ethyl ester (1 g) was dissolved in pyridine (20 ml). Ethylhydrazine (550 mg) was added with stirring and the resulting mixture was allowed to stir overnight. The reaction mixture was concentrated under reduced pressure, and added ether, filtered, washed with ether three times and dried to provide the compound 3BM (1 g).

Step 3: Preparation of 3-(4-bromo-phenyl)-1-ethyl-1H-[1,2,4]triazole

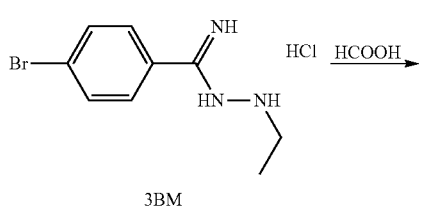

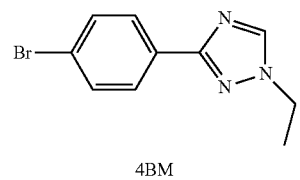

A mixture of compound 3BM (1 g) in formic acid (10 ml) was refluxed overnight and concentrated. The residue was treated with sat. NaHCO$_3$, and extracted with EtOAc three times. The combined organics were dried over MgSO$_4$. After concentration, compound 4BM was obtained as colorless crystals (0.9 g).

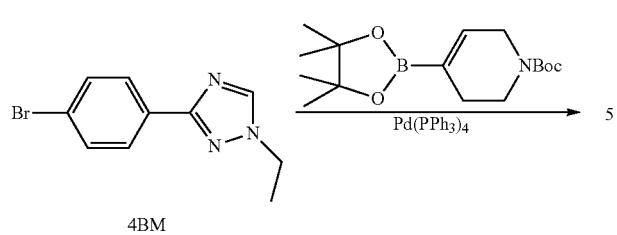

4BM

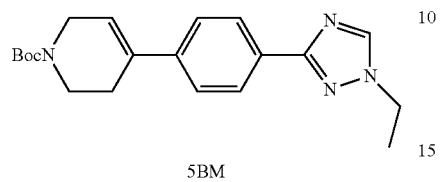

5BM

Step 4: Preparation of 4-[4-(1-ethyl-1H-[1,2,4]triazol-3-yl)-phenyl]-3,6-dihydro-2H-pyridine-1-carboxylic acid tert-butyl ester

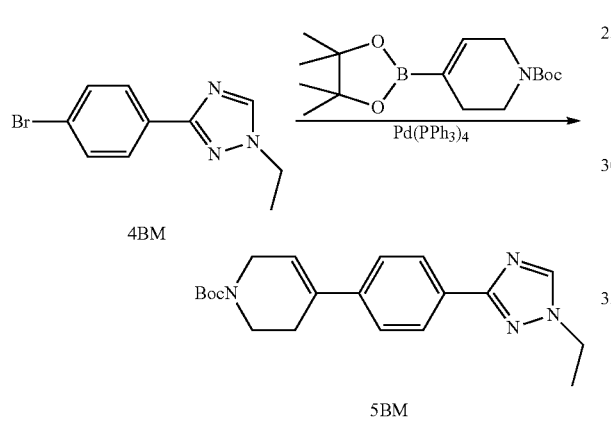

To a large pressure flask were charged compound 4BM (400 mg), 4-(4,4,5,5-tetramethyl-[1,3,2]dioxaborolan-2-yl)-3,6-dihydro-2H-pyridine-1-carboxylic acid tert-butyl ester (540 mg), Pd(PPh$_3$)$_4$ (180 mg), Na$_2$CO$_3$ 2N (3 ml) and Dioxane/EtOH/water (7:3:2, 10 ml). The mixture was briefly degassed with Ar for ~0.5 minute, capped and microwaved at 120° C. for 20 mins. After cooling, the reaction mixture was diluted with EtOAc and brine. Organic layer was isolated, and dried (MgSO$_4$). After concentration, the residue was purified on silica gel. Elution with MeOH/EtOAc (0-10%) gave the desired product 5BM (310 mg).

Step 5: Preparation of 4-[4-(1-ethyl-1H-[1,2,4]triazol-3-yl)-phenyl]-1,2,3,6-tetrahydro-pyridine hydrochloride

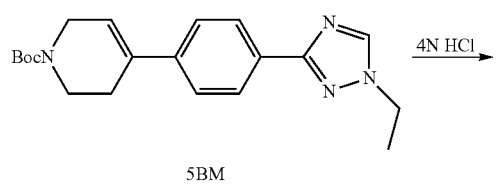

5BM

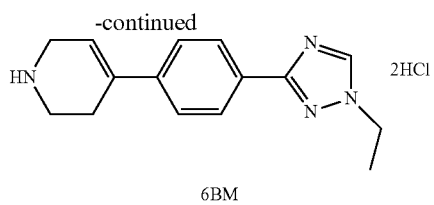

6BM

The Boc group can be removed by treating compound 5BM with 4N HCl in dioxane at rt for two hours. Removal of solvent under vacuum gave compound 6BM.

Synthesis of 1-(2-{4-[4-(1-Ethyl-1H-[1,2,4]triazol-3-yl)-phenyl]-3,6-dihydro-2H-pyridin-1-yl}-2-oxo-ethyl)-3-methoxy-pyrrolidine-3-carboxylic acid [3-(6-isopropoxy-pyridin-3-yl)-1H-indazol-5-yl]-amide

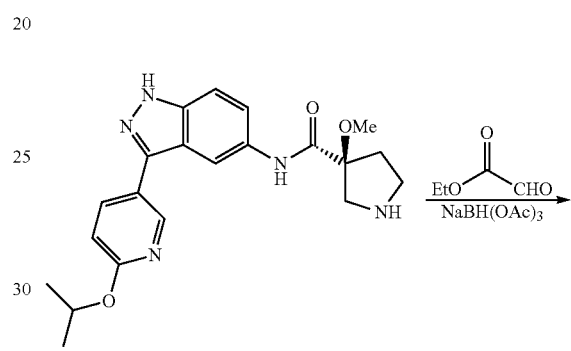

(8BM)

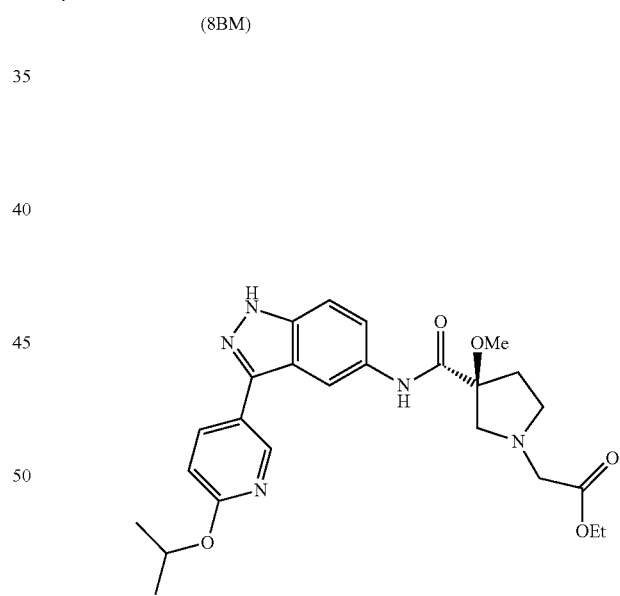

(9BM)

The crude 8BM (5.9 mmol) was stirred in a mixture of dichloromethane/MeOH (1:1, 20 ml), Oxo-acetic acid ethyl ester (10 ml, 50%) and NaBH(OAc)$_3$ (10 ml) at r.t. overnight. The mixture was quenched with saturated aqueous sodium bicarbonate. Solvents were removed in vacuum. Dilute with water and ethyl acetate. Layers were separated and the separated aqueous layer was extracted with ethyl acetate (×3). The combined organic layers were dried (MgSO$_4$), filtered and solvents were removed in vacuum. Column purification gave 8BM as yellow oil.

193

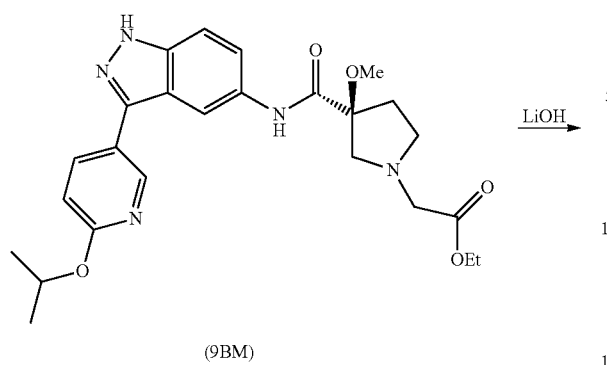

(9BM)

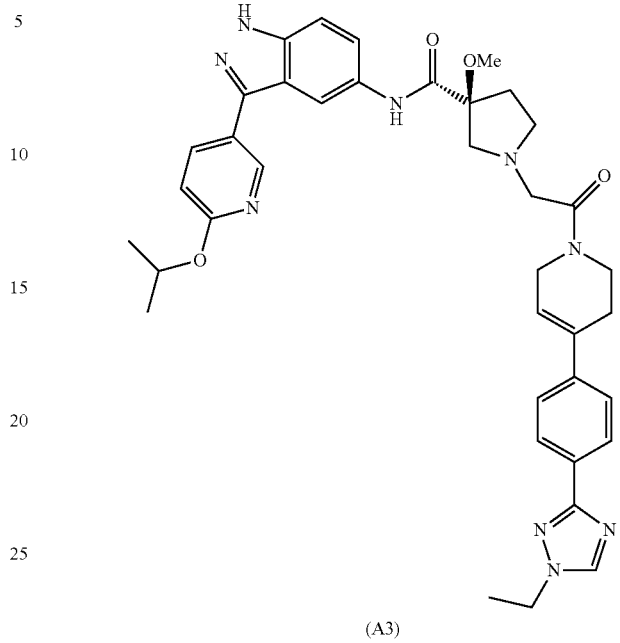

(A3)

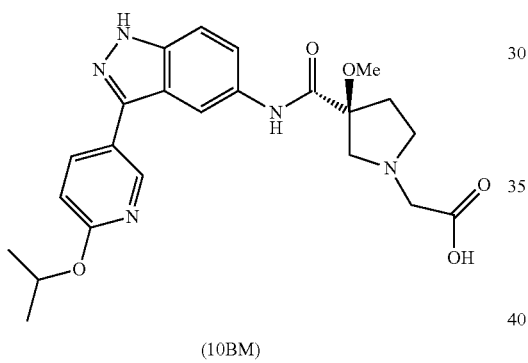

(10BM)

The crude 9BM (235 g) was stirred in a solution of LiOH (1M, 10 ml) and THF (10 ml) at r.t. overnight. The mixture was adjusted to pH 3. Solvents were removed in vacuum. The product was used for next step without purification.

194
-continued

The crude 10BM (49 mg), 4-[4-(1-Ethyl-1H-[1,2,4]triazol-3-yl)-phenyl]-1,2,3,6-tetrahydro-pyridine (25.4 mg), HATU (45 mg) ang triethyl amine (0.1 ml) was stirred in DMF (1 ml at r.t. overnight. The mixture was purified by HPLC to give A3 as yellow oil. Mass spectrum: LCMS M+1=690, retention time=3.47 minutes Example 6

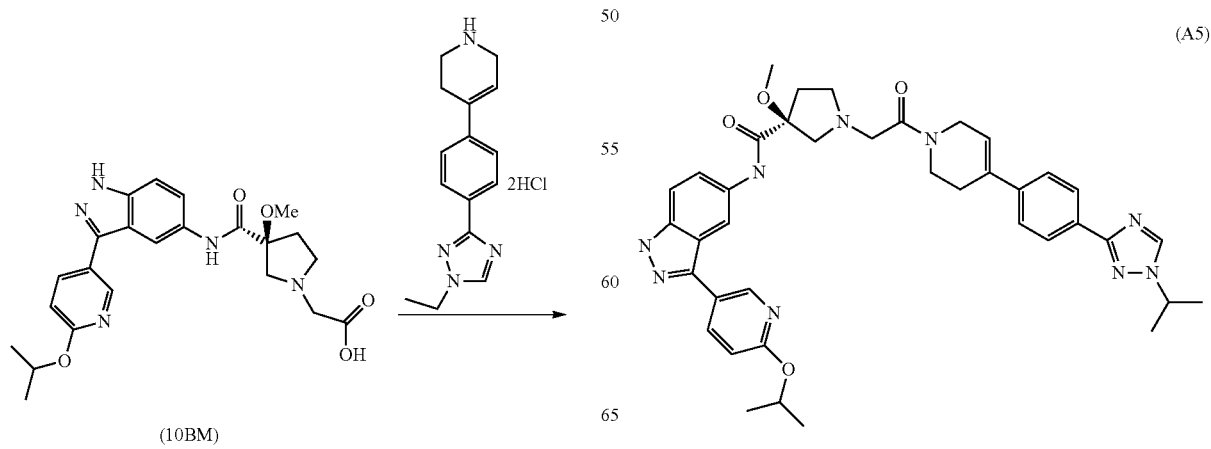

Synthesis of 4-[4-(1-isopropyl-1H-[1,2,4]triazol-3-yl)-phenyl]-1,2,3,6-tetrahydropyridine hydrochloride

Step 1: Preparation of 4-bromo-benzimidic acid ethyl ester

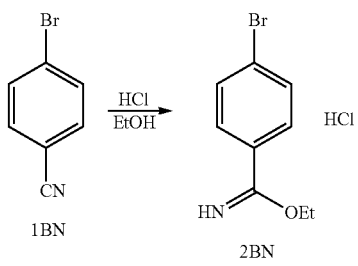 [SMILES: "EtOH" ; N#Cc1ccc(Br)cc1 ; Cl ; CCOC(=N)c1ccc(Br)cc1 ; Cl]

4-Bromo-benzonitrile (5 g) was suspended in absolute EtOH (100 ml) and cooled to 0-5° C. HCl gas was bubbled through, initially vigorously for several minutes and later slowly for 5 hours. The resulting solution was allowed to stir overnight. Most of solvent was removed and the precipitate was filtered, washed with EtOH twice and dried to afford compound 2BN (4.1 g) as white solid. (Note: large scale synthesis may take longer time to get reaction complete. It is better to monitor the disappearance of starting material to get reaction end point.)

Step 2: Preparation of Compound 3BN

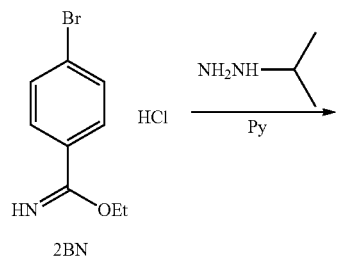

The 4-bromo-benzimidic acid ethyl ester (1 g) was dissolved in pyridine (20 ml). Isopropylhydrazine (550 mg) was added with stirring and the resulting mixture was allowed to stir overnight. The reaction mixture was concentrated under reduced pressure, and added ether, filtered, washed with ether three times and dried to provide the compound 3BN (0.9 g).

Step 3: Preparation of 3-(4-bromo-phenyl)-1-isopropyl-1H-[1,2,4]triazole

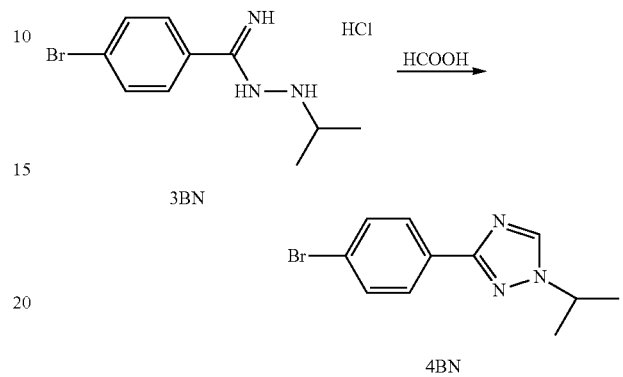

A mixture of compound 3BN (1 g) in formic acid (10 ml) was refluxed overnight and concentrated. The residue was treated with sat. NaHCO$_3$, and extracted with EtOAc three times. The combined organics were dried over MgSO$_4$. After concentration, compound 4BN was obtained as colorless crystals (0.9 g).

Step 4: Preparation of 4-[4-(1-isopropyl-1H-[1,2,4]triazol-3-yl)-phenyl]-3,6-dihydro-2H-pyridine-1-carboxylic acid tert-butyl ester

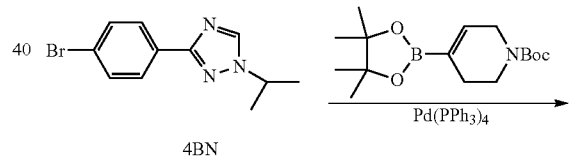

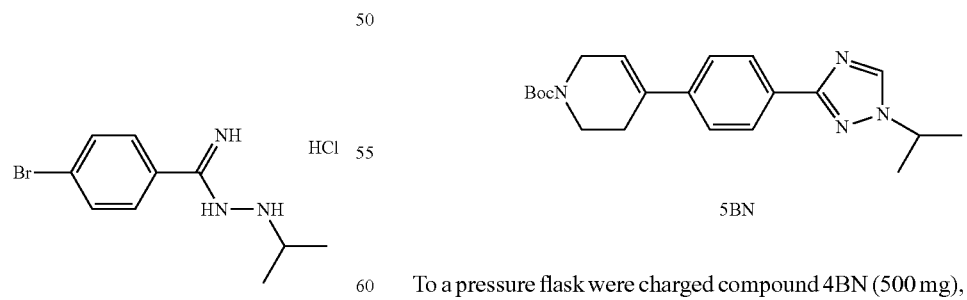

To a pressure flask were charged compound 4BN (500 mg), 4-(4,4,5,5-tetramethyl-[1,3,2]dioxaborolan-2-yl)-3,6-dihydro-2H-pyridine-1-carboxylic acid tert-butyl ester (583 mg), Pd(PPh$_3$)$_4$ (112 mg), Na$_2$CO$_3$ 2N (3 ml) and Dioxane (10 ml). The mixture was briefly degassed with Ar for ~0.5 minute, capped and stirred at 10° C. overnight. After cooling, the reaction mixture was diluted with EtOAc and brine. Organic layer was isolated, and dried (MgSO$_4$). After concentration, the residue was purified on silica gel. Elution with MeOH/EtOAc (0-10%) gave the desired product 5BN (410 mg).

Step 5: Preparation of 4-[4-(1-isopropyl-1H-[1,2,4]triazol-3-yl)-phenyl]-1,2,3,6-tetrahydro-pyridine hydrochloride

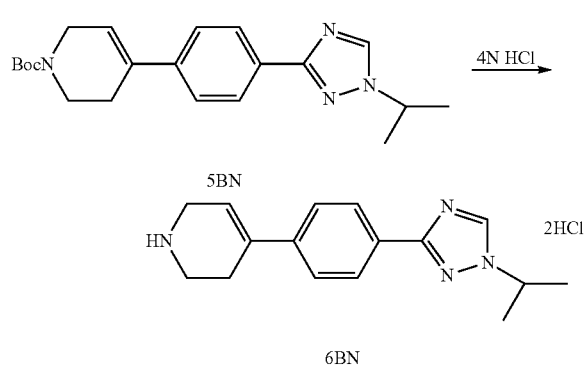

The Boc group can be removed by treating compound 5BN with 4N HCl in dioxane at rt for two hours. Removal of solvent under vacuum gave compound 6BN.

Synthesis of 1-(2-{4-[4-(1-Isopropyl-1H-[1,2,4]triazol-3-yl)-phenyl]-3,6-dihydro-2H-pyridin-1-yl}-2-oxo-ethyl)-3-methoxy-pyrrolidine-3-carboxylic acid [3-(6-isopropoxy-pyridin-3-yl)-1H-indazol-5-yl]-amide

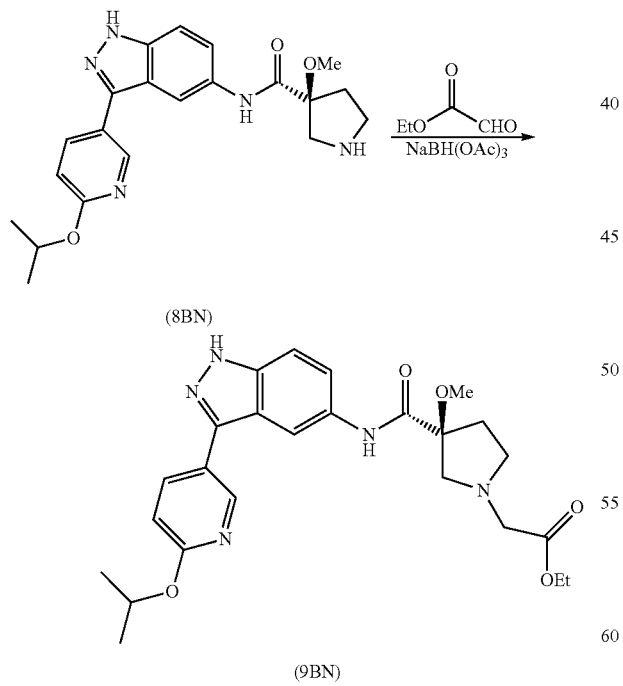

The crude 8BN (5.9 mmol) was stirred in a mixture of dichloromethane/MeOH (1:1, 20 ml), Oxo-acetic acid ethyl ester (10 ml, 50%) and NaBH(OAc)₃ (10 ml) at r.t. overnight. The mixture was quenched with saturated aqueous sodium bicarbonate. Solvents were removed in vacuum. Dilute with water and ethyl acetate. Layers were separated and the separated aqueous layer was extracted with ethyl acetate (×3). The combined organic layers were dried (MgSO₄), filtered and solvents were removed in vacuum. Column purification gave 9BN as yellow oil in 65% yield.

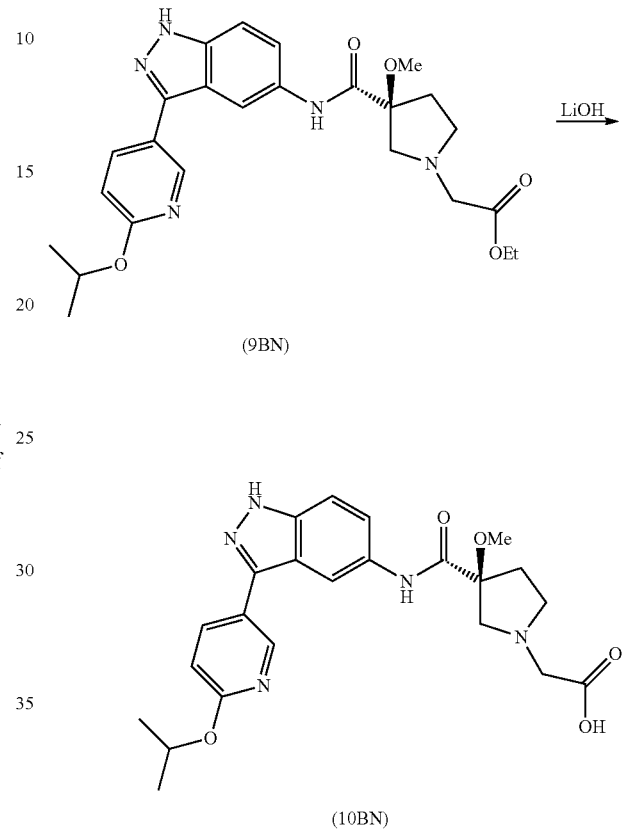

The crude 9BN (2.35 g) was stirred in a solution of LiOH (1M, 10 ml) and THF (10 ml) at r.t. overnight. The mixture was adjusted to pH 3. Solvents were removed in vacuum. The product was used for next step without purification, yield was quantitative.

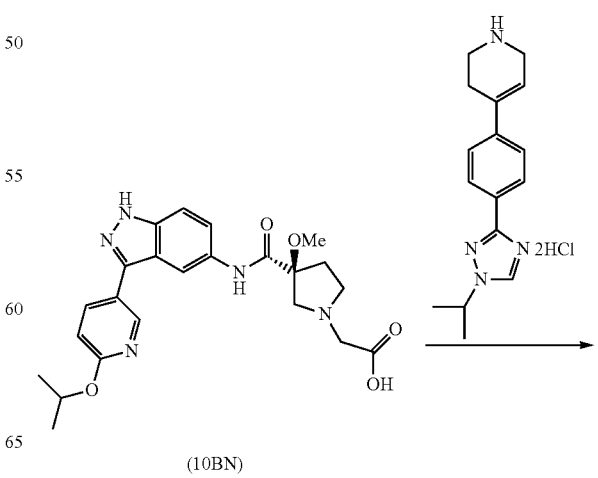

Synthesis of 4-[4-(1-isopropyl-1H-[1,2,4]triazol-3-yl)-phenyl]-1,2,3,6-tetrahydropyridine hydrochloride

Step 1: Preparation of 4-bromo-benzimidic Acid Ethyl Ester

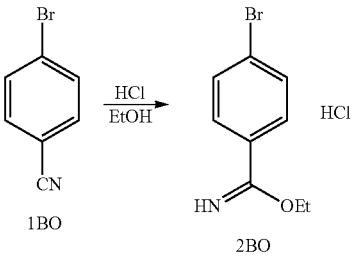 [SMILES: "EtOH" ; N#Cc1ccc(Br)cc1 ; Cl ; CCOC(=N)c1ccc(Br)cc1 ; Cl]

4-Bromo-benzonitrile (5 g) was suspended in absolute EtOH (100 ml) and cooled to 0-5° C. HCl gas was bubbled through, initially vigorously for several minutes and later slowly for 5 hours. The resulting solution was allowed to stir overnight. Most of solvent was removed and the precipitate was filtered, washed with EtOH twice and dried to afford compound 2BO (4.1 g) as white solid.

Step 2: Preparation of Compound 3BO

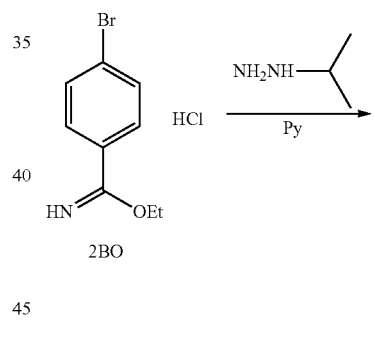

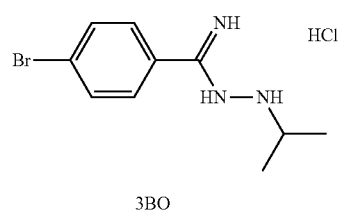

The 4-bromo-benzimidic acid ethyl ester (1 g) was dissolved in pyridine (20 ml). Isopropylhydrazine (550 mg) was added with stirring and the resulting mixture was allowed to stir overnight. The reaction mixture was concentrated under

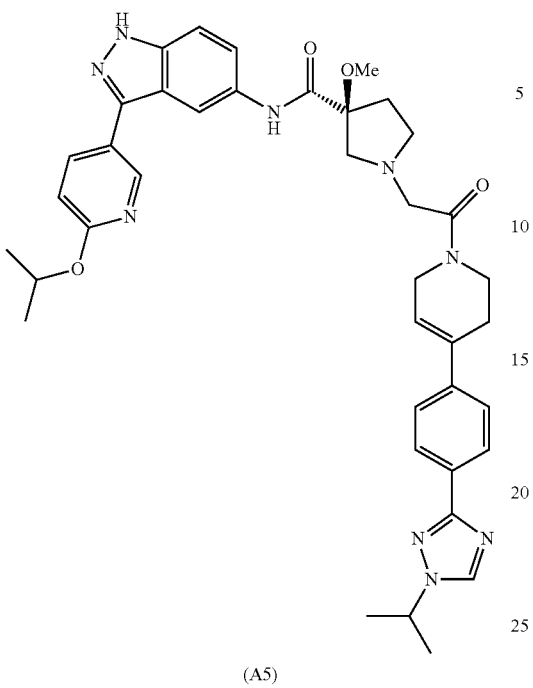

(A5)

The crude 10BN (60 mg), 4-[4-(1-Isopropyl-1H-[1,2,4]triazol-3-yl)-phenyl]-1,2,3,6-tetrahydro-pyridine (35 mg), HATU (52 mg) ang triethyl amine (0.1 ml) was stirred in DMF (1 ml at r.t. overnight. The mixture was purified by HPLC to gave A5 as yellow oil. Mass spectrum: LCMS M+1=704, retention time=3.56 minutes

Example 7

Synthesis of 1-(2-{4-[4-(1-Isopropyl-1H-[1,2,4]triazol-3-yl)-phenyl]-3,6-dihydro-2H-pyridin-1-yl}-2-oxo-ethyl)-3-methoxy-pyrrolidine-3-carboxylic acid [3-(6-isopropoxy-pyridin-3-yl)-1H-indazol-5-yl]-amide

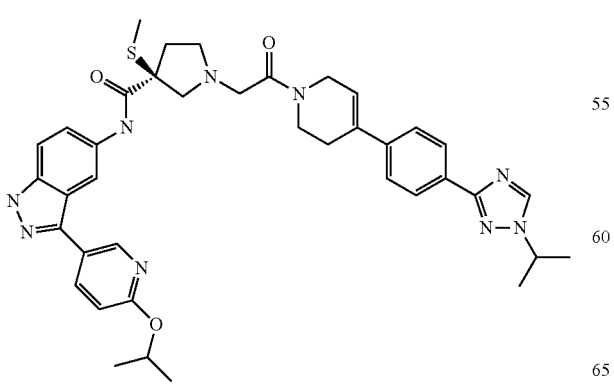

(A7)

reduced pressure, and added ether, filtered, washed with ether three times and dried to provide the compound 3BO (0.9 g).

Step 3: Preparation of 3-(4-bromo-phenyl)-1-isopropyl-1H-[1,2,4]triazole

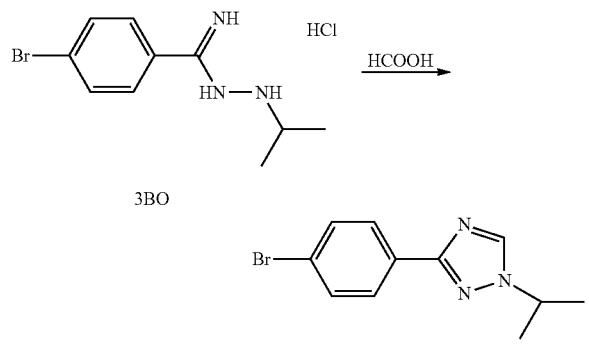

A mixture of compound 3BO (1 g) in formic acid (10 ml) was refluxed overnight and concentrated. The residue was treated with sat. NaHCO₃, and extracted with EtOAc three times. The combined organics were dried over MgSO₄. After concentration, compound 4BO was obtained as colorless crystals (0.9 g). (Note: it was found that the reaction can be done in just two hours. In large scale synthesis, use 10% NaOH to replace NaHCO₃).

Step 4: Preparation of 4-[4-(1-isopropyl-1H-[1,2,4]triazol-3-yl)-phenyl]-3,6-dihydro-2H-pyridine-1-carboxylic acid tert-butyl ester

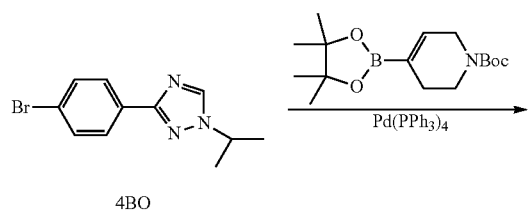

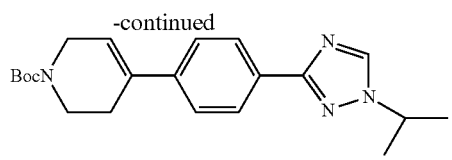

5BO

To a large pressure flask were charged compound 4BO (500 mg), 4-(4,4,5,5-tetramethyl-[1,3,2]dioxaborolan-2-yl)-3,6-dihydro-2H-pyridine-1-carboxylic acid tert-butyl ester (583 mg), Pd(PPh₃)₄ (112 mg), Na₂CO₃ 2N (3 ml) and Dioxane (10 ml). The mixture was briefly degassed with Ar for ~0.5 minute, capped and stirred at 10° C. overnight. After cooling, the reaction mixture was diluted with EtOAc and brine. Organic layer was isolated, and dried (MgSO₄). After concentration, the residue was purified on silica gel. Elution with MeOH/EtOAc (0-10%) gave the desired product 5BO (410 mg).

Step 5: Preparation of 4-[4-(1-isopropyl-1H-[1,2,4]triazol-3-yl)-phenyl]-1,2,3,6-tetrahydro-pyridine hydrochloride

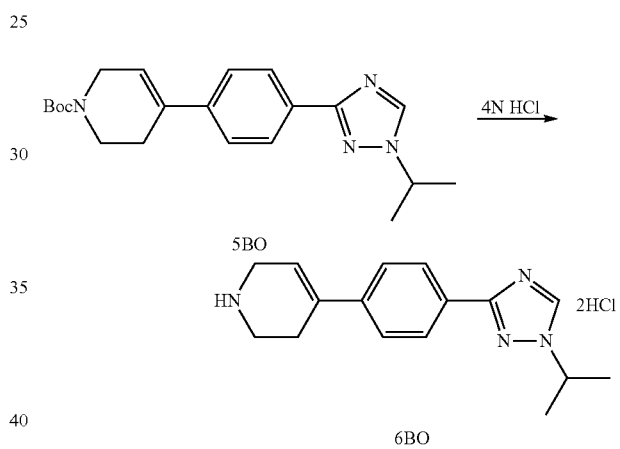

The Boc group can be removed by treating compound 5BO with 4N HCl in dioxane at rt for two hours. Removal of solvent under vacuum gave compound 6BO.

Preparation and Chiral Resolution of 3-Methylsulfanyl-pyrrolidine-3-carboxylic acid methyl ester 4BP

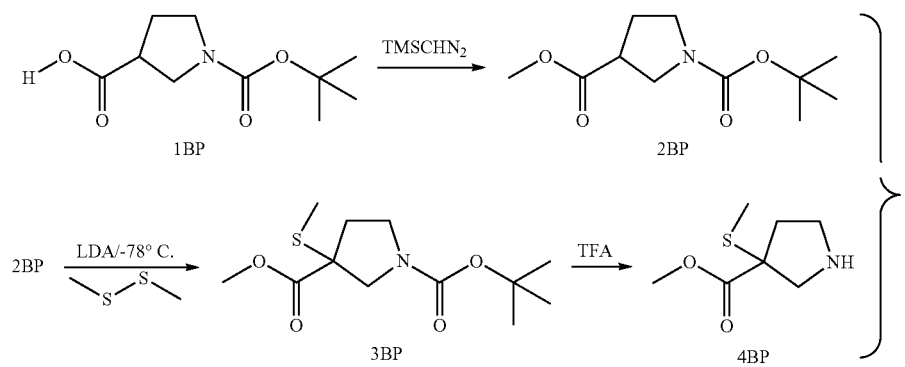

Pyrrolidine-1,3-dicarboxylic acid 1-tert-butyl ester 1BP (4.3 gm, 20 mmol) was dissolved in 28 mL of toluene and 3.5 ml of methanol. Trimethylsilyldiazomethane 2N solution in hexanes (13 ml, 26 mmol) was added drop wise at 0 C and the reaction mixture stirred for 10 min at ambient temperature. The mixture was evaporated to obtain 4.3 gm of oil.

To the oil 2BP (0.5 gm, 2.1 mmol) dissolved in tetrahydrofuran (15 ml) 1.2 ml of lithium diisopropylamide 2N solution in hexanes was added drop wise and the reaction mixture stirred for 1 hr at −78 C. Dimethyldisulfide (0.48 mL, 5.4 mmol) was added slowly and let warm to ambient temperature gradually. The reaction mixture was stirred for 18 hrs. A saturated solution of Ammonium chloride (25 ml) was added and the reaction mixture stirred for 5 min. The reaction mixture was extracted with ethyl acetate three times (3×25 ml), dried over magnesium sulfate, filtered and evaporated to give 0.386 g of title product 3BP after column chromatography.

3-Methylsulfanyl-pyrrolidine-1,3-dicarboxylic acid 1-tert-butyl ester 3-methyl ester (2.15 gm, 8.8 mmol) was dissolved in 20 ml of 50% trifluoroacetic acid/dichloromethane and stirred for 2 hrs. The reaction mixture was evaporated to give 3.35 g of 3-Methylsulfanyl-pyrrolidine-3-carboxylic acid methyl ester 4BP as a gummy solid. Alternatively 4BP can be prepared as follows:

2-Methylsulfanyl-propionic acid methyl ester 5BP (25 g, 0.1 mol) dissolved in chloroform was added sulfuryl chloride (15.1 mL, 0.1 mol) slowly at 0° C. The reaction mixture was stirred at 0° C. for 30 min and then refluxed at 65° C. for 30 min. The reaction mixture then concentrated to dryness to give 23.75 g of 2-Methylsulfanyl-acrylic acid methyl ester 6BP as a liquid.

To a stirred solution of 2-ethoxyacrylate 2-Methylsulfanyl-acrylic acid methyl ester 6BP (136 g, 1.03 mol) and benzyl-methoxymethyl-trimethylsilanylmethyl-amine 7BP (290 g, 1.22 mol) in dichloromethane (2.7 L ml) was added at 0° C. a solution of trifluoroacetic acid (26 mL, 0.3 mol). The resulting solution was warmed to room temperature and stirred for one overnight. The crude product was purified by column chromatography on silica gel eluting with a solution of ethyl acetate in hexane (1:4) to give 1-benzyl-3-methylsulfanyl-pyrrolidine-3-carboxylic acid methyl ester 8BP (131 g, 47%).

To 1-benzyl-3-methylsulfanyl-pyrrolidine-3-carboxylic acid methyl ester 8BP (131 g, 493.7 mmol) dissolved in dichloroethane (2.6 L) at 0° C. was added N,N,N',N'-Tetramethyl-naphthalene-1,8-diamine 9BP (31.8 g, 0.144 mmol) and then 2-Chloropropionyl chloride 10BP (64 mL, 593.1 mmol) sequentially. The reaction mixture was stirred for one overnight at ambient temperature and then concentrated to

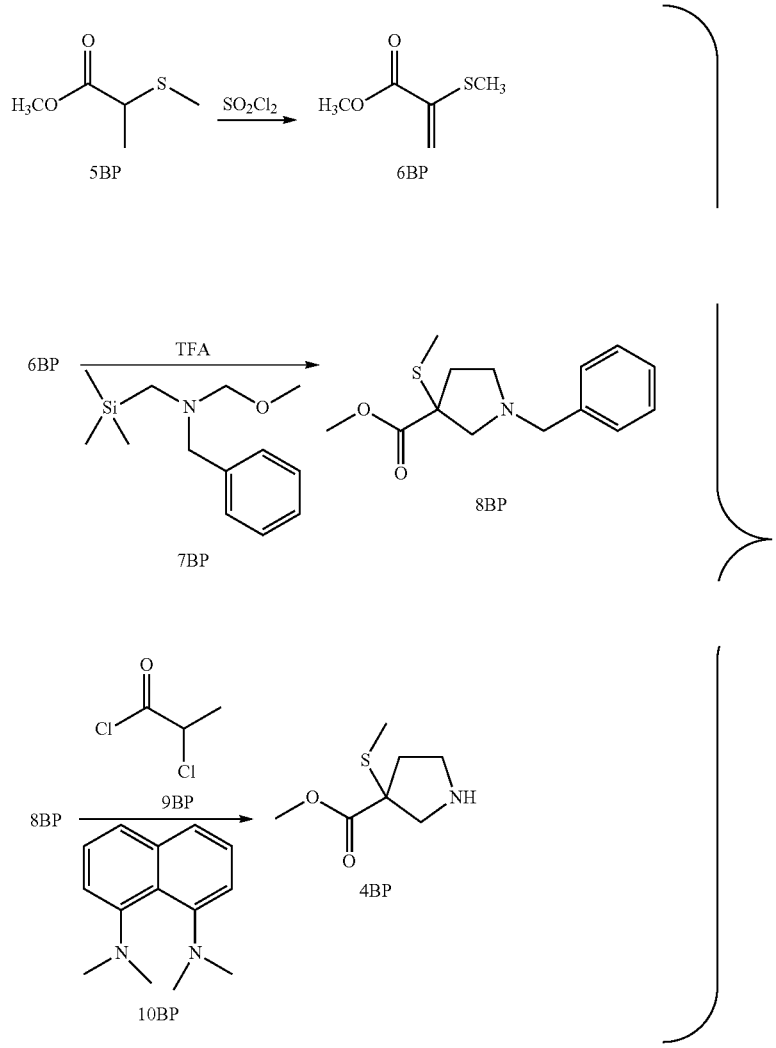

dryness. The residue was dissolved in 2.8 L of methanol and refluxed at 65° C. for 3.5 h. The reaction mixture was then concentrated to dryness and the residue was purified by column chromatography on silica gel eluting with a solution of methanol in dichloromethane (1:9) to give 3-Methylsulfanyl-pyrrolidine-3-carboxylic acid methyl ester 4BP (75 g, 86%).

Chiral resolution of 3-Methylsulfanyl-pyrrolidine-3-carboxylic acid methyl ester 4BP

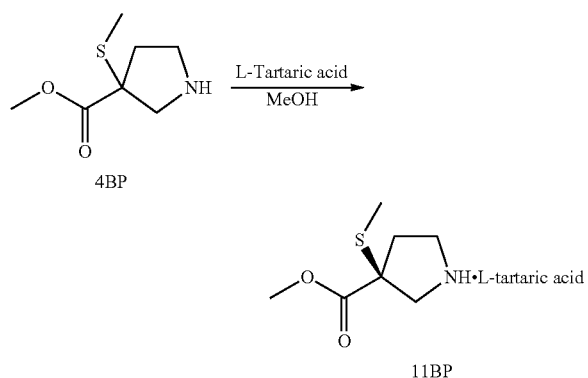

3-Methylsulfanyl-pyrrolidine-3-carboxylic acid methyl ester 4BP (42.9 g, 244.8 mmol) and L-tartaric acid (36.7 g, 244.8 mmol) were placed in a 1 L round bottomed flask and dissolved with 250 mL of methanol. The flask was then attached to a rotavapor at 75° C. The mixture was allowed to gently spin at this temperature for about 20 min. to ensure complete dissolution. After the formation of a clear solution, about 10 mg of authentic crystals of 3-Methylsulfanyl-pyrrolidine-3-carboxylic acid methyl ester 11BP were added (to seed and aid the crystal formation) was allowed to settle gently for crystal formation. After 3 days, 19.4 g of crystals were filtered which was then washed with cold methanol (20-30 mL) to give 18.2 g of crystalline 3-Methylsulfanyl-pyrrolidine-3-carboxylic acid methyl ester 11BP.

The chiral purity of the crystals 3-Methylsulfanyl-pyrrolidine-3-carboxylic acid methyl ester 11BP was determined by derivatizing with 4-nitrobenzyl chloroformate and subjecting it to analytical HPLC (Chiracel AD column) under the conditions of 20% isopropanol/hexane solvent system with a flow rate of 1 mL/min. The purity was found to be >99.9% with a retention time of 16.58 min.

Preparation of 3-Methylsulfanyl-pyrrolidine-1,3-dicarboxylic acid 1-tert-butyl ester

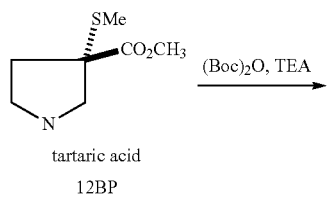

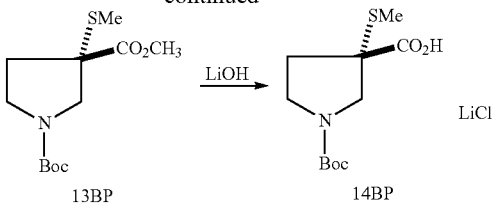

To a cold (0° C.) solution of 12BP (28 g, 90.52 mmol) in dry $CH_2Cl_2$ (250 mL) was added triethylamine (31.5 mL, 226.32 mmol, 2.5 equiv) followed by $(Boc)_2O$ (25.7 g, 117.68 mmol, 1.3 equiv). The resulting mixture was stirred from 0° C. to it for overnight then diluted with $CH_2Cl_2$, which was washed with saturated aqueous $NaHCO_3$ solution and brine, dried ($MgSO_4$) and concentrated. Chromatograph on silica gel (hexanes/ethyl acetate, 4:1) gave 13BP (23.5 mg, 90.52 mmol, 100%) as a colorless oil.

To a stirred solution of 13BP (23.5 mg, 90.52 mmol) in THF/MeOH (175 mL/175 mL) was added 135 mL of LiOH (1M in $H_2O$, 135 mmol, 1.5 equiv). The reaction mixture was stirred at it for overnight, to which 135 mL of 1N HCl was added. The resulting mixture was stirred for additional 15 min and concentrated to give 14BP.

Step 1

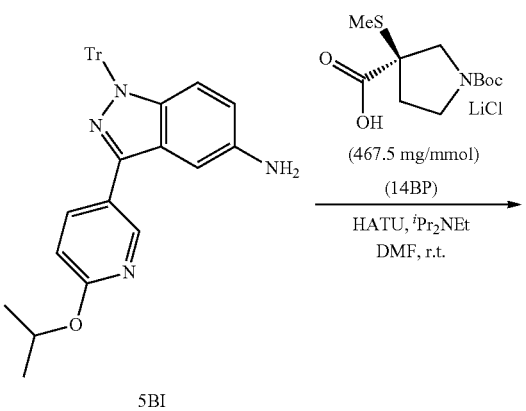

Aminoindazole 5BI (39 g, 0.076 mol) and pyrrolidinecarboxylic acid 14BP (32 g, 0.069 mol) were dissolved in DMF (300 ml) at r.t. HATU (29 g, 0.076 mol) followed by $^i$Pr$_2$NEt (14.5 ml, 0.083 mol) were added. The mixture was stirred at r.t. overnight and was diluted with ethyl acetate and water. Layers were separated. The separated organic layer was washed with water (×2), dried (MgSO$_4$) and filtered. Concentration in vacuum followed by column purification [hexanes-ethyl acetate=4:1 (v/v)] gave crude 7BO as off-white foam.

Step 2

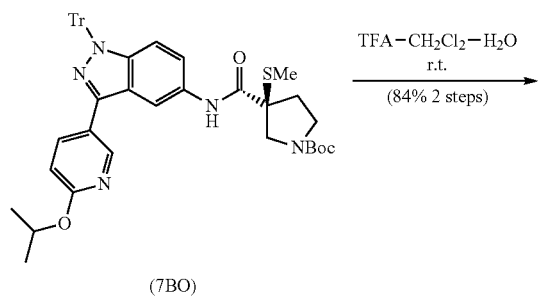

(7BO)

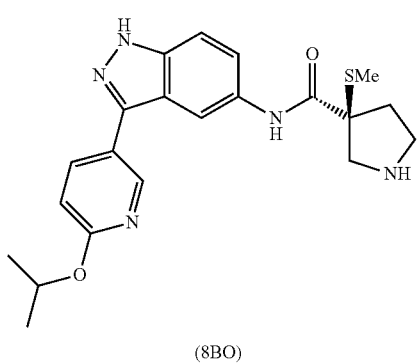

(8BO)

The crude 7BO was stirred in a mixture of dichloromethane (300 ml), trifluoroacetic acid (100 ml) and water (50 ml) at r.t. overnight. The mixture was cooled at 0° C. and quenched carefully with saturated aqueous sodium bicarbonate. Solvents were removed in vacuum. Dilute with water and ethyl acetate. Layers were separated and the separated aqueous layer was extracted with ethyl acetate (×3). The combined organic layers were dried (MgSO$_4$), filtered and solvents were removed in vacuum. Column purification [5 to 10% MeOH (7N ammonia) in dichloromethane] gave pyrrolidine 8BO (23 g, 84%) as off-white solid.

Synthesis of 1-(2-{4-[4-(1-Isopropyl-1H-[1,2,4]triazol-3-yl)-phenyl]-3,6-dihydro-2H-pyridin-1-yl}-2-oxo-ethyl)-3-methylsulfanyl-pyrrolidine-3-carboxylic acid [3-(6-isopropoxy-pyridin-3-yl)-1H-indazol-5-yl]-amide

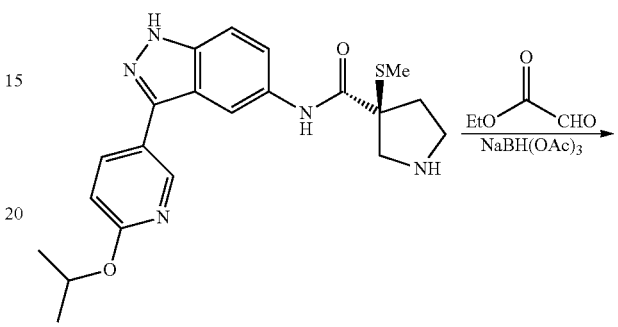

(8BO)

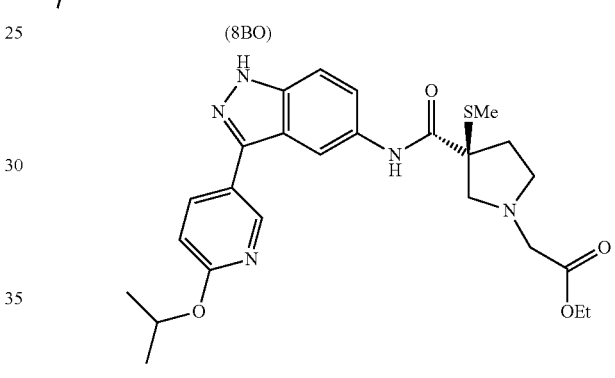

(9BO)

The crude 8BO (5.9 mmol) was stirred in a mixture of dichloromethane/MeOH (1:1, 20 ml), Oxo-acetic acid ethyl ester (10 ml, 50%) and NaBH(OAc)$_3$ (10 ml) at r.t. overnight. The mixture was quenched with saturated aqueous sodium bicarbonate. Solvents were removed in vacuum. Dilute with water and ethyl acetate. Layers were separated and the separated aqueous layer was extracted with ethyl acetate (×3). The combined organic layers were dried (MgSO$_4$), filtered and solvents were removed in vacuum. Column purification gave 9BO as yellow oil.

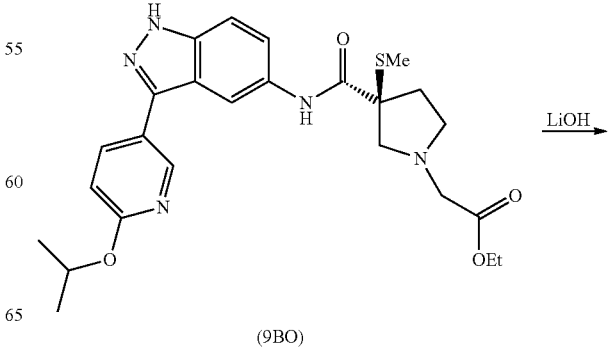

(9BO)

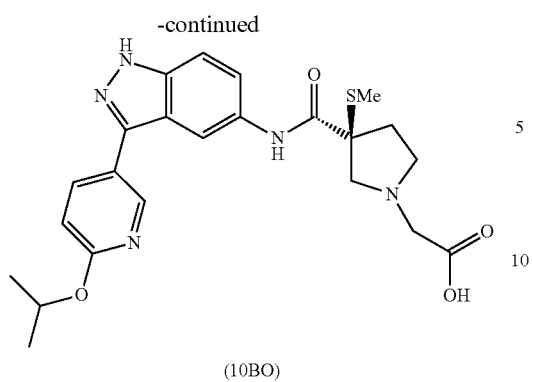

(10BO)

The crude 9BO (2.35 g) was stirred in a solution of LiOH (1M, 10 ml) and THF (10 ml) at r.t. overnight. The mixture was adjusted to pH 3. Solvents were removed in vacuum. The product was used for next step without purification.

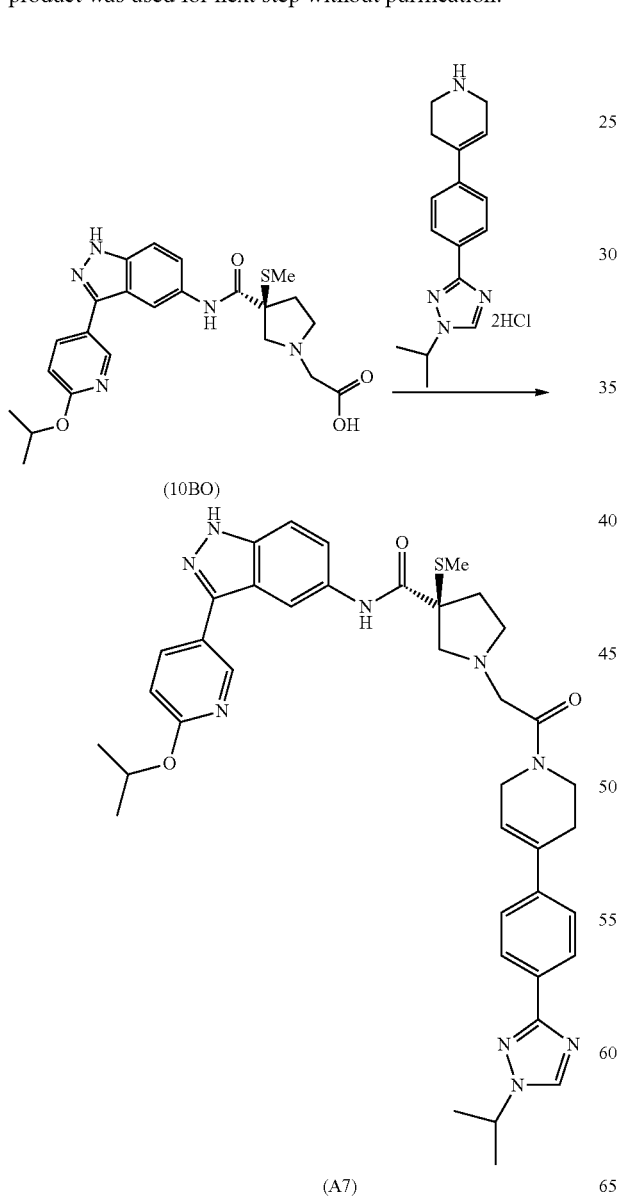

The crude 10BO (60 mg), 4-[4-(1-Isopropyl-1H-[1,2,4] triazol-3-yl)-phenyl]-1,2,3,6-tetrahydro-pyridine (35 mg), HATU (52 mg) ang triethyl amine (0.1 mil) was stirred in DMF (1 ml at r.t. overnight. The mixture was purified by HPLC to gave 11BO as yellow oil. Mass spectrum: LCMS M+1=720, retention time=3.68 minutes.

Example 8

Preparation of 1-[2-(4-{4-[1-(2-Hydroxy-2-methyl-propyl)-1H-[1,2,4]triazol-3-yl]-phenyl}-3,6-dihydro-2H-pyridin-1-yl)-2-oxo-ethyl]-3-methoxy-pyrrolidine-3-carboxylic acid [3-(6-isopropoxy-pyridin-3-yl)-1H-indazol-5-yl]-amide (A9)

Synthesis of 2-chloro-1-{4-[4-(1-ethyl-1H-[1,2,4] triazol-3-yl)-phenyl]-3,6-dihydro-2H-pyridin-1-yl}-ethanone Step 1: Preparation of 4-bromo-benzimidic acid ethyl ester

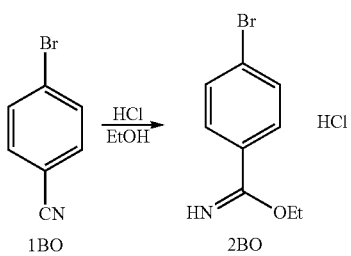 [SMILES: "EtOH" ; N#Cc1ccc(Br)cc1 ; Cl ; CCOC(=N)c1ccc(Br)cc1 ; Cl]

4-Bromo-benzonitrile (5 g) was suspended in absolute EtOH (100 ml) and cooled to 0-5° C. HCl gas was bubbled through, initially vigorously for several minutes and later slowly for 5 hours. The resulting solution was allowed to stir overnight. Most of solvent was removed and the precipitate was filtered, washed with EtOH twice and dried to afford compound 2BO (4.1 g) as white solid.

Step 2: Preparation of Compound 3BQ

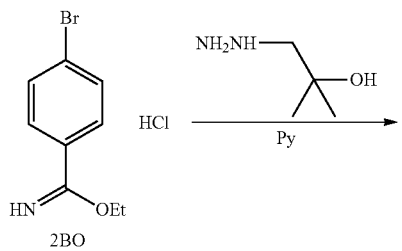

2BO

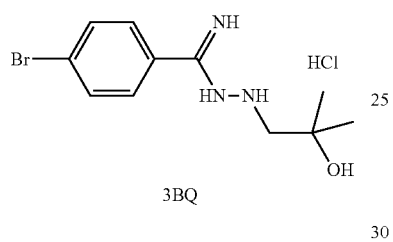

3BQ

The 4-bromo-benzimidic acid ethyl ester (1.68 g) was dissolved in pyridine (10 ml). 1-Hydrazino-2-methyl-propan-2-ol (1 g) was added with stirring and the resulting mixture was allowed to stir overnight. The reaction mixture was concentrated under reduced pressure, and added ether, filtered, washed with ether three times and dried to provide the compound 3BQ (1 g).

Step 3: Preparation of 1-[3-(4-Bromo-phenyl)-[1,2,4]-triazol-1-yl]-2-methyl-propan-2-ol

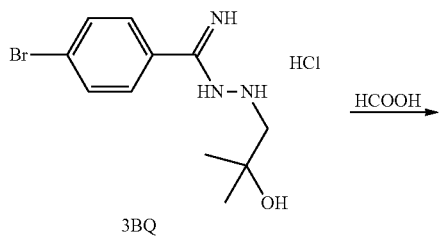

3BQ

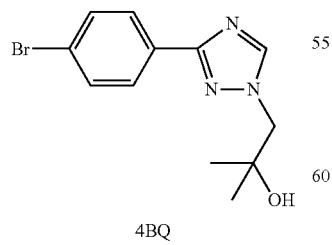

4BQ

A mixture of compound 3BQ (1 g) in formic acid (10 ml) was refluxed overnight and concentrated. The residue was treated with sat. NaHCO$_3$, and extracted with EtOAc three times. The combined organics were dried over MgSO$_4$. After concentration, compound 4BQ was obtained as colorless crystals (0.9 g).

Step 4: Preparation of 4-{4-[1-(2-Hydroxy-2-methyl-propyl)-1H-[1,2,4]triazol-3-yl]-phenyl}-3,6-dihydro-2H-pyridine-1-carboxylic Acid Tert-Butyl Ester

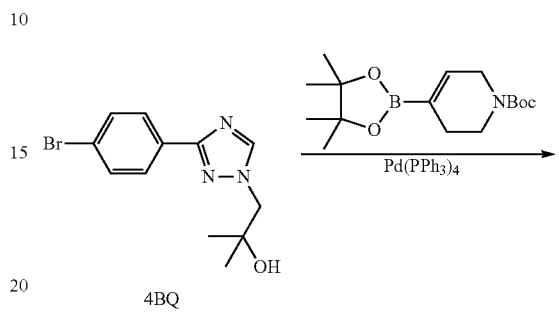

4BQ

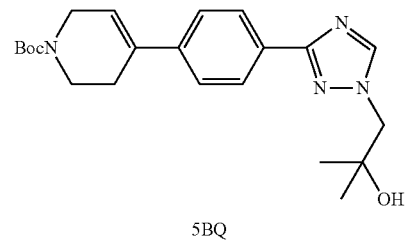

5BQ

To a large pressure flask were charged compound 4BQ (400 mg), 4-(4,4,5,5-tetramethyl-[1,3,2]dioxaborolan-2-yl)-3,6-dihydro-2H-pyridine-1-carboxylic acid tert-butyl ester (540 mg), Pd(PPh$_3$)$_4$ (180 mg), Na$_2$CO$_3$ 2N (3 ml) and Dioxane/EtOH/water (7:3:2, 10 ml). The mixture was briefly degassed with Ar for ~0.5 minute, capped and microwaved at 12° C. for 20 mins. After cooling, the reaction mixture was diluted with EtOAc and brine. Organic layer was isolated, and dried (MgSO$_4$). After concentration, the residue was purified on silica gel. Elution with MeOH/EtOAc (0-10%) gave the desired product 5BQ (310 mg).

Step 5: Preparation of 2-Methyl-1-{3-[4-(1,2,3,6-tetrahydro-pyridin-4-yl)-phenyl]-[1,2,4]triazol-1-yl}-propan-2-ol

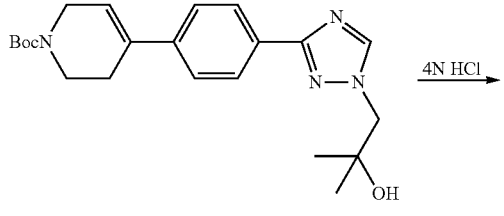

5BQ

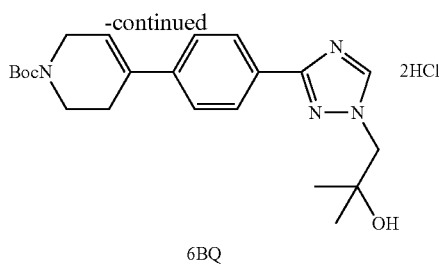

6BQ

The Boc group can be removed by treating compound 5BQ with 4N HCl in dioxane at rt for two hours. Removal of solvent under vacuum gave compound 6BQ.

Synthesis of 1-[2-(4-{4-[1-(2-Hydroxy-2-methyl-propyl)-1H-[1,2,4]triazol-3-yl]-phenyl}-3,6-dihydro-2H-pyridin-1-yl)-2-oxo-ethyl]-3-methoxy-pyrrolidine-3-carboxylic acid [3-(6-isopropoxy-pyridin-3-yl)-1H-indazol-5-yl]-amide

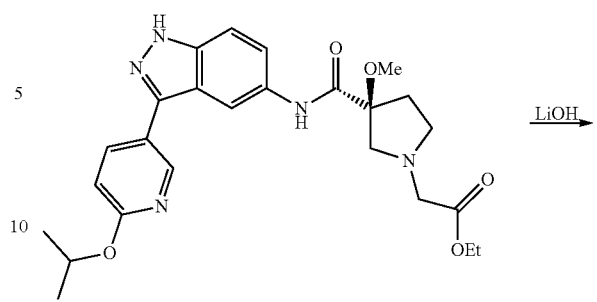

(9BN)

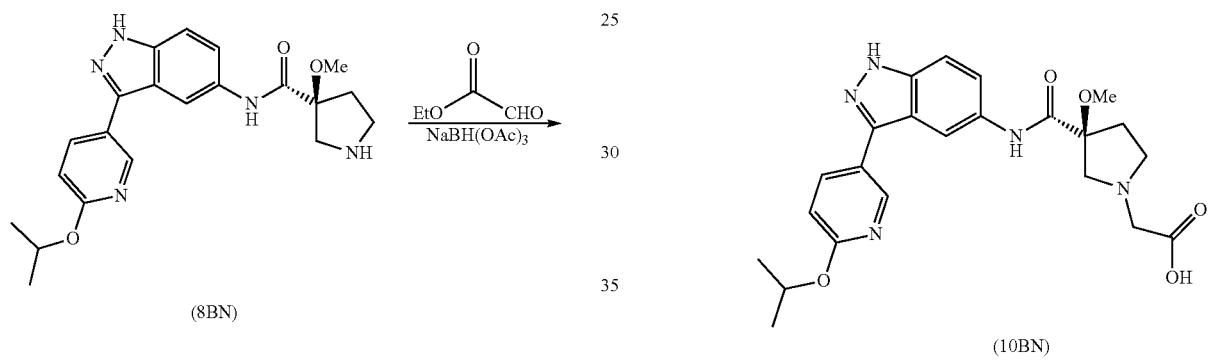

The crude 9BN (2.35 g) was stirred in a solution of LiOH (1M, 10 ml) and THF (10 ml) at r.t. overnight. The mixture was adjusted to pH 3. Solvents were removed in vacuum. The product was used for next step without purification.

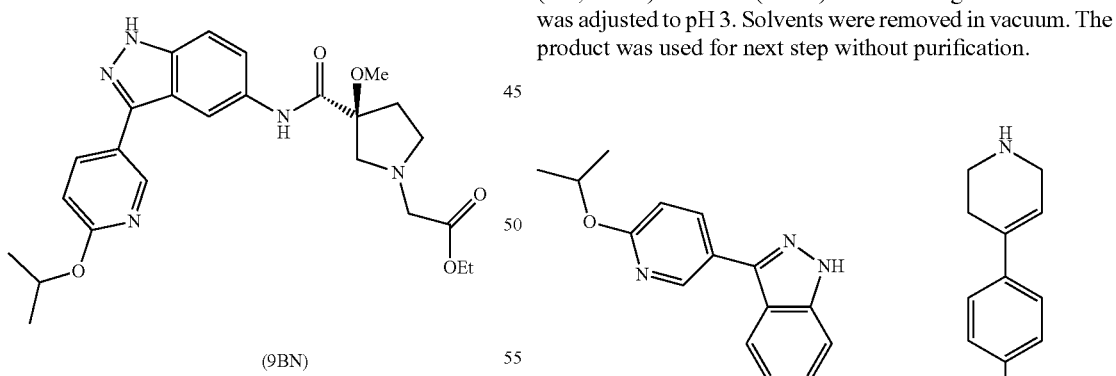

(9BN)

The crude 8BN (5.9 mmol) was stirred in a mixture of dichloromethane/MeOH (1:1, 20 ml), Oxo-acetic acid ethyl ester (10 ml, 50%) and NaBH(OAc)$_3$ (10 ml) at r.t. overnight. The mixture was quenched with saturated aqueous sodium bicarbonate. Solvents were removed in vacuum. Dilute with water and ethyl acetate. Layers were separated and the separated aqueous layer was extracted with ethyl acetate (×3). The combined organic layers were dried (MgSO$_4$), filtered and solvents were removed in vacuum. Column purification gave 9BN as yellow oil.

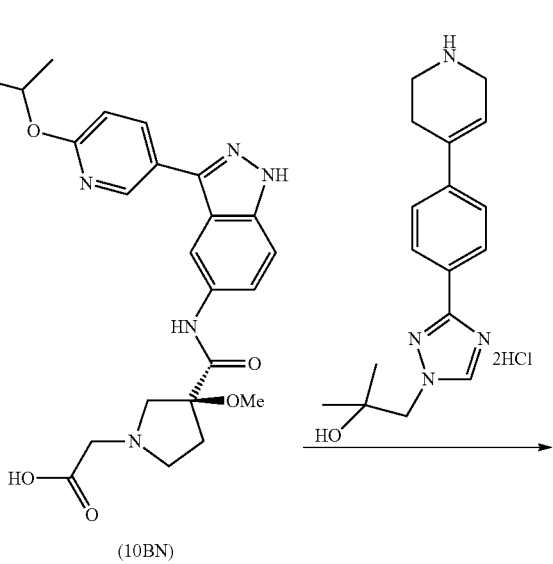

(10BN)

-continued

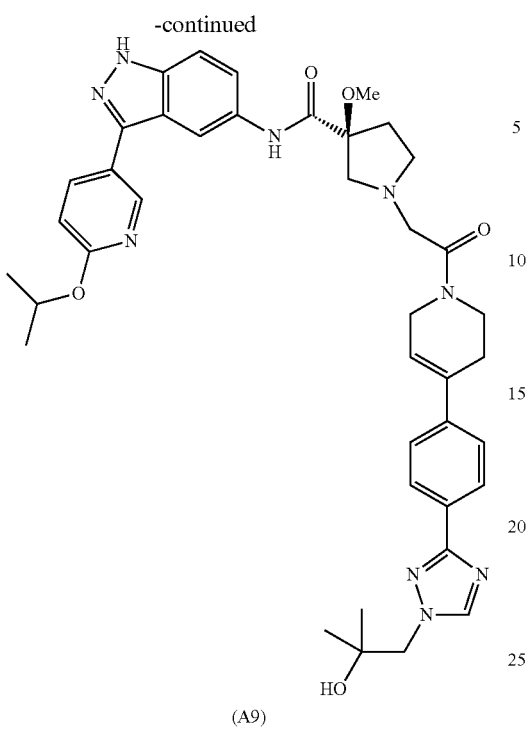

(A9)

The crude 10BN (60 mg), 2-Methyl-1-{3-[4-(1,2,3,6-tetrahydro-pyridin-4-yl)phenyl]-[1,2,4]triazol-1-yl}-propan-2-ol (38 mg), HATU (50 mg) ang triethyl amine (0.1 ml) was stirred in DMF (1 ml at r.t. overnight. The mixture was purified by HPLC to gave A9 as yellow oil, 50%. Mass spectrum: LCMS M+1=734, retention time=3.32 minutes.

Example 9

Preparation of 3-Methoxy-1-(2-{4-[4-(1-methyl-1H-[1,2,4]triazol-3-yl)-phenyl]-3,6-dihydro-2H-pyridin-1-yl}-2-oxo-ethyl)-pyrrolidine-3-carboxylic acid {3-[6-(2-methoxy-ethoxy)-pyridin-3-yl]-1H-indazol-5-yl}-amide (A15)

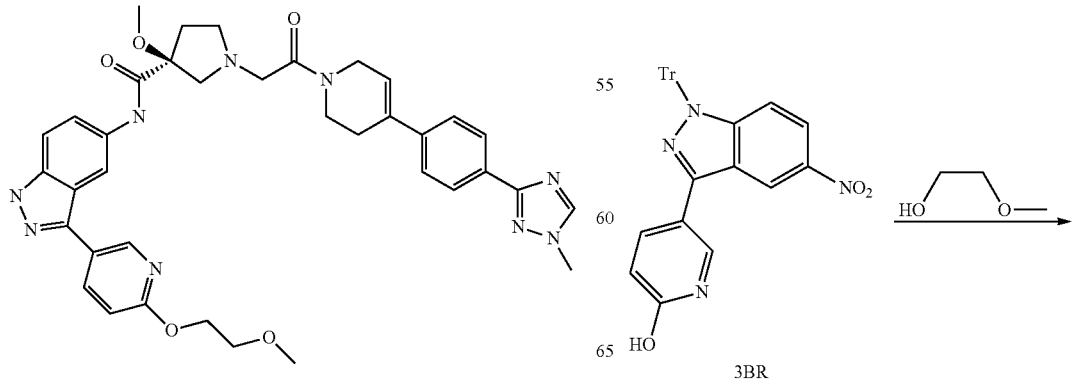

Synthesis of 3-Methoxy-pyrrolidine-3-carboxylic acid {3-[6-(2-methoxy-ethoxy)pyridin-3-yl]-1H-indazol-5-yl}-amide Step 1

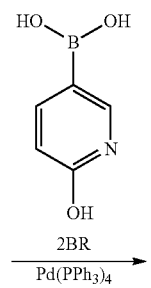

To a pressure flask were charged compound 1BR (1.75 g), 2BR (0.5 g), Pd(PPh$_3$)$_4$ (210 mg), Na$_2$CO$_3$ 2N (10 ml) and Dioxane (10 ml). The mixture was briefly degassed with Ar for ~0.5 minute, capped and stirred at 100° C. overnight. After cooling, the reaction mixture was diluted with EtOAc and brine. Organic layer was isolated, and dried (MgSO$_4$). After concentration, the residue was purified on silica gel. Elution gave the desired product 3BR (0.8 g).

Step 2

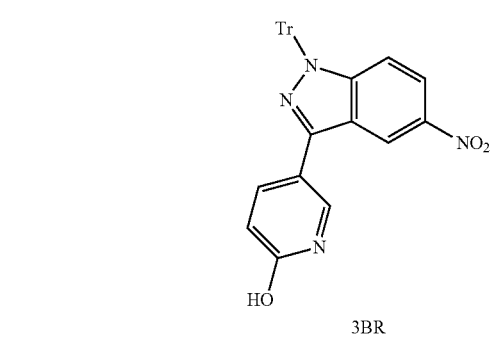

-continued

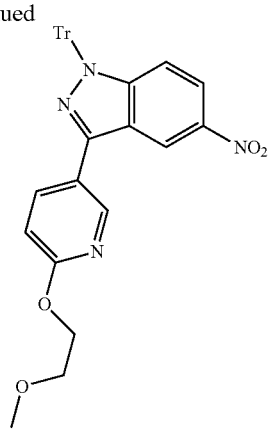

4BR

A mixture of compound 3BR (1.8 g), 2-Methoxy-ethanol (1 g), DEAD (0.8 g) and PPh₃ (1.2 g) in THF (10 ml) was stirred overnight at rt and concentrated. The residue purified by silica gel to gave the desired product 4BR (0.8 g).

Step 3

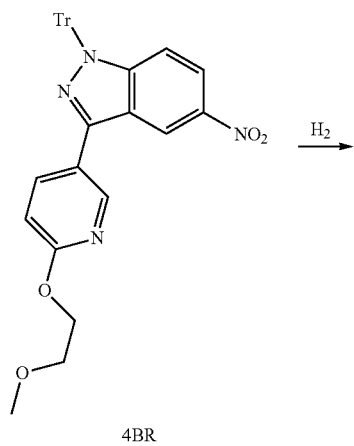

4BR

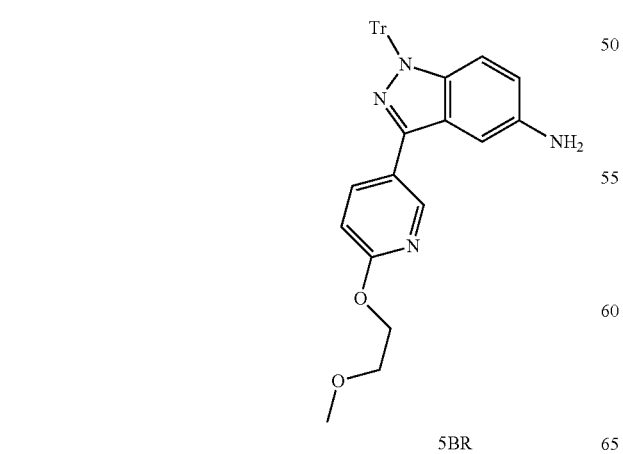

5BR

4BR (0.5 g) in MeOH (20 ml) was reduced by H-cube with Pd/C (10%) column.

Step 4

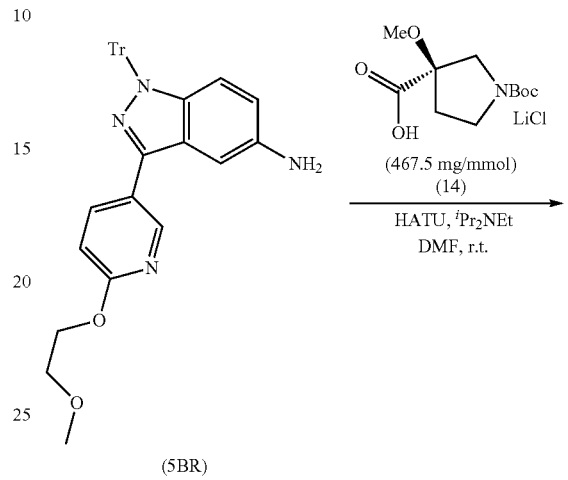

(5BR)

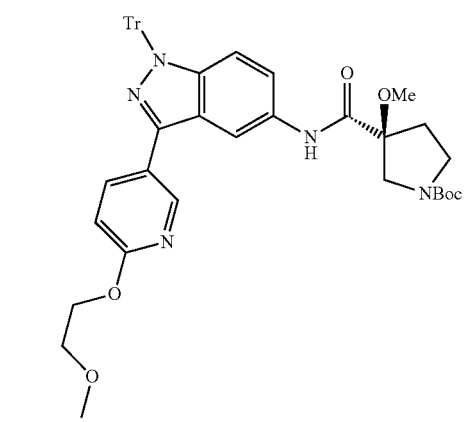

(7BR)

Aminoindazole 5BR (80 mg) and pyrrolidinecarboxylic acid 14BH (38 mg) were dissolved in DMF (1 ml) at r.t. HATU (69 mg) followed by $^i$Pr₂NEt (0.1 ml) were added. The mixture was stirred at r.t. overnight and was diluted with ethyl acetate and water. Layers were separated. The separated organic layer was washed with water (×2), dried (MgSO$_4$) and filtered. Concentration in vacuum gave crude 7BR as off-white foam.

Step 5

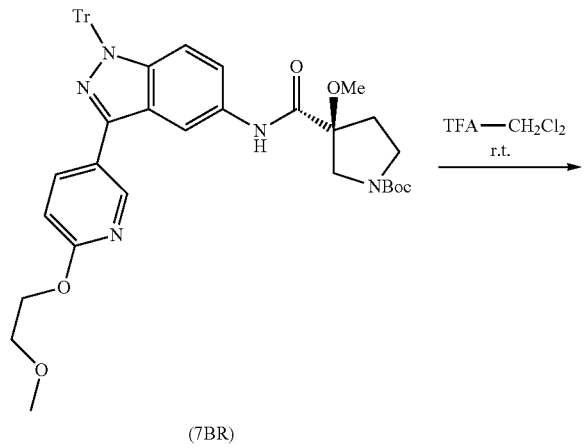

(7BR)

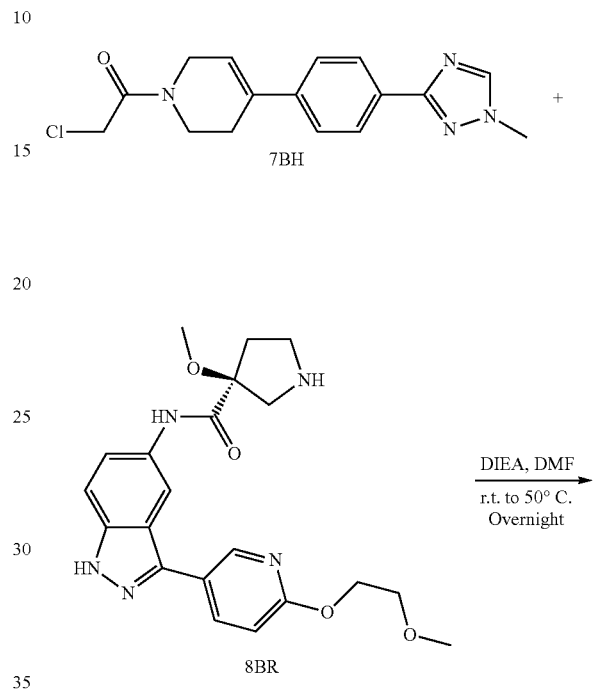

The crude 7BR was stirred in a mixture of dichloromethane (1 ml), trifluoroacetic acid (1 ml) at r.t. for 1 h. The mixture was cooled at 0° C. and quenched carefully with saturated aqueous sodium bicarbonate. Solvents were removed in vacuum. Dilute with water and ethyl acetate. Layers were separated and the separated aqueous layer was extracted with ethyl acetate (×3). The combined organic layers were dried (MgSO$_4$), filtered and solvents were removed in vacuum and gave pyrrolidine 8BR as off-white solid.

Synthesis of 3-Methoxy-1-(2-{4-[4-(1-methyl-1H-[1,2,4]triazol-3-yl)-phenyl]-3,6-dihydro-2H-pyridin-1-yl}-2-oxo-ethyl)-pyrrolidine-3-carboxylic acid {3-[6-(2-methoxy-ethoxy)-pyridin-3-yl]-1H-indazol-5-yl}-amide

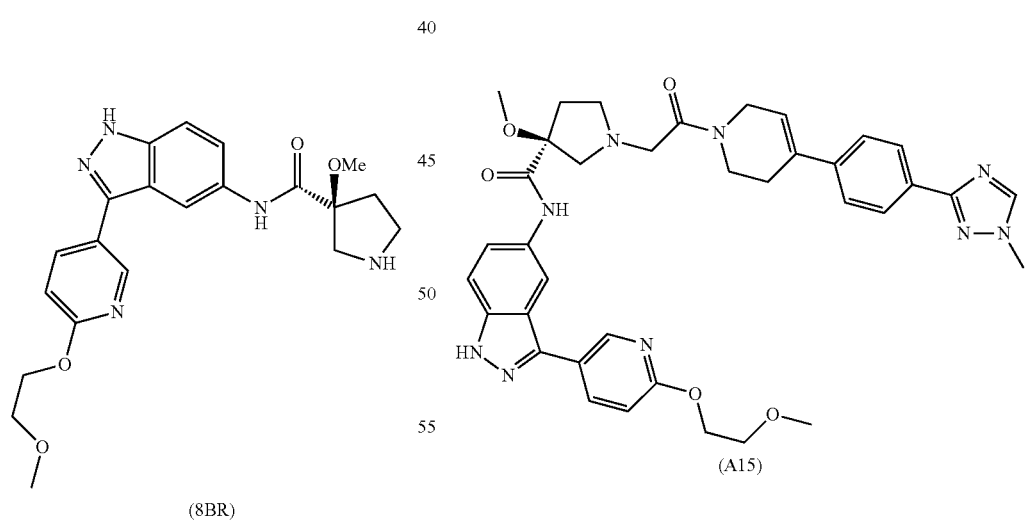

A mixture of compound 7BH (52 mg), compound 8BR (62 mg), and DIEA (0.3 ml) in DMF (1.5 ml) was stirred at room temperature overnight. LCMS shows the reaction is complete. DMF was removed under reduced pressure. The crude was purified by HPLC. (LCMS M+1=692, ret. time=3.00 min.) $^1$H NMR (400 MHz, CDCl$_3$): δ 11.92 (S, 1H), 11.11 (S, 1H), 9.14 (S, 1H), 8.58 (S, 1H), 8.03 (S, 1H), 7.99 (d, 1H, J=8.4 Hz), 7.90 (t, 2H, J=6.8), 7.39 (S, 2H), 7.20 (S, 3H), 6.76 (d, 1H, J=8.0 Hz), 5.85 (d, 1H, J=20 Hz), 4.4 (S, 4H), 4.05 (q, 4H, J=7.2 Hz), 3.8 (S, 3H), 3.50-3.56 (m, 6H), 2.34-2.62 (m, 5H), 2.0 (S, 2H), 1.64-1.49 (m, 3H).

Example 10

Preparation of 1-[2-(4-{4-[1-(2-Hydroxy-ethyl)-1H-[1,2,4]triazol-3-yl]-phenyl}-3,6-dihydro-2H-pyridin-1-yl)-2-oxo-ethyl]-3-methoxy-pyrrolidine-3-carboxylic acid [3-(6-isopropoxy-pyridin-3-yl)-1H-indazol-5-yl]-amide (A2)

Preparation of {3-[3-(6-Isopropoxy-pyridin-3-yl)-1H-inxazol-5-ylcarbamoyl]-3-methoxy-pyrrolidin-1-yl}-acetic acid

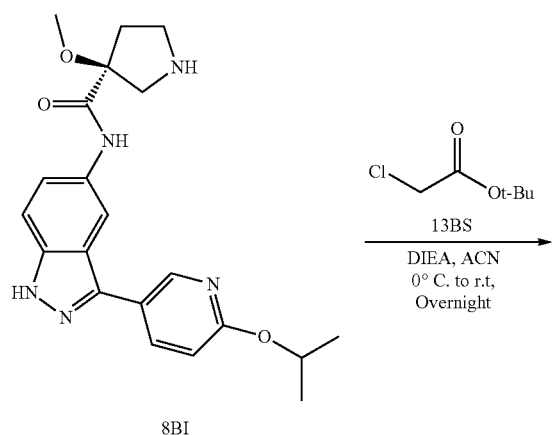

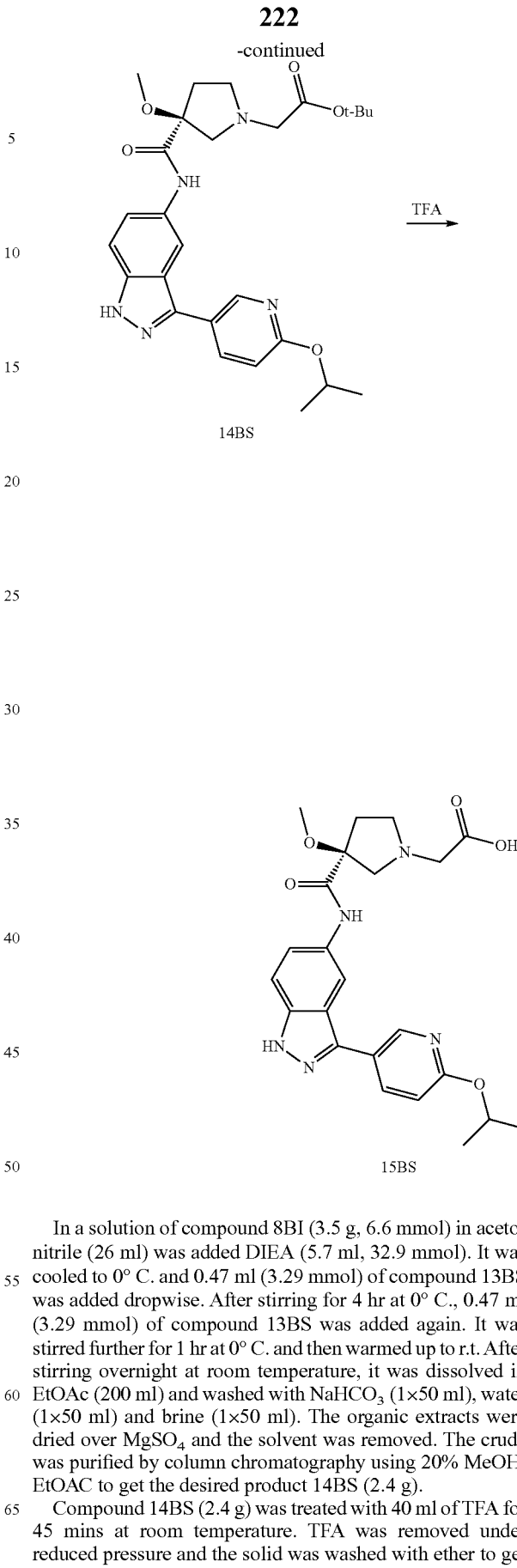

In a solution of compound 8BI (3.5 g, 6.6 mmol) in acetonitrile (26 ml) was added DIEA (5.7 ml, 32.9 mmol). It was cooled to 0° C. and 0.47 ml (3.29 mmol) of compound 13BS was added dropwise. After stirring for 4 hr at 0° C., 0.47 ml (3.29 mmol) of compound 13BS was added again. It was stirred further for 1 hr at 0° C. and then warmed up to r.t. After stirring overnight at room temperature, it was dissolved in EtOAc (200 ml) and washed with NaHCO₃ (1×50 ml), water (1×50 ml) and brine (1×50 ml). The organic extracts were dried over MgSO₄ and the solvent was removed. The crude was purified by column chromatography using 20% MeOH/EtOAC to get the desired product 14BS (2.4 g).

Compound 14BS (2.4 g) was treated with 40 ml of TFA for 45 mins at room temperature. TFA was removed under reduced pressure and the solid was washed with ether to get the desired compound 15BS as a TFA salt (4.4 gm, 95%). Compound 15BS was converted into the HCl salt by adding 4N HCl in water.

Synthesis of Preparation of 2-{3-[[4[(1,2,3,6-Tetrahydro-pyridin-4-yl)-phenyl]-[1,2,4]triazol-1-yl}-ethanol hydrochloride

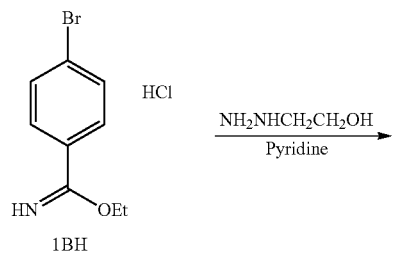

1BH

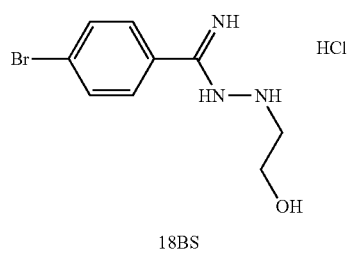

18BS

Preparation of 4-bromo-N'-(2-hydroxyethyl)benzimidohydrazide hydrochloride

The 4-bromo-benzimidic acid ethyl ester 1BH (5 g) was dissolved in pyridine (100 ml). Hydroxyethylhydrazine (1.92 ml) was added with stirring and the resulting mixture was allowed to stir overnight. The precipitate was collected by filtration and mother liquor was concentrated to almost dryness and ether was added. Solid was collected by filtration. Combined solid was washed with ether twice and dried to afford 18BS (5.1 g).

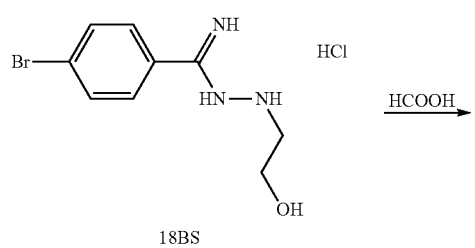

18BS

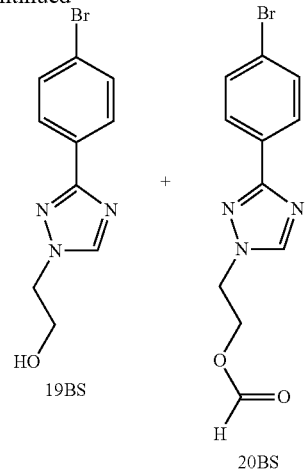

19BS

20BS

Preparation of 2-(3-(4-bromophenyl)-1H-1,2,4-triazol-1-yl)ethanol

A mixture of compound 18BS (3 g) in formic acid (50 ml) was stirred at room temperature for 30 minutes, at 100° C. for 1.5 hours and concentrated. The residue was treated with saturated NaHCO$_3$, and extracted with EtOAc three times. The combined organic extracts were dried over MgSO$_4$. After concentration, the crude was purified on silica gel. Elution with EtOAc gave compound 20BS (2 g), and compound 19BS (262 mg).

Compound 20BS can be easily converted to 19BS by aqueous hydrolysis

Preparation of 4-[4-(1-(2-Hydroxy-ethyl)-1H-[1,2,4]triazol-3-yl)-phenyl]-3,6-dihydro-2H-pyridine-1-carboxylic Acid tert-butyl Ester

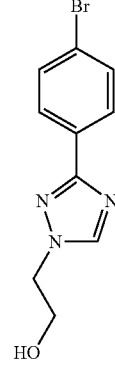

19BS

21BS

To a large pressure flask were charged compound 19BS (1.5 g, 5.6 mmols), 4-(4,4,5,5-tetramethyl-[1,3,2]dioxaborolan-2-yl)-3,6-dihydro-2H-pyridine-1-carboxylic acid tert-butyl ester (1.9 g, 6.2 mmols), [1,1'-bis(diphenylphosphino)ferrocene]dichloropalladium(II), complex with dichloromethane (1:1) (0.22 g, 0.28 mmols), K$_2$CO$_3$ (2.32 g, 16.8 mmols) and DME/water (5:1, 12 ml). The mixture was briefly degassed with Ar for ~0.5 minute, capped and stirred at 80° C. overnight. After cooling, the reaction mixture was diluted with EtOAc and washed with water (1×) and brine (1×). Organic layer was isolated, and dried over MgSO₄. After concentration, the residue was purified on silica gel. Elution with MeOH/EtOAc (0-10%) gave the desired product 21BS (1.4 g, 73%).

Preparation of 2-{3-[[4[(1,2,3,6-Tetrahydro-pyridin-4-yl)-phenyl]-[1,2,4]triazol-1-yl}-ethanol hydrochloride

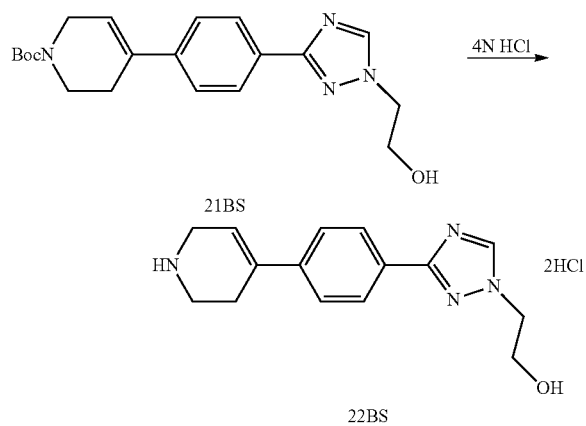

The Boc group can be removed by treating compound 21BS with 4N HCl in dioxane at rt for two hours. Removal of solvent under vacuum gave compound 22BS.

Preparation of 1-[2-(4-{4-[1-(2-Hydroxy-ethyl)-1H-[1,2,4]triazol-3-yl]-phenyl}-3,6-dihydro-2H-pyridin-1-yl)-2-oxo-ethyl]-3-methoxy-pyrrolidine-3-carboxylic acid [3-(6-isopropoxy-pyridin-3-yl)-1H-inxazol-5-yl]-amide

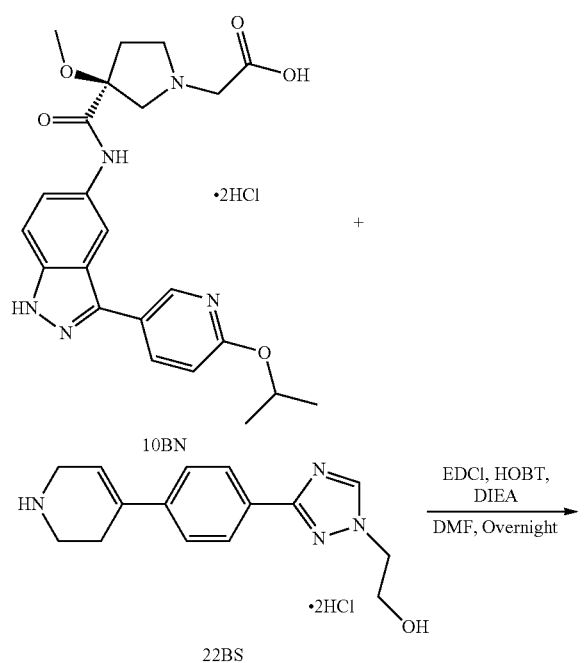

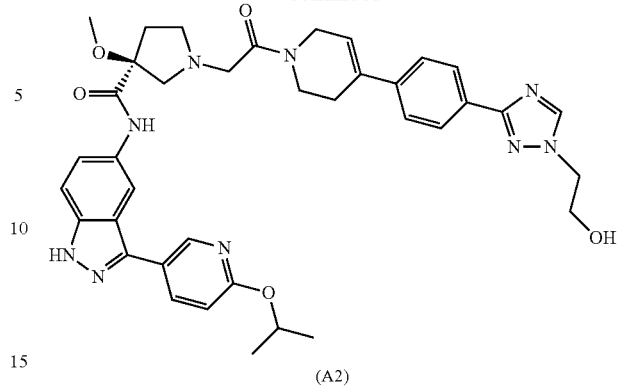

A mixture of compound 10BN (0.49 g, 1 mmol), 1-(3-Dimethyl-aminopropyl)-3-ethylcarbodiimide hydrochloride (0.38 g, 2 mmol), and 1-hydroxybenzotriazole (0.14 g, 1 mmol) was dissolved in DMF (3 ml). After stirring for 20 min at room temperature, compound 16BS (0.34 g, 1 mmol) and DIEA (0.7 ml, 4 mmol) were added. After stirring for overnight at room temperature, it was diluted with DCM (45 ml) and washed with NaHCO₃ (1×7 ml), water (3×7 ml) and brine (1×10 ml). The organic layer was dried over MgSO₄. After concentration, the residue was purified on silica gel. Elution with 2% NH₃ in 20% MeOH/EtOAc gave the desired product A2 (0.3 g). This compound was converted to HCl salt by adding 4N HCl in 1,4-dixoane. (LCMS: M+1=706, ret. time=3.13 min.), ¹H NMR (400 MHz, DMSO-d₆): δ=10.5-10.8 (m, 1H), 10.25 (d, 1H, J=19.2 Hz), 8.60-8.75 (m, 2H), 8.43 (m, 1H), 8.18 (m, 1H), 7.98 (m, 2H), 7.78 (d, 2H, J=20 Hz), 7.5-7.6 (m, 4H), 6.9 (m, 2H), 6.3 (m, 1H), 5.3 (m, 1H), 4.5-4.6 (m, 2H), 4.15-4.3 (m, 4H), 4.0-4.15 (m, 2H), 3.75 (t, 4H, 5.2 Hz), 3.5-3.6 (m, 2H), 3.4-3.3 (m, 1H), 3.29 (s, 2H), 2.5-2.7 (m, 3H), 2.3-2.4 (m, 1H), 1.3 (d, 6H, J=6.4 Hz).

Example 11

Synthesis of 3-Methoxy-1-(2-{4-[4-(1-methyl-1H-[1,2,4]triazol-3-yl)-phenyl]-3,6-dihydro-2H-pyridin-1-yl}-2-oxo-ethyl)-pyrrolidine-3-carboxylic acid [3-(6-ethoxy-pyridin-3-yl)-1H-indazol-5-yl]-amide (Example 1)

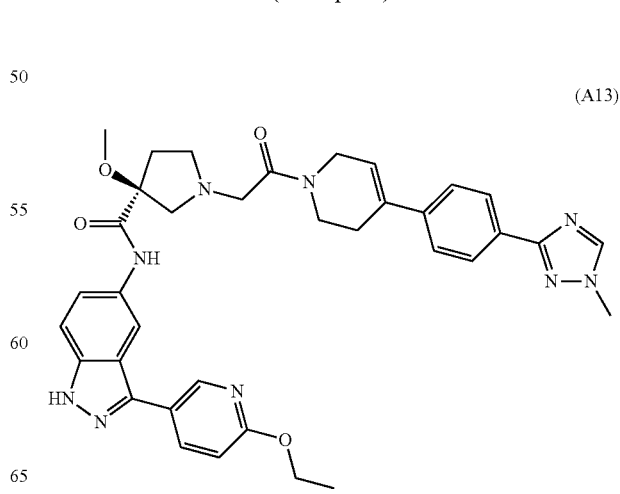

Step 1

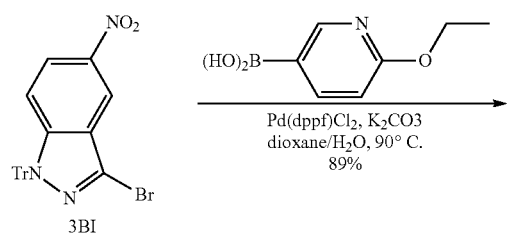

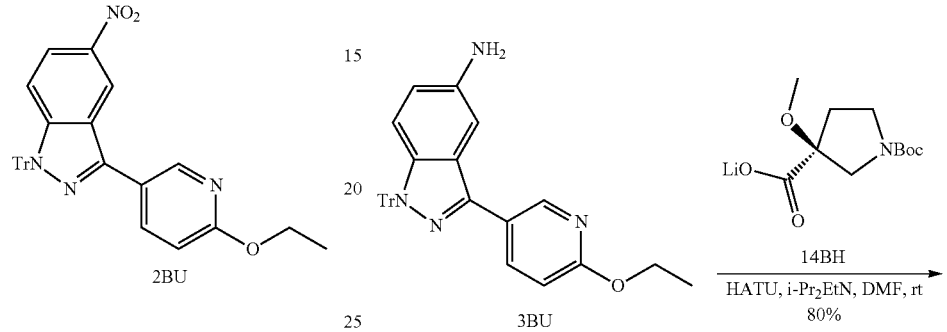

A mixture of 6-ethoxypyridine-3-boronic acid (2.5 g, 14.97 mmol), bromoindazole 3BI (7.25 g, 14.97 mmol), potassium carbonate (6.2 g, 44.91 mmol), PdCl$_2$(dppf$_2$·CH$_2$Cl$_2$ (1.22 g, 1.497 mmol), 1,4-dioxane (40 mL) and water (10 mL), was purged with nitrogen for 15 min at r.t. and then heated at 90° C. for 18 hrs and cooled to r.t. Water (100 mL) and ethyl acetate (300 mL) were added. Solids were filtered through Celite. Layers were separated and the separated organic layer was washed with water (100 mL). The combined organic layers were dried (Na$_2$SO$_4$), filtered and solvents were removed in vacuum. Column purification [Hexanes-ethyl acetate=9:1 (v/v)] gave Compound 2BU (7 g, 89%).

Step 2

Compound 2BU (2 g, 3.8 mmol) and Pd/C (10%, 50% wet, 0.7 g) were stirred in toluene (30 mL) and MeOH (15 mL) under H$_2$ (balloon) at r.t. for 18 hrs. The solid catalyst was filtered through Celite and solvents were removed in vacuum. Column purification using 4% MeOH/CH$_2$Cl$_2$ gave Compound 3BU (1.6 g, 85%).

Step 3

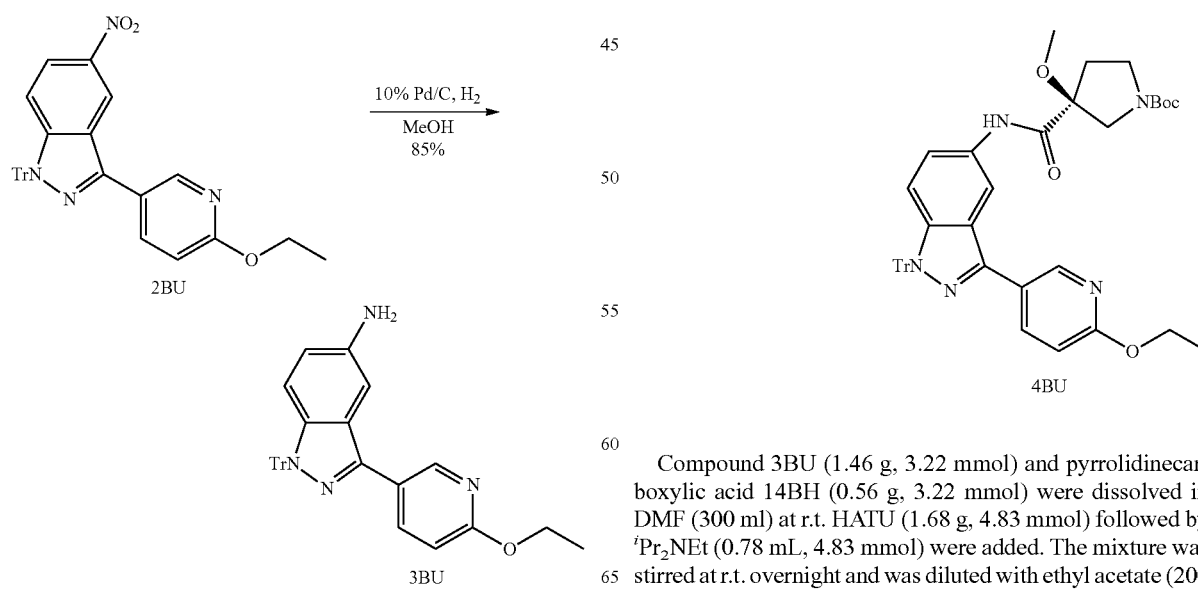

Compound 3BU (1.46 g, 3.22 mmol) and pyrrolidinecarboxylic acid 14BH (0.56 g, 3.22 mmol) were dissolved in DMF (300 ml) at r.t. HATU (1.68 g, 4.83 mmol) followed by $^i$Pr$_2$NEt (0.78 mL, 4.83 mmol) were added. The mixture was stirred at r.t. overnight and was diluted with ethyl acetate (200 mL) and water (100 mL). Layers were separated. The separated organic layer was washed with water (100 mL), dried (Na₂SO₄) and filtered. Concentration in vacuum followed by column purification [hexanes-ethyl acetate=9:1 (v/v)] gave product 4BU.

Step 4

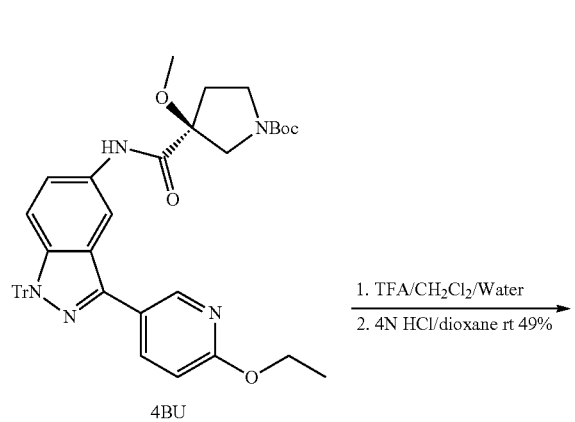

which was converted to mono HCl salt by treating with 4 N HCl/dioxane and evaporating the solution to dryness.

Step 5

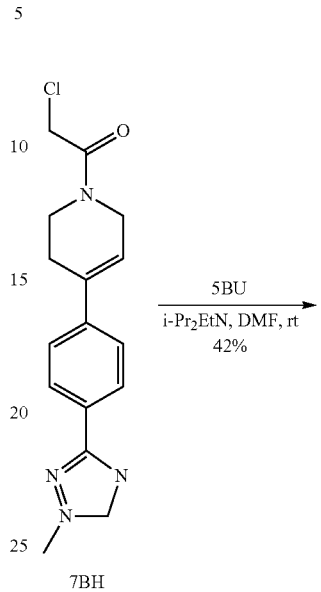

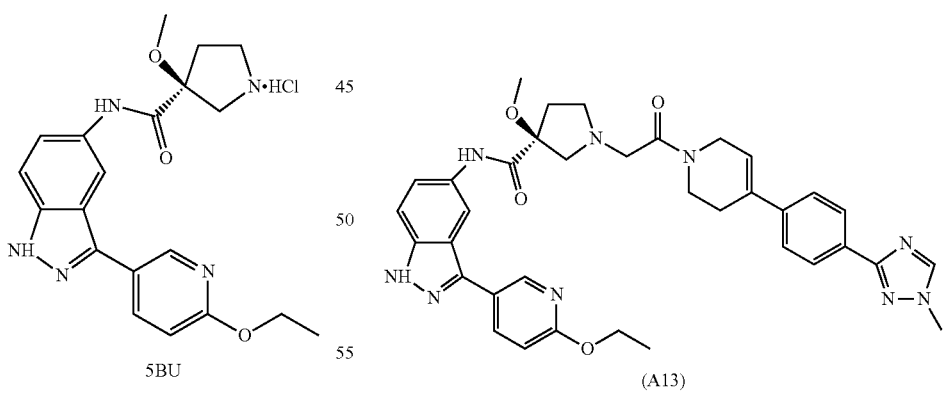

Compound 4BU (1.6 g) was stirred in a mixture of dichloromethane (30 mL), trifluoroacetic acid (4 mL) and few drops of water at r.t. overnight. The mixture was cooled at 0° C. and quenched carefully with 7% MeOH (NH₃)/CH₂Cl₂. Solvents were removed in vacuum. Dilute with water (100 mL) and ethyl acetate (200 mL). Layers were separated. The organic layer was dried (Na₂SO₄), filtered and solvents were removed in vacuum. Column purification [7% MeOH (7N ammonia) in dichloromethane] gave Compound 5BU (0.44 g, 49%)

A mixture of Compound 7BH (46 mg, 0.144 mmol), Compound 5BU (60 mg, 0.144 mmol), DMF (2 mL) and N,N-diisopropylethylamine (0.076 mL, 0.432 mmol) was stirred at room temperature for 18 hours. Diluted with EtOAc (100 mL) and washed with water (2×100 mL). The organic layer was dried over Na₂SO₄, filtered and concentrated. The residue was purified on silica gel eluting with 4% MeOH (NH₃)/CH₂Cl₂ to give the desired product 6BU (40 mg, 42%)

LCMass Spec M+1@ret. time=662@2.57 min .

Example 12

Synthesis of 3-Methylsulfanyl-1-(2-{4-[4-(1-methyl-1H-[1,2,4]triazol-3-yl)-phenyl]-3,6-dihydro-2H-pyridin-1-yl}-2-oxo-ethyl)-pyrrolidine-3-carboxylic acid [3-(6-methoxy-pyridin-3-yl)-1H-indazol-5-yl]-amide (A19)

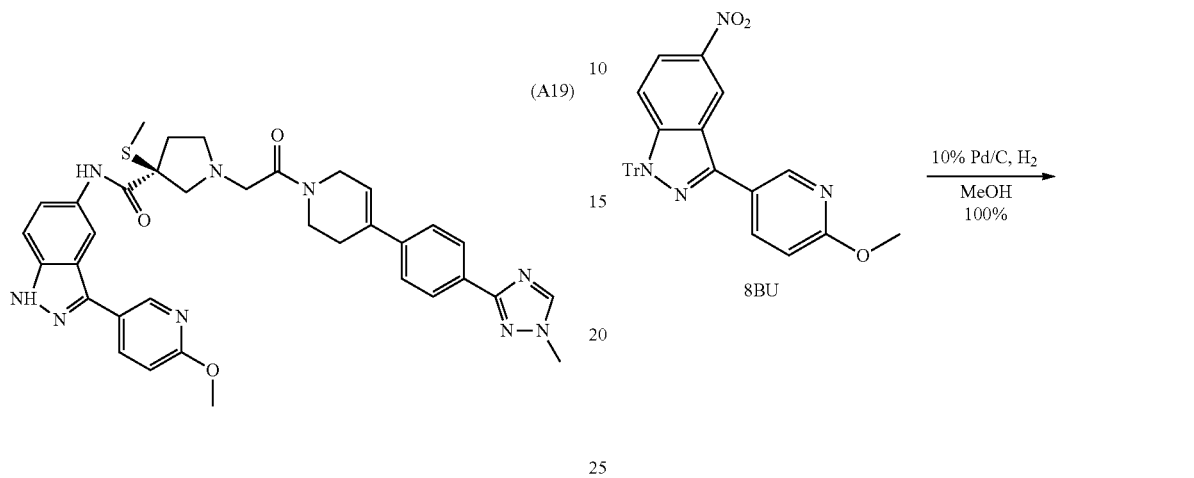

Step 1

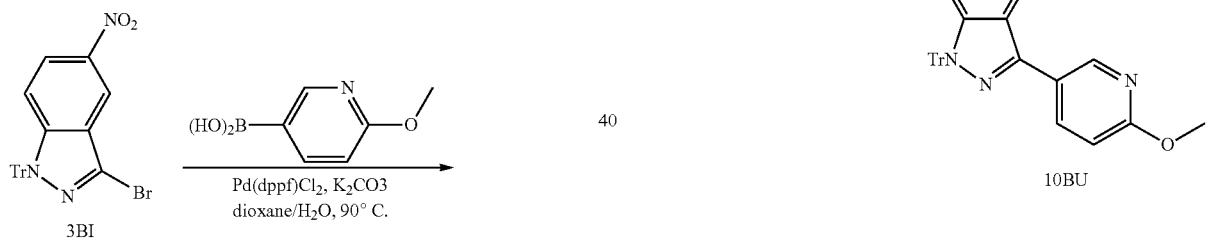

Compound 8BU was prepared from Compound 3BI using essentially the same procedure as described for the preparation of Compound 2BU from Compound 3BI (Example 11, Step 1), using 6-methoxypyridine-3-boronic acid in place of 6-ethoxypyridine-3-boronic acid.

Step 2

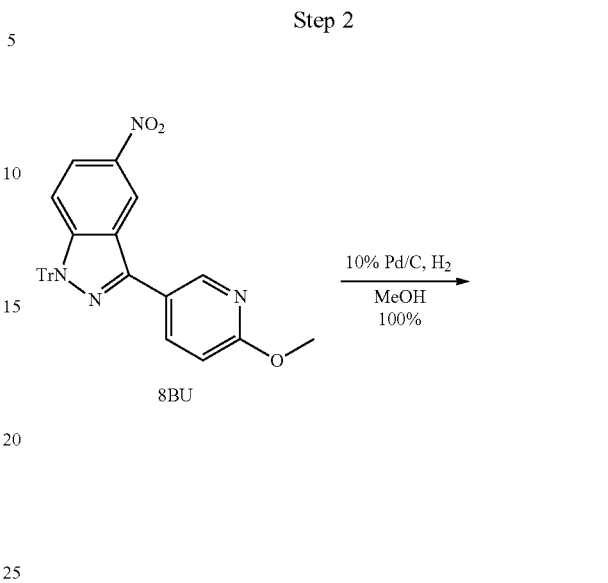

Compound 8BU (3 g, 3.8 mmol) and Pd/C (10%, 50% wet, 1.2 g) were stirred in toluene (30 mL) and MeOH (15 mL) under H$_2$ (balloon) at r.t. for 18 hrs. The solid catalyst was filtered through Celite and solvents were removed in vacuum to give Compound 10BU (2.8 g, 100%).

Step 3

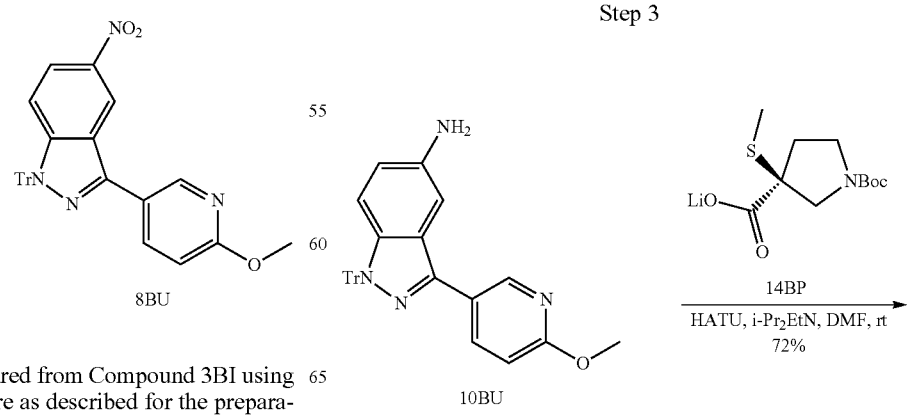

-continued

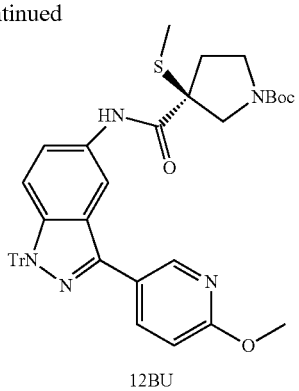

12BU

Compound 10BU (0.6 g, 1.24 mmol) and pyrrolidinecarboxylic acid 14BP (0.33 g, 1.24 mmol) were dissolved in DMF (5 mL) at r.t. HATU (0.71 g, 1.86 mmol) followed by $^i$Pr$_2$NEt (00.66 mL, 3.72 mmol) were added. The mixture was stirred at r.t. overnight and was diluted with ethyl acetate (200 mL) and water (100 mL). Layers were separated. The separated organic layer was washed with water (100 mL), dried (Na$_2$SO$_4$) and filtered. Concentration in vacuum followed by column purification [hexanes-ethyl acetate=9:1 (v/v)] gave product 12BU (0.65 g, 72%).

Step 4

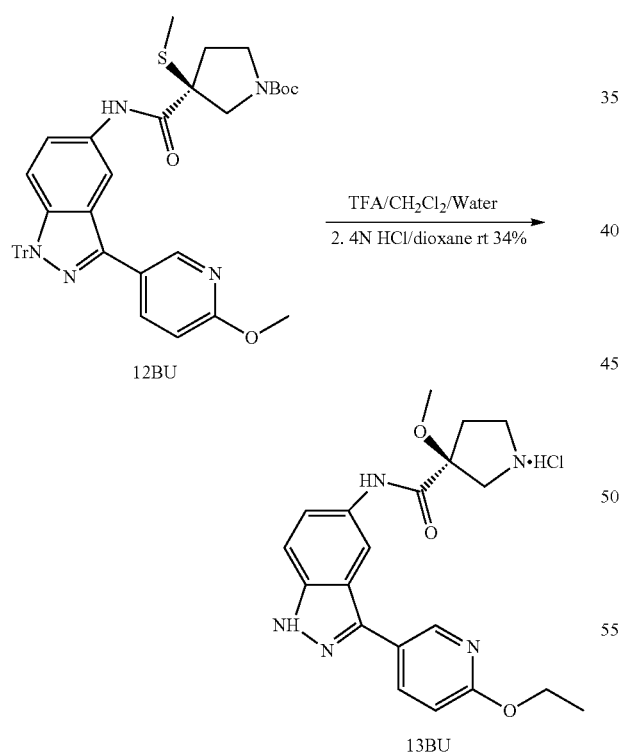

Compound 12BU (0.65 g) was stirred in a mixture of dichloromethane (30 mL), trifluoroacetic acid (4 mL) and few drops of water at r.t. overnight. The mixture was cooled at 0° C. and quenched carefully with 7% MeOH(NH$_3$)/CH$_2$Cl$_2$. Solvents were removed in vacuum. Dilute with water (100 mL) and ethyl acetate (200 mL). Layers were separated. The organic layer was dried (Na$_2$SO$_4$), filtered and solvents were removed in vacuum. Column purification [15% MeOH (7N ammonia) in dichloromethane] gave Compound 13BU (0.22 g, 34%).

Step 5

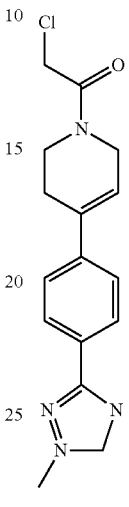

7BH

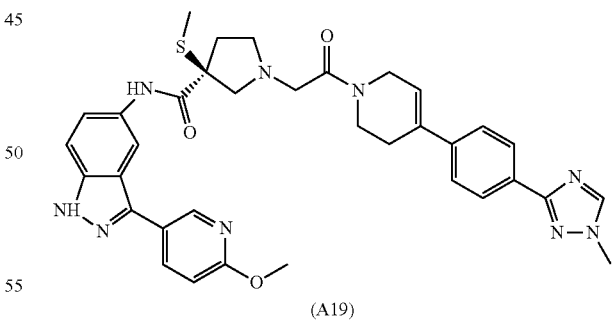

(A19)

A mixture of Compound 7BH (40 mg, 0.126 mmol), Compound 13BU (50 mg, 0.126 mmol), DMF (2 mL) and N,N-diisopropylethylamine (0.045 mL, 0.25 mmol) was stirred at room temperature for 18 hours. Diluted with EtOAc (100 mL) and washed with water (2×100 mL). The organic layer was dried over Na$_2$SO$_4$, filtered and concentrated. The residue was purified on silica gel eluting with 3% MeOH(NH$_3$)/CH$_2$Cl$_2$ to give the desired product A19 (50 mg, 60%)

LCMass Spec M+1@ret. time=664@2.88 min.

Example 13

Synthesis of 3-Methoxy-1-(2-{4-[4-(1-methyl-1H-[1,2,4]triazol-3-yl)-phenyl]-3,6-dihydro-2H-pyridin-1-yl}-2-oxo-ethyl)-pyrrolidine-3-carboxylic acid [3-(2-methoxy-pyridin-4-yl)-1H-indazol-5-yl]-amide (A21)

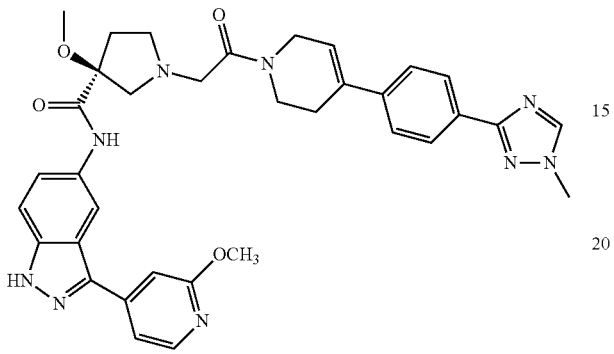

Step 1

Synthesis of 3-(2-Fluoro-pyridin-4-yl)-5-nitro-1-trityl-1H-indazole

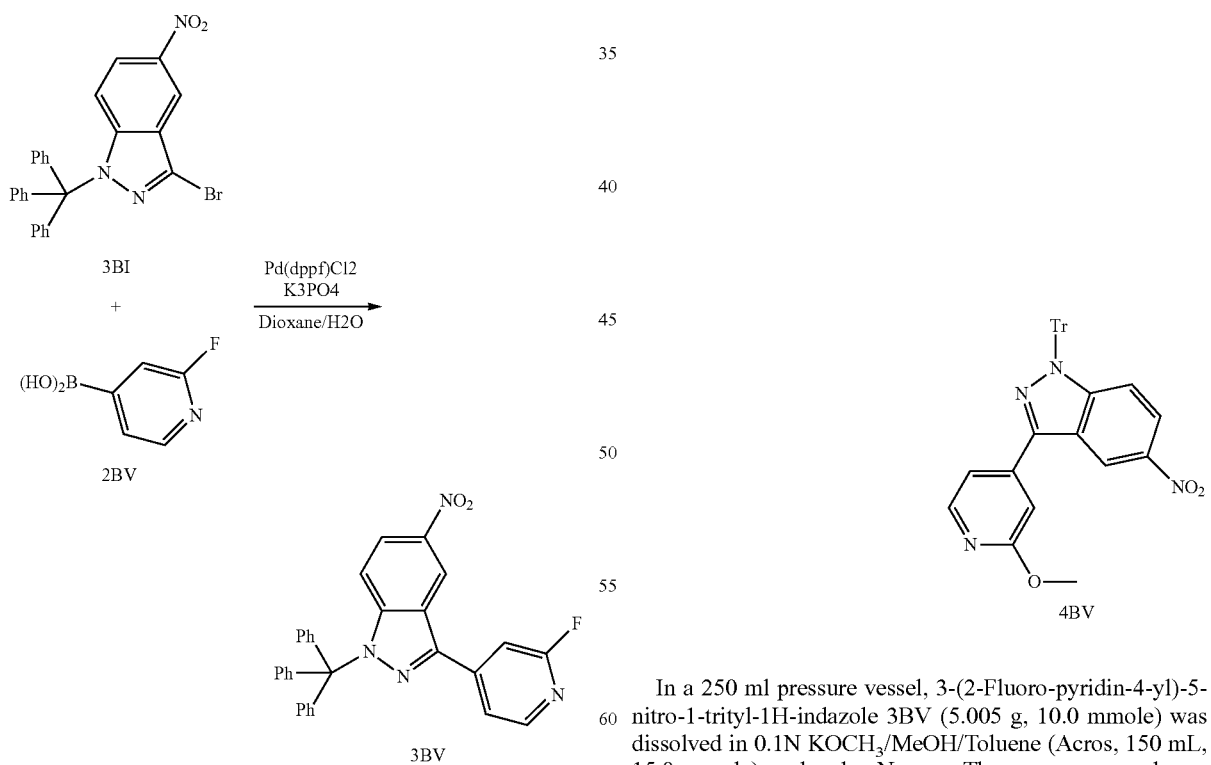

3-Bromo-5-nitro-1-trityl-1H-indazole 3BI (15.64 g, 32.3 mmol), 2-fluoro-4-pyridine boronic acid 2BV (5.0 g, 35.5 mmol), K₃PO₄ (17.1 g, 80.7 mmol) and Pd(dppf)Cl₂ (2.64 g, 3.23 mmol) was mixed in dioxane/H₂O (240 mL/60 mL) at rt and heated at 80° C. overnight. The reaction mixture was cooled to rt and concentrated to a small volume. The residue was partitioned between ethyl acetate (200 mL) and brine (150 mL). The organic layer was washed with brine, dried (MgSO₄) and filtered. The resulting filtrate was concentrated and the residue was purified on silica gel column eluting with hexanes, 5% ethyl acetate in hexanes, 10% ethyl acetate in hexanes sequentially to yield a yellow solid 3BV (3.33 g, 64%).

Step 2

Preparation of 3-(2-Methoxy-pyridin-4-yl)-5-nitro-1-trityl-1H-indazole

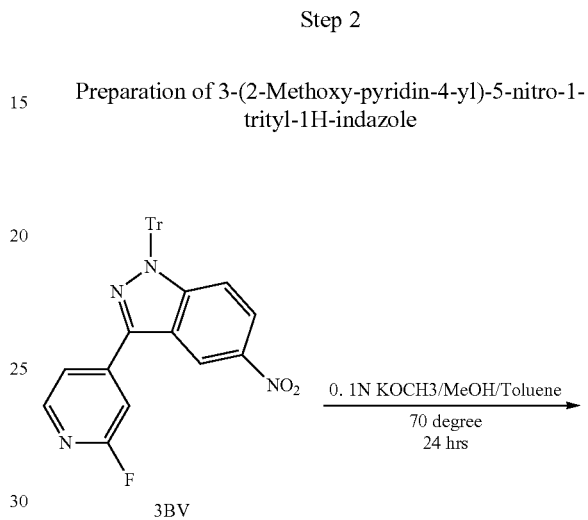

In a 250 ml pressure vessel, 3-(2-Fluoro-pyridin-4-yl)-5-nitro-1-trityl-1H-indazole 3BV (5.005 g, 10.0 mmole) was dissolved in 0.1N KOCH₃/MeOH/Toluene (Acros, 150 mL, 15.0 mmole) under dry N₂ gas. The pressure vessel was tightly sealed and heated under stirring at 70° C. for 24 hours. The pressure vessel was cooled to 0° C. in ice-bath before opening. The contents of the pressure vessel were transferred to 500 ml RBF and evaporated to dryness. The resulting solid was dissolved in CH₂Cl₂ and washed with saturated NaCl

Step 3

Preparation of 3-(2-methoxy-pyridin-4-yl)-1-trityl-1H-indazol-5-ylamine

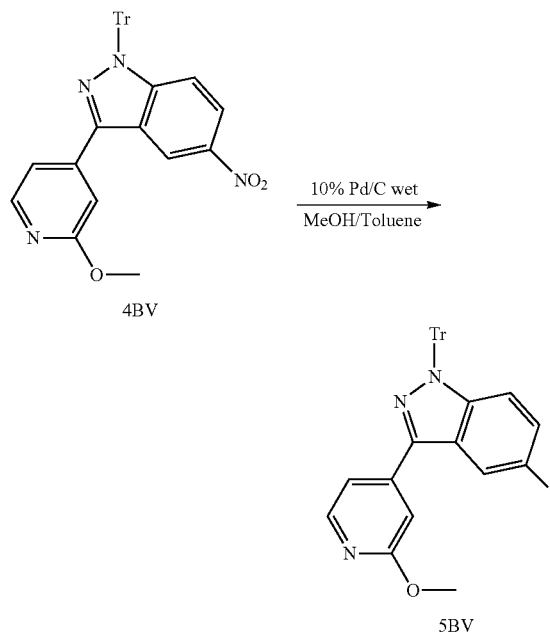

To the stirred suspension of 3-(2-Methoxy-pyridin-4-yl)-5-nitro-1-trityl-1H-indazole 4BV (5.125 g, 10.0 mmole) in MeOH/toluene (50 mL/50 mL) was added 10% Pd/C (Degussa type, 0.5 g) at r.t. under dry $N_2$ gas. The mixture was degassed and was stirred under a balloon inflated with $H_2$ gas overnight. The catalyst was filtered through microfiber filter and was washed with MeOH and $CH_2Cl_2$. The filtrate was evaporated to dryness and a brown solid 5BV was obtained (5.0 g).

Step 4

Preparation 3-Methoxy-3-[3-(2-methoxy-pyridin-4-yl)-1-trityl-1H-indazol-5-ylcarbamoyl]-pyrrolidine-1-carboxylic acid tert-butyl ester

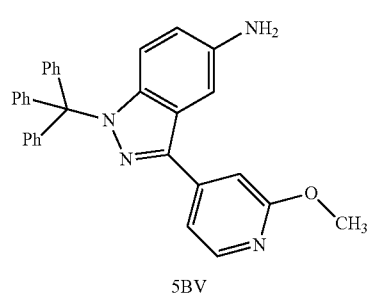

+

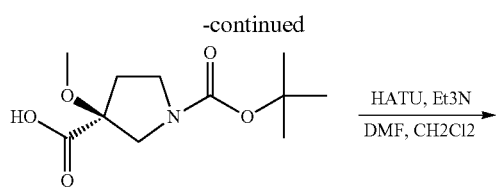

6BV

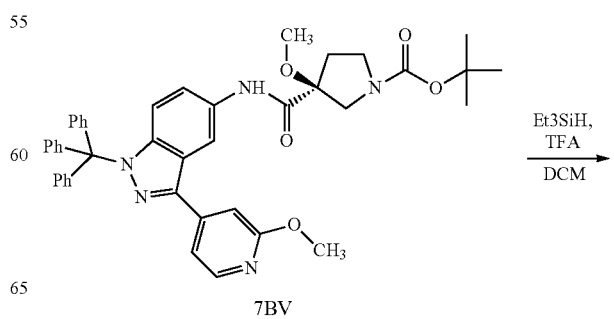

7BV

To the stirred suspension of 3-methoxy-pyrrolidine-1,3-dicarboxylic acid 1-tert-butyl ester 6BV (4.16 mmole, crude) in DMF/DCM (25 mL/25 mL), 3-(2-methoxypyridin-4-yl)-1-trityl-1H-indazol-5-ylamine 5BV (2.008 g, 4.16 mmole) and $Et_3N$ (2.9 mL, 21 mmole) were added at r.t. under dry $N_2$ gas followed by HATU (3.16 g, 8.32 mmole). The mixture was stirred at r.t. under dry $N_2$ gas overnight. The mixture was partitioned between 1:1 EtOAc and sat. $NaHCO_3$ solution. The organic phase was separated, washed with brine, dried over $MgSO_4$ and evaporated to dryness. The crude solid was purified on RediSep 120 g cartridge eluting with 10-25% EtOAc/Hexanes to yield a brown solid 7BV (2.95 g, 100%).

Step 5

Preparation 3-Methoxy-pyrrolidine-3-carboxylic acid [3-(2-methoxy-pyridin-4-yl)-1H-indazol-5-yl]-amide

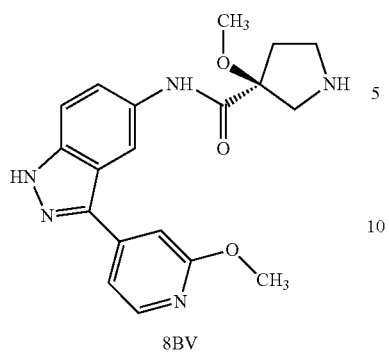

8BV

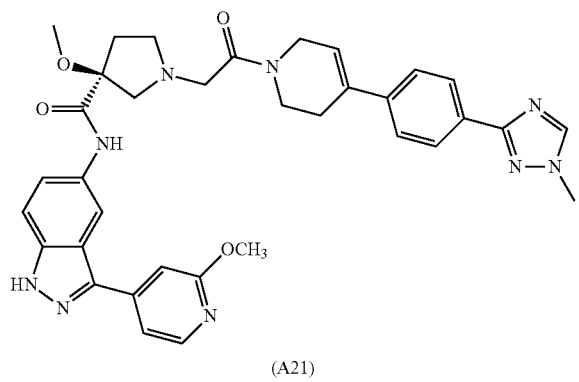

(A21)

To the stirred solution 3-Methoxy-3-[3-(2-methoxy-pyridin-4-yl)-1-trityl-1H-indazol-5-ylcarbamoyl]-pyrrolidine-1-carboxylic acid tert-butyl ester 7BV (2.95 g, 4.16 mmole) in DCM (50 mL) at r.t. was added triethylsilane (1.00 ml, 6.24 mmole) followed by TFA (10 mL). The mixture was stirred at r.t. under dry $N_2$ gas for 4-5 hours. The mixture was evaporated to dryness and co-evaporated with dry toluene (2×75 mL). The resulting crude solid was purified on RediSep 120 g cartridge eluting with 2.5%-6% 2M $NH_3$-MeOH/$CH_2Cl_2$ to yield an off-white solid 8BV (1.23 g, 80%).

Step 6

Synthesis of 3-Methoxy-1-(2-{4-[4-(1-methyl-1H-[1,2,4]triazol-3-yl)-phenyl]-3,6-dihydro-2H-pyridin-1-yl}-2-oxo-ethyl)-pyrrolidine-3-carboxylic acid [3-(2-methoxy-pyridin-4-yl)-1H-indazol-5-yl]-amide A mixture of compound 8BV (40 mg, 0.11 mmol), compound 9BV (41.6 mg, 0.13 mmol) and triethylamine (0.1 mL) in DMF (3 mL) was heated at 45° C. with stirring overnight. The reaction mixture was then concentrated in vacuo and the resulting crude was purified on silica gel column eluting with 2% and 4% 2N $NH_3$/MeOH in $CH_2Cl_2$ to isolate a yellow solid A21 (39.6 mg, 55%). (LCMS M+1=648, ret. time=2.34 min.) $^1$H-NMR (400 MHz, CDCl$_3$): δ 10.54 (br, 1H), 9.51 & 9.44 (s, s, 1H), 8.46 (dd, 1H, J=8.2 Hz & 1.4 Hz), 8.27 (d, 1H, J=5.3 Hz), 8.07 (s, 1H), 8.05 (m, 2H), 7.76 (m, 1H), 7.54 (m, 1H), 7.44 (m, 3H), 7.37 (br, 1H), 6.20 & 6.11 (t, t, 1H, J=2.5 Hz), 4.27 (m, 2H), 4.00 & 3.98 (s, s, 6H), 3.96 & 3.86 (m, m, 1H), 3.74 (m, 1H), 3.47-3.60 (m, 2H), 3.453 & 3.446 (s, s, 3H), 3.32 (d, 1H, 9.9 Hz), 3.02 (m, 1H), 2.97 (dd, 1H, J=10.1 Hz & 1.0 Hz), 2.91 (m, 1H), 2.64 (m, 2H), 2.47 (m, 1H), 2.19 (m, 1H).

Example 14

Synthesis of 3-Methylsulfanyl-1-(2-{4-[4-(1-methyl-1H-[1,2,4]triazol-3-yl)-phenyl]-3,6-dihydro-2H-pyridin-1-yl}-2-oxo-ethyl)-pyrrolidine-3-carboxylic acid [3-(2-ethoxy-pyridin-4-yl)-1H-indazol-5-yl]-amide (A22)

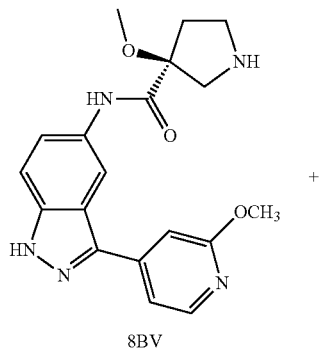

8BV

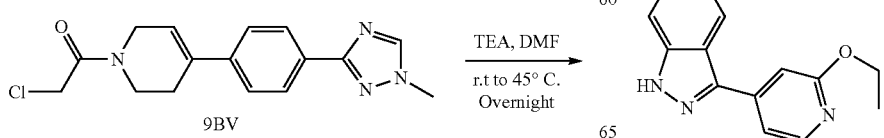

9BV

TEA, DMF
r.t to 45° C.
Overnight

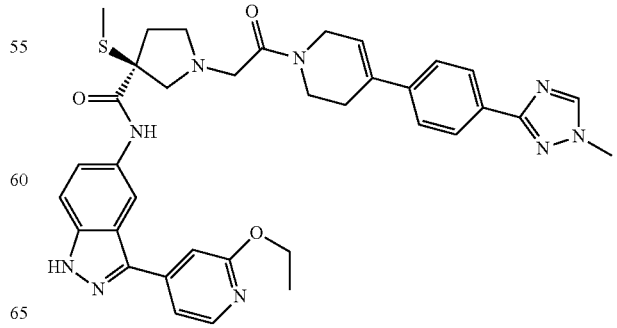

Step 1

Preparation of 3-(2-Ethoxy-pyridin-4-yl)-5-nitro-1-trityl-1H-indazole

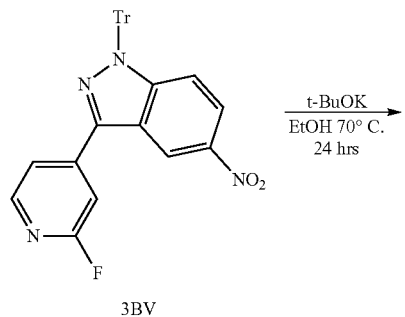

In a 150 mL pressure vessel, to the stirred solution of 3-(2-Fluoro-pyridin-4-yl)-5-nitro-1-trityl-1H-indazole 3BV (2.0 g, 4.0 mmole) in anhydrous EtOH (40 mL), solid potassium tert-butoxide (12 g, 10.0 mmole) was added under dry $N_2$ gas. The pressure vessel was tightly sealed and heated at 80° C. for 24 hours. The pressure vessel was cooled to 0° C. in ice-bath before opening. The contents of the pressure vessel were transferred to 250 mL RBF and concentrated to a small volume. The resulting mixture was partitioned between EtOAc and $H_2O$. The organic phase was separated, washed with saturated NaCl solution and dried over $MgSO_4$. The solvent was evaporated to dryness to give a crude solid 11BV (1.5 g, 71%).

Step 2

Preparation of 3-(2-ethoxy-pyridin-4-yl)-1-trityl-1H-indazol-5-ylamine

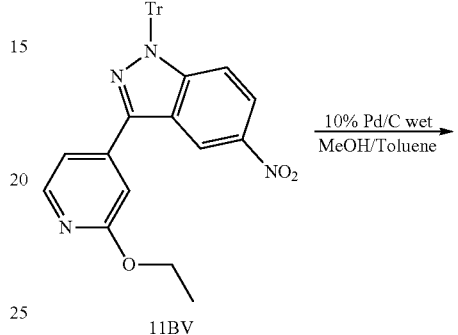

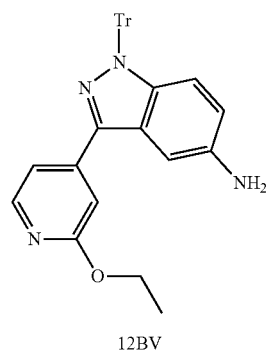

12BV was prepared by using essentially the same procedure as in Example 13, Step 3, except using 11BV instead of 4BV.

Step 3

Preparation of 3-[3-(2-Ethoxy-pyridin-4-yl)-1-trityl-1H-indazol-5-ylcarbamoyl]-3-methylsulfanyl-pyrrolidine-1-carboxylic acid tert-butyl ester

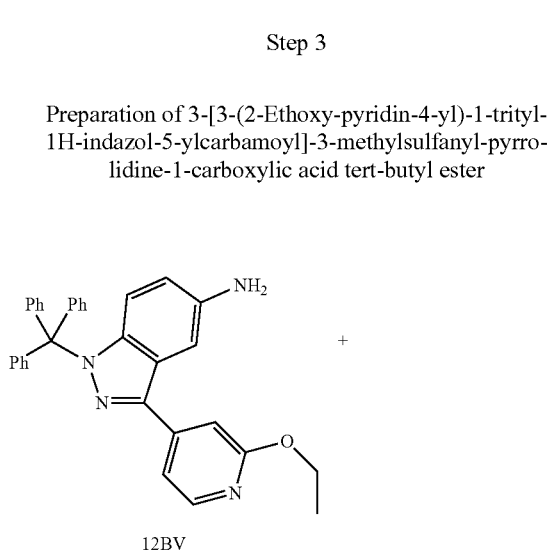

243

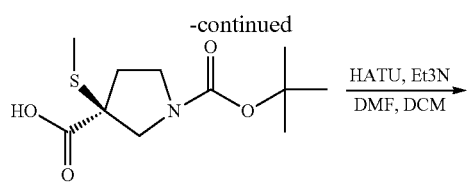

14BP

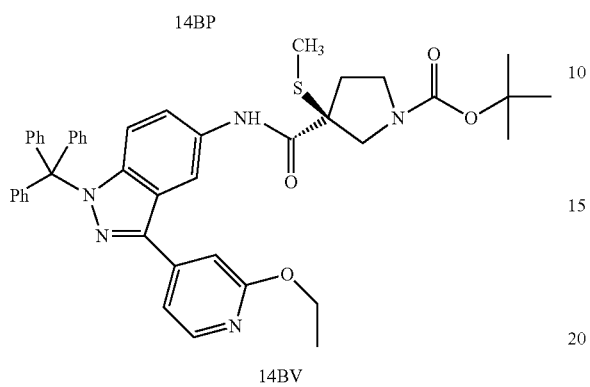

14BV

14BV, with a yield of 88%, was prepared using essentially the same procedure as in Example 13, Step 4, except using 12BV and 14BP instead of 5BV and 6BV.

Step 4

Preparation of 3-Methylsulfanyl-pyrrolidine-3-carboxylic acid [3-(2-ethoxypyridin-4-yl)-1H-indazol-5-yl]-amide

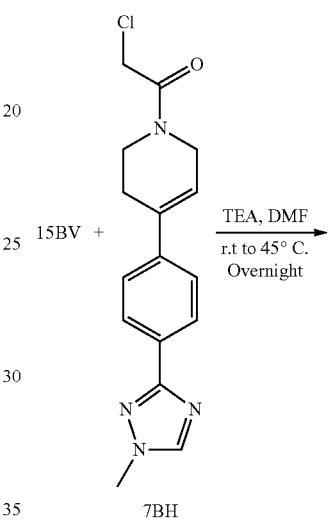

15BV

244

15BV, with a yield of 80%, was prepared using essentially the same procedure as in Example 13, Step 5, except using 14BV instead of 7BV.

Step 5

Preparation of 3-Methylsulfanyl-1-(2-{4-[4-(1-methyl-1H-[1,2,4]triazol-3-yl)phenyl]-3,6-dihydro-2H-pyridin-1-yl}-2-oxo-ethyl)-pyrrolidine-3-carboxylic acid [3-(2-ethoxy-pyridin-4-yl)-1H-indazol-5-yl]-amide

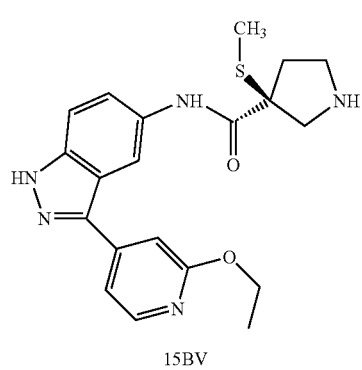

7BH

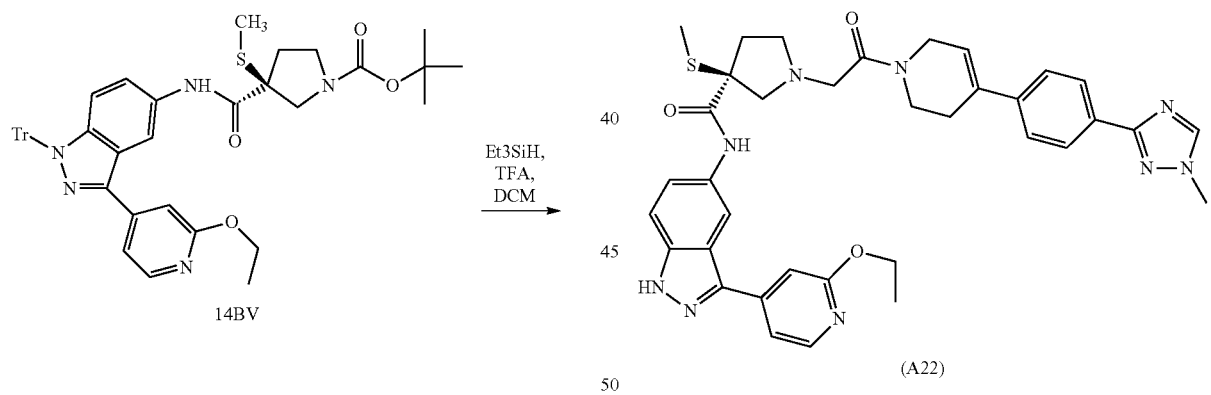

(A22)

A mixture of compound 15BV (40 mg, 0.10 mmol), compound 7BH (41.6 mg, 0.13 mmol) and triethylamine (0.1 mL) in DMF (3 mL) was heated at 45° C. with stirring overnight. The reaction mixture was then concentrated in vacuo and the resulting crude was purified on silica gel column eluting with 2% and 4% 2N $NH_3$/MeOH in $CH_2Cl_2$ to isolate a yellow solid A22 (36.0 mg, 53%). (LCMS M+1=678, ret. time=2.41 min.) $^1$H-NMR (400 MHz, $CDCl_3$): δ 10.55 (br, 1H), 10.01 & 9.84 (s, s, 1H), 8.50 & 8.44 (d, d, 1H, J=1 Hz), 8.25 (d, 1H, J=5.2 Hz), 8.08 (s, 1H), 8.04 (d, 1H, J=8.2 Hz), 8.00 (d, 1H, J=8.2 Hz), 7.75 (m, 1H), 7.53 (m, 1H), 7.43 (d, 1H, J=8.2 Hz), 7.39 (m, 2H), 7.34 (d, 1H, J=5.2 Hz), 6.18 & 6.11 (t, t, 1H, J=2.5 Hz), 4.42 (q, 2H, J=7.0 Hz), 4.35 & 4.30 (m, m, 1H), 4.22 (m, 1H), 3.99 (s, 3H), 3.92 (t, 1H, J=5.6 Hz), 3.72 (m, 3H), 3.42 (m, 1H), 3.12 (m, 1H), 2.84 (q, 1H, J=7.9 Hz), 2.76

(d, 1H, J=9.9 Hz), 2.70 (m, 1H), 2.63 (m, 2H), 2.15 (s, 3H), 2.11 (m, 1H), 1.44 (t, 3H, J=7.0 Hz).

Example 15

Synthesis of 3-Methoxy-1-(2-{4-[4-(1-methyl-1H-[1,2,4]triazol-3-yl)-phenyl]-3,6-dihydro-2H-pyridin-1-yl}-2-oxo-ethyl)-pyrrolidine-3-carboxylic acid [3-(2-isopropoxy-pyridin-4-yl)-1H-indazol-5-yl]-amide

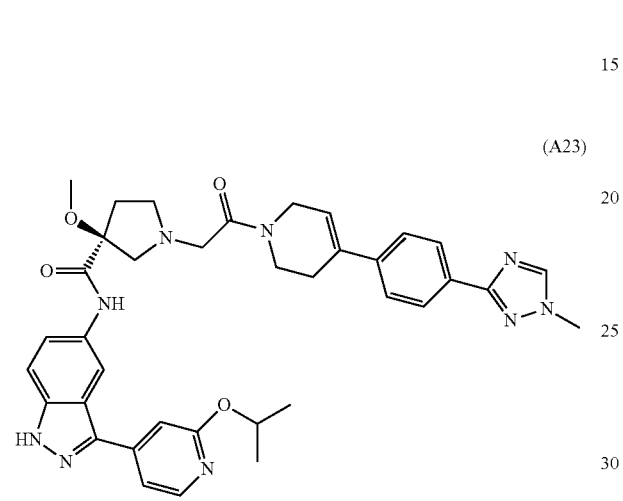

(A23)

Step 1

Preparation of 4-Bromo-2-Isopropoxy-pyridine

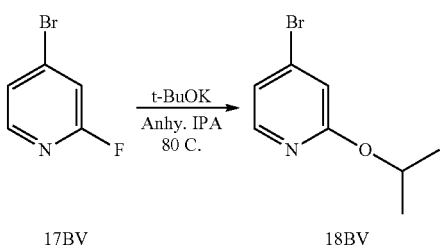

To the stirred solution of 4-bromo-2-fluoro-pyridine 17BV (4.12 g, 23.41 mmole) in 50 mL anhydrous IPA in a 150 mL pressure vessel was added 2.627 g (23.41 mmole) of solid potassium tert-butoxide under dry $N_2$ gas. The pressure vessel was tightly sealed and heated at 80° C. for 3 hours. The pressure vessel was cooled to 0° C. in ice-bath before opening. The contents of the pressure vessel were transferred to 250 mL RBF and concentrated to a small volume. The resulting mixture was partitioned between EtOAc and $H_2O$. The organic phase was separated, washed with saturated NaCl solution and dried over $MgSO_4$. The solvent was evaporated and resulting clear oil was purified on RediSep 80 g cartridge eluting with 20:1 Hexanes/EtOAc to give clear oil 18BV (4.2 g, 83%).

Step 2

Preparation of 3-(2-Isopropoxy-pyridin-4-yl)-5-nitro-1-trityl-1H-indazole

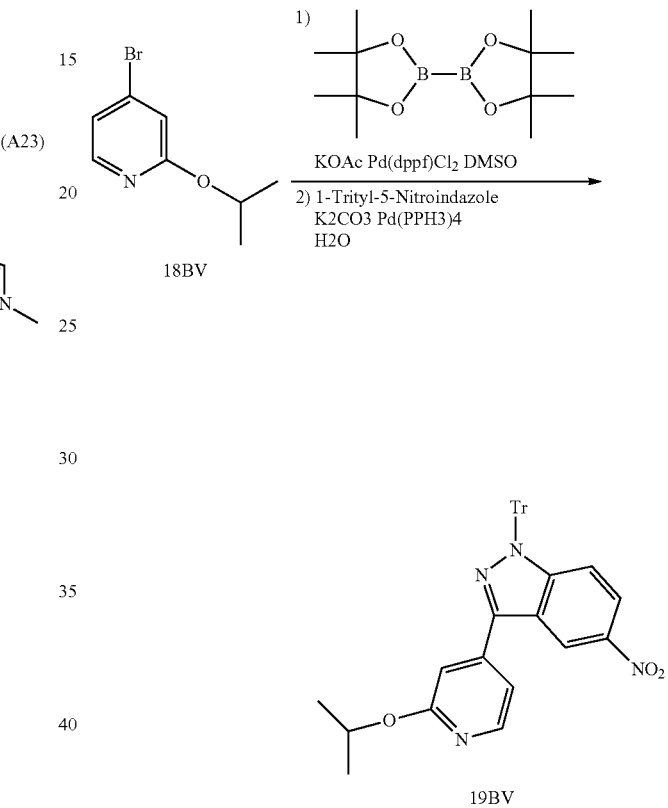

To the stirred solution of 4.20 g (19.4 mmole) 4-bromo-2-isopropoxy-pyridine

18BV in 150 mL anhydrous DMSO, 7.39 g (29.1 mmole) of bis(pinacolato)diboron, 5.704 g (58.2 mmole) of potassium acetate, and 1.584 g (1.94 mmole) of Pd(dppf)Cl$_2$ were added at r.t. under dry $N_2$ gas. The mixture was degassed couple of times with dry $N_2$ gas. The dark orange mixture was heated at 100° C. for 2 hours. The dark colored mixture was allowed to cool to r.t. 75 mL of $H_2O$ was added followed by 9.396 g (19.4 mmole) of 1-Trityl-5-Nitroindazole, 13.401 g (96.96 mmole) of potassium carbonate, and 2.246 g (1.94 mmole) of PdTetrakis(Triphenylphosphine) were added at r.t. under dry $N_2$ gas. The mixture was degassed couple of times with dry $N_2$ gas. The dark colored mixture was heated at 100° C. overnight. The mixture was allowed to cool to r.t. and diluted with 1:1 mixture of $H_2O$/EtOAc. The diluted mixture was filtered through the pad of Celite and Celite pad was liberally washed with EtOAc. The contents were transferred to a separation funnel and shaken well. The organic phase was separated and washed couple of times with saturated NaCl solution, dried over $MgSO_4$ and evaporated to dryness. The dark colored gum was purified on RediSep 330 g cartridge eluting with Hexanes, 5% EtOAc/Hexane and 10% EtOAc/Hexanes, gave 3.24 g (31%) pale yellow solid 19BV.

Step 3

Preparation of 3-(2-Isopropoxy-pyridin-4-yl)-1-trityl-1H-indazol-5-ylamine

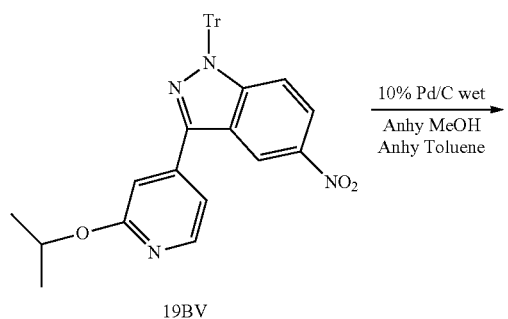

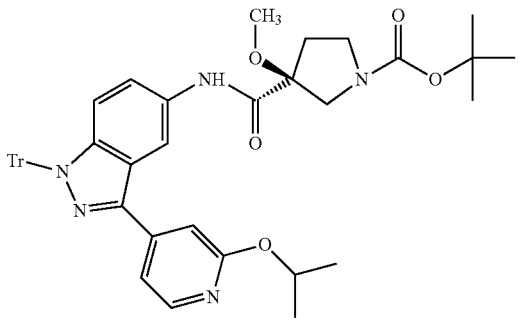

21BV was prepared using essentially the same procedure as in Example 13, Step 4, starting with 20BV instead of 5BV.

Step 5

Preparation of 3-Methoxy-pyrrolidine-3-carboxylic acid [3-(2-isopropoxy-pyridin-4-yl)-1H-indazol-5-yl]-amide

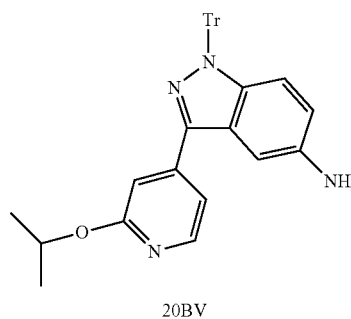

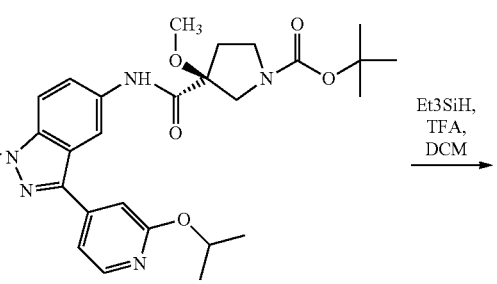

20BV was prepared, with a crude yield of 100%, using essentially the same procedure as in Example 13, Step 3, except using 19BV instead of 4BV.

Step 4

Preparation of 3-[3-(2-Isopropoxy-pyridin-4-yl)-1-trityl-1H-indazol-5-ylcarbamoyl]-3-methoxy-pyrrolidine-1-carboxylic acid tert-butyl ester

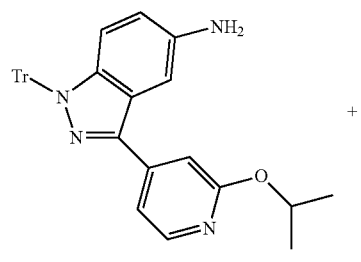

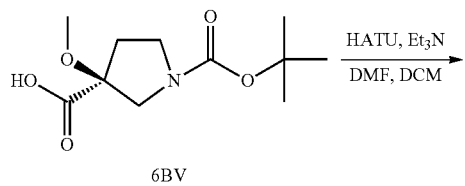

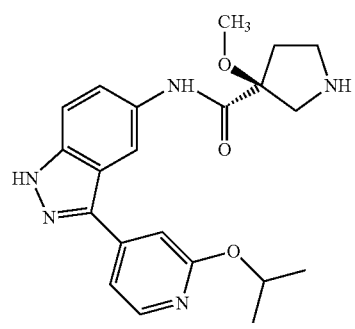

22BV was prepared using essentially the same procedure as in Example 13, Step 5, using 21BV instead of 7BV.

Step 6

Preparation of 3-Methoxy-1-(2-{4-[4-(1-methyl-1H-[1,2,4]triazol-3-yl)-phenyl]-3,6-dihydro-2H-pyridin-1-yl}-2-oxo-ethyl)-pyrrolidine-3-carboxylic acid [3-(2-isopropoxy-pyridin-4-yl)-1H-indazol-5-yl]-amide

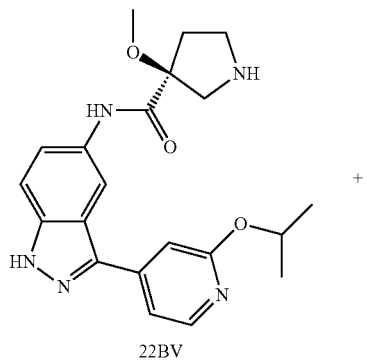

22BV

+

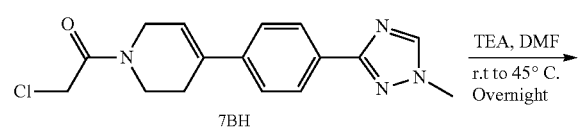

7BH

TEA, DMF
r.t to 45° C.
Overnight

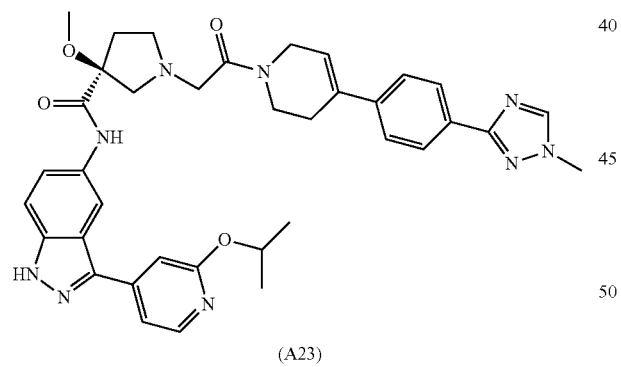

(A23)

A mixture of compound 22BV (40 mg, 0.10 mmol), compound 7BH (41.6 mg, 0.13 mmol) and triethylamine (0.1 mL) in DMF (3 mL) was heated at 45° C. with stirring overnight. The reaction mixture was then concentrated in vacuo and the resulting crude was purified on silica gel column eluting with 2% and 4% 2N NH₃/MeOH in CH₂Cl₂ to isolate a yellow solid 23BV (35.0 mg, 52%). LCMS M+1=676, ret. time=2.45 min. $^1$H-NMR (400 MHz, CDCl₃): δ 10.42 (br, 1H), 9.41 & 9.34 (s, s, 1H), 8.43 (dd, 1H, J=10.7 Hz & 1.2 Hz), 8.25 (d, 1H, J=5.2 Hz), 8.07 (s, 1H), 8.05 (m, 2H), 7.74 (m, 1H), 7.49 (m, 1H), 7.44 (m, 3H), 7.29 (br, 1H), 6.20 & 6.11 (t, t, 1H, J=2.5 Hz), 5.37 (m, 1H), 4.27 (m, 2H), 3.98 (s, 3H), 3.80-3.98 (m, 1H), 3.74 (m, 1H), 3.53 (d, 1H, J=6.6 Hz), 3.49 (br, 1H), 3.47 & 3.46 (s, s, 3H), 3.28 (d, 1H, J=10 Hz), 3.02 (m, 2H), 2.88 (m, 1H), 2.64 (m, 2H), 2.47 (m, 1H), 2.19 (m, 1H), 1.40 (d, 6H, J=6.1 Hz).

Example 16

Synthesis of 3-Methylsulfanyl-1-(2-{4-[5-(1-methyl-1H-[1,2,4]triazol-3-yl)thiophen-2-yl]-3,6-dihydro-2H-pyridin-1-yl}-2-oxo-ethyl)-pyrrolidine-3-carboxylic acid [3-(6-isopropoxy-pyridin-3-yl)-1H-indazol-5-yl]-amide

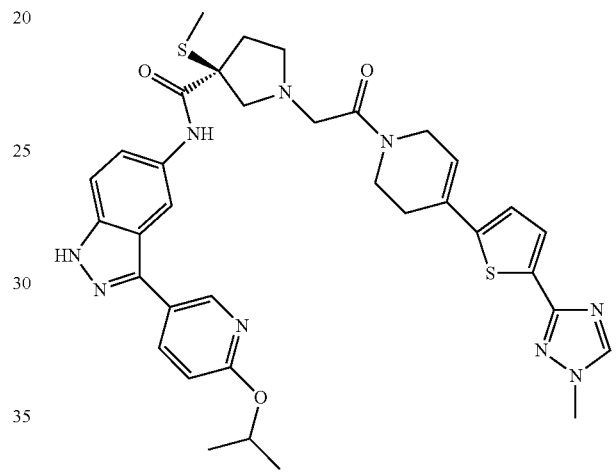

(A24)

Synthesis of 2-Chloro-1-{4-[5-(1-methyl-1H-[1,2,4]triazol-3-yl)-thiophen-2-yl]-3,6-dihydro-2H-pyridin-1-yl}-ethanone Step 1

Preparation of 5-bromo-thiophene-2-carboxylic acid amide

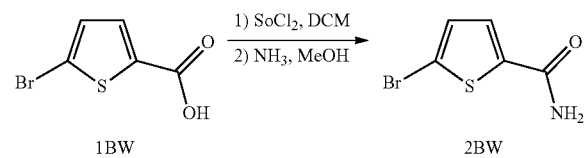 [SMILES: O=C(O)c1ccc(Br)s1 ; NC(=O)c1ccc(Br)s1]

5-Bromo-thiophene 2-carboxylic acid (1BW) (6 g) was suspended in dichloromethane (30 ml) and thionyl chloride (30 ml). The resulting solution was allowed to reflux for overnight at 80° C. Solvent was removed under reduced pressure and the precipitate was dissolved in dichloromethane which was added dropwise to the cooled solution of ammonia in methanol (100 mL) reaction was monitored by TLC and LC-MS. Solvent was removed under reduced pressure to yield 5-bromo-thiophene 2-carboxylic acid amide (2BW).

Step 2

Preparation of 5-bromo-thiophene 2-carboximidic acid ethyl ester

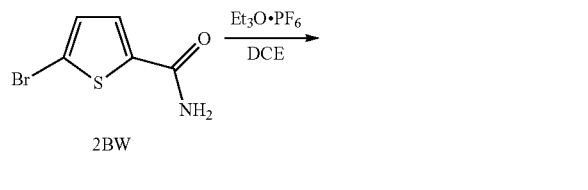

The 5-bromo-thiophene 2-carboxylic acid amide (2BW) (7 g, 34.1 mmols) was dissolved in dichloroethane (170 ml). Triethyloxonium hexafluorophosphate (10.16 g, 40.97 mmols) was added and the resulting mixture was refluxed for 1 hr at 90° C. The reaction mixture was concentrated under reduced pressure, and was taken directly to next step.

Step 3

Preparation of 5-bromo-thiophene 2-carboximidic-N'-methyl-hydrazide

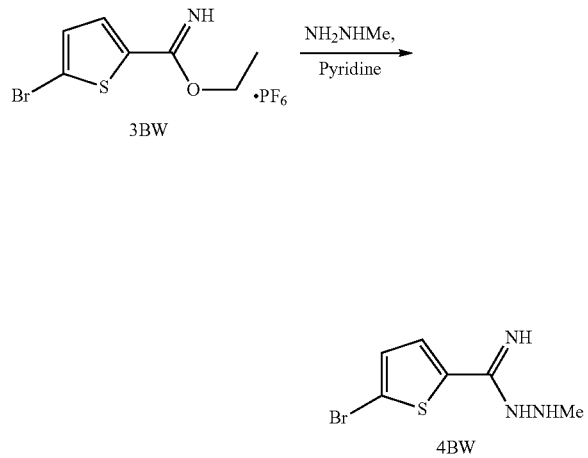

The 5-bromo-thiophene 2-carboximidic acid ethyl ester (3BW) (13 g, 34.3 mmols) was dissolved in pyridine (100 ml). Methylhydrazine (2.7, 51.45 mmols) was added with stirring and the resulted mixture was allowed to stir overnight. The reaction mixture was concentrated under reduced pressure, and added ether, filtered, washed with ether three times and dried to provide the titled compound (4BW) (13 g).

Step 4

Preparation of 3-(5-bromo-thiophen-2-yl)-1-methyl-1H-[1,2,4]triazole

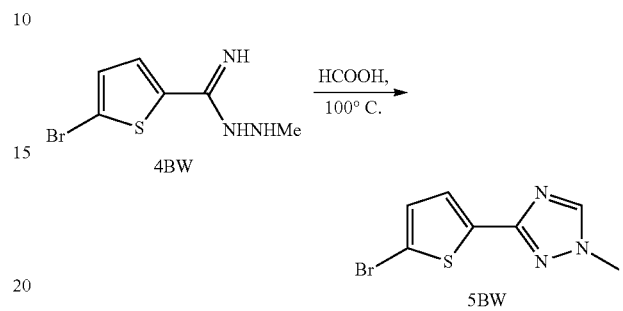

A mixture of compound 5-bromo-thiophene 2-carboximidic-N'-methyl-hydrazide (4BW) (13 g) in formic acid (100 ml) was refluxed overnight and concentrated. The residue was treated with sat. NaHCO$_3$, and extracted with EtOAc three times. The combined organics were dried over MgSO$_4$. After concentration, compound 5BW was purified by column using 80% EtoAc/hexane to yield light yellow colored solid.

Step 5

Preparation of 4-[5-(1-methyl-1H-[1,2,4]triazol-3-yl)-thiophen-2-yl]-3,6-dihydro-2H-pyridine-1-carboxylic acid tert-butyl ester

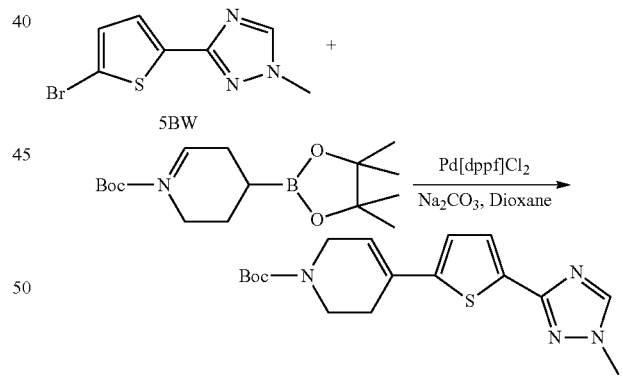

To a large pressure flask were charged compound 3-(5-bromo-thiophen-2-yl)-1-methyl-1H-[1,2,4]triazole (3.1 g, 12.8 mmols) (5BW), 4-(4,4,5,5-tetramethyl-[1,3,2]dioxaborolan-2-yl)-3,6-dihydro-2H-pyridine-1-carboxylic acid tert-butyl ester (3.6 g, 11.65 mmols), [1,1'-bis(diphenylphosphino)-ferrocene]dichloro-palladium (II), complex with dichloromethane (1:1) (0.475 g, 0.89 mmols), Na$_2$CO$_3$ (8.5 ml) and dioxane (40 ml). The mixture was briefly degassed with Ar for ~0.5 minute, capped and stirred at 80° C. overnight. After cooling, the reaction mixture was diluted with EtOAc and brine. Organic layer was isolated, and dried MgSO₄. After concentration, the residue was purified on silica gel. Elution with EtOAc (100%) gave the desired product (6BW) (3.5 g).

Step 6

Preparation of 4-[5-(1-methyl-1H-[1,2,4]triazol-3-yl)-thiophen-2-yl]-1,2,3,6-tetrahydro-pyridine hydrochloride

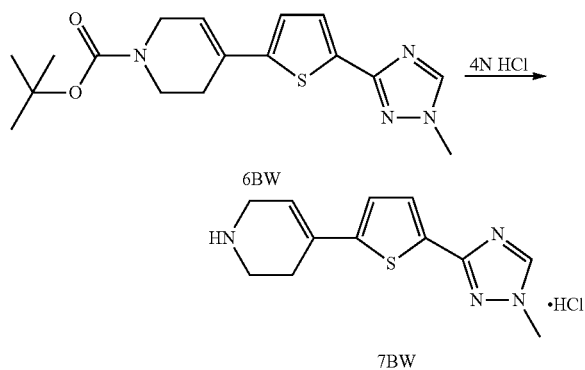

The Boc group on 6BW can be removed by treating compound 4-[5-(1-methyl-1H-[1,2,4]triazol-3-yl)-thiophen-2-yl]-3,6-dihydro-2H-pyridine-1-carboxylic acid tert-butyl ester with 4N HCl in dioxane at room temperature for two hours. Removal of solvent under vacuum followed by ether wash yielded the desired compound (7BW).

Step 7

Preparation of 2-chloro-1-{4-[5-(1-methyl-1H-[1,2,4]triazol-3-yl)-thiophen-2-yl]-3,6-dihydro-2H-pyridin-1-yl}-ethanone

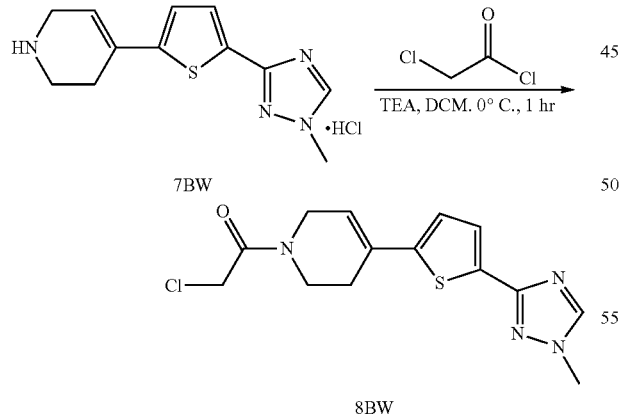

To a cold (0° C.) solution of 4-[5-(1-methyl-1H-[1,2,4]triazol-3-yl)-thiophen-2-yl]-1,2,3,6-tetrahydro-pyridine (7BW) (1.5 g, 4.72 mmol) in dichloromethane (50 ml) was added TEA (4.5 ml, 28.32 mmol) dropwise. After stirred at 0° C. for 10 min, chloroacetyl chloride (1.12 ml, 14.2 mmol) was added to the reaction mixture. The resulting mixture was stirred at 0° C. for 1 hr., and quenched with water (15.6 ml). The reaction mixture was diluted with dichloromethane (200 ml). The organic layer was separated and washed with brine, dried over MgSO₄. Reaction mixture was concentrated to ~50 ml, ether was added and the solid was filtered out to get the desired product (8BW).

Step 8

Synthesis of 3-Methoxy-1-(2-{4-[4-(1-methyl-1H-[1,2,4]triazol-3-yl)-phenyl]-3,6-dihydro-2H-pyridin-1-yl}-2-oxo-ethyl)-pyrrolidine-3-carboxylic acid [3-(6-isopropoxy-pyridin-3-yl)-1H-indazol-5-yl]-amide

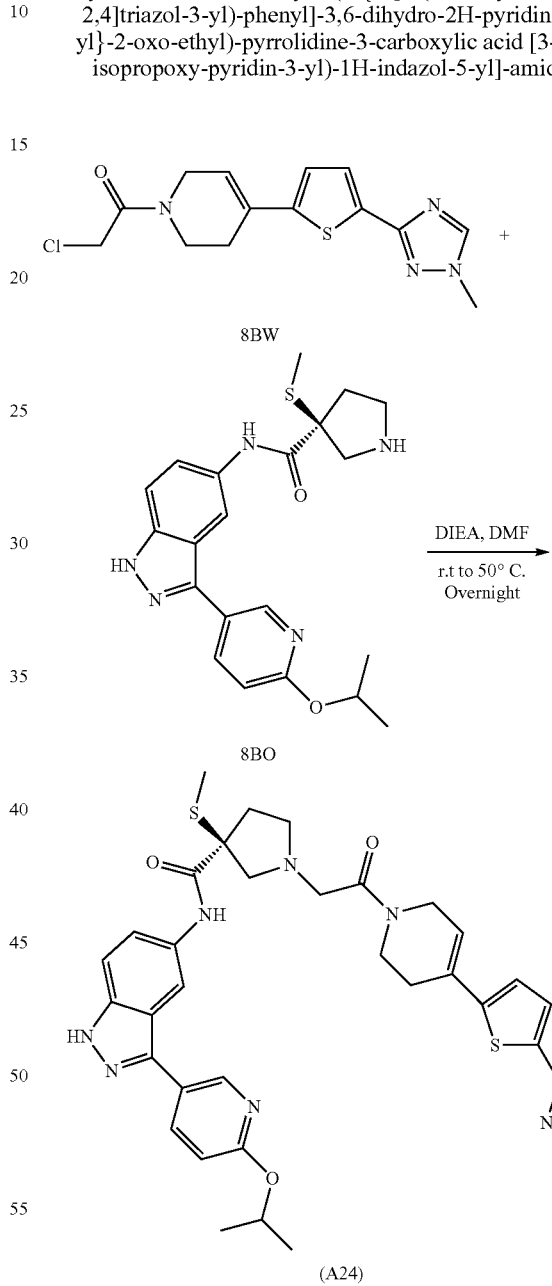

A mixture of 2-chloro-1-{4-[5-(1-methyl-1H-[1,2,4]triazol-3-yl)-thiophen-2-yl]-3,6-dihydro-2H-pyridin-1-yl}-ethanone (8BW) (0.522 gm, 0.863 mmol), 3-Methylsulfanyl-pyrrolidine-3-carboxylic acid [3-(6-isopropoxy-pyridin-3-yl)-1H-indazol-5-yl]-amide (8BO) (0.463 gm, 0.95 mmol), and DIEA (0.9 ml, 5.2 mmol) in DMF (10 ml) was stirred at room temperature for overnight. DMF was removed under reduced pressure. The crude reaction mixture was precipitated in 30 ml ice cold water, filtered, dried, and purified by column chromatography using 10% MeOH/EtOAc to get desired product A24 as a yellow solid (70%). (LCMS M+1=698, ret. time=3.6 min.) $^1$H NMR (400 MHz, DMSO): ᵟ 8.67 (S, 1H), 8.64 (S, 1H), 8.36 (S, 1H), 8.15 (S, 1H), 7.64 (d, 1H, J=8.8 Hz), 7.52 (S, 1H), 7.49 (d, 1H J=5.2 Hz), 7.40 (d, 1H J=8.8 Hz), 7.02 (m, 1H), 6.18 (d, 1H, J=18.8 Hz), 5.08 (m, 1H), 4.41 (d, 2H, J=7.6 Hz), 4.34 (d, 1H, J=6.4 Hz)), 4.12 (S, 1H), 3.96 (s, 2H), 3.84 (S, 3H), 3.76 (S, 2H), 3.52 (S, 2H), 2.76 (S, 1H), 2.58 (d, 2H J=20.4 Hz), 2.13 (S, 3H), 1.94 (t, 2H J=2.8 Hz), 1.39 (d, 6H, J=4.8 Hz).

Examples 17 to 25

Compounds A4, A6, A8, A10-A12, A18, A25 and A26 were prepared following the procedures indicated in the Table 1 below.

TABLE 1

| Ex. | Compound Prepared | Procedure Followed |
|---|---|---|
| 17 | A4 | Essentially the same procedure as in Example 4 except substituting hydrazine for hydroxyethyl-hydrazine in the preparation of 4BL |
| 18 | A6 | Essentially the same procedure as in Example 1 except substituting 11BP for 14BH |
| 19 | A8 | Essentially the same procedure as in Example 10 except substituting 8BO for 8BN in the preparation of 10BN |
| 20 | A10 | Essentially the same procedure as in Example 8 except substituting 8BO for 8BN in the preparation of 10BN |
| 21 | A11 | Essentially the same procedure as in Example 4 except substituting hydroxyethylhydrazine for methoxyethylhydrazine |
| 22 | A12 | Essentially the same procedure as in Example 21 except substituting except substituting 8BO for 8BN in the preparation of 10BN |

TABLE 1-continued

| Ex. | Compound Prepared | Procedure Followed |
|---|---|---|
| 23 | A18 | Essentially the same procedure as in Example 7 using commercially available 5-(4-Bromo-phenyl)-2H-[1,2,4]triazol-3-ylamine for 4BN. |
| 24 | A25 | Essentially the same procedure as in Example 14 except substituting 4BV for 11BV |
| 25 | A26 | Essentially the same procedure as in Example 14 except substituting 20BV for 11BV |

The LCMS data for compounds in Table 1 are given in Table 2 below.

TABLE 2

| Compound | LCMS Retention Time (Minutes) | LCMS M + 1 |
|---|---|---|
| A4 | 3.08 | 680 |
| A6 | 3.36 | 692 |
| A8 | 3.16 | 722 |
| A10 | 3.41 | 750 |
| A11 | 3.23 | 724 |
| A12 | 3.19 | 740 |
| A18 | 3.21 | 693 |
| A25 | 2.24 | 664 |
| A26 | 2.49 | 692 |

Example 26

Preparation of (S)—N-(3-(6-isopropoxypyridin-3-yl)-1H-indazol-5-yl)-3-methoxy-1-(2-(4-(5-(1-methyl-1H-1,2,4-triazol-3-yl)pyridin-2-yl)-5,6-dihydropyridin-1(2H)-yl)-2-oxoethyl)pyrrolidine-3-carboxamide

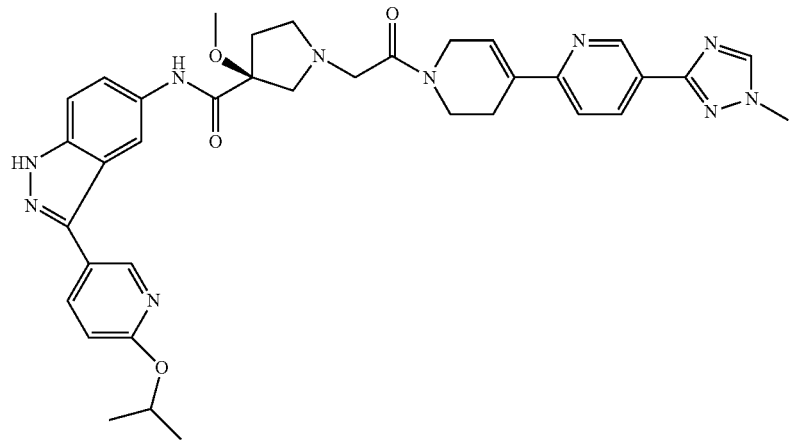

(A27)

Step 1: Methyl 6-chloronicotinimidate (1BX)

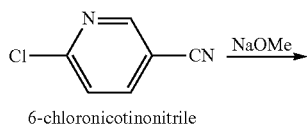

6-chloronicotinonitrile

methyl 6-chloronicotinimidate
1BX

Sodium methoxide (725 mg, 13.42 mmol) was added to a solution of 2-Chloro pyridine-5-carbonitrile (1.8 g, 13.04 mmol) in MeOH:dioxane (40 ml, 1:1) at 0° C., then stirred for 30 minutes at 0° C., and 1 hour at room temperature. The reaction was diluted with EtOAc (200 ml) and H$_2$O (100 ml), organic layer separated, dried over Na$_2$SO$_4$, filtered and solvent evaporated to yield title compound 1BX as a white solid (2.6 g, 100%) MS (MH 171)

Step 2: 6-chloro-N'-methylnicotinimidohydrazide (2BX)

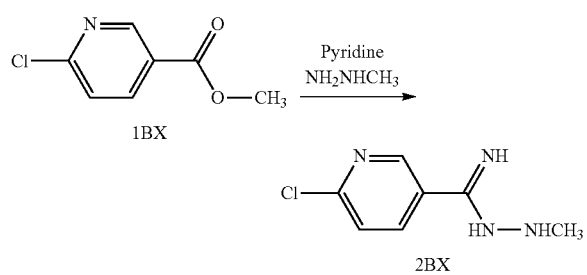

Methyl hydrazine (750 mg, 16.30 mmol) was added to a solution of Methyl 6-chloronicotinimidate (1BX) (2.6 g, 15.29 mmol) in Pyridine (10 ml) at room temperature, then stirred for 1 hour. The solvent was evaporated, and residual solid triturated with cold Ether (2×10 ml) yielding title product 2BX as a yellow powder (2.4 g, 85%) MS (MH, 185)

Step 3: 2-chloro-5-(1-methyl-1H-1,2,4-triazol-3-yl) pyridine (3BX)

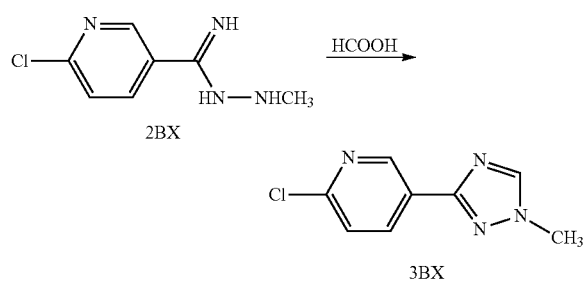

A solution of 6-chloro-N'-methylnicotinimidohydrazide (2BX) (2.4 g, 13 mmol) in Formic Acid (99%, 10 ml) was stirred at reflux temperature for 1 hour. Reaction was cooled and solvent evaporated. The residue was extracted with EtOAc (100 ml) and Aqueous NaHCO$_3$ (50 ml), organic layer was separated, dried over Na$_2$SO$_4$, filtered and solvent evaporated. The residue chromatographed on silica gel eluting with 10% MeOH:CH$_2$Cl$_2$ yielding title product as a solid (1.8 g, 72%) MS (MH, 195)

Step 4: Tert-butyl 4-(5-(1-methyl-1H-1,2,4-triazol-3-yl)pyridin-2-yl)-5,6-dihydropyridine-1(2H)-carboxylate (4BX)

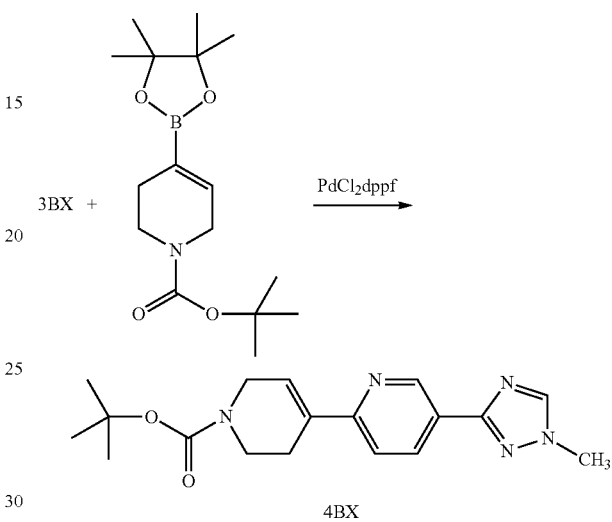

A mixture of 2-chloro-5-(1-methyl-1H-1,2,4-triazol-3-yl) pyridine (3BX) (400 mg, 2.06 mmol); N-Tert-Butoxycarbonyl-1,2,3,6-tetrahydropyridine-4-boronic acid, pinacol ester (1.4 g, 4.53 mmol); Cesium carbonate (2.3 g, 7.07 mmol) and PdCl$_2$dppf (100 mg) in dioxane/H$_2$O (v/v 10:1, 20 ml) was stirred at 100° C. for 2 hours. The reaction was cooled, diluted with CH$_2$Cl$_2$ (300 ml) and H$_2$O (100 ml), organic layer separated, dried over Na$_2$SO$_4$, filtered and solvent evaporated yielding a residue which chromatographed on silica gel eluting with EtOAc yielding title product 4BX as a solid (400 mg, 57%) MS (MH, 342).

Step 5: 5-(1-methyl-1H-1,2,4-triazol-3-yl)-2-(1,2,3, 6-tetrahydropyridin-4-yl)pyridine dihydrochloride (5BX)

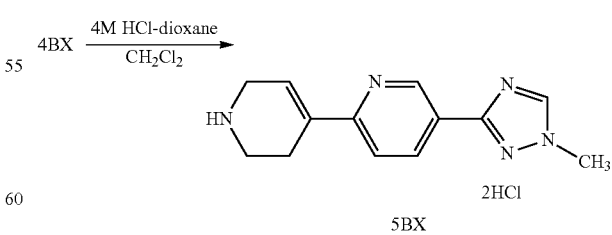

4M HCl in dioxane (20 ml) was added to a solution of Tert-butyl 4-(5-(1-methyl-1H-1,2,4-triazol-3-yl)pyridin-2-yl)-5,6-dihydropyridine-1(2H)-carboxylate (4BX) (4 g, 11.67 mmol) in CH$_2$Cl$_2$ (50 ml) at room temperature. The mixture was stirred for 3 hours then solvent was evaporated yielding title product as a white solid (3.8 g).

Step 6: 2-chloro-1-(4-(5-(1-methyl-1H-1,2,4-triazol-3-yl)pyridin-2-yl)-5,6-dihydropyridin-1(2H)-yl)ethanone (6BX)

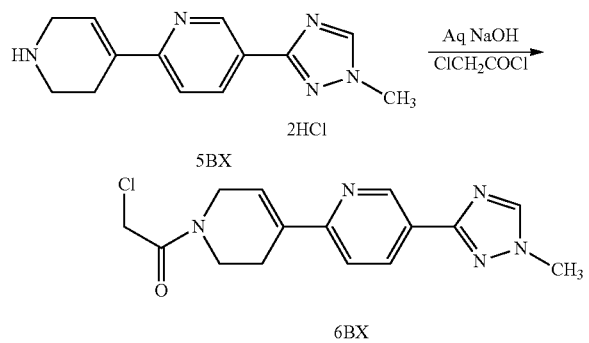

Added 1N NaOH (50 ml, 50 mmol) and Chloroacetyl chloride (3 ml, 37.7 mmol) in CH$_2$Cl$_2$ (50 ml) dropwise to a solution of 5-(1-methyl-1H-1,2,4-triazol-3-yl)-2-(1,2,3,6-tetrahydropyridin-4-yl)pyridine dihydrochloride (5BX) (1 g, 3.60 mmol) in CH$_2$Cl$_2$ (50 ml at 0° C., maintaining pH at >12. Mixture was stirred for 2 hours at 0° C., then reaction was diluted with CH$_2$Cl$_2$ (200 ml) and H$_2$O (100 ml). The organic layer was separated, washed with H$_2$O (50 ml), dried (Na$_2$SO$_4$), filtered and solvent evaporated yielding title product as a white solid (1.1 g, 100%) MS (MH, 318)

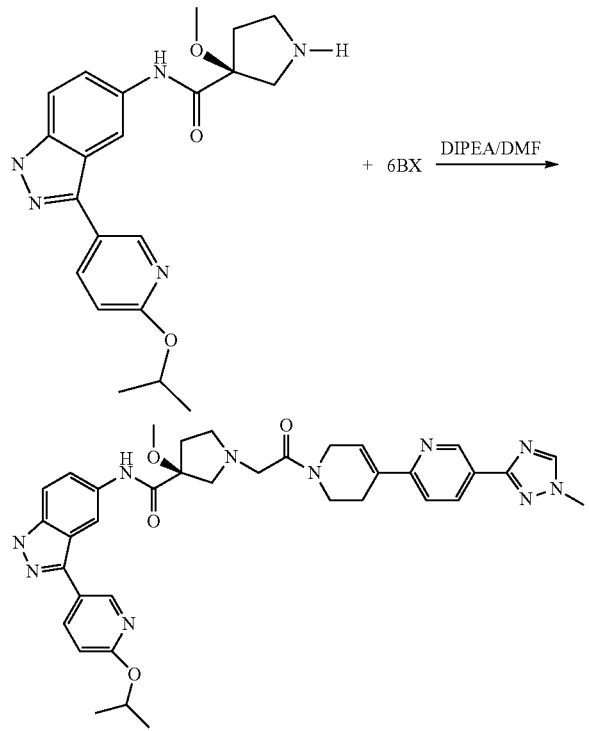

Added a solution of 2-chloro-1-(4-(5-(1-methyl-1H-1,2,4-triazol-3-yl)pyridin-2-yl)-5,6-dihydropyridin-1(2H)-yl) ethanone (6BX) (0.85 g, 2.68 mmol) in CH$_2$Cl$_2$ (10 ml) to a solution of the Indazole (1 g, 2.53 mmol) in DMF (10 ml) at room temperature, then stirred at 50° C. for 3 hours. The reaction was diluted with EtOAc (300 ml) and H$_2$O (100 ml), then the organic layer was separated, dried over Na$_2$SO$_4$, filtered and evaporated solvent. The residue chromatographed on silica gel eluting with 10% v/v MeOH/CH$_2$Cl$_2$/NH$_4$OH yielding product A27 as a white solid (1.3 g, 76%) MS (MH, 677)

LCMS Elution time=2.61 minutes

Example 27

Preparation of (S)—N-(3-(6-isopropoxypyridin-3-yl)-1H-indazol-5-yl)-3-methoxy-1-(2-(4-(5-(1-methyl-1H-1,2,4-triazol-3-yl)thiazol-2-yl)-5,6-dihydropyridin-1(2H)-yl)-2-oxoethyl)pyrrolidine-3-carboxamide

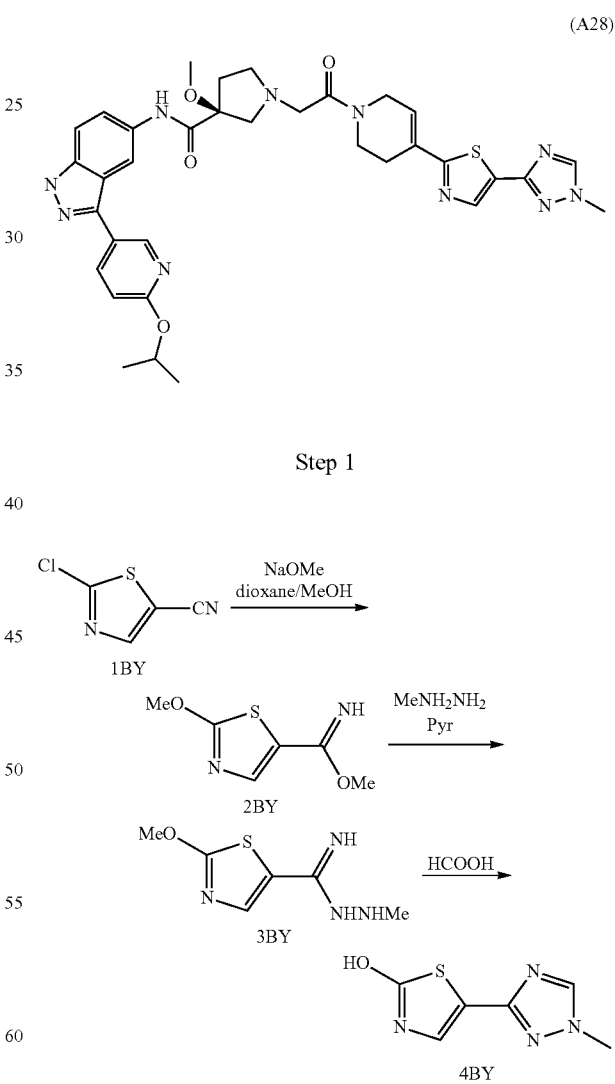

To a stirred mixture of 2-chlorothiazole-carbonitrile (1 g, 6.92 mmol) in MeOH was added NaOMe (745 mg, 13.8 mmol, 2 equiv.) and the reaction mixture was stirred at 0° C. for 15 min and warmed to rt for another 15 min, quenched with water, extracted with EtOAc. The combined organic layer was washed with brine, dried over Na₂SO₄ and concentrated to give crude 2BY (1.2 g) as a yellow oil. To the stirred solution of crude 2BY in pyridine (1 ml) was added methyl hydrazine (363 μL, 6.9 mmol, 1 equiv.), the resulting mixture was stirred at 0° C. for 15 min and quenched with HCOOH (5 ml). The resulting mixture was then transferred to a sealed tube and stirred at 110° C. for overnight, cooled to rt, to which water was added. The resulting mixture was extracted with CH₂Cl₂. The combined organic layer was washed with brine, dried and concentrated to give a yellow solid, which was filtered and washed with CH₂Cl₂. The resulting yellow solid (375 mg) is desired product 4BY. The filtrate was concentrated and could be further purified on column to provide more product.

Step 2

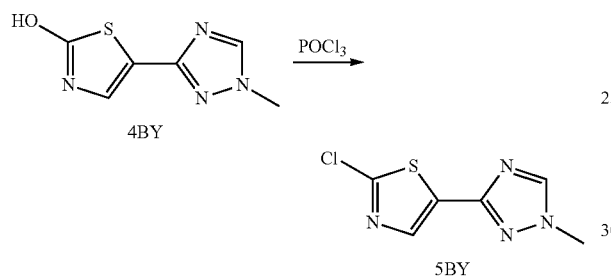

A mixture of 4BY (130 mg) in POCl₃ was stirred under N₂ at 120° C. for 2 d. The initial heterogeneous mixture became a clear brown solution, which was concentrated and purified on silica gel (CH₂Cl₂/MeOH, 50/1) to give 5BY (143 mg) as a yellow solid.

Step 3

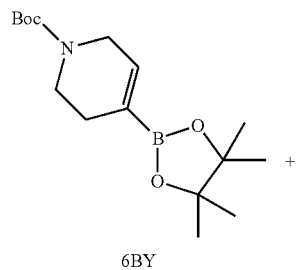

+

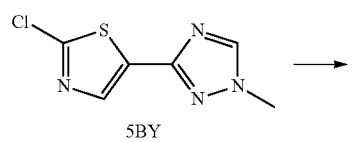

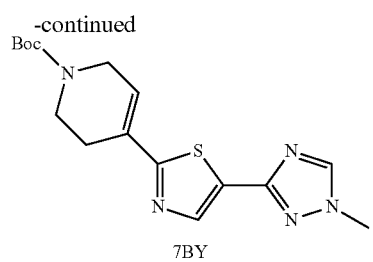

A mixture of 5BY (118 mg, 0.59 mmol), 6BY (274 mg, 0.89 mmol, 1.5 equiv.), 2 M Na₂CO₃ (590 μL, 1.18 mmol, 2 equiv.) and Pd(PPh₃)₄ (34 mg, 0.05 equiv.) in benzene/MeOH (5 mL, 4/1) was degassed and stirred under N₂ at 80° C. for overnight. The reaction mixture was then concentrated and purified on silica gel (CH₂Cl₂/MeOH, 30/1) to give 7BY (150 mg) as a yellow solid.

Step 4

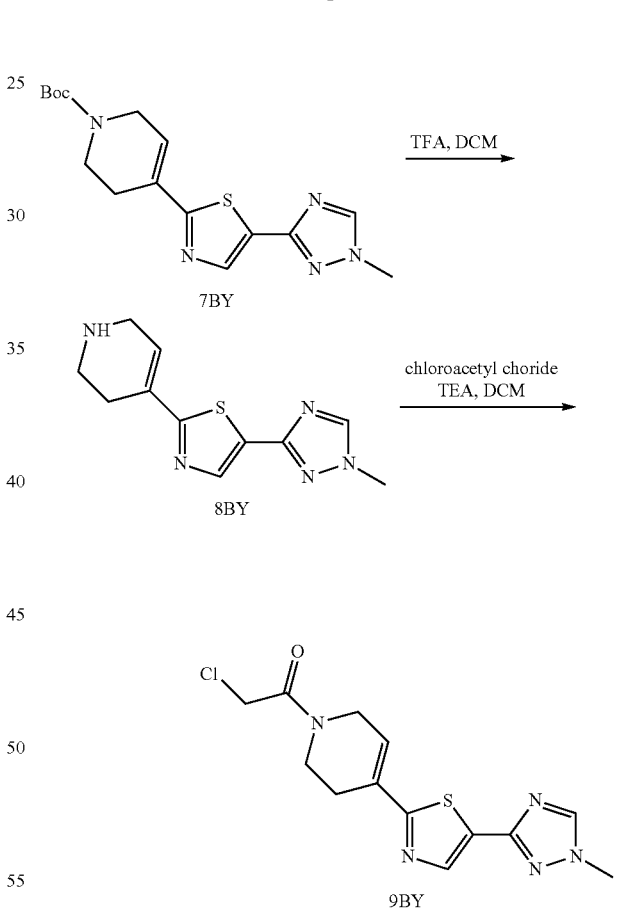

A mixture of 7BY (150 mg, 0.43 mmol) and TFA (1.5 mL) was stirred at rt for 1 h and concentrated. Chromatograph on silica gel (CH₂Cl₂/MeOH, 15/1) gave the 8BY (98 mg). To a stirred mixture of 8BY (98 mg, 0.4 mmol) and triethylamine (335 μL, 2.4 mmol, 6 equiv.) in CH₂Cl₂/MeOH (6 mL, 2/1) at 0° C. was added chloroacetyl chloride (126 μL, 1.6 mmol, 4 equiv.). The reaction mixture was stirred at 0° C. for 1 h and concentrated. Chromatograph on silica gel (CH₂Cl₂/MeOH, 25/1) gave the 9BY (103 mg) as a white solid.

Step 5

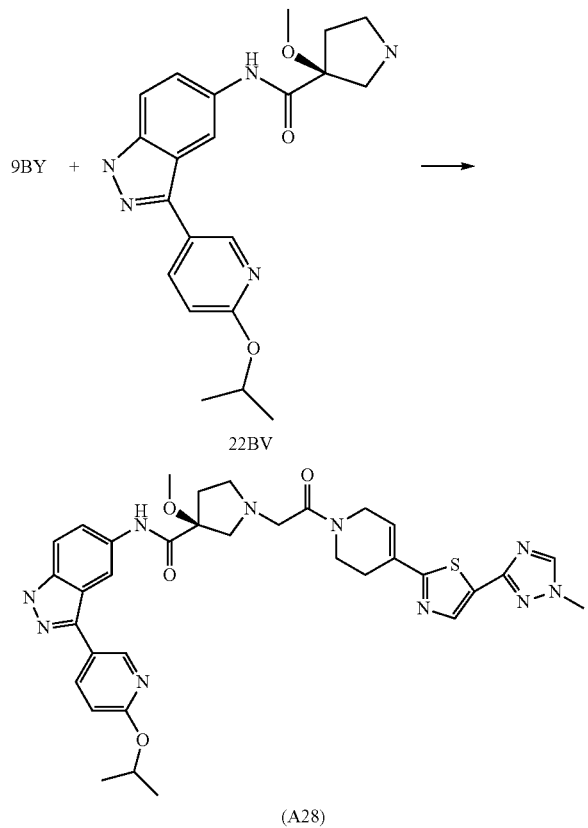

(A28)

Compound 9BY was substituted for compound 7BH in Example 15 step 6 to obtain A28. LCMS MH=683.4, Retention time=2.77 minutes

Example 28

Preparation of (S)—N-(3-(6-isopropoxypyridin-3-yl)-1H-indaol-5-yl)-3-(methylthio)-1-(2-oxo-2-(4-(5-(6-oxopyridazin-1(6H)-yl)-5,6-dihydropyridin-1(2H)-yl)ethyl)pyrrolidine-3-carboxamide) (A29)

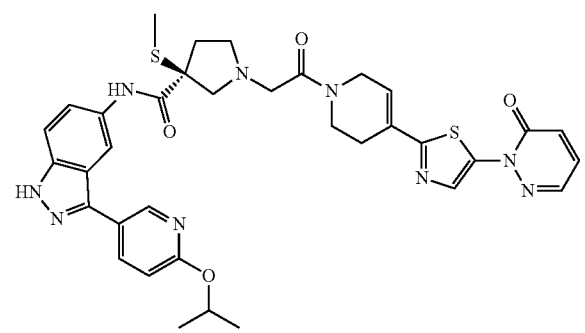

(A29)

Step 1: Preparation of 2-(5-bromothiophen-2-yl)pyridazin-3(2H)-one

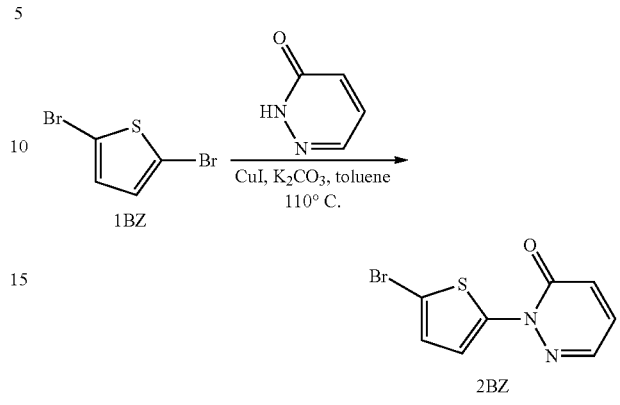

A mixture of 2,5-dibromothiophene (1.5 g, 6.2 mmol), pyridazin-3(2H)-one (0.4 g, 4.1 mmol), copper(I) iodide (0.24 g, 1.2 mmol), potassium carbonate (1.7 g, 12.4 mmol), trans-N,N'-dimethylcyclohexane-1,2-diamine (0.2 mL, 1.2 mmol) and toluene (15 mL) was degassed for 15 minutes and then heated in a sealed tube at 110° C. for 18 hours. Cooled to room temperature, filtered through celite and washed with EtOAc. The filterate was washed with water (100 mL×2). The organic layer was dried over Na₂SO₄, filtered and concentrated give the desired product 2BZ (0.9 g, 90%). The residue was purified on silica gel eluting with 80% EtOAc/hexane to give the desired product 2BZ (0.7 g, 67%).

Step 2: Preparation of tert-butyl 4-(5-(6-oxopyridazin-1(6H)-yl)thiophen-2-yl)-5,6-dihydropyridine-1(2H)-carboxylate

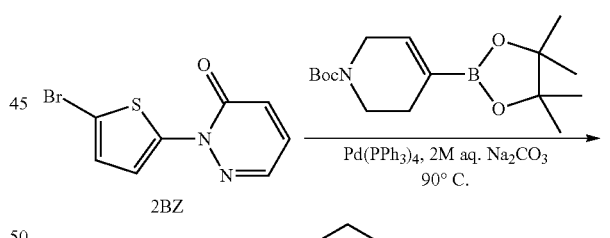

A mixture of Compound 2BZ (0.7 g, 2.7 mmol), 4-(4,4,5,5-tetramethyl-[1,3,2]dioxaborolan-2-yl)-3,6-dihydro-2H-pyridine-1-carboxylic acid tert-butyl ester (0.84 g, 2.7 mmol), 2M aq. sodium carbonate solution (6.8 mL, 13.6 mmol), Pd(PPh₃)₄ (0.31 g, 0.27 mmol) and 1/1/toluene/ethanol (20 mL) was degassed for 15 minutes. Then it was heated at 90° C. for overnight. Cooled to room temperature and diluted with EtOAc (200 ml). The organic layer was washed with water (100 ml), dried over Na₂SO₄, filtered and concentrated. The residue was purified on silica gel eluting with 60% EtOAc/hexane to give the desired product 3BZ (0.63 g, 65%).

Step 4: Preparation of 2-(5-(1,2,3,6-tetrahydropyridin-4-yl)thiophen-2-yl)pyridazin-3(2H)-one

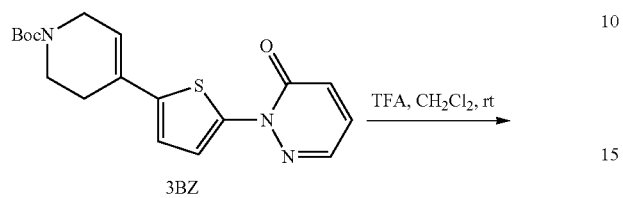

A mixture of Compound 3BZ (0.63 g, 1.75 mmol), CH$_2$Cl$_2$ (20 mL) and TFA (23 mL) was stirred at room temperature for 18 hours. Concentrated and purified on silica gel eluting with 5% MeOH(NH$_3$)/CH$_2$Cl$_2$ to give the desired product 4BZ (0.4 g, 89%).

Step 5: Preparation of 2-(5-(1-(2-chloroacetyl)-1,2,3,6-tetrahydropyridin-4-yl)thiophen-2-yl)pyridazin-3(2H)-one

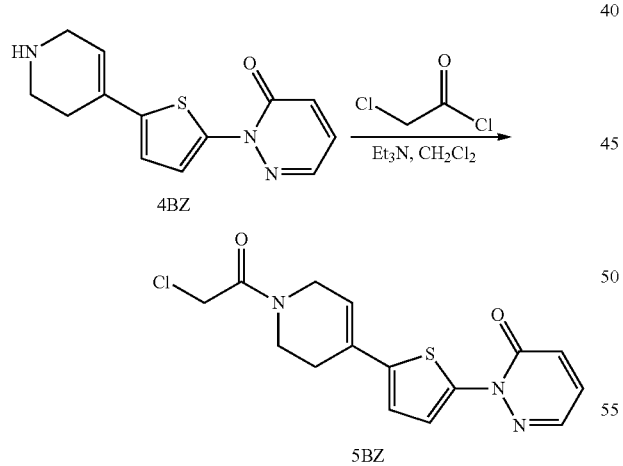

To a mixture of Compound 4BZ (0.62 g, 2.39 mmol), CH$_2$Cl$_2$ (10 mL), MeOH (3 mL) and triethyl amine (0.67 mL, 4.78 mmol) at −78° C. was added chloroacetyl chloride (0.19 mL, 2.39 mmol). Reaction mixture was stirred at −78° C. for 10 minutes then warm to 0° C. and stirred for 1 hour. Diluted with CH$_2$Cl$_2$ (100 mL) and washed with saturated aq. NaHCO$_3$ (100 mL). The organic layer was dried over Na$_2$SO$_4$, filtered and concentrated. The residue was taken in CH$_2$Cl$_2$ and added ether. Resulting solid was filtered and washed with ether and dried to give the desired product 5BZ (0.56 g, 70%).

Step 6

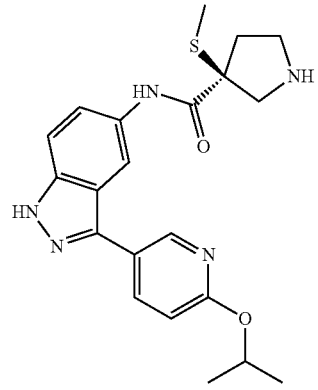

A mixture of Compound 5BZ (0.04 g, 0.12 mmol), compound 6BZ (0.05 g, 0.12 mmol), DMF (2 mL) and N,N-diisopropylethylamine (0.042 mL, 0.24 mmol) was stirred at room temperature for 18 hours. Diluted with EtOAc (100 mL) and washed with water (2×100 mL). The organic layer was dried over Na$_2$SO$_4$, filtered and concentrated. The residue was purified on silica gel eluting with 3% MeOH(NH$_3$)/CH$_2$Cl$_2$ to give the desired product A29 (0.083 g, 97%).

LCMS MH=711, Retention time=3.26 minutes.

Example 29
Preparation of (S)—N-(3-(6-isopropoxypyridin-3-yl)-1H-indaol-5-yl)-1-(2-(4-(5-(3-methyl-6-oxopyridazin-1 (6H)-yl)thiophen-2-yl)-5,6-dihydropyridin-1(2H)-yl)-2-oxoethyl)-3-(methylthio)pyrolidine-3-carboxamide (A30)
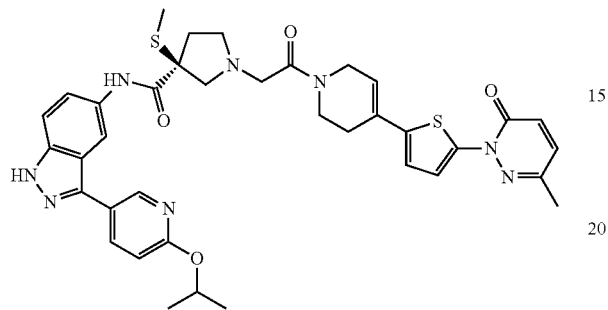
(A30)
Compound A30 was prepared using a procedure similar to that in Example 28 except that 6-methylpyridazin-3(2H)-one was used in place of pyridazin-3(2H)-one in Step 1.
LCMS MH=725, Retention time=3.21 minutes.
Example 30
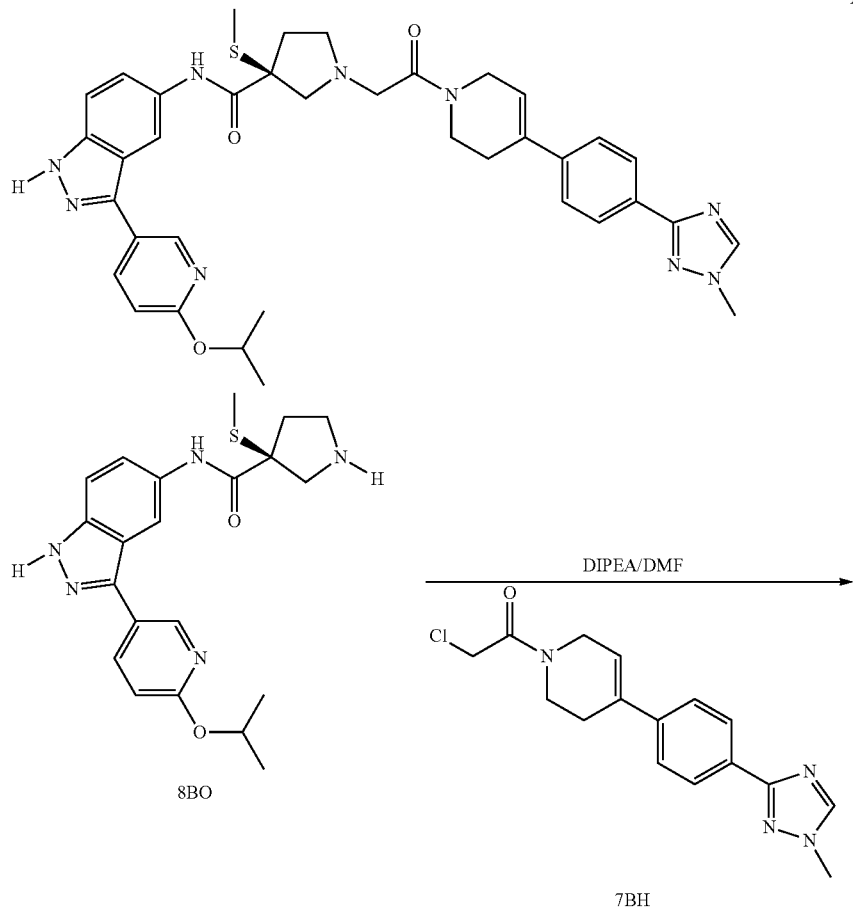

-continued

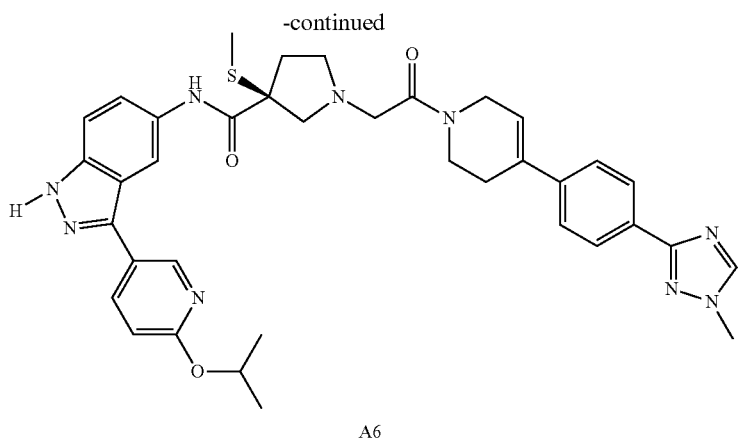

A6

8BO (4.25 g, 10.33 mmol) was dissolved in N,N-dimethylformamide (40 ml) at room temperature. Diisopropylethylamine (5.1 mL, 30.99 mmol) was added followed by 7BH (3.27 g, 10.33 mmol). The reaction mixture was stirred for 1 hr. overnite at ambient temperature. Brine was added to the reaction mixture which was then extracted with ethylacetate (3×100 mL). The ethylacetate extracts were dried over magnesium sulfate, filtered and evaporated to obtain crude title product. The crude product was chromatographed to obtain 4.95 g (69%) of title product (A6)(10% 2N $NH_3$ in MeOH: $CH_2Cl_2$).

Example 31

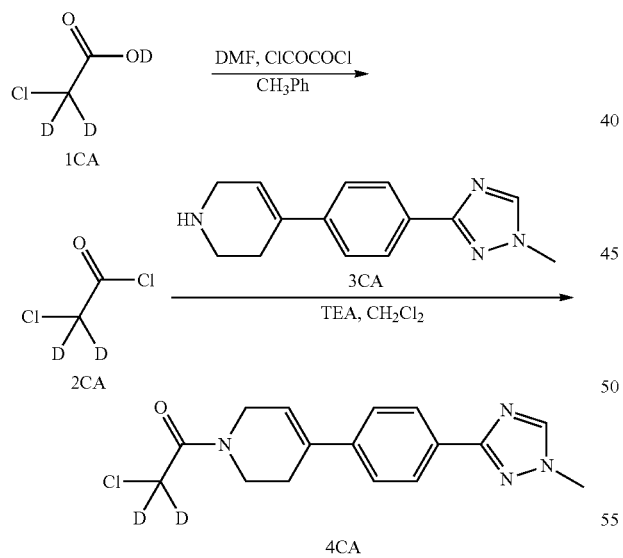

To $CH_3Ph$ (3 mL) solution of 1CA (140 mg, 1.4 mmol) was added a drop of DMF followed by addition of oxalyl chloride (0.14 mL, 1.6 mmol) at r.t. After 30 mins, the resulting clear solution was added to a $CH_2Cl_2$ solution of 3CA (240 mg, 1 mmol) and triethyl amine (0.5 mL). After stirring at r.t. for 30 mins, it was quenched with sat. $NaHCO_3$, extracted with $CH_2Cl_2$ and conc. to get an off white solid as a crude 4CA (312 mg) which was used directly in next reactions. In 1CA, 2CA, and 4CA "D" represents deuterium.

Compounds A31 and A32, were prepared by a method similar to the method for preparing Compound A1 and A6 substituting 4CA for 7BH. Compounds A45 and A48 were prepared by a method similar to the method for preparing A23 and A25 substituting 4CA for 7BH. In A31, A32, A45 and A48 "D" represents deuterium.

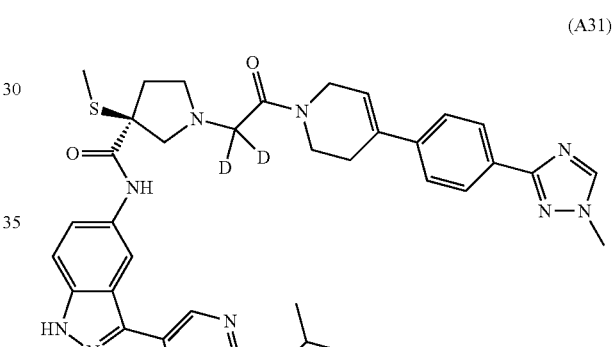

LCMS 3.95 min M + 1 = 694.4

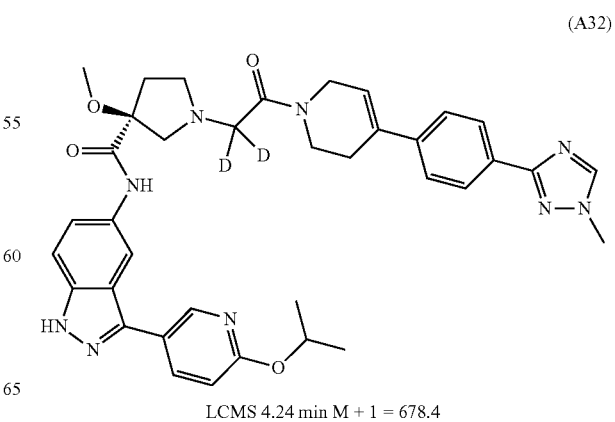

LCMS 4.24 min M + 1 = 678.4

(A45)
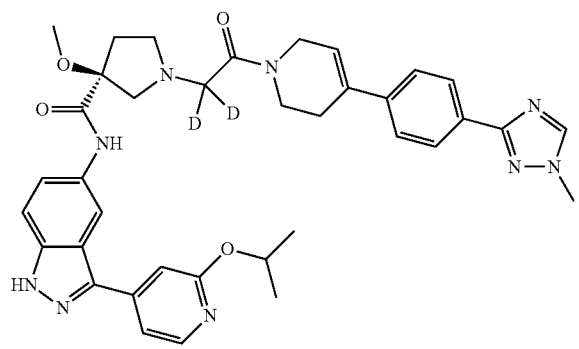
LCMS 3.94 min M + 1 = 674
(A48)
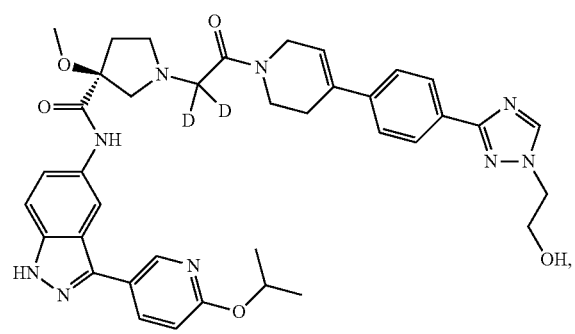
LCMS 3.61 min M + 1 = 664
Example 32
If one were to follow a procedure similar to the procedure in Example 31, Compounds A33 to A44, A46, and A47 below would be obtained. In A33 to A44, A46, and A47 "D" represents deuterium.
(A33)
(A34)
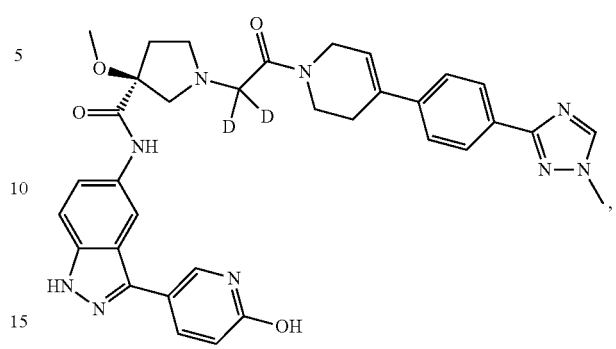
(A35)
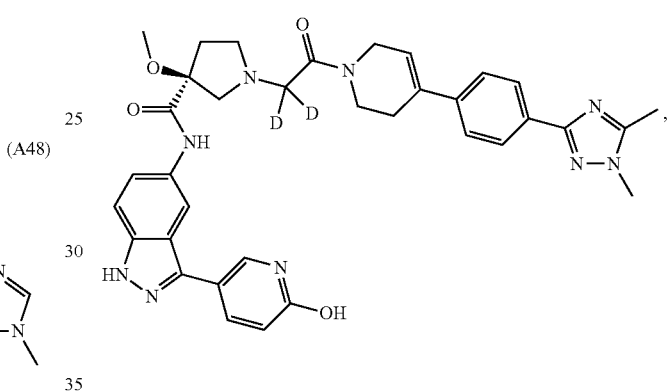
(A36)
(A37)
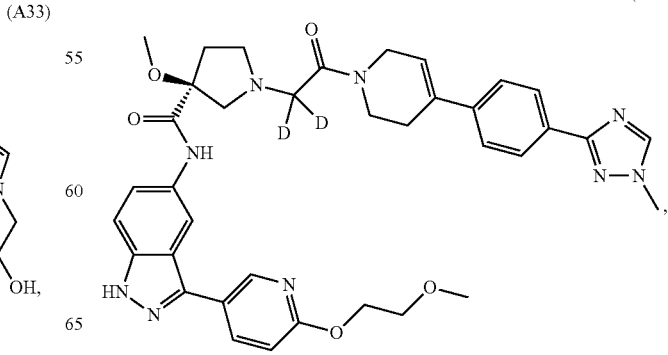

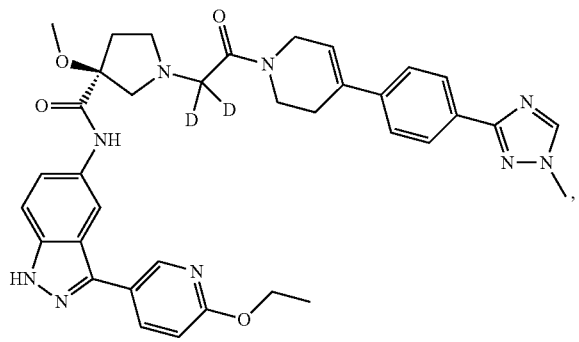 (A38)
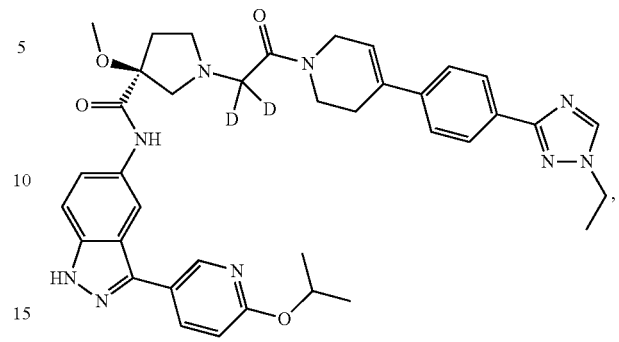 (A42)
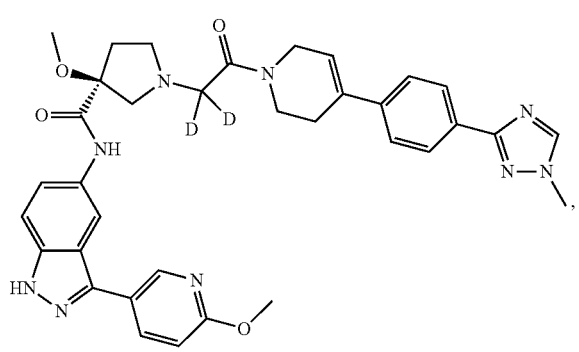 (A39)
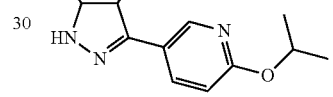 (A43)
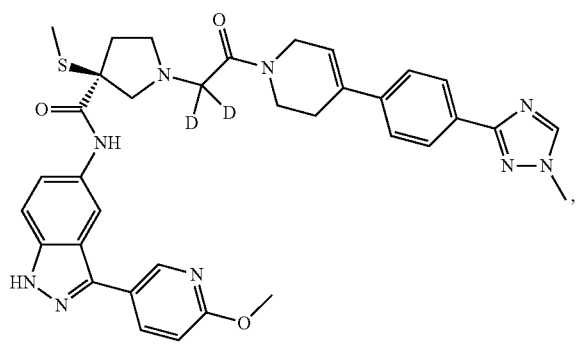 (A40)
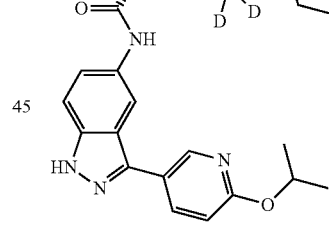 (A44)
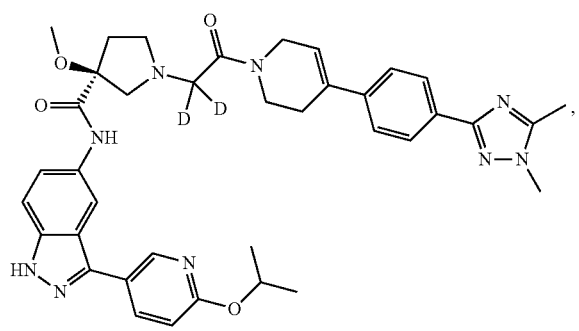 (A41)
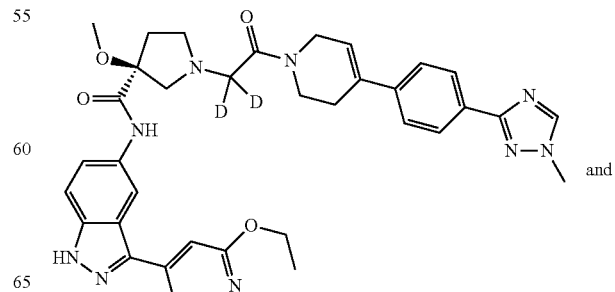 (A46)
and (A47)

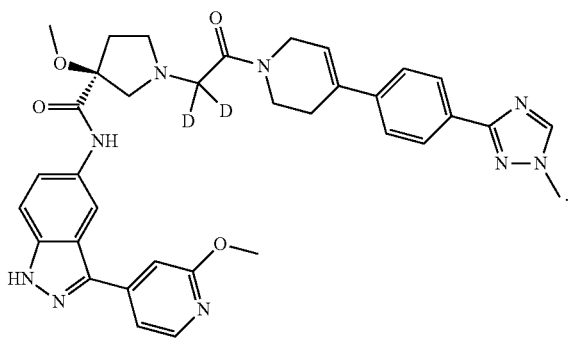

(A45)

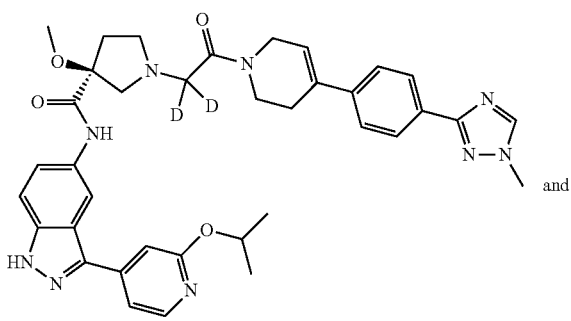

and (A48)

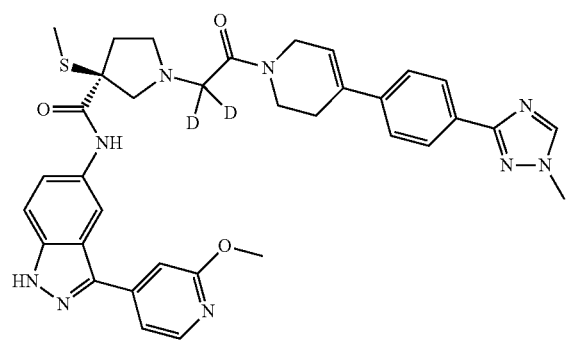

In A33 to A44, A46, and A47 "D" represents deuterium.

Assays

Coupled ERK2 Assay:

Activity of compounds against inactive ERK2 can be tested in a coupled MEK1/ERK2 IMAP assay as follows: Compounds can be diluted to 25× final test concentration in 100% DMSO. 14 μl of kinase buffer (10 mM Tris.HCl pH 7.2, 10 mM $MgCl_2$, 0.01% Tween-20, 1 mM DTT) containing 0.4 ng unphosphorylated Mouse ERK2 protein can be added to each well of a black 384-well assay plate. 1 μl of 25× compound can be added to each well and incubated at room temperature for 30 minutes to allow an opportunity for the compound to bind to the inactive enzyme. DMSO concentration during initial incubation is 6.7%. ERK2 activity can be determined to be insensitive to DMSO concentrations up to 20%. ERK2 can then be activated and it's kinase activity can be measured by the addition of 10 μl kinase buffer with the following components (final concentration per reaction): 2 ng active (phosphorylated) human MEK1 protein and 4 μM (total) ERK2 IMAP substrate peptides (3.9 μM unlabeled IPT-TPITTTYFFFK-$CONH_2$ and 100 nM IPTTPITTTYFFFK (5-carboxyfluorescein)-CON $H_2$) and 30 μM ATP. DMSO concentration during ERK activation can be 4%. After one hour, reactions can be terminated by addition of 60 μl IMAP detections beads in binding buffer (Molecular Devices). Binding can be allowed to equilibrate for 30 minutes before reading the plate on an LJL Analyst Fluorescence Polarization plate reader. Compound inhibition can be calculated relative to DMSO and fully inhibited standards. Active compounds can be reconfirmed in an independent assay.

Active ERK2 Assay:

Activated ERK2 activity was also determined in the IMAP assay format using the procedure outlined above. 1 μl of 25× compound was added to 14 μl of kinase buffer containing 0.25 ng fully phosphorylated, active Mouse ERK2 protein. Following a 30 minute incubation, the reactions were initiated by addition of 10 μl of kinase buffer containing 1 μM ERK2 IMAP substrate peptide (0.9 μM unlabeled IPTTPITTTY-FFFK-$CONH_2$ and 100 nM IPTTPITTTYFFFK(5-carboxyfluorescein)-$CONH_2$) and 30 μM ATP. Reactions proceeded for 30 minutes before termination by addition of 60 μl IMAP detection beads in binding buffer. Plates were read as above after 30 minute binding equilibration. Active compounds were reconfirmed in an independent assay.

Soft Agar Assay:

Anchorage-independent growth is a characteristic of tumorigenic cell lines. Human tumor cells can be suspended in growth medium containing 0.3% agarose and an indicated concentration of a farnesyl transferase inhibitor. The solution can be overlayed onto growth medium solidified with 0.6% agarose containing the same concentration of ERK1 and ERK2 inhibitor as the top layer. After the top layer is solidified, plates can be incubated for 10-16 days at 37° C. under 5% $CO_2$ to allow colony outgrowth. After incubation, the colonies can be stained by overlaying the agar with a solution of MTT (3-[4,5-dimethyl-thiazol-2-yl]-2,5-diphenyltetrazolium bromide, Thiazolyl blue) (1 mg/mL in PBS). Colonies can be counted and the $IC_{50}$'s can be determined.

The AUC (Area Under the Concentration-Time Curve During the First 6 Hours ($AUC_{6hr}$) was Determined Using the Protocol of Cassette Accelerating Rapid Rat Screen (CARRS)

Animal Dosing and Sample Collection

Male Sprague-Dawley rats (Charles River, Co.) were pre-cannulated (femoral artery) in order to facilitate precise blood sampling times, and to reduce the stress on the animals caused by serial bleedings. Following an overnight fast, two rats were dosed orally with one compound at a dose of 10 mg/kg in a 5-mL/kg dose volume. Blood was collected into heparin-containing tubes serially from each animal at 0.5, 1, 2, 3, 4 and 6 h post-dosing and centrifuged to generate plasma. Approximately 100 μL of plasma were collected at the individual time points. The plasma samples were stored at −20° C. until analysis.

Plasma Sample and Standard Curve Preparation

A set of 12 rat plasma samples was generated for each NCE (i.e. 6 timepoints and n=2 rats). These 12 samples were pooled across the two rats at each timepoint to provide 6 pooled samples (one sample per time point) for each NCE. The pooled samples were assayed as cassettes of six (36 samples total) to provide data on the six compounds. The 50-μL aliquots of the 36 plasma samples were placed into individual wells of a 96-well plate. An additional compound (often a structural analog of the test compounds) was selected as the internal standard. A mini-calibration curve was prepared (three points plus a zero) for each compound assayed. Drug-free rat plasma was measured into 1-mL aliquots and each aliquot was spiked with known concentrations of the compounds to generate standards of the desired concentrations. The concentrations of the standards were chosen to bracket the expected concentration of the pooled samples based on historical data from previous studies on other compounds. For this work, the standards were set to contain concentrations of 25, 250 and 2500 ng NCE/mL plasma. The plasma standards were precipitated in duplicate along with the samples, Protein precipitation occurred after addition of 150 μL of acetonitrile containing the internal standard at a concentration of 1 ng/mL into each sample well using the Tomtec Quadra 96 system. The precipitated samples and standards were vortexed and centrifuged in the 96-well plate. Approximately 50-100 μL of the supernatant were removed and placed into a fresh 96-well plate using the Tomtec Quadra 96 system. A volume of 5-10 μL of the supernatant was used for analysis by HPLC-MS/MS. The mini-standard curve was run in duplicate, once before and once after the samples. Thus, a total of 14 study samples plus standards were analyzed per compound. In addition, solvent blanks were injected before and after each set of 14 and after the highest calibration standard for each compound; therefore, a total of 103 injections were made into each HPLC system for each set of six compounds. Multiple solvent blank injections could be made from a single well. Twelve solvent blank wells were designated in each 96-well plate. Thus, one batch (cassette) of six NCEs was prepared and assayed using one 96-well plate format.

HPLC-MS/MS Analysis

All the compounds were analyzed using selected reaction monitoring (SRM) methods with LC/MS/MS instruments. Once the method development had been completed, the assay was quickly set up using a standard injection sequence template for the CARRS assay.

Compounds A1 to A16, A18, A20, A21, A23, A25, A26, and A27 to A30 had an AERK2 IC50 in the range of 1.2 to 50 nM.

Compounds A1-A3, A6, A8-A11, A13-A16, A20-A24, A26 and A27 to A30 had an AUC in the range of 36 to 50,999 nM.hr in the CARRS assay.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington: The Science and Practice of Pharmacy, 20$^{th}$ Edition, (2000), Lippincott Williams & Wilkins, Baltimore, Md.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparations subdivided into suitably sized unit doses containing appropriate quantities of the active component, e.g., an effective amount to achieve the desired purpose.

The quantity of active compound in a unit dose of preparation may be varied or adjusted from about 0.01 mg to about 1000 mg, preferably from about 0.01 mg to about 750 mg, more preferably from about 0.01 mg to about 500 mg, and most preferably from about 0.01 mg to about 250 mg according to the particular application.

The actual dosage employed may be varied depending upon the requirements of the patient and the severity of the condition being treated. Determination of the proper dosage regimen for a particular situation is within the skill in the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.04 mg/day to about 4000 mg/day, in two to four divided doses.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:
1. A compound of the formula:

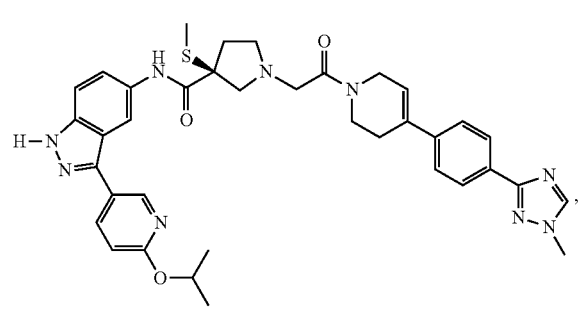

A6 or a pharmaceutically acceptable salt thereof.

2. The compound of claim 1 wherein said compound is:

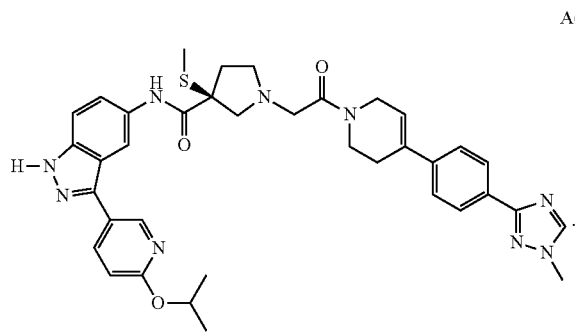
(A6)

3. A compound of the formula:

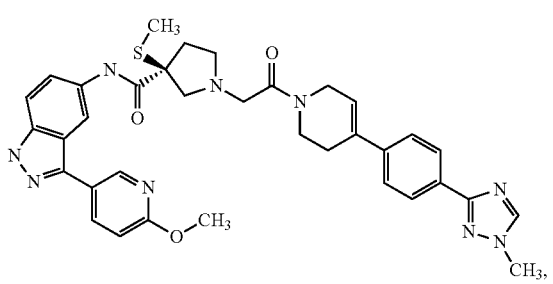
(A19)

or a pharmaceutically acceptable salt thereof.

4. The compound of claim 3 wherein said compound is:

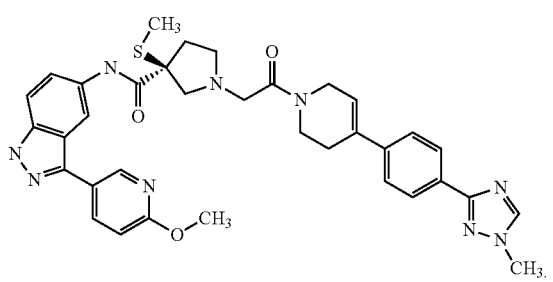
(A19)

5. A compound of the formula:

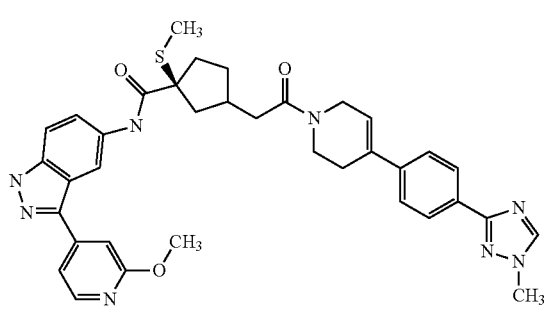
(A25)

or a pharmaceutically acceptable salt thereof.

6. The compound of claim 5 wherein said compound is:

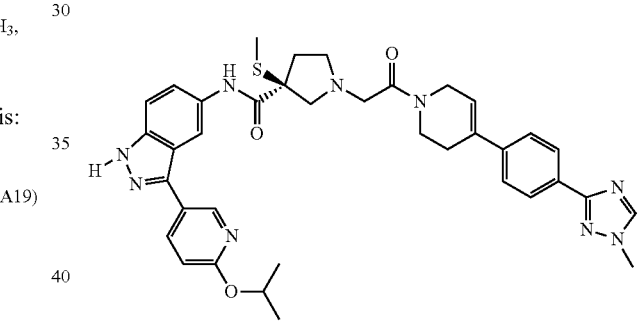
(A25)

7. A pharmaceutical composition comprising the compound of claim 1.

8. A pharmaceutical composition comprising the compound of claim 3.

9. A pharmaceutical composition comprising the compound of claim 5.

10. A compound of the formula:

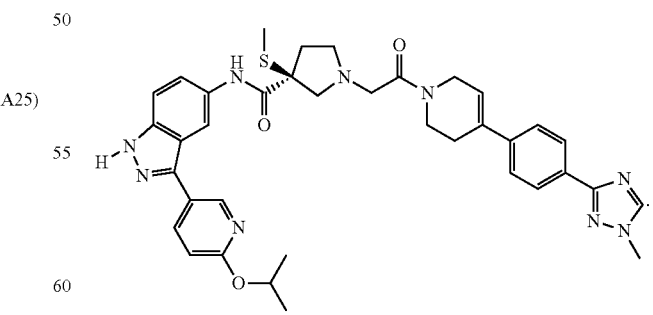

or a pharmaceutically acceptable salt thereof.

11. The compound of claim 10 wherein the compound is:

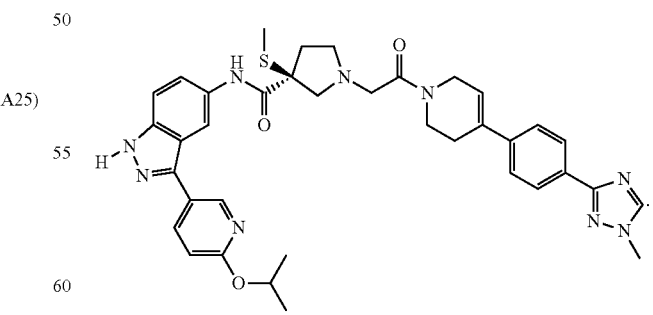

12. A pharmaceutical composition comprising the compound of claim 10.

* * * * *

UNITED STATES PATENT AND TRADEMARK OFFICE
CERTIFICATE OF CORRECTION

| | | | |
|---|---|---|---|
| PATENT NO. | : | 8,716,483 B2 | Page 1 of 1 |
| APPLICATION NO. | : | 12/918099 | |
| DATED | : | May 6, 2014 | |
| INVENTOR(S) | : | Cooper et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 644 days.

Signed and Sealed this
Twenty-ninth Day of September, 2015

Michelle K. Lee
*Director of the United States Patent and Trademark Office*